US006861506B1

(12) United States Patent
Frudakis et al.

(10) Patent No.: US 6,861,506 B1
(45) Date of Patent: Mar. 1, 2005

(54) COMPOSITIONS AND METHODS FOR THE TREATMENT AND DIAGNOSIS OF BREAST CANCER

(75) Inventors: Tony N. Frudakis, Sarasota, FL (US); John M. Smith, Columbia Heights, MN (US); Steven G. Reed, Bellevue, WA (US); Lynda E. Misher, Seattle, WA (US); Marc W. Retter, Carnation, WA (US); Davin C. Dillon, Issaquah, WA (US)

(73) Assignee: Corixa Corporation, Seattle, WA (US)

( * ) Notice: Subject to any disclaimer, the term of this patent is extended or adjusted under 35 U.S.C. 154(b) by 29 days.

(21) Appl. No.: 09/534,825

(22) Filed: Mar. 23, 2000

Related U.S. Application Data

(63) Continuation-in-part of application No. 09/429,755, filed on Oct. 28, 1999, which is a continuation-in-part of application No. 09/289,198, filed on Apr. 9, 1999, which is a continuation-in-part of application No. 09/062,451, filed on Apr. 17, 1998, which is a continuation-in-part of application No. 08/991,789, filed on Dec. 11, 1997, which is a continuation-in-part of application No. 08/838,762, filed as application No. PCT/US97/00485 on Jan. 10, 1997, now abandoned, and a continuation-in-part of application No. 08/700,014, filed on Aug. 20, 1996, which is a continuation-in-part of application No. 08/585,392, filed on Jan. 1, 1996.

(51) Int. Cl.$^7$ .......................... A61K 38/00; C07K 1/00; C07K 14/00; C07K 17/00; C07K 2/00
(52) U.S. Cl. .......................... 530/350; 530/300; 536/1; 536/18.7; 536/22.1; 536/23.1; 536/23.5; 514/1; 514/2; 514/12; 514/13; 514/14; 514/15; 514/16; 514/17; 514/18; 514/19; 424/9.1; 424/9.2
(58) Field of Search ................................ 530/300, 350; 514/1, 2, 12, 13, 14, 15, 16, 17, 18, 19; 536/1, 18.7, 22.1, 23.1, 23.5; 424/9.1, 9.2

(56) References Cited

U.S. PATENT DOCUMENTS

| | | | |
|---|---|---|---|
| 5,231,012 A | 7/1993 | Mosmann et al. | 435/69.52 |
| 5,428,145 A | 6/1995 | Okamoto et al. | 536/23.72 |
| 5,516,650 A | 5/1996 | Foster et al. | 435/68.1 |
| 5,523,225 A | 6/1996 | Kraus | 435/240.1 |
| 5,585,270 A | 12/1996 | Grotendorst et al. | 435/252.3 |
| 5,811,535 A | 9/1998 | Adamou et al. | 536/23.5 |
| 5,872,237 A | 2/1999 | Feder et al. | 536/23.5 |
| 6,329,505 B1 * | 12/2001 | Xu et al. | |

FOREIGN PATENT DOCUMENTS

| | | |
|---|---|---|
| CA | 2044940 A1 | 12/1992 |
| EP | 0475623 A1 | 3/1992 |
| GB | 2 273 099 A | 6/1994 |
| WO | WO 91/02062 | 2/1991 |
| WO | WO 92/10573 | 6/1992 |
| WO | WO 92/15680 | 9/1992 |
| WO | WO 98/11514 | 5/1994 |
| WO | WO 95/10777 | 4/1995 |
| WO | WO 95/19369 | 7/1995 |
| WO | WO 95/32311 | 11/1995 |
| WO | WO 96/38463 | 12/1996 |
| WO | WO 97/06256 | 2/1997 |
| WO | WO 97/25426 | 7/1997 |
| WO | WO 97/25431 | 7/1997 |
| WO | WO 98/45328 | 10/1998 |
| WO | WO 00/61753 | 10/2000 |

OTHER PUBLICATIONS

Gencore, Amino acid database, Sequence 376 of U.S. Patent 6,329,505. Dec. 11, 2001.*
GenCore database sheet, nucleic acid and amino acid databases showing polypeptide from WO 9845328. Jan. 22, 1999.*
Ezzell, Carol. Cancer "vaccines": an idea whose time has come? The Journal of NIH Research, 7:46–49, Jan. 1995.*
Adams et al., Genbank Accession No. Q60347, 1993.
Adams et al., Genbank Accession No. Q61250, 1993.
Anderson et al., "Sequence and organization of the human mitochondrial genome," *Nature* 290:457–465, 1981.
Bauer et al., "Identification of differentially expressed mRNA species by an improved display technique (DDRT–PCR)," *Nucleic Acids Research* 21(18):4272–4280, 1993.
Bernard et al., "Cloning and Sequencing of Pro–α1(XI) Collagen cDNA Demonstrates That Type XI Belongs to the Fibrillar Class of Collagens and Reveals That the Expression of the Gene Is Not Restricted to Cartilagenous Tissue," *J. Biol. Chem.* 263(32):17159–17166, 1988.
Bratthauer et al., "Expression of LINE–1 Retrotransposons in Human Breast Cancer," *Cancer* 73:2333–2336, 1994.
Byrne et al., "A Screening Method to Identify Genes Commonly Overexpressed in Carcinomas and the Identification of a Novel Complementary DNA Sequence," *Cancer Research* 55:2869–2903, 1995.
Chai et al., Genbank Accession No. U03644, 1994.
Charnock–Jones et al., "Extension of incomplete cDNAs (ESTs) by biotin/streptavidin–mediated walking using polymerase chain reaction," *J. Biotechno.* 35:205–215, Jun. 1994.
Chen and Sager, "Differential Expression of Human Tissue Factor in Normal Mammary Epithelial Cells and in Carcinomas," *Molecular Medicine* 1(2):153–160, 1995.

(List continued on next page.)

Primary Examiner—Alana M. Harris
(74) Attorney, Agent, or Firm—Seed IP Law Group PLLC

(57) ABSTRACT

Compositions and methods for the detection and therapy of breast cancer are disclosed. The compounds provided include nucleotide sequences that are preferentially expressed in breast tumor tissue, as well as polypeptides encoded by such nucleotide sequences. Vaccines and pharmaceutical compositions comprising such compounds are also provided and may be used, for example, for the prevention and treatment of breast cancer. The polypeptides may also be used for the production of antibodies, which are useful for diagnosing and monitoring the progression of breast cancer in a patient.

9 Claims, 19 Drawing Sheets

OTHER PUBLICATIONS

Cordonnier et al., "Isolation of Novel Human Endogenous Retrovirus–Like Elements with Foamy Virus–Related pol Sequence," *Journal of Virology* 69(9):5890–5897, 1995.

Databank Genebank Accession No. Z34289, 1995.

Ezzell, "Cancer "Vaccines": An Idea Whose Time Has Come?," *The Journal of NIH Research* 7:46–49, 1995.

Frank et al., Genbank Accession No. Q70049, 1994.

Gura, "Systems for Identifying New Drugs Are Often Faulty," *Science* 278:1041–1042, 1997.

Haltmeier et al., "Identification of S71–Related Human Endogenous Retroviral Sequences with Full–Length pol Genes," *Virology* 209:550–560, 1995.

Hillier et al., Genbank Accession No. H80165, 1995.

Hillier et al., Genbank Accession No. R19532, 1995.

Hillier et al., Genbank Accession No. R55637, 1995.

Hillier et al., Genbank Accession No. R60426, 1995.

Hillier et al., Genbank Accession No. T83348, 1995.

Hillier et al., Genbank Accession No. R35308, 1995.

Keydar et al., "Properties of retrovirus–like particles produced by a human breast carcinoma cell line: Immunological relationship with mouse mammary tumor virus proteins," *Proc. Natl. Acad. Sci.* USA 81:4188–92, 1984.

Leib–Mösch and Seifarth, "Evolution and Biological Significance of Human Retroelements," *Virus Genes* 11(2/3):133–145, 1996.

Leib–Mösch et al., "Endogenous Retroviral Elements in Human DNA," *Cancer Research* 50:5636s–5642s, 1994.

Leib–Mösch et al., "Genomic Distribution and Transcription of Solitary HERV–K LTRs," *Genomics* 18:261–269, 1993.

Liang et al., "Differential Display of Eukaryotic Messenger RNA by Means of the Polymerase Chain Reaction," *Science* 257:967–971, 1992.

Matsubara et al., Genbank Accession No. T24124, 1995.

Wang et al., "Detection of Mammary Tumor Virus ENV Gene–like Sequences in Human Breast Cancer," *Cancer Research* 55:5173–5179, 1995.

Watson and Fleming, "Isolation of Differentially Expressed Sequence Tags from Human Breast Cancer," *Cancer Research* 54(17):4598–4602, 1994.

Werner et al., "S71 Is a Phylogenetically Distinct Human Endogenous Retroviral Element with Structural and Sequence Homology to Simian Sarcoma Virus (SSV)," *Virology* 174:225–238, 1990.

Yoshioka et al., "Pro–α1(XI) Collagen. Structure Of The Amino–Terminal Propeptide And Expression Of The Gene In Tumor Cell Lines," *J. Biol. Chem.* 265(11):6423–6426, 1990.

Critical Synergy: The Biotechnology Industry and Intellectual Property Protection, Presentation of the Intellectual Property Committee of the Biotechnology Industry Organization at the Oct. 17, 1994, Hearing of the U.S. Patent and Trademark Office, San Diego, CA, published by the Biotechnology Industry Organization, Washington, D.C., pp. 75, 100–107.

Ahmed et al., "Characterization of a retrovirus isolated form normal mink cells co–cultivated with a dog mammary tumour," *J. Gen. Virol.* 42:179–184, 1979.

Bakker et al., "Generation of antimelanoma cytotoxic T lymphocytes for healthy donors after presentation of melanoma–associated antigen–derived epitopes by dendritic cells in vivo," *Cancer Research* 55:5330–5334, Nov. 15, 1995.

Cease et al., "T cell clones specific for an amphipathic α–helical region of sperm whale myoglobin show differing fine specificities for synthetic peptides," *Journal of Experimental Medicine* 164:1779–1784, Nov. 1986.

Derks et al., "Synthesis of a viral protein with molecular weight of 30,000 (p30) by leukemic cells and antibodies cross–reacting with simian sarcoma virus p30 in serum of a chronic myeloid leukemia patient," *Cancer Research* 42:681–686, Feb. 1982.

Hehlmann et al., "Detection and biochemical characterization of antigens in human leukemic sera that cross–react with primate C–type viral proteins (M 30,000)[1]," *Cancer Research* 43:392–399, Jan. 1983.

Herbrink et al., "Detection of antibodies cross–reactive with type C RNA tumor viral p30 protein in human sera and exudate fluids," *Cancer Research* 40:166–173, Jan. 1980.

Hopp, T., "Computer prediction of protein surface features and antigenic determinants," *Molecular Basis of Cancer* Part B: Macromolecular Recognition, Chemotherapy, and Immunology:367–377, 1985.

Jerabek et al., "Detection and immunochemical characterization of a primate type C retrovirus–related p30 protein in normal human placentas," *Proc. Natl. Acad. Sci.* USA 81:6501–6505, Oct. 1984.

Kast et al., "Role of HLA–A motifs in identification of potential CTL epitopes in human papillmavirus type 16 E6 and E7 proteins," *J. Immunol.* 152:3904–3912, 1994.

Kawakami et al., "Recognition of multiple epitopes in the human melanoma antigen gp100 by tumor–infiltrating T lymphocytes associated with in vivo tumor regression," *J. Immunol.* 154:3961–3968, 1995.

Maeda et al., "Serum antibody reacting with placental syncytiotrophoblast in sera of patients with autoimmune diseases—a possible relation to type C RNA retroviruses," *Clin. Exp. Immunol.* 60:645–653, 1985.

Margalit et al., "Prediction of immunodominant helper T cell antigenic sites from the primary sequence," *The Journal of Immunology* 138(7):2213–2229, Apr. 1, 1987.

McCombs, R., "Role of oncornaviruses in carcinoma of the prostate," *Cancer Treatment Reports* 61(2):131–132, Mar./Apr. 1977.

Porter–Jordan and Lippman et al., "Overview of the biologic markers of breast cancer," *Breast Cancer* 8(1):73–100, Feb. 1994.

Rammensee et al., "MHC ligands and peptide motifs: first listing," *Immunogenetics* 41:178–228, 1995.

Rothbard and Taylor, "A sequence pattern common to T cell epitopes," *The EMBO Journal* 7(1):93–100, Jan. 1988.

Sette et al., "The relationship between class I binding affinity and immunogenicity of potential cytotoxic T cell epitopes," *J. Immunol.* 153:5586–5592, 1994.

Smith et al., "Expression of antigenic crossreactivity to RD114 p30 protein in a human fibrosarcoma cell line," *Proc. Natl. Acad. Sci.* USA 74(2): 744–748, Feb. 1977.

Spouge et al., "Strong conformational propensities enhance T cell antigenicity," *The Journal of Immunology* 138(1):204–212, Jan. 1987.

Tsai et al., "In vitro immunization and expansion of antigen–specific cytotoxic T–lymphocytes for adoptive immunotherapy using peptide pulsed dendritic cells," *Critical Reviews in Immunology 18*:65–75, 1998.

Vaczi and Toth, "Studies on antigens of C–type primate viruses and antibodies to them at patients wit myeloid leukemia and potentially preleukemic hematological disorders," *Arch. Geschwulstforsch 50*(8):769–777, 1980.

Visseren et al., "CTL specific for the tyrosinase autoantigen can be induced form healthy donor blood to lyse melanoma cells," *J. Immunol 154*:3991–3998, 1995.

Vitiello et al., "Analysis of the HLA–restricted influenza specific cytotoxic T lymphcyte response in transgenic mice carrying a chimeric human–mouse class I major histocompatability complex," *J. Exp. Med. 173*:1007–1015, Apr. 1991.

Wiley and Cunningham, "A steady state model for analyzing the cellular binding, internalization and degradation of polypeptide ligands," *Cell 25*:433–440, Aug. 1981.

GenBank Accession No. Z34289, "*H. sapiens* mRNA for nucleolar phosphoprotein p130," Jun. 1, 1995.

\* cited by examiner

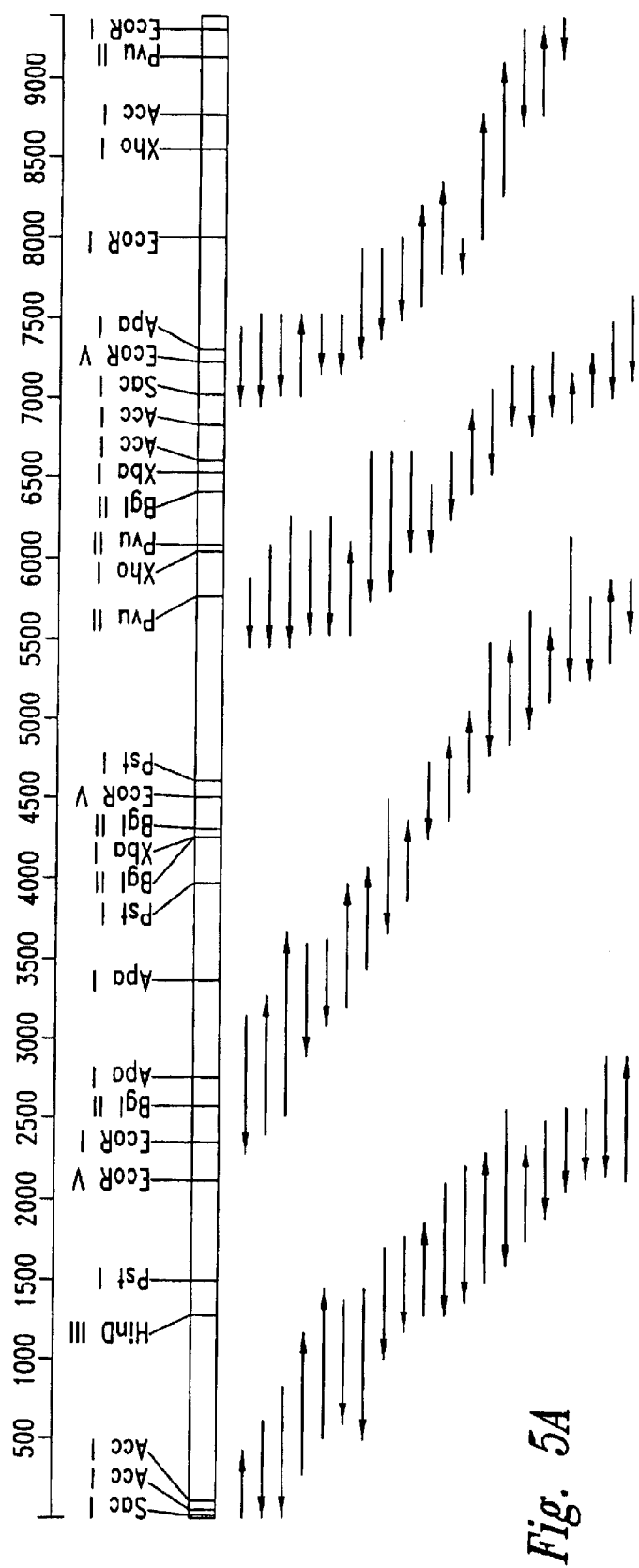
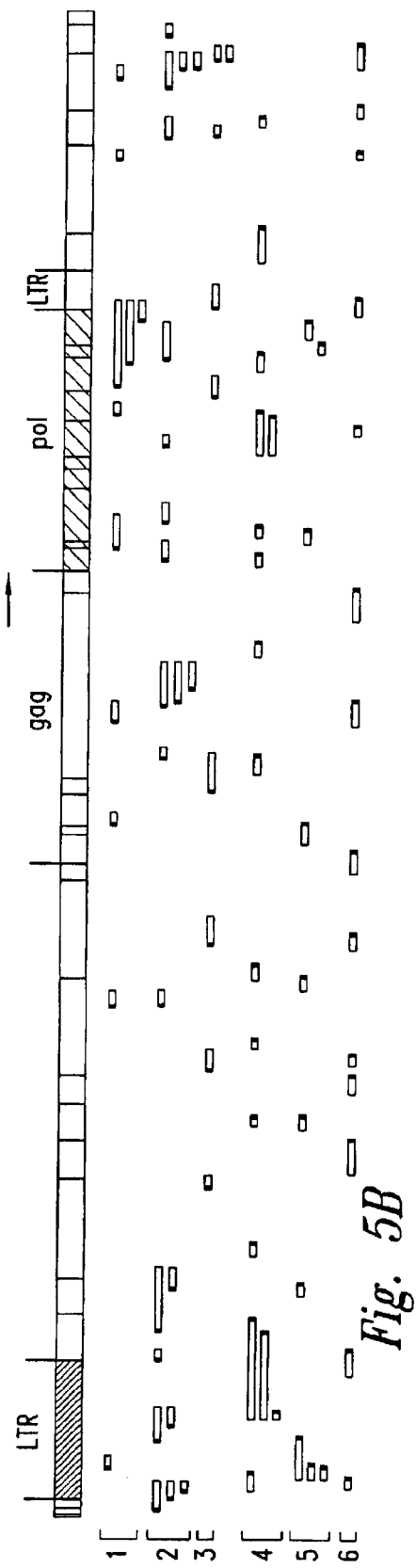
Fig. 5A
Fig. 5B

NUCLEOTIDE SEQUENCE OF THE REPRESENTATIVE BREAST-TUMOR SPECIFIC cDNA B18Ag1

```
TTA GAG ACC CAA TTG GGA CCT AAT TGG GAC CCA AAT TTC TCA AGT GGA   48
Leu Glu Thr Gln Leu Gly Pro Asn Trp Asp Pro Asn Phe Ser Ser Gly
 1           5                  10                  15

GGG AGA ACT TTT GAC GAT TTC CAC CGG TAT CTC CTC GTG GGT ATT CAG   96
Gly Arg Thr Phe Asp Asp Phe His Arg Tyr Leu Leu Val Gly Ile Gln
            20                  25                  30

GGA GCT GCC CAG AAA CCT ATA AAC TTG TCT AAG GCG ATT GAA GTC GTC  144
Gly Ala Ala Gln Lys Pro Ile Asn Leu Ser Lys Ala Ile Glu Val Val
        35                  40                  45

CAG GGG CAT GAT GAG TCA CCA GGA GTG TTT TTA GAG CAC CTC CAG GAG  192
Gln Gly His Asp Glu Ser Pro Gly Val Phe Leu Glu His Leu Gln Glu
    50                  55                  60

GCT TAT CGG ATT TAC ACC CCT TTT GAC CTG GCA GCC CCC GAA AAT AGC  240
Ala Tyr Arg Ile Tyr Thr Pro Phe Asp Leu Ala Ala Pro Glu Asn Ser
65                  70                  75                  80

CAT GCT CTT AAT TTG GCA TTT GTG GCT CAG GCA GCC CCA GAT AGT AAA  288
His Ala Leu Asn Leu Ala Phe Val Ala Gln Ala Ala Pro Asp Ser Lys
            85                  90                  95

AGG AAA CTC CAA AAA CTA GAG GGA TTT TGC TGG AAT GAA TAC CAG TCA  336
Arg Lys Leu Gln Lys Leu Glu Gly Phe Cys Trp Asn Glu Tyr Gln Ser
        100                 105                 110

GCT TTT AGA GAT AGC CTA AAA GGT TTT                              363
Ala Phe Arg Asp Ser Leu Lys Gly Phe
    115                 120
```

*Fig. 6*

NUCLEOTIDE SEQUENCE OF THE REPRESENTATIVE BREAST-TUMOR SPECIFIC cDNA B17Ag1

```
GC TGGGCACAGT GGCTCATACC TGTAATCCTG ACCGTTTCAG AGGCTCAGGT        60

CG CTTGAGCCCA AGATTTCAAG ACTAGTCTGG GTAACATAGT GAGACCCTAT       120

AA AAATAAAAAA ATGAGCCTGG TGTAGTGGCA CACACCAGCT GAGGAGGGAG       180

CT AGGAGA                                                       196
```

*Fig. 7*

NUCLEOTIDE SEQUENCE OF THE REPRESENTATIVE
BREAST-TUMOR SPECIFIC cDNA B17Ag2

GC TTGGGGGCTC TGACTAGAAA TTCAAGGAAC CTGGGATTCA AGTCCAACTG  60

AC TTACACTGTG GNCTCCAATA AACTGCTTCT TTCCTATTCC CTCTCTATTA  120

AA GGAAAACGAT GTCTGTGTAT AGCCAAGTCA GNTATCCTAA AAGGAGATAC  180

AT TAAATATCAG AATGTAAAAC CTGGGAACCA GGTTCCCAGC CTGGGATTAA  240

CA AGAAGACTGA ACAGTACTAC TGTGAAAAGC CCGAAGNGGC AATATGTTCA  300

TT GAAGGATGGC TGGGAGAATG AATGCTCTGT CCCCCAGTCC CAAGCTCACT  360

CT CCTTTATAGC CTAGGAGA                                    388

*Fig. 8*

NUCLEOTIDE SEQUENCE OF THE REPRESENTATIVE
BREAST-TUMOR SPECIFIC cDNA B13Ag2a

GC CTATAATCAT GTTTCTCATT ATTTTCACAT TTTATTAACC AATTTCTGTT  60

AA AATATGAGGG AAATATATGA AACAGGGAGG CAATGTTCAG ATAATTGATC  120

TG ATTTCTACAT CAGATGCTCT TTCCTTTCCT GTTTATTTCC TTTTTATTTC  180

GG TCGAATGTAA TAGCTTTGTT TCAAGAGAGA GTTTTGGCAG TTTCTGTAGC  240

CT GCTCATGTCT CCAGGCATCT ATTTGCACTT TAGGAGGTGT CGTGGGAGAC  300

CT ATTTTTTCCA TATTTGGGCA ACTACTA                          337

*Fig. 9*

NUCLEOTIDE SEQUENCE OF THE REPRESENTATIVE
BREAST-TUMOR SPECIFIC cDNA B13Ag1b

| | |
|---|---|
| GC CATACAGTGC CTTTCCATTT ATTTAACCCC CACCTGAACG GCATAAACTG | 60 |
| GC TGGTGTTTTT TACTGTAAAC AATAAGGAGA CTTTGCTCTT CATTTAAACC | 120 |
| AT TTCATATTTT ACGCTCGAGG GTTTTTACCG GTTCCTTTTT ACACTCCTTA | 180 |
| TT TAAGTCGTTT GGAACAAGAT ATTTTTTCTT TCCTGGCAGC TTTTAACATT | 240 |
| TT TGTGTCTGGG GGACTGCTGG TCACTGTTTC TCACAGTTGC AAATCAAGGC | 300 |
| CC AAGAAAAAAA AATTTTTTTG TTTATTTGA AACTGGACCG GATAAACGGT | 360 |
| CG GCTGCTGTAT ATAGTTTTAA ATGGTTTATT GCACCTCCTT AAGTTGCACT | 420 |
| GG GGGGNTTTTG NATAGAAAGT NTTTANTCAC ANAGTCACAG GGACTTTTNT | 480 |
| NA CTGAGCTAAA AAGGGCTGNT TTTCGGGTGG GGGCAGATGA AGGCTCACAG | 540 |
| TC TCTTAGAGGG GGGAACTNCT A | 571 |

Fig. 10

NUCLEOTIDE SEQUENCE OF THE REPRESENTATIVE
BREAST-TUMOR SPECIFIC cDNA B13Ag1a

| | |
|---|---|
| TA ATAACTTAAA TATATTTTGA TCACCCACTG GGGTGATAAG ACAATAGATA | 60 |
| TT TCCAAAAAGC ATAAAACCAA AGTATCATAC CAAACCAAAT TCATACTGCT | 120 |
| CC GCACTGAAAC TTCACCTTCT AACTGTCTAC CTAACCAAAT TCTACCCTTC | 180 |
| GG TGCGTGCTCA CTACTCTTTT TTTTTTTTTT TTTNTTTTGG AGATGGAGTC | 240 |
| CA GCCCAGGGGT GGAGTACAAT GGCACAACCT CAGCTCACTG NAACCTCCGC | 300 |
| TT CATGAGATTC TCCTGNTTCA GCCTTCCCAG TAGCTGGGAC TACAGGTGTG | 360 |
| TG CCTGGNTAAT CTTTTTTNGT TTTNGGGTAG AGATGGGGGT TTTACATGTT | 420 |
| TG GTNTCGAACT CCTGACCTCA AGTGATCCAC CCACCTCAGG CTCCCAAAGT | 480 |
| TA CAGACATGAG CCACTGNGCC CAGNCCTGGT GCATGCTCAC TTCTCTAGGC | 540 |

*Fig. 11*

NUCLEOTIDE SEQUENCE OF THE REPRESENTATIVE
BREAST-TUMOR SPECIFIC cDNA B11Ag1

| | |
|---|---|
| TG CACATGCAGA ATATTCTATC GGTACTTCAG CTATTACTCA TTTTGATGGC | 60 |
| AG CCTATCCTCA AGATGAGTAT TTAGAAAGAA TTGATTTAGC GATAGACCAA | 120 |
| GC ACTCTGACTA CACGAAATTG TTCAGATGTG ATGGATTTAT GACAGTTGAT | 180 |
| GA GATTATTAAG TGATTATTTT AAAGGGAATC CATTAATTCC AGAATATCTT | 240 |
| TC AAGATGATAT AGAAATAGAA CAGAAAGAGA CTACAAATGA AGATGTATCA | 300 |
| TA TTGAAGAGCC TATAGTAGAA AATGAATTAG CTGCATTTAT TAGCCTTACA | 360 |
| TT TTCCTGATGA ATCTTATATT CAGCCATCGA CATAGCATTA CCTGATGGGC | 420 |
| GA ATAATAGAAA CTGGGTGCGG GGCTATTGAT GAATTCATCC NCAGTAAATT | 480 |
| AC AAAATATAAC TCGATTGCAT TTGGATGATG GAATACTAAA TCTGGCAAAA | 540 |
| GG AGCTACTAGT AACCTCTCTT TTTGAGATGC AAAATTTTCT TTTAGGGTTT | 600 |
| CT ACTTTACGGA TATTGGAGCA TAACGGGA | 638 |

*Fig. 12*

NUCLEOTIDE SEQUENCE OF THE REPRESENTATIVE
BREAST-TUMOR SPECIFIC cDNA B3CA3c

| | | | | | |
|---|---|---|---|---|---|
| ACTGATGGAT | GTCGCCGGAG | GCGAGGGGCC | TTATCTGATG | CTCGGCTGCC | TGTTCGTGAT | 60 |
| GTGCGCGGCG | ATTGGGCTGT | TTATCTCAAA | CACCGCCACG | GCGGTGCTGA | TGGCGCCTAT | 120 |
| TGCCTTAGCG | GCGGCGAAGT | CAATGGGCGT | CTCACCCTAT | CCTTTTGCCA | TGGTGGTGGC | 180 |
| GATGGCGGCT | TCGGCGGCGT | TTATGACCCC | GGTCTCCTCG | CCGGTTAACA | CCCTGGTGCT | 240 |
| TGGCCCTGGC | AAGTACTCAT | TTAGCGATTT | TGTCAAAATA | GGCGTG | | 286 |

*Fig. 13*

NUCLEOTIDE SEQUENCE OF THE REPRESENTATIVE
BREAST-TUMOR SPECIFIC cDNA B9CG1

| | | | | | |
|---|---|---|---|---|---|
| AG CAGCCCCTTC | TTCTCAATTT | CATCTGTCAC | TACCCTGGTG | TAGTATCTCA | 60 |
| CA TTTTTATAGC | CTCCTCCCTG | GTCTGTCTTT | TGATTTTCCT | GCCTGTAATC | 120 |
| AC ATAACTGCAA | GTAAACATTT | CTAAAGTGTG | GTTATGCTCA | TGTCACTCCT | 180 |
| AA ATAGTTTCCA | TTACCGTCTT | AATAAAATTC | GGATTTGTTC | TTTNCTATTN | 240 |
| CA CCTATGACCG AA | | | | | 262 |

*Fig. 14*

NUCLEOTIDE SEQUENCE OF THE REPRESENTATIVE
BREAST-TUMOR SPECIFIC cDNA B9CG3

```
AG CAAAGCCAGT GGTTTGAGCT CTCTACTGTG TAAACTCCTA AACCAAGGCC    60

TA AATGGTGGCA GGATTTTTAT TATAAACATG TACCCATGCA AATTTCCTAT   120

GA TATATTCTTC TACATTTAAA CAATAAAAAT AATCTATTTT TAAAAGCCTA   180

AG TTAGGTAAGA GTGTTTAATG AGAGGGTATA AGGTATAAAT CACCAGTCAA   240

TG CCTATGACCG A                                             261
```

*Fig. 15*

NUCLEOTIDE SEQUENCE OF THE REPRESENTATIVE
BREAST-TUMOR SPECIFIC cDNA B2CA2

```
CGACGTCGGT AAAATCGGAC ATGAAGCCAC CGCTGGTCTT TTCGTCCGAG CGATAGGCGC    60

CGGCCAGCCA GCGGAACGGT TGCCCGGATG GCGAAGCGAG CCGGAGTTCT TCGGACTGAG   120

TATGAATCTT GTTGTGAAAA TACTCGCCGC CTTCGTTCGA CGACGTCGCG TCGAAATCTT   180

AATCATGGTT GAGCCGGATG CTGCCCCGA AGCCCT                              276
```

*Fig. 16*

NUCLEOTIDE SEQUENCE OF THE REPRESENTATIVE BREAST-TUMOR SPECIFIC cDNA B3CA1

```
CCCAGGTCAA CCAGGCTGCA ACACGCAGGT CCTTGGATTG GGCACGAAGC AGCGCTTCGC    60

TGTTTTCCAG GATTTTCAAC CAGTCGGTCT GGCCGTTCTC ATGGAGCGAG AGCGCCTTGC   120

CCAGCTCATT TTCCAGCGCC TCGTATTCGC TGGAAAAACG CACATCCTCA CCCGCAAAGA   180

CATCCTTTGA AATCGGCTGT TCCGCGAGTT CCAGATANTG CGAGGAGAGC TTGCTCGAAT   240

AGGTCATCCT AACCCTTCAA TGCACACCAT GTGCGCCAAT GAATATCTTA ACAATTCAAC   300

TAGTTGGCAT AANAACCGAA CGAAAATCCC AATAGTCTGA AGAGCTCTTT TG           352
```

Fig. 17

NUCLEOTIDE SEQUENCE OF THE REPRESENTATIVE BREAST-TUMOR SPECIFIC cDNA B3CA2

```
CTGCATGTCC ACGGCCTGGA TTTACGGGTG GTCGGCGTTC ACCCCTGGCA GCTGGCGGCTC    60

TTCCCGACCA GGCCCAGCAG GATGTGTGGG GCAAGGATAA CGGCGTGCGC ATCGCCTCGA   120

CCTATATGCC TACTGGCAAG GCCGAGCCCG TGGAAGGCGG ATTCAGGTTC ANCGGTCGCT   180

GGAGCTTTTC CACCGGCTCC ATGCATTGTG ACTGGCTGTT TCTAGGCGGT CTGTTGCCCA   240

AGCGTGATGG TACGTCTGGC CTGGAGCATG TGACTTTCTG                         280
```

Fig. 18

NUCLEOTIDE SEQUENCE OF THE REPRESENTATIVE
BREAST-TUMOR SPECIFIC cDNA B3CA3

AG GGAGCAAGGA GAAGGCATGG AGAGGCTCAN GCTGGTCCTG GCCTACGACT    60

CT GTCGCCGGGG ATGGTGGAGA ACTGAAGCGG GACCTCCTCG AGGTCCTCCG   120

TC NCCGTCCAGG AGGAGGGTCT TTCCGTGGTC TNGGAGGAGC GGGGGGAGAA   180

TC ATGGTCNACA TCCC                                          204

*Fig. 19*

NUCLEOTIDE SEQUENCE OF THE REPRESENTATIVE
BREAST-TUMOR SPECIFIC cDNA B4CA1

TC AGGAGCGGGT AGAGTGGCAC CATTGAGGGG ATATTCAAAA ATATTATTTT    60

TG ATAGTTGCTG AGTTTTTCTT TGACCCATGA GTTATATTGG AGTTTATTTT   120

CC AATCGCATGG ACATGTTAGA CTTATTTTCT GTTAATGATT NCTATTTTTA   180

GA TTTGAGAAAT TGGTTNTTAT TATATCAATT TTTGGTATTT GTTGAGTTTG   240

GC TTAGTATGTG ACCA                                          264

*Fig. 20*

SEQUENCE LISTING

<160> NUMBER OF SEQ ID NOS: 317

<210> SEQ ID NO 1
<211> LENGTH: 363
<212> TYPE: DNA
<213> ORGANISM: Homo sapien

<400> SEQUENCE: 1
ttagagaccc aattgggacc taattgggac ccaaatttct caagtggagg gagaactttt        60
gacgatttcc accggtatct cctcgtgggt attcagggag ctgcccagaa acctataaac       120
ttgtctaagg cgattgaagt cgtccagggg catgatgagt caccaggagt gtttttagag       180
cacctccagg aggcttatcg gatttacacc ccttttgacc tggcagcccc cgaaaatagc       240
catgctctta atttggcatt tgtggctcag gcagcccag atagtaaaag gaaactccaa       300

```
aaactagagg gattttgctg gaatgaatac cagtcagctt ttagagatag cctaaaaggt    360
ttt                                                                  363
```

<210> SEQ ID NO 2
<211> LENGTH: 121
<212> TYPE: PRT
<213> ORGANISM: Homo sapien

<400> SEQUENCE: 2

```
Leu Glu Thr Gln Leu Gly Pro Asn Trp Asp Pro Asn Phe Ser Ser Gly
 1               5                  10                  15

Gly Arg Thr Phe Asp Asp Phe His Arg Tyr Leu Leu Val Gly Ile Gln
                20                  25                  30

Gly Ala Ala Gln Lys Pro Ile Asn Leu Ser Lys Ala Ile Glu Val Val
            35                  40                  45

Gln Gly His Asp Glu Ser Pro Gly Val Phe Leu Glu His Leu Gln Glu
        50                  55                  60

Ala Tyr Arg Ile Tyr Thr Pro Phe Asp Leu Ala Ala Pro Glu Asn Ser
65                  70                  75                  80

His Ala Leu Asn Leu Ala Phe Val Ala Gln Ala Ala Pro Asp Ser Lys
                85                  90                  95

Arg Lys Leu Gln Lys Leu Glu Gly Phe Cys Trp Asn Glu Tyr Gln Ser
            100                 105                 110

Ala Phe Arg Asp Ser Leu Lys Gly Phe
        115                 120
```

<210> SEQ ID NO 3
<211> LENGTH: 1080
<212> TYPE: DNA
<213> ORGANISM: Homo sapien
<220> FEATURE:
<221> NAME/KEY: misc_feature
<222> LOCATION: (1)...(1080)
<223> OTHER INFORMATION: n = A,T,C or G

<400> SEQUENCE: 3

```
tcttagaatc ttcatacccc gaactcttgg gaaaacttta atcagtcacc tacagtctac     60
cacccattta ggaggagcaa agctacctca gctcctccgg agccgtttta agatccccca    120
tcttcaaagc ctaacagatc aagcagctct ccggtgcaca acctgcgccc aggtaaatgc    180
caaaaaaggt cctaaaccca gcccaggcca ccgtctccaa gaaaactcac caggagaaaa    240
gtgggaaatt gactttacag aagtaaaacc acaccgggct gggtacaaat accttctagt    300
actggtagac accttctctg gatggactga agcatttgct accaaaaacg aaactgtcaa    360
tatggtagtt aagttttttac tcaatgaaat catccctcga cgtgggctgc ctgttgccat    420
agggtctgat aatggaacgg ccttcgcctt gtctatagtt taatcagtca gtaaggcgtt    480
aaacattcaa tggaagctcc attgtgccta tcgacccaga gctctgggca agtagaacgc    540
atgaactgca ccctaaaaaa acactcttac aaaattaatc ttaaaaaccg tgttaattg     600 tgttagtctc cttcccttag ccctacttag agttaaggtg cacccttac tgggctgggt    660 tctttacctt tgaaatcat ntttggaag gggctgccta tctttncttta actaaaaaan    720 gcccatttgg caaaaatttc ncaactaatt tntacgtncc tacgtctccc caacaggtan    780
aaaaatctnc tgccctttc aaggaaccat cccatccatt cctnaacaaa aggcctgccn    840
ttcttccccc agtaactnt tttttnttaa aattcccaaa aaangaaccn cctgctggaa    900
aaacnccccc ctccaanccc cggccnaagn ggaaggttcc cttgaatccc nccccncna    960
```

```
anggcccgga accnttaaan tngttccngg gggtnnggcc taaaagnccn atttggtaaa      1020
cctanaaatt ttttcttttn taaaaaccac nntttnnttt ttcttaaaca aaaccctntt      1080
```

<210> SEQ ID NO 4
<211> LENGTH: 1087
<212> TYPE: DNA
<213> ORGANISM: Homo sapien
<220> FEATURE:
<221> NAME/KEY: misc_feature
<222> LOCATION: (1)...(1087)
<223> OTHER INFORMATION: n = A,T,C or G

<400> SEQUENCE: 4

```
tctagagctg cgcctggatc ccgccacagt gaggagacct gaagaccaga gaaaacacag       60
caagtaggcc ctttaaacta ctcacctgtg ttgtcttcta atttattctg ttttattttg      120
tttccatcat tttaaggggt taaaatcatc ttgttcagac ctcagcatat aaaatgaccc      180
atctgtagac ctcaggctcc aaccatacccc caagagttgt ctggttttgt ttaaattact    240
gccaggtttc agctgcagat atccctggaa ggaatattcc agattccctg agtagtttcc    300
aggttaaaat cctataggct tcttctgttt tgaggaagag ttcctgtcag agaaaaacat    360
gattttggat ttttaacttt aatgcttgtg aaacgctata aaaaaaattt tctaccccta    420
gctttaaagt actgttagtg agaaattaaa attccttcag gaggattaaa ctgccatttc    480
agttacccta attccaaatg ttttggtggt tagaatcttc tttaatgttc ttgaagaagt    540
gttttatatt ttcccatcna gataaattct ctcncncctt nnttttntnt ctnnttttttt   600 aaaacggant cttgctccgt tgtccangct gggaattttn ttttggccaa tctccgctnc    660
cttgcaanaa tnctgcntcc caaaattacc nccttttttcc cacctccacc ccnnggaatt    720
acctggaatt anaggccccc ncccccccccc cggctaatttt gtttttgttt ttagtaaaaa    780
acgggtttcc tgttttagtt aggatggccc anntctgacc cntnatcnt cccctcngc        840 cctcnaatnt tnggnntang gcttacccccc cccngnngtt tttcctccat tnaaatttt    900 tntggantct tgaatnncgg gttttccctt ttaaaccnat tttttttttn nnccccan       960 ttttnccctcc cccntntnta anggggtttt cccaanccgg gtccncccc angtccccaa      1020 tttttctccc ccccctctt ttttctttnc cccaaaantc ctatcttttc ctnnaaatat     1080 cnantnt                                                             1087
```

<210> SEQ ID NO 5
<211> LENGTH: 1010
<212> TYPE: DNA
<213> ORGANISM: Homo sapien
<220> FEATURE:
<221> NAME/KEY: misc_feature
<222> LOCATION: (1)...(1010)
<223> OTHER INFORMATION: n = A,T,C or G

<400> SEQUENCE: 5

```
tctagaccaa gaaatgggag gatttttagag tgactgatga tttctctatc atctgcagtt     60
agtaaacatt ctccacagtt tatgcaaaaa gtaacaaaac cactgcagat gacaaacact    120
aggtaacaca catactatct cccaaatacc tacccacaag ctcaacaatt ttaaactgtt    180
aggatcactg gctctaatca ccatgacatg aggtcaccac caaaccatca agcgctaaac    240
agacagaatg tttccactcc tgatccactg tgtgggaaga agcaccgaac ttacccactg    300
gggggcctgc ntcanaanaa aagcccatgc ccccgggtnt nccttttnaac cggaacgaat     360 naacccacca tccccacanc tcctctgttc ntgggccctg catcttgtgg cctcntntnc    420
```

| | |
|---|---|
| tttngggggan acntgggggaa ggtacccat ttcnttgacc ccncnanaaa accccngtgg | 480 |
| ccctttgccc tgattcncnt gggccttttc tcttttccct tttgggttgt ttaaattccc | 540 |
| aatgtccccn gaaccctctc cntnctgccc aaaacctacc taaattnctc nctangnntt | 600 |
| ttcttggtgt tnctttttcaa aggtnacctt ncctgttcan ncccnacnaa aatttnttcc | 660 |
| ntatnntggn cccnnaaaaa nnnatcnncc cnaattgccc gaattggttn ggttttcct | 720 |
| nctgggggaa acccttaaaa tttcccccctt ggccggcccc cctttttcc ccccttnga | 780 |
| aggcaggngg ttcttcccga acttccaatt ncaacagccn tgcccattgn tgaaaccctt | 840 |
| ttcctaaaat taaaaatan ccggttnngg nnggcctctt tccctccng gngggnngng | 900 |
| aaantcctta ccccnaaaaa ggttgcttag ccccngtcc ccactccccc nggaaaaatn | 960 |
| aaccttttcn aaaaaaggaa tataantttn ccactccttn gttctcttcc | 1010 |

<210> SEQ ID NO 6
<211> LENGTH: 950
<212> TYPE: DNA
<213> ORGANISM: Homo sapien
<220> FEATURE:
<221> NAME/KEY: misc_feature
<222> LOCATION: (1)...(950)
<223> OTHER INFORMATION: n = A,T,C or G

<400> SEQUENCE: 6

| | |
|---|---|
| tctagagctc gcggccgcga gctctaatac gactcactat agggcgtcga ctcgatctca | 60 |
| gctcactgca atctctgccc ccggggtcat gcgattctcc tgcctcagcc ttccaagtag | 120 |
| ctgggattac aggcgtgcaa caccacaccc ggctaatttt gtatttttaa tagagatggg | 180 |
| gttttcccct gttggccann atggtctcna acccctgacc tcnngtgatc ccccncccn | 240 |
| nganctcnna ctgctgggga tnccgnnnn nnncctcccn ncncnnnnnn ncncnntccn | 300 |
| tnntccttnc tcnnnnnnnn cnntcnntcc nncttctcnc cnnntnttnt cnncnnccnn | 360 |
| cnnnccncnt ncccncnnnt tcncntncnn tntccnncnn nntcnncnnn cnnnncntnn | 420 |
| ccnntacntc ntnnncnnnt cctctntnn cctcnncnnt cnctncncnt tntctcctcn | 480 |
| ntnnnnnnct ccnnnnntct cntcncnncn tncctcnntn nccncnccc ncctcncnnc | 540 |
| ctnntttnnn cnncnnntcc ntnccnttcn nntcnntnn cnncntcncn nncntnttc | 600 |
| ccncntnttc cttcncntn nntntcnn cncntcnntc ntttctcct nnntcccnnc | 660 |
| tcnnttcncc cnnntccncc cccncctnt ctctcncccn nntnnntntn nnncntccnc | 720 |
| tntcncttc ntcnntncnt tnctntcnnc nncntncnc tnccntntnt ctnntcncn | 780 |
| tcncntntcn cctcnttn ctntctcctn tntccttccc ctcncctnct cnttcnccnc | 840 |
| ccnntntntn tnncnccnnt nctnnncnnc cntcntttcn tctctnctnn nnntnncctc | 900 |
| nnccntncc ctnntncnct nctnntaccn tnctnctccn tcttccttcc | 950 |

<210> SEQ ID NO 7
<211> LENGTH: 1086
<212> TYPE: DNA
<213> ORGANISM: Homo sapien
<220> FEATURE:
<221> NAME/KEY: misc_feature
<222> LOCATION: (1)...(1086)
<223> OTHER INFORMATION: n = A,T,C or G

<400> SEQUENCE: 7

| | |
|---|---|
| tctagagctc gcggccgcga gctcaattaa ccctcactaa agggagtcga ctcgatcaga | 60 |
| ctgttactgt gtctatgtag aaagaagtag acataagaga ttccattttg ttctgtacta | 120 |

-continued

```
agaaaaattc ttctgccttg agatgctgtt aatctgtaac cctagcccca accctgtgct    180
cacagagaca tgtgctgtgt tgactcaagg ttcaatggat ttagggctat gctttgttaa    240
aaaagtgctt gaagataata tgcttgttaa aagtcatcac cattctctaa tctcaagtac    300
ccagggacac aatacactgc ggaaggccgc agggacctct gtctaggaaa gccaggtatt    360
gtccaagatt tctccccatg tgatagcctg agatatggcc tcatgggaag ggtaagacct    420
gactgtcccc cagcccgaca tcccccagcc cgacatcccc cagcccgaca cccgaaaagg    480
gtctgtgctg aggaagatta ntaaaagagg aaggctcttt gcattgaagt aagaagaagg    540
ctctgtctcc tgctcgtccc tgggcaataa aatgtcttgg tgttaaaccc gaatgtatgt    600
tctacttact gagaatagga gaaacatcc ttagggctgg aggtgagaca ccctggcggc     660
atactgctct ttaatgcacg agatgtttgt ntaattgcca tccagggcca nccccttcc    720 ttaacttttt atganacaaa aactttgttc ncttttcctg cgaacctctc ccctattan    780 cctattggcc tgcccatccc ctccccaaan ggtgaaaana tgttcntaaa tncgagggaa    840
tccaaaacnt tttcccgttg gtccccttc caaccccgtc cctgggccnn tttcctcccc    900
aacntgtccc ggntccttcn ttcccncccc cttcccngan aaaaaacccc gtntganggn    960 gcccctcaa attataacct ttccnaaaca aannggttcn aaggtggttt gnttccggtg    1020
cggctggcct tgaggtcccc cctncacccc aatttggaan ccngttttttt ttattgcccn   1080 ntcccc                                                              1086
```

<210> SEQ ID NO 8
<211> LENGTH: 1177
<212> TYPE: DNA
<213> ORGANISM: Homo sapien
<220> FEATURE:
<221> NAME/KEY: misc_feature
<222> LOCATION: (1)...(1177)
<223> OTHER INFORMATION: n = A,T,C or G

<400> SEQUENCE: 8

```
nccntttaga tgttgacaan ntaaacaagc ngctcaggca gctgaaaaaa gccactgata     60
aagcatcctg gagtatcaga gtttactgtt agatcagcct catttgactt cccctcccac    120
atggtgttta aatccagcta cactacttcc tgactcaaac tccactattc ctgttcatga    180
ctgtcaggaa ctgttggaaa ctactgaaac tggccgacct gatcttcaaa atgtgcccct    240
aggaaaggtg gatgccaccg tgttcacaga cagtaccncc ttcctcgaga agggactacg    300 agggccggt gcanctgtta ccaaggagac tnatgtgttg tgggctcagg ctttaccanc     360
aaacacctca ncncnnaagg ctgaattgat cgccctcact caggctctcg gatgggtaa     420 gggatattaa cgttaacact gacagcaggt acgcctttgc tactgtgcat gtacgtggag    480
ccatctacca ggagcgtggg ctactcactc ggcaggtggc tgtnatccac tgtaaangga    540
catcaaaagg aaaacnggc tgttgcccgt ggtaaccana aanctgatcn ncagctcaaa    600
gatgctgtgt tgactttcac tcncnccctct taaacttgct gcccacantc tccttccca    660 accagatctg cctgacaatc cccatactca aaaaaaaaan aanactggcc ccgaacccna    720
accaataaaa acggggangg tnggtnganc nncctgaccc aaaaataatg gatcccccgg    780
gctgcaggaa ttcaattcan ccttatcnat accccccaacn ngngnggggg ggccngtncc    840 cattnccccct ntattnattc tttnncccc ccccggcnt ccttttttnaa ctcgtgaaag    900 ggaaaacctg ncttaccaan ttatcncctg gaccntcccc ttccncggtn gnttanaaaa    960 aaaagccccnc antcccntcc naaatttgca cngaaaggna aggaatttaa cctttatttt   1020
```

-continued

| | |
|---|---|
| ttnntcctttt antttgtnnn ccccctttta cccaggcgaa cngccatcnt ttaanaaaaa | 1080 |
| aaanagaang tttatttttc cttngaacca tcccaatana aancacccgc nggggaacgg | 1140 |
| ggnggnaggc cnctcaccc ctttntgtng gngggnc | 1177 |

<210> SEQ ID NO 9
<211> LENGTH: 1146
<212> TYPE: DNA
<213> ORGANISM: Homo sapien
<220> FEATURE:
<221> NAME/KEY: misc_feature
<222> LOCATION: (1)...(1146)
<223> OTHER INFORMATION: n = A,T,C or G

<400> SEQUENCE: 9

| | |
|---|---|
| nccnnttnnt gatgttgtct ttttggcctc tctttggata ctttccctct cttcagaggt | 60 |
| gaaagggtc aaaaggagct gttgacagtc atcccaggtg ggccaatgtg tccagagtac | 120 |
| agactccatc agtgaggtca aagcctgggg cttttcagag aagggaggat tatggttttt | 180 |
| ccaattatac aagtcagaag tagaaagaag ggacataaac caggaagggg gtggagcact | 240 |
| catcacccag agggacttgt gcctctctca gtggtagtag aggggctact tcctcccacc | 300 |
| acggttgcaa ccaagaggca atgggtgatg agcctacagg ggacatancc gaggagacat | 360 |
| gggatgaccc taagggagta ggctggtttt aaggcggtgg gactgggtga gggaaactct | 420 |
| cctcttcttc agagagaagc agtacagggc gagctgaacc ggctgaaggt cgaggcgaaa | 480 |
| acaggtctg gctcaggaag accttggaag taaaattatg aatggtgcat gaatggagcc | 540 |
| atggaagggg tgctcctgac caaactcagc cattgatcaa tgttagggaa actgatcagg | 600 |
| gaagccggga atttcattaa caacccgcca cacagcttga acattgtgag gttcagtgac | 660 |
| ccttcaaggg gccactccac tccaactttg gccattctac tttgcnaaat ttccaaaact | 720 |
| tccttttta aggccgaatc cntantccct naaaaacnaa aaaaaatctg cncctattct | 780 |
| ggaaaaggcc canccctac caggctggaa gaaattttnc cttttttttt tttttgaagg | 840 |
| cntttnttaa attgaacctn aattcncccc cccaaaaaaa aacccnccng ggggcggat | 900 |
| ttccaaaaac naattccctt accaaaaaac aaaaacccnc ccttnttccc ttccnccctn | 960 |
| ttcttttaat tagggagaga tnaagccccc caatttccng gnctngatnn gtttcccccc | 1020 |
| cccccatttt ccnaaactttt ttcccancna ggaanccncc ctttttttng gtcngattna | 1080 |
| ncaaccttcc aaaccatttt tccnnaaaaa ntttgntngg ngggaaaaan acctnntttt | 1140 |
| atagan | 1146 |

<210> SEQ ID NO 10
<211> LENGTH: 545
<212> TYPE: DNA
<213> ORGANISM: Homo sapien

<400> SEQUENCE: 10

| | |
|---|---|
| cttcattggg tacgggcccc ctcgaggtcg acggtatcga taagcttgat atcgaattcc | 60 |
| tgcagcccgg gggatccact agttctagag tcaggaagaa ccaccaacct tcctgatttt | 120 |
| tattggctct gagttctgag gccagttttc ttcttctgtt gagtatgcgg gattgtcagg | 180 |
| cagatctggc tgtggaaagg agactgtggg cagcaagttg agaggcgtga ctgaaagtca | 240 |
| cactgcatct tgagctgctg aatcagctt ctggttacca cgggcaacag ccgtgttttc | 300 |
| cttttgatgt cctttacagt ggattacagc cacctgctga ggtgagtagc ccacgctcct | 360 |
| ggtagatggc tccacgtaca tgcacagtag caaaggcgta cctgctgtca gtgttaacgt | 420 |

| | |
|---|---:|
| taatatcctt acccatcgg agagcctgag tgagggcgat caattcagcc cttttgtgct | 480 |
| gaggtgtttg ctggttaagc cctgaaccca caacacatct gtctccatgg taacagctgc | 540 |
| accgg | 545 |

<210> SEQ ID NO 11
<211> LENGTH: 196
<212> TYPE: DNA
<213> ORGANISM: Homo sapien

<400> SEQUENCE: 11

| | |
|---|---:|
| tctcctaggc tgggcacagt ggctcatacc tgtaatcctg accgtttcag aggctcaggt | 60 |
| gggggatcg cttgagccca agatttcaag actagtctgg gtaacatagt gagaccctat | 120 |
| ctctacgaaa aataaaaaa atgagcctgg tgtagtggca cacaccagct gaggagggag | 180 |
| aatcgagcct aggaga | 196 |

<210> SEQ ID NO 12
<211> LENGTH: 388
<212> TYPE: DNA
<213> ORGANISM: Homo sapien
<220> FEATURE:
<221> NAME/KEY: misc_feature
<222> LOCATION: (1)...(388)
<223> OTHER INFORMATION: n = A,T,C or G

<400> SEQUENCE: 12

| | |
|---|---:|
| tctcctaggc ttgggggctc tgactagaaa ttcaaggaac ctgggattca agtccaactg | 60 |
| tgacaccaac ttacactgtg gnctccaata aactgcttct ttcctattcc ctctctatta | 120 |
| aataaaataa ggaaaacgat gtctgtgtat agccaagtca gntatcctaa aaggagatac | 180 |
| taagtgacat taaatatcag aatgtaaaac ctgggaacca ggttcccagc ctgggattaa | 240 |
| actgacagca agaagactga acagtactac tgtgaaaagc ccgaagnggc aatatgttca | 300 |
| ctctaccgtt gaaggatggc tgggagaatg aatgctctgt cccccagtcc caagctcact | 360 |
| tactataccct cctttatagc ctaggaga | 388 |

<210> SEQ ID NO 13
<211> LENGTH: 337
<212> TYPE: DNA
<213> ORGANISM: Homo sapien

<400> SEQUENCE: 13

| | |
|---|---:|
| tagtagttgc ctataatcat gtttctcatt attttcacat tttattaacc aatttctgtt | 60 |
| taccctgaaa aatatgaggg aaatatatga acagggagg caatgttcag ataattgatc | 120 |
| acaagatatg atttctacat cagatgctct ttcctttcct gtttatttcc ttttatttc | 180 |
| ggttgtgggg tcgaatgtaa tagctttgtt tcaagagaga gttttggcag tttctgtagc | 240 |
| ttctgacact gctcatgtct ccaggcatct atttgcactt taggaggtgt cgtgggagac | 300 |
| tgagaggtct attttttcca tatttgggca actacta | 337 |

<210> SEQ ID NO 14
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 14

```
tagtagttgc catacagtgc ctttccattt atttaacccc cacctgaacg gcataaactg      60
agtgttcagc tggtgttttt tactgtaaac aataaggaga ctttgctctt catttaaacc     120
aaaatcatat ttcatatttt acgctcgagg gtttttaccg gttcctttt acactcctta     180 aaacagtttt taagtcgttt ggaacaagat attttttctt tcctggcagc ttttaacatt     240
atagcaaatt tgtgtctggg ggactgctgg tcactgtttc tcacagttgc aaatcaaggc     300
atttgcaacc aagaaaaaaa aatttttttg ttttatttga aactggaccg gataaacggt     360
gtttggagcg gctgctgtat atagtttaa atggtttatt gcacctcctt aagttgcact     420
tatgtggggg ggggnttttg natagaaagt ntttantcac anagtcacag ggacttttnt     480
cttttggnna ctgagctaaa aagggctgnt ttcgggtgg gggcagatga aggctcacag     540
gaggcctttc tcttagaggg gggaactnct a                                    571
```

<210> SEQ ID NO 15
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 15

```
tatatattta ataacttaaa tatattttga tcacccactg gggtgataag acaatagata      60
taaaagtatt tccaaaaagc ataaaaccaa agtatcatac caaaccaaat tcatactgct     120
tcccccaccc gcactgaaac ttcaccttct aactgtctac ctaaccaaat tctacccttc     180
aagtctttgg tgcgtgctca ctactctttt tttttttttt tttnttttgg agatgggagtc     240 tggctgtgca gcccagggt ggagtacaat ggcacaacct cagctcactg naacctccgc     300
ctcccaggtt catgagattc tcctgnttca gccttcccag tagctgggac tacaggtgtg     360
catcaccatg cctggntaat cttttttngt tttngggtag agatgggggt tttacatgtt     420
ggccaggntg gtntcgaact cctgacctca agtgatccac ccacctcagg ctcccaaagt     480
gctaggatta cagacatgag ccactgngcc cagncctggt gcatgctcac ttctctaggc     540
aactacta                                                             548
```

<210> SEQ ID NO 16
<211> LENGTH: 638
<212> TYPE: DNA
<213> ORGANISM: Homo sapien
<220> FEATURE:
<221> NAME/KEY: misc_feature
<222> LOCATION: (1)...(638)
<223> OTHER INFORMATION: n = A,T,C or G

<400> SEQUENCE: 16

```
ttccgttatg cacatgcaga atattctatc ggtacttcag ctattactca ttttgatggc      60
gcaatccgag cctatcctca agatgagtat ttagaaagaa ttgatttagc gatagaccaa     120
gctggtaagc actctgacta cacgaaattg ttcagatgtg atggatttat gacagttgat     180 cttttggaaga gattattaag tgattatttt aaagggaatc cattaattcc agaatatctt     240
ggtttagctc aagatgatat agaaatagaa cagaaagaga ctacaaatga agatgtatca     300
ccaactgata ttgaagagcc tatagtagaa atgaattag ctgcatttat tagccttaca     360
catagcgatt ttcctgatga atcttatatt cagccatcga catagcatta cctgatgggc     420
```

-continued

| aaccttacga ataatagaaa ctgggtgcgg ggctattgat gaattcatcc ncagtaaatt | 480 |
| tggatatnac aaaatataac tcgattgcat ttggatgatg gaatactaaa tctggcaaaa | 540 |
| gtaactttgg agctactagt aacctctctt tttgagatgc aaaattttct tttagggttt | 600 |
| cttattctct actttacgga tattggagca taacggga | 638 |

<210> SEQ ID NO 17
<211> LENGTH: 286
<212> TYPE: DNA
<213> ORGANISM: Homo sapien

<400> SEQUENCE: 17

| actgatggat gtcgccggag gcgaggggcc ttatctgatg ctcggctgcc tgttcgtgat | 60 |
| gtgcgcggcg attgggctgt ttatctcaaa caccgccacg gcggtgctga tggcgcctat | 120 |
| tgccttagcg gcggcgaagt caatgggcgt ctcaccctat cctttgcca tggtggtggc | 180 |
| gatggcggct tcggcggcgt ttatgacccc ggtctcctcg ccggttaaca ccctggtgct | 240 |
| tggccctggc aagtactcat ttagcgattt tgtcaaaata ggcgtg | 286 |

<210> SEQ ID NO 18
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 18

| tcggtcatag cagccccttc ttctcaattt catctgtcac taccctggtg tagtatctca | 60 |
| tagccttaca tttttatagc ctcctccctg gtctgtcttt tgattttcct gcctgtaatc | 120 |
| catatcacac ataactgcaa gtaaacattt ctaaagtgtg gttatgctca tgtcactcct | 180 |
| gtgncaagaa atagtttcca ttaccgtctt aataaaattc ggatttgttc tttnctattn | 240 |
| tcactcttca cctatgaccg aa | 262 |

<210> SEQ ID NO 19
<211> LENGTH: 261
<212> TYPE: DNA
<213> ORGANISM: Homo sapien

<400> SEQUENCE: 19

| tcggtcatag caaagccagt ggtttgagct ctctactgtg taaactccta aaccaaggcc | 60 |
| atttatgata aatggtggca ggattttat tataaacatg tacccatgca aatttcctat | 120 |
| aactctgaga tatattcttc tacatttaaa caataaaaat aatctatttt taaaagccta | 180 |
| atttgcgtag ttaggtaaga gtgtttaatg agagggtata aggtataaat caccagtcaa | 240 |
| cgtttctctg cctatgaccg a | 261 |

<210> SEQ ID NO 20
<211> LENGTH: 294
<212> TYPE: DNA
<213> ORGANISM: Homo sapien
<220> FEATURE:
<221> NAME/KEY: misc_feature
<222> LOCATION: (1)...(294)
<223> OTHER INFORMATION: n = A,T,C or G

<400> SEQUENCE: 20

```
tacaacgagg cgacgtcggt aaaatcggac atgaagccac cgctggtctt ttcgtccgag      60
cgataggcgc cggccagcca gcggaacggt tgcccggatg gcgaagcgag ccggagttct     120
tcggactgag tatgaatctt gttgtgaaaa tactcgccgc cttcgttcga cgacgtcgcg     180
tcgaaatctt cganctcctt acgatcgaag tcttcgtggg cgacgatcgc ggtcagttcc     240
gccccaccga aatcatggtt gagccggatg ctgnccccga agncctcgtt tgtn           294
```

<210> SEQ ID NO 21
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 21

```
ttggtaaagg gcatggacgc agacgcctga cgtttggctg aaaatctttc attgattcgt      60
atcaatgaat aggaaaattc ccaaagaggg aatgtcctgt tgctcgccag tttttntgtt    120
gttctcatgg anaaggcaan gagctcttca gactattggn attntcgttc ggtcttctgc    180
caactagtcg ncttgcnang atcttcat                                        208
```

<210> SEQ ID NO 22
<211> LENGTH: 287
<212> TYPE: DNA
<213> ORGANISM: Homo sapien
<220> FEATURE:
<221> NAME/KEY: misc_feature
<222> LOCATION: (1)...(287)
<223> OTHER INFORMATION: n = A,T,C or G

<400> SEQUENCE: 22

```
nccnttgagc tgagtgattg agatntgtaa tggttgtaag ggtgattcag gcggattagg      60
gtggcgggtc acccggcagt gggtctcccg acaggccagc aggatttggg gcaggtacgg    120
ngtgcgcatc gctcgactat atgctatggc aggcgagccg tggaaggngg atcaggtcac    180
ggcgctggag cttccacgg tccatgnatt gngatggctg ttctaggcgg ctgttgccaa     240
gcgtgatggt acgctggctg gagcattgat ttctggtgcc aaggtgg                  287
```

<210> SEQ ID NO 23
<211> LENGTH: 204
<212> TYPE: DNA
<213> ORGANISM: Homo sapien
<220> FEATURE:
<221> NAME/KEY: misc_feature
<222> LOCATION: (1)...(204)
<223> OTHER INFORMATION: n = A,T,C or G

<400> SEQUENCE: 23

```
ttgggtaaag ggagcaagga gaaggcatgg agaggctcan gctggtcctg gcctacgact      60
gggccaagct gtcgccgggg atggtggaga actgaagcgg gacctcctcg aggtcctccg    120
ncgttacttc nccgtccagg aggagggtct ttccgtggtc tnggaggagc ggggggagaa    180
gatnctcctc atggtcnaca tccc                                            204
```

<210> SEQ ID NO 24
<211> LENGTH: 264
<212> TYPE: DNA
<213> ORGANISM: Homo sapien

```
<220> FEATURE:
<221> NAME/KEY: misc_feature
<222> LOCATION: (1)...(264)
<223> OTHER INFORMATION: n = A,T,C or G

<400> SEQUENCE: 24
tggattggtc aggagcgggt agagtggcac cattgagggg atattcaaaa atattatttt       60
gtcctaaatg atagttgctg agttttttctt tgacccatga gttatattgg agtttatttt    120
ttaactttcc aatcgcatgg acatgttaga cttattttct gttaatgatt nctattttta     180
ttaaattgga tttgagaaat tggttnttat tatatcaatt tttggtattt gttgagtttg     240
acattatagc ttagtatgtg acca                                            264

<210> SEQ ID NO 25
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 25
ttacaacgag gggaaactcc gtctctacaa aaattaaaaa attagccagg tgtggtggtg      60
tgcacccgca atcccagcta cttgggaggt tgagacacaa gantcaccta natgtgggag    120
gtcaaggttg catgagtcat gattgtgcca ctgcactcca gcctgggtga cagaccgaga    180
ccctgcctca anaganaang aataggaagt tcagaaatcn tggntgtggn gcccagcaat    240
ctgcatctat ncaaccccctg caggcaangc tgatgcagcc tangttcaag agctgctgtt   300
tctggaggca gcagttnggg cttccatcca gtatcacggc cacactcgca cnagccatct    360
gtcctccgtn tgtnac                                                    376

<210> SEQ ID NO 26
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 26
ttacaacgag gggaaactcc gtctctacaa aaattaaaaa attagccagg tgtggtggtg      60
tgcacctgta atcccagcta cttgggcggc tgagacacaa gaaccaccta aatgtgggag    120
ggtcaaggtt gcatgagtca tgatcgcgcc actgcactcc agcctgggtg acagactgag    180
accctgcctc aaaagaaaaa gaataggaag ttcagaaacc ctgggtgtgg ngcccagcaa    240
tctgcattta acaatccct gcaggcaatg ctgatgcagc ctaagttcaa gagctgctgt     300
tctggaggca gnagtaaggg cttccatcca gcatcacggn caacactgca aaagcacctg    360
tcctcgttgg ta                                                        372

<210> SEQ ID NO 27
<211> LENGTH: 477
<212> TYPE: DNA
<213> ORGANISM: Homo sapien
```

```
<400> SEQUENCE: 27
ttctgtccac atctacaagt tttatttatt ttgtgggttt tcagggtgac taagtttttc      60
cctacattga aaagagaagt tgctaaaagg tgcacaggaa atcatttttt taagtgaata     120
tgataatatg ggtccgtgct taatacaact gagacatatt tgttctctgt tttttagag     180 tcacctctta aagtccaatc ccacaatggt gaaaaaaaaa tagaaagtat tgttctacc     240 tttaaggaga ctgcagggat tctccttgaa aacggagtat ggaatcaatc ttaaataaat     300
atgaaattgg ttggtcttct gggataagaa attcccaact cagtgtgctg aaattcacct     360
gacttttttt gggaaaaaat agtcgaaaat gtcaatttgg tccataaaat acatgttact     420
attaaaagat atttaaagac aaattcttc agagctctaa gattggtgtg gacagaa        477

<210> SEQ ID NO 28
<211> LENGTH: 438
<212> TYPE: DNA
<213> ORGANISM: Homo sapien
<220> FEATURE:
<221> NAME/KEY: misc_feature
<222> LOCATION: (1)...(438)
<223> OTHER INFORMATION: n = A,T,C or G

<400> SEQUENCE: 28
tctncaacct cttgantgtc aaaaaccttn taggctatct ctaaaagctg actggtattc      60
attccagcaa aatccctcta gttttggag tttccttta ctatctgggg ctgcctgagc     120
cacaaatgcc aaattaagag catggctatt tcgggggct gacaggtcaa aagggtgta     180 aatccgataa gcctcctgga ggtgctctaa aaacactcct ggtgactcat catgcccctg     240
gacgacttca atcgncttag acaagtttat aggtttctgg gcagctccct gaatacccac     300
gaggagatac cggtggaaat cgtcaaaagt tctccctcca cttgagaaat ttgggtccca     360
attaggtccc aattgggtct ctaatcacta ttcctctagc ttcctcctcc ggnctattgg     420
ttgatgtgag gttgaaga                                                   438

<210> SEQ ID NO 29
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 29
aagagggtac cagccccaag ccttgacaac ttccataggg tgtcaagcct gtgggtgcac      60
agaagtcaaa aattgagttt tgggatcctc agcctagatt tcagaggata taagaaaca     120 cctaacacct agatattcag acaaaagttt actacaggga tgaagctttc acggaaaacc     180
tctactagga aagtacagaa gagaaatgtg ggtttggagc ccccaaacag aatcccctct     240
agaacactgc ctaatgaaac tgtgagaaga tggccactgt catccagaca ccagaatgat     300
agacccacca aaaactatg ccatattgcc tataaaacct acagacactc aatgccagcc     360
ccatgaaaaa aaaactgaga agaagactgt ncctacaat gccaccggag cagaactgcc     420
ccaggccatg gaagcacagc tcttatatca atgtgacctg gatgttgaga catggaatcc     480
nangaaatcn ttttaanact tccacggttn aatgactgcc ctattanatt cngaacttan     540
atccnggcct gtgacctctt tgctttggcc attccccctt tttggaatgg ctntttttt     600 cccatgcctg tncccctctta                                              620
```

<210> SEQ ID NO 30
<211> LENGTH: 100
<212> TYPE: DNA
<213> ORGANISM: Homo sapien

<400> SEQUENCE: 30

| | | | | |
|---|---|---|---|---|
| ttacaacgag ggggtcaatg tcataaatgt cacaataaaa caatctcttc tttttttttt | | | | 60 |
| tttttttttt tttttttttt tttttttttt tttttttttt | | | | 100 |

<210> SEQ ID NO 31
<211> LENGTH: 762
<212> TYPE: DNA
<213> ORGANISM: Homo sapien
<220> FEATURE:
<221> NAME/KEY: misc_feature
<222> LOCATION: (1)...(762)
<223> OTHER INFORMATION: n = A,T,C or G

<400> SEQUENCE: 31

| | |
|---|---|
| tagtctatgc gccggacaga gcagaattaa attggaagtt gccctccgga ctttctaccc | 60 |
| acactcttcc tgaaaagaga aagaaaagag gcaggaaaga ggttaggatt tcattttcaa | 120 |
| gagtcagcta attaggagag cagagtttag acagcagtag gcaccccatg atacaaacca | 180 |
| tggacaaagt ccctgtttag taactgccag acatgatcct gctcaggttt tgaaatctct | 240 |
| ctgcccataa aagatggaga gcaggagtgc catccacatc aacacgtgtc caagaaagag | 300 |
| tctcagggag acaagggtat caaaaaacaa gattcttaat gggaaggaaa tcaaaccaaa | 360 |
| aaattagatt tttctctaca tatatataat atacagatat ttaacacatt attccagagg | 420 |
| tggctccagt ccttggggct tgagagatgg tgaaaacttt tgttccacat taacttctgc | 480 |
| tctcaaattc tgaagtatat cagaatggga caggcaatgt tttgctccac actggggcac | 540 |
| agacccaaat ggttctgtgc ccgaagaaga gaagcccgaa agacatgaag gatgcttaag | 600 |
| gggggttggg aaagccaaat tggtantatc ttttcctcct gcctgtgttc cngaagtctc | 660 |
| cnctgaagga attcttaaaa ccctttgtga ggaaatgccc ccttaccatg acaantggtc | 720 |
| ccattgcttt tagggngatg gaaacaccaa gggttttgat cc | 762 |

<210> SEQ ID NO 32
<211> LENGTH: 276
<212> TYPE: DNA
<213> ORGANISM: Homo sapien

<400> SEQUENCE: 32

| | |
|---|---|
| tagtctatgc gtgtattaac ctcccctccc tcagtaacaa ccaaagaggc aggagctgtt | 60 |
| attaccaacc ccattttaca gatgcatcaa taatgacaga gaagtgaagt gacttgcgca | 120 |
| cacaaccagt aaattggcag agtcagattt gaatccatgg agtctggtct gcactttcaa | 180 |
| tcaccgaata ccctttctaa gaaacgtgtg ctgaatgagt gcatggataa atcagtgtct | 240 |
| actcaacatc tttgcctaga tatcccgcat agacta | 276 |

<210> SEQ ID NO 33
<211> LENGTH: 477
<212> TYPE: DNA
<213> ORGANISM: Homo sapien

<400> SEQUENCE: 33

| | |
|---|---|
| tagtagttgc caaatatttg aaaatttacc cagaagtgat tgaaaacttt ttggaaacaa | 60 |
| aaacaaataa agccaaaagg taaaataaaa atatctttgc actctcgtta ttacctatcc | 120 |

-continued

| | |
|---|---|
| ataactttttt caccgtaagc tctcctgctt gttagtgtag tgtggttata ttaaactttt | 180 |
| tagttattat ttttattca cttttccact agaaagtcat tattgattta gcacacatgt | 240 |
| tgatctcatt tcatttttc tttttatagg caaaatttga tgctatgcaa caaaaatact | 300 |
| caagcccatt atcttttttc cccccgaaat ctgaaaattg caggggacag agggaagtta | 360 |
| tcccattaaa aaattgtaaa tatgttcagt ttatgtttaa aaatgcacaa aacataagaa | 420 |
| aattgtgttt acttgagctg ctgattgtaa gcagtttat ctcaggggca actacta | 477 |

<210> SEQ ID NO 34
<211> LENGTH: 631
<212> TYPE: DNA
<213> ORGANISM: Homo sapien

<400> SEQUENCE: 34

| | |
|---|---|
| tagtagttgc caattcagat gatcagaaat gctgctttcc tcagcattgt cttgttaaac | 60 |
| cgcatgccat ttggaacttt ggcagtgaga agccaaaagg aagaggtgaa tgacatatat | 120 |
| atatatatat attcaatgaa agtaaaatgt atatgctcat atactttcta gttatcagaa | 180 |
| tgagttaagc tttatgccat tgggctgctg catatttaa tcagaagata aagaaaatc | 240 |
| tgggcatttt tagaatgtga tacatgtttt tttaaaactg ttaaatatta tttcgatatt | 300 |
| tgtctaagaa ccggaatgtt cttaaaattt actaaaacag tattgtttga ggaagagaaa | 360 |
| actgtactgt ttgccattat tacagtcgta caagtgcatg tcaagtcacc cactctctca | 420 |
| ggcatcagta tccacctcat agctttacac attttgacgg ggaatattgc agcatcctca | 480 |
| ggcctgacat ctgggaaagg ctcagatcca cctactgctc cttgctcgtt gatttgtttt | 540 |
| aaaatattgt gcctggtgtc acttttaagc cacagccctg cctaaaagcc agcagagaac | 600 |
| agaacccgca ccattctata ggcaactact a | 631 |

<210> SEQ ID NO 35
<211> LENGTH: 578
<212> TYPE: DNA
<213> ORGANISM: Homo sapien

<400> SEQUENCE: 35

| | |
|---|---|
| tagtagttgc catcccatat tacagaaggc tctgtataca tgacttattt ggaagtgatc | 60 |
| tgttttctct ccaaacccat ttatcgtaat ttcaccagtc ttggatcaat cttggtttcc | 120 |
| actgatacca tgaaacctac ttggagcaga cattgcacag ttttctgtgg taaaaactaa | 180 |
| aggtttattt gctaagctgt catcttatgc ttagtatttt ttttttacag tggggaattg | 240 |
| ctgagattac attttgttat tcattagata ctttgggata acttgacact gtcttcttt | 300 |
| tttcgctttt aattgctatc atcatgcttt tgaaacaaga acacattagt cctcaagtat | 360 |
| tacataagct tgcttgttac gcctggtggt ttaaaggact atctttggcc tcaggttcac | 420 |
| aagaatgggc aaagtgtttc cttatgttct gtagttctca ataaaagatt gccagggggcc | 480 |
| gggtactgtg gctcgcactg taatcccagc actttgggaa gctgaggctg gcggatcatg | 540 |
| ttagggcagg tgttcgaaac cagcctgggc aactacta | 578 |

<210> SEQ ID NO 36
<211> LENGTH: 583
<212> TYPE: DNA
<213> ORGANISM: Homo sapien

<400> SEQUENCE: 36

```
tagtagttgc ctgtaatccc agcaactcag gaggctgggg caggagaatc agttgaacct      60
gggaggcaga agttgtaatt agcaaagatc gcaccattgc acttcagcct gggcaacaag     120
agtgagattc catctcaaaa acaaaaaaaa gaaaagaaa agaaaggaa aaacgtata        180
aacccagcca aaacaaaatg atcattcttt taataagcaa gactaattta atgtgtttat     240
ttaatcaaag cagttgaatc ttctgagtta ttggtgaaaa tacccatgta gttaatttag     300
ggttcttact tgggtgaacg tttgatgttc acaggttata aatggttaa caaggaaaat      360
gatgcataaa gaatcttata aactactaaa aataaataaa atataaatgg ataggtgcta     420
tggatggagt ttttgtgtaa tttaaaatct tgaagtcatt ttggatgctc attggttgtc     480
tggtaatttc cattaggaaa aggttatgat atggggaaac tgtttctgga aattgcggaa     540
tgtttctcat ctgtaaaatg ctagtatctc agggcaacta cta                      583
```

<210> SEQ ID NO 37
<211> LENGTH: 716
<212> TYPE: DNA
<213> ORGANISM: Homo sapien
<220> FEATURE:
<221> NAME/KEY: misc_feature
<222> LOCATION: (1)...(716)
<223> OTHER INFORMATION: n = A,T,C or G

<400> SEQUENCE: 37

```
gatctactag tcatntggat tctatccatg gcagctaagc ctttctgaat ggattctact      60
gctttcttgt tctttaatcc agacccttat atatgtttat gttcacaggc agggcaatgt     120
ttagtgaaaa caattctaaa tttttttattt tgcattttca tgctaatttc cgtcacactc    180
cagcaggctt cctgggagaa taaggagaaa tacagctaaa gacattgtcc ctgcttactt     240
acagcctaat ggtatgcaaa accacttcaa taaagtaaca ggaaaagtac taaccaggta     300
gaatggacca aaactgatat agaaaaatca gaggaagaga ggaacaaata tttactgagt     360
cctagaatgt acaaggcttt ttaattacat attttatgta aggcctgcaa aaaacaggtg     420
agtaatcaac atttgtccca ttttacatat aaggaaactg aagcttaaat tgaataattt     480
aatgcataga ttttatagtt agaccatgtt caggtcccta tgttatactt actagctgta     540
tgaatatgag aaaataattt tgttatttc ttggcatcag tattttcatc tgcaaaataa      600
agctaaagtt atttagcaaa cagtcagcat agtgcctgat acatagtagg tgctccaaac     660
atgattacnc tantattngg tattanaaaa atccaatata ggcntggata aaaccg         716
```

<210> SEQ ID NO 38
<211> LENGTH: 688
<212> TYPE: DNA
<213> ORGANISM: Homo sapien
<220> FEATURE:
<221> NAME/KEY: misc_feature
<222> LOCATION: (1)...(688)
<223> OTHER INFORMATION: n = A,T,C or G

<400> SEQUENCE: 38

```
ttctgtccac atatcatccc actttaattg ttaatcagca aactttcaa tgaaaaatca      60
tccatttaa ccaggatcac accaggaaac tgaaggtgta ttttttttta ccttaaaaaa     120
aaaaaaaaa accaaacaaa ccaaaacaga ttaacagcaa agagttctaa aaaatttaca    180
tttctcttac aactgtcatt cagagaacaa tagttcttaa gtctgttaaa tcttggcatt    240
aacagagaaa cttgatgaan agttgtactt ggaatattgt ggatttttt ttttgtctaa    300
```

-continued

```
tctcccccta ttgttttgcc aacagtaatt taagtttgtg tggaacatcc ccgtagttga      360
agtgtaaaca atgtatagga aggaatatat gataagatga tgcatcacat atgcattaca      420
tgtagggacc ttcacaactt catgcactca gaaaacatgc ttgaagagga ggagaggacg      480
gcccagggtc accatccagg tgccttgagg acagagaatg cagaagtggc actgttgaaa      540
tttagaagac catgtgtgaa tggtttcagg cctgggatgt ttgccaccaa gaagtgcctc      600
cgagaaattt ctttcccatt tggaatacag ggtggcttga tgggtacggt gggtgaccca      660
acgaagaaaa tgaaattctg ccctttcc                                         688
```

<210> SEQ ID NO 39
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 39

```
tagtagttgc cgcnnaccta aaanttggaa agcatgatgt ctaggaaaca tantaaaata      60
gggtatgcct atgtgctaca gagagatgtt agcatttaaa gtgcatantt ttatgtattt     120
tgacaaatgc atatncctct ataatccaca actgattacg aagctattac aattaaaaag     180
tttggccggg cgtggtgggc ggtggctgac gcctgtaatc ccagcacttt gggaggccga     240
ggcacgcgga tcacgaggtc gggagttcaa gaccatcctg gctaacacgg tgaaagtcca     300
tctctactaa aaatacgaaa aaattacccc ggcgtggtgg cgggcgcctg tagtcccagc     360
tactccggag gctgaggcag gagaatggcg tgaacccagg acacggagct gcagtgtgc      420 caacatcacg tcactgccct ccagcctggg ggacaggaac aagantcccg tcctcanaaa     480
agaaaaatac tactnatant ttcnacttta ttttaantta cacagaactn cctcttggta     540
cccccttacc attcatctca cccacctcct atagggcacn nctaa                    585
```

<210> SEQ ID NO 40
<211> LENGTH: 475
<212> TYPE: DNA
<213> ORGANISM: Homo sapien

<400> SEQUENCE: 40

```
tctgtccaca ccaatcttag aagctctgaa aagaatttgt ctttaaatat cttttaatag      60
taacatgtat tttatggacc aaattgacat tttcgactgt tttttccaaa aaagtcaggt     120
gaatttcagc acactgagtt gggaatttct tatcccagaa gaccaaccaa tttcatattt     180
atttaagatt gattccatac tccgttttca aggagaatcc ctgcagtctc cttaaaggta     240
gaacaaatac ttcctatttt ttttcacca ttgtgggatt ggactttaag aggtgactct     300
aaaaaaacag agaacaaata tgtctcagtt gtattaagca cggacccata ttatcatatt     360
cacttaaaaa aatgatttcc tgtgcacctt ttggcaactt ctcttttcaa tgtagggaaa     420
aacttagtca ccctgaaaac ccacaaaata aataaaactt gtagatgtgg acaga         475
```

<210> SEQ ID NO 41
<211> LENGTH: 423
<212> TYPE: DNA
<213> ORGANISM: Homo sapien

<400> SEQUENCE: 41

```
taagagggta catcgggtaa gaacgtaggc acatctagag cttagagaag tctggggtag    60
gaaaaaaatc taagtattta aagggtata ggtaacattt aaaagtaggg ctagctgaca    120
ttatttagaa agaacacata cggagagata agggcaaagg actaagacca gaggaacact    180
aatatttagt gatcacttcc attcttggta aaaatagtaa cttttaagtt agcttcaagg    240
aagatttttg gccatgatta gttgtcaaaa gttagttctc ttgggtttat attactaatt    300
ttgttttaag atccttgtta gtgctttaat aaagtcatgt tatatcaaac gctctaaaac    360
attgtagcat gttaaatgtc acaatatact taccatttgt tgtatatggc tgtaccctct    420
cta                                                                  423
```

<210> SEQ ID NO 42
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 42

```
tctcctaggc taatgtgtgt gtttctgtaa aagtaaaaag ttaaaaattt taaaaataga    60
aaaaagctta tagaataaga atatgaagaa agaaaatatt tttgtacatt tgcacaatga   120
gtttatgttt taagctaagt gttattacaa aagagccaaa aaggttttaa aaattaaaac   180
gtttgtaaag ttacagtacc cttatgttaa tttataattg aagaaagaaa actttttttt   240
tataaatgta gtgtagccta agcatacagt atttataaag tctggcagtg ttcaataatg   300
tcctaggcct tcacattcac tcactgactc acccagagca acttccagtc ctgtaagctc   360
cattcgtggt aagtgcccta tacaggtgca ccatttattt tacagtattt ttactgtacc   420
ttctctatgt ttccatatgt ttcgatatac aaataccact ggttactatn gcccnacagg   480
taattccagt aacacggcct gtatacgtct ggtanccctc gngaaga               527
```

<210> SEQ ID NO 43
<211> LENGTH: 331
<212> TYPE: DNA
<213> ORGANISM: Homo sapien

<400> SEQUENCE: 43

```
tcttcaacct cgtaggacaa ctctcatatg cctgggcact attttttaggt tactaccttg    60 gctgcccttc tttaagaaaa aaaaagaag aaaaagaac ttttccacaa gtttctcttc    120
ctctagttgg aaaattagag aaatcatgtt tttaattttg tgttatttca gatcacaaat    180
tcaaacactt gtaaacatta agcttctgtt caatcccctg ggaagaggat tcattctgat    240
atttacggtt caaagaagt tgtaatattg tgcttggaac acagagaacc agttattaac    300
ttcctactac tattatataa taaataataa c                                  331
```

<210> SEQ ID NO 44
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

```
<400> SEQUENCE: 44
ggcttagtag ttgccaggca aaatarcgtt gattctcctc aggagccacc cccaacaccc        60
ctgtttgctt ctagacctat acctagacta aagtcccagc agaccctag aggtgaggtt       120 cagagtgacc cttgaggaga tgtgctacac tagaaaagaa ctgcttgagt tttctaattt       180
atataagcag aaatctggag aagagtcata ggaatggata ttaagggtgt gagataatgg       240
cggaaggaat atagagttgg atcaggctgg acttattgat ttgaacccac taagtagaga       300
ttctgctttt gatgttgcag ctcagggagt taaaaaggt tttaatggtt ctaatagttt       360
atttgcttgg ttagctgaaa tatggataaa agatggccca ctgtgagcaa gctggaaatg       420
cctgatctct ctcagtttaa tgtagaggaa gggatccaaa agtttaggga ganttggatg       480
ctggraktgg attggtcact ttgrgaccta cccwtcccag ctgggagggt ccagaagata       540 caccttgac caacgctttg cgaaatggat ttgtgatggc ggcaactact aa               592

<210> SEQ ID NO 45
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 45
ggcttagtag ttgccattgc gagtgcttgc tcaacgagcg ttgaacatgg cggattgtct        60
agattcaacg gatttgagtt ttaccagcaa agcgaaccaa gcgcggccca gagaattatg       120
ggttggttgg ctttgaaaag atggaaatcc tgtaggccta gtcagaaaag ccttcttgca       180
gaacagttgg ttctcgggcg aacgctcatc aagatgccca ttggaaaggc tagcgtgtat       240
ttgggagagc ctgatagcgt gtcttctgat gatgtttgtg cttggacagt gacaaaagat       300
atgcaaagca agtccgaact agacgtcaag cttcgtgagc aaattattgt agactcctac       360
ttatactgtg aggaatgata gccaagggtg gggactttaa gactaaggtg gttttgtactt       420 gcgccgatga tcccaggcag aaagamctga tcgctagttt tatacgggca actactaagc       480
cgaattccag cacactggcg gccgttacta attggatccg anctcggtac cagcttgatg       540
catascttga gttwtctata ntgtcnc                                         567

<210> SEQ ID NO 46
<211> LENGTH: 908
<212> TYPE: DNA
<213> ORGANISM: Homo sapien
<220> FEATURE:
<221> NAME/KEY: misc_feature
<222> LOCATION: (1)...(908)
<223> OTHER INFORMATION: n = A,T,C or G

<400> SEQUENCE: 46
gagcgaaaga ccgagggcag ngnntangng cgangaagcg gagagggcca aaaagcaacc        60
gctttccccg ggggtgccg attcattaag gcaggtggag gacaggtttc ccgatggaag       120
gcggcagggg cgcaagcaat taatgtgagt aggccattca ttagcacccg ggcttaacat       180
ttaagcttcg ggttggtatg tggtgggaat tgtgagcgga taacaatttc acacaggaaa       240
cagctatgac catgattacg ccaagctatt taggtgacat tatagaataa ctcaagttat       300
gcatcaagct tggtaccgag ttcggatcca ctagtaacgg ccgccagtgt gtggaattcg       360
gcttagtagt tgccgaccat ggagtgctac ctaggctaga atacctgagy tcctcccctag       420
```

```
cctcactcac attaaattgt atcttttcta cattagatgt cctcagcgcc ttatttctgc      480
tggacwatcg ataaattaat cctgatagga tgatagcagc agattaatta ctgagagtat      540
gttaatgtgt catccctcct atataacgta tttgcatttt aatggagcaa ttctggagat      600
aatccctgaa ggcaaaggaa tgaatcttga gggtgagaaa gccagaatca gtgtccagct      660
gcagttgtgg gagaaggtga tattatgtat gtctcagaag tgacaccata tgggcaacta      720
ctaagcccga attccagcac actggcgggc gttactaatg gatccgagct cggtaccaag      780
cttgatgcat agcttgagta tctatagtgt cactaaatag cctggcgtta tcatggtcat      840
agctgtttcc tgtgtgaaat tgttatccgc tcccaattcc ccccaccata cgagccggaa      900
cataaagt                                                              908

<210> SEQ ID NO 47
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 47
tgccaacaag gaaagtttta aatttcccct tgaggattct tggtgatcat caaattcagt      60
ggtttttaag gttgttttct gtcaaataac tctaacttta agccaaacag tatatggaag      120
cacagataka atattacaca gataaaagag gagttgatct aaagtaraga tagttggggg      180
ctttaatttc tggaacctag gtctccccat cttcttctgt gctgaggaac ttcttggaag      240
cggggattct aaagttcttt ggaagacagt ttgaaaacca ccatgttgtt ctcagtacct      300
ttatttttaa aaagtaggtg aacattttga gagagaaaag ggcttggttg agatgaagtc      360 ccccccccc cttttttttt ttttagctga aatagatacc ctatgttnaa rgaarggatt      420
attatttacc atgccaytar scacatgctc tttgatgggc nyctccstac cctccttaag      480

<210> SEQ ID NO 48
<211> LENGTH: 591
<212> TYPE: DNA
<213> ORGANISM: Homo sapien

<400> SEQUENCE: 48
aagagggtac cgagtggaat ttccgcttca ctagtctggt gtggctagtc ggtttcgtgg      60
tggccaacat tacgaacttc caactcaacc gttcttggac gttcaagcgg gagtaccggc      120
gaggatggtg gcgtgaattc tggcctttct ttgccgtggg atcggtagcc gccatcatcg      180
gtatgtttat caagatcttc tttactaacc cgacctctcc gatttacctg cccgagccgt      240
ggtttaacga ggggagggg atccagtcac gcgagtactg gtcccagatc ttcgccatcg      300
tcgtgacaat gcctatcaac ttcgtcgtca ataagttgtg gaccttccga acggtgaagc      360
actccgaaaa cgtccggtgg ctgctgtgcg gtgactccca aaatcttgat aacaacaagg      420
taaccgaatc gcgctaagga accccggcat ctcgggtact ctgcatatgc gtacccctta      480
agccgaattc cagcacactg gcggccgtta ctaattggat ccgaactccg taaccaagcc      540
tgatgcgtaa cttgagttat tctatagtgt ccctaaaata acctggcgtt a              591

<210> SEQ ID NO 49
<211> LENGTH: 454
<212> TYPE: DNA
<213> ORGANISM: Homo sapien
```

<400> SEQUENCE: 49

```
aagagggtac ctgccttgaa atttaaatgt ctaaggaaar tgggagatga ttaagagttg      60
gtgtggcyta gtcacaccaa aatgtattta ttacatcctg ctcctttcta gttgacagga     120
aagaaagctg ctgtggggaa aggagggata aatactgaag ggatttacta aacaaatgtc     180
catcacagag ttttccttttt tttttttttg agacagagtc ttgctctgtc acccaggctg     240
gaatgaagwg gtatgatctc agttgaatgc aacctctacc tcctaggttc aagcgattct     300
catgcctcag cctcctgagc agctgggact ataggcgcat gctaccatgc caggctaatt     360
tttatatttt tattagagac gggtgttgc catgttggcc aggcaggtct cgaactcctg      420
ggcctcagat gatctgcccc accgtaccct ctta                                 454
```

<210> SEQ ID NO 50
<211> LENGTH: 463
<212> TYPE: DNA
<213> ORGANISM: Homo sapien

<400> SEQUENCE: 50

```
aagagggtac caaaaaaaag aaaaaggaaa aaaagaaaaa caacttgtat aaggctttct      60
gctgcataca gctttttttt tttaaataaa tggtgccaac aaatgttttt gcattcacac     120
caattgctgg ttttgaaatc gtactcttca aggtatttg tgcagatcaa tccaatagtg      180
atgccccgta ggttttgtgg actgcccacg ttgtctacct tctcatgtag agccattga     240
gagactgttt ggacatgcct gtgttcatgt agccgtgatg tccggggggcc gtgtacatca    300
tgttaccgtg gggtggggtc tgcattggct gctgggcata tggctgggtg cccatcatgc    360
ccatctgcat ctgcataggg tattggggcg tttgatccat atagccatga ttgctgtggt    420
agccactgtt catcattggc tgggacatgc tgttaccctc tta                      463
```

<210> SEQ ID NO 51
<211> LENGTH: 399
<212> TYPE: DNA
<213> ORGANISM: Homo sapien

<400> SEQUENCE: 51

```
cttcaacctc ccaaagtgct gggattacag gactgagcca ccacgctcag cctaagcctc      60
tttttcacta ccctctaagc gatctaccac agtgatgagg ggctaaagag cagtgcaatt     120
tgattacaat aatggaactt agattttatta attaacaatt tttccttagc atgttggttc    180
cataattatt aagagtatgg acttacttag aaatgagctt tcattttaag aatttcatct    240
ttgaccttct ctattagtct gagcagtatg acactatacg tatttttattt aactaaccta    300
ccttgagcta ttactttta aaaggctata tacatgaatg tgtattgtca actgtaaagc     360
cccacagtat ttaattatat catgatgtct ttgaggttg                            399
```

<210> SEQ ID NO 52
<211> LENGTH: 392
<212> TYPE: DNA
<213> ORGANISM: Homo sapien

<400> SEQUENCE: 52

```
cttcaacctc aatcaacctt ggtaattgat aaaatcatca cttaactttc tgatataatg      60
gcaataatta tctgagaaaa aaaagtggtg aaagattaaa cttgcatttc tctcagaatc     120
ttgaaggata tttgaataat tcaaaagcgg aatcagtagt atcagccgaa gaaactcact    180
tagctagaac gttggaccca tggatctaag tccctgccct tccactaacc agctgattgg    240
```

```
ttttgtgtaa acctcctaca cgcttgggct tggtcgcctc atttgtcaaa gtaaaggctg      300
aaataggaag ataatgaacc gtgtcttttt ggtctctttt ccatccatta ctctgatttt      360
acaaagaggc ctgtattccc ctggtgaggt tg                                    392
```

```
<210> SEQ ID NO 53
<211> LENGTH: 179
<212> TYPE: DNA
<213> ORGANISM: Homo sapien
<220> FEATURE:
<221> NAME/KEY: misc_feature
<222> LOCATION: (1)...(179)
<223> OTHER INFORMATION: n = A,T,C or G

<400> SEQUENCE: 53
ttcgggtgat gcctcctcag gctacagtga agactggatt acagaaaggt gccagcgaga       60
tttcagattc ctgtaaacct ctaaagaaaa ggagtcgcgc ctcaactgat gtagaaatga      120
ctagttcagc atacngagac acntctgact ccgattctag aggactgagt gacctgcan      179
```

```
<210> SEQ ID NO 54
<211> LENGTH: 112
<212> TYPE: DNA
<213> ORGANISM: Homo sapien
<220> FEATURE:
<221> NAME/KEY: misc_feature
<222> LOCATION: (1)...(112)
<223> OTHER INFORMATION: n = A,T,C or G

<400> SEQUENCE: 54
ttcgggtgat gcctcctcag gctacatcat natagaagca aagtagaana atcnngtttg       60
tgcattttcc cacanacaaa attcaaatga ntggaagaaa ttgggganagt at             112
```

```
<210> SEQ ID NO 55
<211> LENGTH: 225
<212> TYPE: DNA
<213> ORGANISM: Homo sapien

<400> SEQUENCE: 55
tgagcttccg cttctgacaa ctcaatagat aatcaaagga caactttaac agggattcac       60
aaaggagtat atccaaatgc caataaacat ataaaaagga attcagcttc atcatcatca      120
gaagwatgca aattaaaacc ataatgagaa accactatgt cccactagaa tagataaaat      180
cttaaaagac tggtaaaacc aagtgttggt aaggcaagag gagca                     225
```

```
<210> SEQ ID NO 56
<211> LENGTH: 175
<212> TYPE: DNA
<213> ORGANISM: Homo sapien

<400> SEQUENCE: 56
gctcctcttg ccttaccaac acattctcaa aaacctgtta gagtcctaag cattctcctg       60
ttagtattgg gattttaccc ctgtcctata aagatgttat gtaccaaaaa tgaagtggag      120
ggccataccc tgagggaggg gagggatctc tagtgttgtc agaagcggaa gctca           175
```

```
<210> SEQ ID NO 57
<211> LENGTH: 223
<212> TYPE: DNA
<213> ORGANISM: Homo sapien
```

```
<400> SEQUENCE: 57
agccatttac cacccatgga tgaatggatt ttgtaattct agctgttgta ttttgtgaat      60
ttgttaattt tgttgttttt ctgtgaaaca catacattgg atatgggagg taaaggagtg     120
tcccagttgc tcctggtcac tccctttata gccattactg tcttgtttct tgtaactcag    180
gttaggtttt ggtctctctt gctccactgc aaaaaaaaaa aaa                      223

<210> SEQ ID NO 58
<211> LENGTH: 211
<212> TYPE: DNA
<213> ORGANISM: Homo sapien

<400> SEQUENCE: 58
gttcgaaggt gaacgtgtag gtagcggatc tcacaactgg ggaactgtca aagacgaatt     60
aactgacttg gatcaatcaa atgtgactga ggaaacacct gaaggtgaag aacatcatcc    120
agtggcagac actgaaaata aggagaatga agttgaagag gtaaaagagg agggtccaaa    180
agagatgact ttggatgggt ggtaaatggc t                                   211

<210> SEQ ID NO 59
<211> LENGTH: 208
<212> TYPE: DNA
<213> ORGANISM: Homo sapien

<400> SEQUENCE: 59
gctcctcttg ccttaccaac tttgcaccca tcatcaacca tgtggccagg tttgcagccc     60
aggctgcaca tcaggggact gcctcgcaat acttcatgct gttgctgctg actgatggtg    120
ctgtgacgga tgtggaagcc acacgtgagg ctgtggtgcg tgcctcgaac ctgcccatgt    180
cagtgatcat tatgggtggt aaatggct                                       208

<210> SEQ ID NO 60
<211> LENGTH: 171
<212> TYPE: DNA
<213> ORGANISM: Homo sapien

<400> SEQUENCE: 60
agccatttac cacccatact aaattctagt tcaaactcca acttcttcca taaaacatct     60
aaccactgac accagttggc aatagcttct tccttcttta acctcttaga gtatttatgg    120
tcaatgccac acatttctgc aactgaataa agttggtaag gcaagaggag c             171

<210> SEQ ID NO 61
<211> LENGTH: 134
<212> TYPE: DNA
<213> ORGANISM: Homo sapien
<220> FEATURE:
<221> NAME/KEY: misc_feature
<222> LOCATION: (1)...(134)
<223> OTHER INFORMATION: n = A,T,C or G

<400> SEQUENCE: 61
cgggtgatgc ctcctcaggc tttggtgtgt ccactcnact cactggcctc ttctccagca     60
actggtgaan atgtcctcan gaaaancncc acacgcngct cagggtgggg tgggaancat    120
canaatcatc nggc                                                      134

<210> SEQ ID NO 62
<211> LENGTH: 145
<212> TYPE: DNA
<213> ORGANISM: Homo sapien
```

<400> SEQUENCE: 62

```
agagggtaca tatgcaacag tatataaagg aagaagtgca ctgagaggaa cttcatcaag      60
gccatttaat caataagtga tagagtcaag gctcaaccca ggtgtgacgg attccaggtc     120
ccaagctcct tactggtacc ctctt                                           145
```

<210> SEQ ID NO 63
<211> LENGTH: 297
<212> TYPE: DNA
<213> ORGANISM: Homo sapien

<400> SEQUENCE: 63

```
tgcactgaga ggaattcaaa gggtttatgc caaagaacaa accagtcctc tgcagcctaa      60
ctcatttgtt tttgggctgc gaagccatgt agagggcgat caggcagtag atggtccctc     120
ccacagtcag cgccatggtg gtccggtaaa gcatttggtc aggcaggcct cgtttcaggt     180
agacgggcac acatcagctt tctggaaaaa cttttgtagc tctggagctt tgttttccc     240
agcataatca tacactgtgg aatcggaggt cagtttagtt ggtaaggcaa gaggagc        297
```

<210> SEQ ID NO 64
<211> LENGTH: 300
<212> TYPE: DNA
<213> ORGANISM: Homo sapien

<400> SEQUENCE: 64

```
gcactgagag gaacttccaa tactatgttg aataggagtg gtgagagagg gcatccttgt      60
cttgtgccgg ttttcaaagg gaatgcttcc agcttttgcc cattcagtat aatattaaag     120
aatgttttac cattttctgt cttgcctgtt tttctgtgtt tttgttggtc tcttcattct     180
ccatttttag gcctttacat gttaggaata tatttctttt aatgatactt cacctttggt     240
atcttttgtg agactctact catagtgtga taagcactgg gttggtaagg caagaggagc     300
```

<210> SEQ ID NO 65
<211> LENGTH: 203
<212> TYPE: DNA
<213> ORGANISM: Homo sapien

<400> SEQUENCE: 65

```
gctcctcttg ccttaccaac tcacccagta tgtcagcaat tttatcrgct ttacctacga      60
aacagcctgt atccaaacac ttaacacact cacctgaaaa gttcaggcaa caatcgcctt     120
ctcatgggtc tctctgctcc agttctgaac cttttctcttt cctagaaca tgcatttarg    180
tcgatagaag ttcctctcag tgc                                              203
```

<210> SEQ ID NO 66
<211> LENGTH: 344
<212> TYPE: DNA
<213> ORGANISM: Homo sapien

<400> SEQUENCE: 66

```
tacggggacc cctgcattga gaaagcgaga ctcactctga agctgaaatg ctgttgccct      60
tgcagtgctg gtagcaggag ttctgtgctt tgtgggctaa ggctcctgga tgacccctga     120
catggagaag gcagagttgt gtgcccctcc tcatggcctc gtcaaggcat catggactgc     180
cacacacaaa atgccgtttt tattaacgac atgaaattga aggagagaac acaattcact     240
gatgtggctc gtaaccatgg atatggtcac atacagaggt gtgattatgt aaaggttaat    300
tccacccacc tcatgtggaa actagcctca atgcagggt ccca                      344
```

<210> SEQ ID NO 67
<211> LENGTH: 157
<212> TYPE: DNA
<213> ORGANISM: Homo sapien

<400> SEQUENCE: 67
gcactgagag gaacttcgta gggaggttga actggctgct gaggaggggg aacaacaggg          60
taaccagact gatagccatt ggatggataa tatggtggtt gaggagggac actacttata         120
gcagagggtt gtgtatagcc tgaggaggca tcacccg                                  157

<210> SEQ ID NO 68
<211> LENGTH: 137
<212> TYPE: DNA
<213> ORGANISM: Homo sapien

<400> SEQUENCE: 68
gcactgagag gaacttctag aaagtgaaag tctagacata aaataaaata aaaatttaaa          60
actcaggaga gacagcccag cacggtggct cacgcctgta atcccagaac tttgggagcc         120
tgaggaggca tcacccg                                                        137

<210> SEQ ID NO 69
<211> LENGTH: 137
<212> TYPE: DNA
<213> ORGANISM: Homo sapien

<400> SEQUENCE: 69
cgggtgatgc ctcctcaggc tgtattttga agactatcga ctggacttct tatcaactga          60
agaatccgtt aaaaatacca gttgtattat ttctacctgt caaaatccat ttcaaatgtt         120
gaagttcctc tcagtgc                                                        137

<210> SEQ ID NO 70
<211> LENGTH: 220
<212> TYPE: DNA
<213> ORGANISM: Homo sapien
<220> FEATURE:
<221> NAME/KEY: misc_feature
<222> LOCATION: (1)...(220)
<223> OTHER INFORMATION: n = A,T,C or G

<400> SEQUENCE: 70
agcatgttga gcccagacac gcaatctgaa tgagtgtgca cctcaagtaa atgtctacac          60
gctgcctggt ctgacatggc acaccatcnc gtggagggca casctctgct cngcctacwa         120
cgagggcant ctcatwgaca ggttccaccc accaaactgc aagaggctca nnaagtactr         180
ccagggtmya sggacmasgg tgggaytyca ycacwcatct                               220

<210> SEQ ID NO 71
<211> LENGTH: 353
<212> TYPE: DNA
<213> ORGANISM: Homo sapien
<220> FEATURE:
<221> NAME/KEY: misc_feature
<222> LOCATION: (1)...(353)
<223> OTHER INFORMATION: n = A,T,C or G

<400> SEQUENCE: 71
cgttagggtc tctatccact gctaaaccat acacctgggt aaacagggac catttaacat          60
tcccanctaa atatgccaag tgacttcaca tgtttatctt aaagatgtcc aaaacgcaac         120
tgattttctc ccctaaacct gtgatggtgg gatgattaan cctgagtggt ctacagcaag         180

-continued

| | |
|---|---|
| ttaagtgcaa ggtgctaaat gaangtgacc tgagatacag catctacaag gcagtacctc | 240 |
| tcaacncagg gcaactttgc ttctcanagg gcatttagca gtgtctgaag taatttctgt | 300 |
| attacaactc acggggcggg gggtgaatat ctantggana gnagaccc ta acg | 353 |

<210> SEQ ID NO 72
<211> LENGTH: 343
<212> TYPE: DNA
<213> ORGANISM: Homo sapien

<400> SEQUENCE: 72

| | |
|---|---|
| gcactgagag gaacttccaa tacyatkatc agagtgaaca rgcarccyac agaacaggag | 60 |
| aaaatgttyg caatctctcc atctgacaaa aggctaatat ccagawtcta awaggaactt | 120 |
| aaacaaattt atgagaaaag aacaracaac ctcawcaaaa agtgggtgaa ggawatgcts | 180 |
| aaargaagac atytattcag ccagtaaaca yatgaaaaaa aggctcatsa tcactgawca | 240 |
| ttagagaaat gcaaatcaaa accacaatga gataccatct yayrccagtt agaayggtga | 300 |
| tcattaaaar stcaggaaac aacagatgct ggacaaggtg tca | 343 |

<210> SEQ ID NO 73
<211> LENGTH: 321
<212> TYPE: DNA
<213> ORGANISM: Homo sapien
<220> FEATURE:
<221> NAME/KEY: misc_feature
<222> LOCATION: (1)...(321)
<223> OTHER INFORMATION: n = A,T,C or G

<400> SEQUENCE: 73

| | |
|---|---|
| gcactgagag gaacttcaga gagagagaga gagttccacc ctgtacttgg ggagagaaac | 60 |
| agaaggtgag aaagtctttg gttctgaagc agcttctaag atcttttcat ttgcttcatt | 120 |
| tcaaagttcc catgctgcca aagtgccatc ctttggggta ctgttttctg agctccagtg | 180 |
| ataactcatt tatacaaggg agatacccag aaaaaaagtg agcaaatctt aaaaggtgg | 240 |
| cttgagttca gccttaaata ccatcttgaa atgacacaga gaaagaanga tgttgggtgg | 300 |
| gagtggatag agaccctaac g | 321 |

<210> SEQ ID NO 74
<211> LENGTH: 321
<212> TYPE: DNA
<213> ORGANISM: Homo sapien

<400> SEQUENCE: 74

| | |
|---|---|
| gcactgagag gaacttcaga gagagagaga gagttccacc ctgtacttgg ggagagaaac | 60 |
| agaaggtgag aaagtctttg gttctgaagc agcttctaag atcttttcat ttgcttcatt | 120 |
| tcaaagttcc catgctgcca aagtgccatc ctttggggta ctgttttctg agctccagtg | 180 |
| ataactcatt tatacaaggg agatacccag aaaaaaagtg agcaaatctt aaaaggtgg | 240 |
| cttgagttca gycttaaata ccatcttgaa atgamacaga gaagaagga tgttgggtgg | 300 |
| gagtggatag agaccctaac g | 321 |

<210> SEQ ID NO 75
<211> LENGTH: 317
<212> TYPE: DNA
<213> ORGANISM: Homo sapien

```
<400> SEQUENCE: 75
gcactgagag gaacttccac atgcactgag aaatgcatgt tcacaaggac tgaagtctgg      60
aactcagttt ctcagttcca atcctgattc aggtgtttac cagctacaca accttaagca     120
agtcagataa ccttagcttc ctcatatgca aaatgagaat gaaaagtact catcgctgaa     180
ttgttttgag gattagaaaa acatctggca tgcagtagaa attcaattag tattcatttt     240
cattcttcta aattaaacaa ataggatttt tagtggtgga acttcagaca ccagaaatgg     300
gagtggatag agaccct                                                    317

<210> SEQ ID NO 76
<211> LENGTH: 244
<212> TYPE: DNA
<213> ORGANISM: Homo sapien

<400> SEQUENCE: 76
cgttagggtc tctatccact cccactactg atcaaactct atttatttaa ttatttttat      60
catactttaa gttctgggat acacgtgcag catgcgcagg tttgttgcat aggtatacac     120
ttgccatggt ggtttgctgc acccatcagt ccatcatcta cattaggtat ttctcctaat     180
gctatccctc ccctagcccc ttacaccccc aacaggctct agtgtgtgaa gttcctctca     240
gtgc                                                                  244

<210> SEQ ID NO 77
<211> LENGTH: 254
<212> TYPE: DNA
<213> ORGANISM: Homo sapien

<400> SEQUENCE: 77
cgttagggtc tctatccact gaaatctgaa gcacaggagg aagagaagca gtyctagtga      60
gatggcaagt tcwtttacca cactcttttaa catttgtttt agttttaacc tttatttatg    120
gataataaag gttaatatta ataatgattt atttttaaggc attcccraat ttgcataatt    180
ctccttttgg agatacccctt ttatctccag tgcaagtctg gatcaaagtg atasamagaa    240
gttcctctca gtgc                                                       254

<210> SEQ ID NO 78
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 78
ttcgatacag gcaaacatga actgcaggag ggtggtgacg atcatgatgt tgccgatggt      60
ccggatggnc acgaagacgc actggancac gtgcttacgt ccttttgctc tgttgatggc    120
cctgagggga cgcaggaccc ttatgaccct cagaatcttc acaacgggag atggcactgg    180
attgantccc antgacacca gagacacccc aaccaccagn atatcantat attgatgtag    240
ttcctgtaga nggcccccctt gtggaggaaa gctccatnag ttggtcatct tcaacaggat    300
ctcaacagtt tccgatggct gtgatgggca tagtcatant taaccntgtn tcgaa         355

<210> SEQ ID NO 79
<211> LENGTH: 406
<212> TYPE: DNA
<213> ORGANISM: Homo sapien
```

<400> SEQUENCE: 79

```
taagagggta ccagcagaaa ggttagtatc atcagatagc atcttatacg agtaatatgc      60
ctgctatttg aagtgtaatt gagaaggaaa attttagcgt gctcactgac ctgcctgtag     120
ccccagtgac agctaggatg tgcattctcc agccatcaag agactgagtc aagttgttcc     180
ttaagtcaga acagcagact cagctctgac attctgattc gaatgacact gttcaggaat     240
cggaatcctg tcgattagac tggacagctt gtggcaagtg aatttgcctg taacaagcca     300
gattttttaa aatttatatt gtaaataatg tgtgtgtgtg tgtgtgtata tatatatata     360
tgtacagtta tctaagttaa tttaaaagtt gtttggtacc ctctta                    406
```

<210> SEQ ID NO 80
<211> LENGTH: 327
<212> TYPE: DNA
<213> ORGANISM: Homo sapien

<400> SEQUENCE: 80

```
tttttttttt tttactcggc tcagtctaat cctttttgta gtcactcata ggccagactt      60
agggctagga tgatgattaa taagagggat gacataacta ttagtggcag gttagttgtt     120
tgtagggctc atggtagggg taaaaggagg gcaatttcta gatcaaataa taagaaggta     180
atagctacta agaagaattt tatggagaaa gggacgcggg cggggatat agggtcgaag      240 ccgcactcgt aagggtggga tttttctatg tagccgttga gttgtggtag tcaaaatgta     300
ataattatta gtagtaagcc taggaga                                         327
```

<210> SEQ ID NO 81
<211> LENGTH: 318
<212> TYPE: DNA
<213> ORGANISM: Homo sapien

<400> SEQUENCE: 81

```
tagtctatgc ggttgattcg gcaatccatt atttgctgga ttttgtcatg tgttttgcca      60
attgcattca taatttatta tgcatttatg cttgtatctc ctaagtcatg gtatataatc     120
catgcttttt atgttttgtc tgacataaac tcttatcaga gccctttgca cacagggatt     180
caataaatat taacacagtc tacatttatt tggtgaaatat tgcatatctg ctgtactgaa    240
agcacattaa gtaacaaagg caagtgagaa gaatgaaaag cactactcac aacagttatc     300
atgattgcgc atagacta                                                   318
```

<210> SEQ ID NO 82
<211> LENGTH: 338
<212> TYPE: DNA
<213> ORGANISM: Homo sapien

<400> SEQUENCE: 82

```
tcttcaacct ctactcccac taatagcttt ttgatgactt ctagcaagcc tcgctaacct      60
cgccttaccc cccactatta acctactggg agaactctct gtgctagtaa ccacgttctc     120
ctgatcaaat atcactctcc tacttacagg actcaacata ctagtcacag ccctatactc     180
cctctacata tttaccacaa cacaatgggg ctcactcacc caccacatta acaacataaa     240
accctcattc acacgagaaa acaccctcat gttcatacac ctatccccca ttctcctcct     300
atccctcaac ccgacatca ttaccgggtt ttcctctt                              338
```

<210> SEQ ID NO 83
<211> LENGTH: 111
<212> TYPE: DNA
<213> ORGANISM: Homo sapien

<400> SEQUENCE: 83
agccatttac cacccatcca caaaaaaaaa aaaaaaaaag aaaaatatca aggaataaaa    60
atagactttg aacaaaaagg aacatttgct ggcctgagga ggcatcaccc g            111

<210> SEQ ID NO 84
<211> LENGTH: 224
<212> TYPE: DNA
<213> ORGANISM: Homo sapien

<400> SEQUENCE: 84
tcgggtgatg cctcctcagg ccaagaagat aaagcttcag acccctaaca catttccaaa    60
aaggaagaaa ggagaaaaaa gggcatcatc cccgttccga agggtcaggg aggaggaaat   120
tgaggtggat tcacgagttg cggacaactc ctttgatgcc aagcgaggtg cagccggaga   180
ctggggagag cgagccaatc aggttttgaa gttcctctca gtgc                    224

<210> SEQ ID NO 85
<211> LENGTH: 348
<212> TYPE: DNA
<213> ORGANISM: Homo sapien

<400> SEQUENCE: 85
gcactgagag gaacttcgtt ggaaacgggt ttttttcatg taaggctaga cagaagaatt    60
ctcagtaact tccttgtgtt gtgtgtattc aactcacasa gttgaacgat cctttacaca   120
gagcagactt gtaacactct twttgtggaa tttgcaagtg gagatttcag scgctttgaa   180
gtsaaaggta gaaaaggaaa tatcttccta taaaaactag acagaatgat tctcagaaac   240
tcctttgtga tgtgtgcgtt caactcacag agtttaacct ttcwttcat agaagcagtt    300 aggaaacact ctgtttgtaa agtctgcaag tggatagaga ccctaacg                 348

<210> SEQ ID NO 86
<211> LENGTH: 293
<212> TYPE: DNA
<213> ORGANISM: Homo sapien

<400> SEQUENCE: 86
gcactgagag gaacttcytt gtgwtgtktg yattcaactc acagagttga asswtsmttt    60
acabagwkca ggcttkcaaa cactcttttt gtmgaatytg caagwggaka tttsrrccrc   120
tttgwggycw wysktmgaaw mggrwatatc ttcwyatmra amctagacag aaksattctc   180
akaawstyyy ytgtgawgws tgcrttcaac tcacagagkt kaacmwtyct kytsatrgag   240
cagttwkgaa actctmtttc tttggattct gcaagtggat agagaccctaa acg          293

<210> SEQ ID NO 87
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 87
ctcctaggct                                                           10

```
<210> SEQ ID NO 88
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 88
agtagttgcc                                                              10

<210> SEQ ID NO 89
<211> LENGTH: 11
<212> TYPE: DNA
<213> ORGANISM: Artificial Sequence
<220> FEATURE:
<223> OTHER INFORMATION: Primer for amplification from breast tumor cDNA

<400> SEQUENCE: 89
ttccgttatg c                                                            11

<210> SEQ ID NO 90
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 90
tggtaaaggg                                                              10

<210> SEQ ID NO 91
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 91
tcggtcatag                                                              10

<210> SEQ ID NO 92
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 92
tacaacgagg                                                              10

<210> SEQ ID NO 93
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 93
tggattggtc                                                              10

<210> SEQ ID NO 94
<211> LENGTH: 10
<212> TYPE: DNA
<213> ORGANISM: Artificial Sequence
<220> FEATURE:
<223> OTHER INFORMATION: Primer for amplification from breast tumor cDNA
```

-continued

<400> SEQUENCE: 94
ctttctaccc 10

```
<210> SEQ ID NO 95
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 95
ttttggctcc 10

<210> SEQ ID NO 96
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 96
ggaaccaatc 10

<210> SEQ ID NO 97
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 97
tcgatacagg 10

<210> SEQ ID NO 98
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 98
ggtactaagg 10

<210> SEQ ID NO 99
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 99
agtctatgcg 10

<210> SEQ ID NO 100
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 100
ctatccatgg 10
```

```
<210> SEQ ID NO 101
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 101
tctgtccaca                                                              10

<210> SEQ ID NO 102
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 102
aagagggtac                                                              10

<210> SEQ ID NO 103
<211> LENGTH: 10
<212> TYPE: DNA
<213> ORGANISM: Artificial Sequence
<220> FEATURE:
<223> OTHER INFORMATION: Primer for amplification from breast tumor cDNA

<400> SEQUENCE: 103
cttcaacctc                                                              10

<210> SEQ ID NO 104
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 104
gctcctcttg ccttaccaac                                                   20

<210> SEQ ID NO 105
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 105
gtaagtcgag cagtgtgatg                                                   20

<210> SEQ ID NO 106
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 106
gtaagtcgag cagtctgatg                                                   20

<210> SEQ ID NO 107
<211> LENGTH: 20
<212> TYPE: DNA
<213> ORGANISM: Artificial Sequence
<220> FEATURE:
<223> OTHER INFORMATION: Primer for amplification from breast tumor cDNA
```

```
<400> SEQUENCE: 107
gacttagtgg aaagaatgta                                              20

<210> SEQ ID NO 108
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 108
gtaattccgc caaccgtagt                                              20

<210> SEQ ID NO 109
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 109
atggttgatc gatagtggaa                                              20

<210> SEQ ID NO 110
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 110
acggggaccc ctgcattgag                                              20

<210> SEQ ID NO 111
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 111
tattctagac cattcgctac                                              20

<210> SEQ ID NO 112
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 112
acataaccac tttagcgttc                                              20

<210> SEQ ID NO 113
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 113
cgggtgatgc ctcctcaggc                                              20
```

-continued

```
<210> SEQ ID NO 114
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 114
agcatgttga gcccagacac                                                   20

<210> SEQ ID NO 115
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 115
gacaccttgt ccagcatctg                                                   20

<210> SEQ ID NO 116
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 116
tacgctgcaa cactgtggag                                                   20

<210> SEQ ID NO 117
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 117
cgttagggtc tctatccact                                                   20

<210> SEQ ID NO 118
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 118
agactgactc atgtcccta                                                    20

<210> SEQ ID NO 119
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 119
tcatcgctcg gtgactcaag                                                   20

<210> SEQ ID NO 120
<211> LENGTH: 20
<212> TYPE: DNA
<213> ORGANISM: Artificial Sequence
<220> FEATURE:
<223> OTHER INFORMATION: Primer for amplification from breast tumor cDNA
```

```
<400> SEQUENCE: 120
caagattcca taggctgacc                                                    20

<210> SEQ ID NO 121
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 121
acgtactggt cttgaaggtc                                                    20

<210> SEQ ID NO 122
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 122
gacgcttggc cacttgacac                                                    20

<210> SEQ ID NO 123
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 123
gtatcgacgt agtggtctcc                                                    20

<210> SEQ ID NO 124
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 124
tagtgacatt acgacgctgg                                                    20

<210> SEQ ID NO 125
<211> LENGTH: 20
<212> TYPE: DNA
<213> ORGANISM: Artificial Sequence
<220> FEATURE:
<223> OTHER INFORMATION: Primer for amplification from breast tumor cDNA

<400> SEQUENCE: 125
cgggtgatgc ctcctcaggc                                                    20

<210> SEQ ID NO 126
<211> LENGTH: 23
<212> TYPE: DNA
<213> ORGANISM: Artificial Sequence
<220> FEATURE:
<223> OTHER INFORMATION: Primer for amplification from breast tumor cDNA

<400> SEQUENCE: 126
atggctattt tcgggggctg aca                                                23
```

```
<210> SEQ ID NO 127
<211> LENGTH: 22
<212> TYPE: DNA
<213> ORGANISM: Artificial Sequence
<220> FEATURE:
<223> OTHER INFORMATION: Primer for amplification from breast tumor cDNA

<400> SEQUENCE: 127
ccggtatctc ctcgtgggta tt                                          22

<210> SEQ ID NO 128
<211> LENGTH: 18
<212> TYPE: DNA
<213> ORGANISM: Artificial Sequence
<220> FEATURE:
<223> OTHER INFORMATION: Primer for amplification from breast tumor cDNA

<400> SEQUENCE: 128
ctgcctgagc cacaaatg                                               18

<210> SEQ ID NO 129
<211> LENGTH: 24
<212> TYPE: DNA
<213> ORGANISM: Artificial Sequence
<220> FEATURE:
<223> OTHER INFORMATION: Primer for amplification from breast tumor cDNA

<400> SEQUENCE: 129
ccggaggagg aagctagagg aata                                        24

<210> SEQ ID NO 130
<211> LENGTH: 14
<212> TYPE: DNA
<213> ORGANISM: Artificial Sequence
<220> FEATURE:
<223> OTHER INFORMATION: Primer

<400> SEQUENCE: 130
tttttttttt ttag                                                   14

<210> SEQ ID NO 131
<211> LENGTH: 18
<212> TYPE: PRT
<213> ORGANISM: Artificial Sequence
<220> FEATURE:
<223> OTHER INFORMATION: Predicited Th Motifs (B-cell epitopes)

<400> SEQUENCE: 131

Ser Ser Gly Gly Arg Thr Phe Asp Asp Phe His Arg Tyr Leu Leu Val
 1               5                  10                  15

Gly Ile

<210> SEQ ID NO 132
<211> LENGTH: 22
<212> TYPE: PRT
<213> ORGANISM: Artificial Sequence
<220> FEATURE:
<223> OTHER INFORMATION: Predicited Th Motifs (B-cell epitopes)
<221> NAME/KEY: VARIANT
<222> LOCATION: (1)...(22)
<223> OTHER INFORMATION: Xaa = Any Amino Acid
```

-continued

```
<400> SEQUENCE: 132

Gln Gly Ala Ala Gln Lys Pro Ile Asn Leu Ser Lys Xaa Ile Glu Val
1               5                   10                  15

Val Gln Gly His Asp Glu
            20

<210> SEQ ID NO 133
<211> LENGTH: 23
<212> TYPE: PRT
<213> ORGANISM: Artificial Sequence
<220> FEATURE:
<223> OTHER INFORMATION: Predicted Th Motifs (B-cell epitopes)

<400> SEQUENCE: 133

Ser Pro Gly Val Phe Leu Glu His Leu Gln Glu Ala Tyr Arg Ile Tyr
1               5                   10                  15

Thr Pro Phe Asp Leu Ser Ala
            20

<210> SEQ ID NO 134
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 134

Tyr Leu Leu Val Gly Ile Gln Gly Ala
1               5

<210> SEQ ID NO 135
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 135

Gly Ala Ala Gln Lys Pro Ile Asn Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)
<221> NAME/KEY: VARIANT
<222> LOCATION: (1)...(9)
<223> OTHER INFORMATION: Xaa = Any Amino Acid

<400> SEQUENCE: 136

Asn Leu Ser Lys Xaa Ile Glu Val Val
1               5

<210> SEQ ID NO 137
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 137

Glu Val Val Gln Gly His Asp Glu Ser
1               5
```

```
<210> SEQ ID NO 138
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 138

His Leu Gln Glu Ala Tyr Arg Ile Tyr
 1               5

<210> SEQ ID NO 139
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 139

Asn Leu Ala Phe Val Ala Gln Ala Ala
 1               5

<210> SEQ ID NO 140
<211> LENGTH: 9
<212> TYPE: PRT
<213> ORGANISM: Artificial Sequence
<220> FEATURE:
<223> OTHER INFORMATION: Predicted HLA A2.1 Motifs (T-cell epitopes)

<400> SEQUENCE: 140

Phe Val Ala Gln Ala Ala Pro Asp Ser
 1               5

<210> SEQ ID NO 141
<211> LENGTH: 9388
<212> TYPE: DNA
<213> ORGANISM: Homo sapien

<400> SEQUENCE: 141
gctcgcggcc gcgagctcaa ttaaccctca ctaaagggag tcgactcgat cagactgtta      60
ctgtgtctat gtagaaagaa gtagacataa gagattccat tttgttctgt actaagaaaa     120
attcttctgc cttgagatgc tgttaatctg taaccctagc cccaaccctg tgctcacaga     180
gacatgtgct gtgttgactc aaggttcaat ggatttaggg ctatgctttg ttaaaaaagt     240
gcttgaagat aatatgcttg ttaaaagtca tcaccattct ctaatctcaa gtacccaggg     300
acacaataca ctgcggaagg ccgcagggac ctctgtctag gaaagccagg tattgtccaa     360
gatttctccc catgtgatag cctgagatat ggcctcatgg gaagggtaag acctgactgt     420
cccccagccc gacatccccc agcccgacat ccccccagccc gacacccgaa aagggtctgt     480
gctgaggagg attagtaaaa gaggaaggcc tctttgcagt tgaggtaaga ggaaggcatc     540
tgtctcctgc tcgtccctgg gcaatagaat gtcttggtgt aaaacccgat tgtatgttct     600
acttactgag ataggagaaa acatccttag ggctggaggt gagacacgct ggcggcaata     660 ctgctctttta atgcaccgag atgtttgtat aagtgcacat caaggcacag cacctttcct     720
taaacttatt tatgacacag agacctttgt tcacgttttc ctgctgaccc tctccccact     780
attaccctat tggcctgcca catccccctc tccgagatgt agagataat gatcaataaa      840 tactgaggga actcagagac cagtgtccct gtaggtcctc cgtgtgctga gcgccggtcc     900
cttgggctca cttttctttc tctatacttt gtctctgtgt ctctttcttt tctcagtctc     960
tcgttccacc tgacgagaaa tacccacagg tgtggagggg caggccaccc cttcaataat    1020
```

```
ttactagcct gttcgctgac aacaagactg gtggtgcaga aggttgggtc ttggtgttca    1080
ccgggtggca ggcatgggcc aggtgggagg gtctccagcg cctggtgcaa atctccaaga    1140
aagtgcagga aacagcacca aggtgattg taaattttga tttggcgcgg caggtagcca    1200
ttccagcgca aaaatgcgca ggaaagcttt tgctgtgctt gtaggcaggt aggccccaag    1260
cacttcttat tggctaatgt ggaggaacc tgcacatcca ttggctgaaa tctccgtcta    1320
tttgaggctg actgagcgcg ttcctttctt ctgtgttgcc tggaaacgga ctgtctgcct    1380
agtaacatct gatcacgttt cccattggcc gccgtttccg aagcccgcc ctcccatttc    1440
cggaagcctg gcgcaaggtt ggtctgcagg tggcctccag gtgcaaagtg ggaagtgtga    1500
gtcctcagtc ttgggctatt cggccacgtg cctgccggac atggacgct ggagggtcag    1560
cagcgtggag tcctggcctt ttgcgtccac gggtgggaaa ttggccattg ccacggcggg    1620
aactgggact caggctgccc cccggccgtt tctcatccgt ccaccggact cgtgggcgct    1680
cgcactggcg ctgatgtagt ttcctgacct ctgacccgta ttgtctccag attaaaggta    1740
aaaacgggc ttttcagcc cactcgggta aaacgccttt tgatttctag gcaggtgttt    1800
tgttgcacgc ctgggaggga gtgacccgca ggttgaggtt tattaaaata cattcctggt    1860
ttatgttatg tttataataa agcaccccaa cctttacaaa atctcacttt ttgccagttg    1920
tattatttag tggactgtct ctgataagga cagccagtta aaatgaatt ttgttgttgc    1980
taattaaacc aattttagt tttggtgttt gtcctaatag caacaacttc tcaggcttta    2040
taaaaccata ttcttgggg gaaatttctg tgtaaggcac agcgagttag tttggaattg    2100
ttttaaagga agtaagttcc tggttttgat atcttagtag tgtaatgccc aacctggttt    2160
ttactaaccc tgttttttaga ctctcccttt ccttaaatca cctagccttg tttccacctg    2220
aattgactct cccttagcta agagcgccag atggactcca tcttggctct ttcactggca    2280
gccccttcct caaggactta acttgtgcaa gctgactccc agcacatcca agaatgcaat    2340
taactgttaa gatactgtgg caagctatat ccgcagttcc gaggaattca tccgattgat    2400
tatgcccaaa agccccgcgt ctatcacctt gtaataatct taaagcccct gcacctggaa    2460
ctattaactt tcctgtaacc atttatcctt ttaacttttt tgcttacttt atttctgtaa    2520
aattgtttta actagacctc ccctccccttt tctaaaccaa agtataaaag aagatctagc    2580
cccttcttca gagcggagag aattttgagc attagccatc tcttggcggc cagctaaata    2640
aatggacttt taatttgtct caaagtgtgg cgttttctct aactcgctca ggtacgacat    2700
ttggaggccc cagcgagaaa cgtcaccggg agaaacgtca ccgggcgaga gccgggcccg    2760
ctgtgtgctc ccccggaagg acagccagct tgtaggggg agtgccacct gaaaaaaaaa    2820
tttccaggtc cccaaagggt gaccgtcttc cggaggacag cggatcgact accatgcggg    2880
tgcccaccaa aattccacct ctgagtcctc aactgctgac cccggggtca ggtaggtcag    2940
atttgacttt ggttctggca gagggaagcg accctgatga gggtgtccct cttttgactc    3000
tgcccatttc tctaggatgc tagagggtag agccctggtt ttctgttaga cgcctctgtg    3060
tctctgtctg ggagggaagt ggccctgaca ggggccatcc cttgagtcag tccacatccc    3120
aggatgctgg gggactgagt cctggttct ggcagactgg tctctctctc tctctttttc    3180
tatctctaat ctttccttgt tcaggttct tggagaatct ctgggaaaga aaaagaaaa    3240
actgttataa actctgtgtg aatggtgaat gaatggggga ggacaagggc ttgcgcttgt    3300
cctccagttt gtagctccac ggcgaaagct acggagttca agtgggccct cacctgcggt    3360
tccgtggcga cctcataagg cttaaggcag catccggcat agctcgatcc gagccgggg    3420
```

-continued

```
tttataccgg cctgtcaatg ctaagaggag cccaagtccc ctaaggggga gcggccaggc    3480
gggcatctga ctgatcccat cacgggaccc cctcccttg tttgtctaaa aaaaaaaaaa    3540
gaagaaactg tcataactgt ttacatgccc tagggtcaac tgtttgtttt atgtttattg    3600
ttctgttcgg tgtctattgt cttgtttagt ggttgtcaag gttttgcatg tcaggacgtc    3660
gatattgccc aagacgtctg ggtaagaact tctgcaaggt ccttagtgct gattttttgt    3720
cacaggaggt taaatttctc atcaatcatt taggctggcc accacagtcc tgtcttttct    3780
gccagaagca agtcaggtgt tgttacggga atgagtgtaa aaaacattc gcctgattgg    3840 gatttctggc accatgatgg ttgtatttag attgtcatac cccacatcca ggttgattgg    3900
acctcctcta aactaaactg gtggtgggtt caaaacagcc accctgcaga tttccttgct    3960
cacctctttg gtcattctgt aacttttcct gtgcccttaa atagcacact gtgtaggaa    4020 acctaccctc gtactgcttt acttcgttta gattcttact ctgttcctct gtggctactc    4080
tcccatctta aaaacgatcc aagtggtcct tttcctcctc cctgccccct accccacaca    4140
tctcgttttc cagtgcgaca gcaagttcag cgtctccagg acttggctct gctctcactc    4200
cttgaaccct aaaagaaaa agctgggttt gagctatttg cctttgagtc atggagacac    4260
aaaaggtatt tagggtacag atctagaaga agagagagaa cacctagatc caactgaccc    4320
aggagatctc gggctggcct ctagtcctcc tccctcaatc ttaaagctac agtgatgtgg    4380
caagtggtat ttagctgttg tggtttttct gctctttctg gtcatgttga ttctgttctt    4440
tcgatactcc agccccccag gggtgagtt tctctgtctg tgctgggttt gatatctatg    4500
ttcaaatctt attaaattgc cttcaaaaaa aaaaaaaaaa gggaaacact tcctcccagc    4560
cttgtaaggg ttggagccct ctccagtata tgctgcagaa ttttctctc ggtttctcag    4620 aggattatgg agtccgcctt aaaaaaggca agctctggac actctgcaaa gtagaatggc    4680
caaagtttgg agttgagtgg cccccttgaag ggtcactgaa cctcacaatt gttcaagctg    4740
tgtggcgggt tgttactgaa actcccggcc tccctgatca gtttccctac attgatcaat    4800
ggctgagttt ggtcaggagc acccccttcca tggctccact catgcaccat tcataatttt    4860
acctccaagg tcctcctgag ccagaccgtg ttttcgcctc gaccctcagc cggttcagct    4920
cgccctgtac tgcctctctc tgaagaagag gagagtctcc ctcacccagt cccaccgcct    4980
taaaaccagc ctactcccctt agggtcatcc catgtctcct cggctatgtc ccctgtaggc    5040
tcatcaccca ttgcctcttg gttgcaaccg tggtgggagg aagtagcccc tctactacca    5100
ctgagagagg cacaagtccc tctgggtgat gagtgctcca ccccttcct ggtttatgtc    5160 ccttctttct acttctgact tgtataattg gaaaacccat aatcctccct tctctgaaaa    5220
gccccaggct ttgacctcac tgatggagtc tgtactctgg acacattggc ccacctggga    5280
tgactgtcaa cagctccttt tgacccttt cacctctgaa gagagggaaa gtatccaaag    5340
agaggccaaa agtacaacc tcacatcaac caataggccg gaggaggaag ctagaggaat    5400
agtgattaga gacccaattg ggacctaatt gggacccaaa tttctcaagt ggagggagaa    5460
cttttgacga tttccaccgg tatctcctcg tgggtattca gggagctgct cagaaaccta    5520
taaacttgtc taaggcgact gaagtcgtcc aggggcatga tgagtcacca ggagtgtttt    5580
tagagcacct ccaggaggct tatcggattt acaccccttt tgacctggca gccccgaaa    5640 atagccatgc tcttaatttg gcatttgtgg ctcaggcagc cccagatagt aaaaggaaac    5700
tccaaaaact agagggattt tgctggaatg aataccagtc agcttttaga gatagcctaa    5760 aaggttttg acagtcaaga ggttgaaaaa caaaaacaag cagctcaggc agctgaaaaa    5820
```

```
agccactgat aaagcatcct ggagtatcag agtttactgt tagatcagcc tcatttgact    5880
tcccctccca catggtgttt aaatccagct acactacttc ctgactcaaa ctccactatt    5940
cctgttcatg actgtcagga actgttggaa actactgaaa ctggccgacc tgatcttcaa    6000
aatgtgcccc taggaaaggt ggatgccacc gtgttcacag acagtagcag cttcctcgag    6060
aagggactac gaaaggccgg tgcagctgtt accatggaga cagatgtgtt gtgggctcag    6120
gctttaccag caaacacctc agcacaaaag ctgaattga tcgccctcac tcaggctctc     6180
cgatggggta aggatattaa cgttaacact gacagcaggt acgcctttgc tactgtgcat    6240
gtacgtggag ccatctacca ggagcgtggg ctactcacct cagcaggtgg ctgtaatcca    6300
ctgtaaagga catcaaaagg aaaacacggc tgttgcccgt ggtaaccaga aagctgattc    6360
agcagctcaa gatgcagtgt gactttcagt cacgcctcta aacttgctgc ccacagtctc    6420
ctttccacag ccagatctgc ctgacaatcc cgcatactca acagaagaag aaaactggcc    6480
tcagaactca gagccaataa aaatcaggaa ggttggtgga ttcttcctga ctctagaatc    6540
ttcataccccc gaactcttgg gaaaacttta atcagtcacc tacagtctac cacccattta   6600
ggaggagcaa agctacctca gctcctccgg agccgtttta agatccccca tcttcaaagc    6660
ctaacagatc aagcagctct ccggtgcaca acctgcgccc aggtaaatgc caaaaaggt     6720
cctaaaccca gcccaggcca ccgtctccaa gaaaactcac caggagaaaa gtgggaaatt    6780
gactttacag aagtaaaacc acaccgggct gggtacaaat accttctagt actggtagac    6840
accttctctg gatggactga agcatttgct accaaaaacg aaactgtcaa tatggtagtt    6900
aagtttttac tcaatgaaat catccctcga cgtgggctgc ctgttgccat agggtctgat    6960
aatggaccgg ccttcgcctt gtctatagtt tagtcagtca gtaaggcgtt aaacattcaa    7020
tggaagctcc attgtgccta tcgaccccag agctctgggc aagtagaacg catgaactgc    7080
accctaaaaa acactcttac aaaattaatc ttagaaaccg gtgtaaattg tgtaagtctc    7140
cttcctttag ccctacttag agtaaggtgc acccttact gggctgggtt cttacctttt     7200
gaaatcatgt atgggagggc gctgcctatc ttgcctaagc taagagatgc ccaattggca    7260
aaaatatcac aaactaattt attacagtac ctacagtctc cccaacaggt acaagatatc    7320
atcctgccac ttgttcgagg aacccatccc aatccaattc ctgaacagac agggccctgc    7380
cattcattcc cgccaggtga cctgttgttt gttaaaaagt tccagagaga aggactccct    7440
cctgcttgga agagacctca caccgtcatc acgatgccaa cggctctgaa ggtggatggc    7500
attcctgcgt ggattcatca ctcccgcatc aaaaaggcca acggagccca actagaaaca    7560
tgggtccccca gggctgggtc aggccccttta aaactgcacc taagttgggt gaagccatta   7620
gattaattct ttttcttaat tttgtaaaac aatgcatagc ttctgtcaaa cttatgtatc    7680
ttaagactca atataacccc cttgttataa ctgaggaatc aatgatttga ttccccaaaa    7740
acacaagtgg ggaatgtagt gtccaacctg gtttttacta accctgtttt tagactctcc    7800
ctttccttta atcactcagc cttgtttcca cctgaattga ctctccctta gctaagagcg    7860
ccagatggac tccatcttgg ctctttcact ggcagccgct tcctcaagga cttaacttgt    7920
gcaagctgac tcccagcaca tccaagaatg caattaactg ataagatact gtggcaagct    7980
atatccgcag ttcccaggaa ttcgtccaat tgattacacc caaaagcccc gcgtctatca    8040
ccttgtaata atcttaaagc ccctgcacct ggaactatta acgttcctgt aaccatttat    8100
ccttttaact tttttgccta ctttatttct gtaaaattgt tttaactaga ccccccctct    8160
cctttctaaa ccaaagtata aaagcaaatc tagcccttc ttcaggccga gagaatttcg     8220
```

-continued

```
agcgttagcc gtctcttggc caccagctaa ataaacggat tcttcatgtg tctcaaagtg    8280
tggcgttttc tctaactcgc tcaggtacga ccgtggtagt attttcccca acgtcttatt    8340
tttagggcac gtatgtagag taacttttat gaaagaaacc agttaaggag gttttgggat    8400
ttcctttatc aactgtaata ctggttttga ttatttattt atttatttat tttttttgag    8460
aaggagtttc actcttgttg cccaggctgg agtgcaatgg tgcgatcttg gctcactgca    8520
acttccgcct cccaggttca gcgattctc ctgcctcagc ctcgagagta gctgggatta    8580
taggcatgcg ccaccacacc cagctaattt tgtattttta gtaaagatgg gtttcttca    8640 tgttggtcaa gctggtctgg aactcccgc ctcgggtgat ctgcccgcct cggcctccga    8700
aagtgctggg attacaggtg tgatccacca cacccagccg atttatatgt atataaatca    8760
cattcctcta accaaaatgt agtgtttcct tccatcttga ataggctg tagacccgt    8820 gggtatggga cattgttaac agtgagacca cagcagtttt tatgtcatct gacagcatct    8880
ccaaatagcc ttcatggttg tcactgcttc ccaagacaat tccaaataac acttcccagt    8940
gatgacttgc tacttgctat tgttacttaa tgtgttaagg tggctgttac agacactatt    9000
agtatgtcag gaattacacc aaatttagt ggctcaaaca atcattttat tatgtatgtg    9060
gattctcatg gtcaggtcag gatttcagac agggcacaag ggtagcccac ttgtctctgt    9120
ctatgatgtc tggcctcagc acaggagact caacagctgg ggtctgggac catttggagg    9180
cttgttccct cacatctgat acctggcttg ggatgttgga agaggggtg agctgagact    9240 gagtgcctat atgtagtgtt tccatatggc cttgacttcc ttacagcctg gcagcctcag    9300
ggtagtcaga attcttagga ggcacagggc tccagggcag atgctgaggg gtcttttatg    9360
aggtagcaca gcaaatccac ccaggatc                                       9388
```

<210> SEQ ID NO 142
<211> LENGTH: 419
<212> TYPE: DNA
<213> ORGANISM: Homo sapien

<400> SEQUENCE: 142

```
tgtaagtcga gcagtgtgat ggaaggaatg gtctttggag agagcatatc catctcctcc     60
tcactgcctc ctaatgtcat gaggtacact gagcagaatt aaacagggta gtcttaacca    120
cactattttt agctaccttg tcaagctaat ggttaaagaa cacttttggt ttacacttgt    180
tgggtcatag aagttgcttt ccgccatcac gcaataagtt tgtgtgtaat cagaaggagt    240
taccttatgg tttcagtgtc attctttagt taacttggga gctgtgtaat ttaggctttg    300
cgtattattt cacttctgtt ctccacttat gaagtgattg tgtgttcgcg tgtgtgtgcg    360
tgcgcatgtg cttccggcag ttaacataag caaataccca acatcacact gctcgactt    419
```

<210> SEQ ID NO 143
<211> LENGTH: 402
<212> TYPE: DNA
<213> ORGANISM: Homo sapien

<400> SEQUENCE: 143

```
tgtaagtcga gcagtgtgat gtccactgca gtgtgttgct gggaacagtt aatgagcaaa     60
ttgtatacaa tggctagtac attgaccggg atttgttgaa gctggtgagt gttatgactt    120
agcctgttag actagtctat gcacatggct ctggtcaact accgctctct catttctcca    180
gataaatccc ccatgcttta tattctcttc caaacatact atcctcatca ccacatagtt    240
cctttgttaa tgctttgttc tagactttcc cttttctgtt ttcttattca aacctatatc    300
```

| tctttgcata gattgtaaat tcaaatgccc tcagggtgca ggcagttcat gtaagggagg | 360 |
| gaggctagcc agtgagatct gcatcacact gctcgactta ca | 402 |

<210> SEQ ID NO 144
<211> LENGTH: 224
<212> TYPE: DNA
<213> ORGANISM: Homo sapien

<400> SEQUENCE: 144

| tcgggtgatg cctcctcagg ccaagaagat aaagcttcag acccctaaca catttccaaa | 60 |
| aaggaagaaa ggagaaaaaa gggcatcatc cccgttccga agggtcaggg aggaggaaat | 120 |
| tgaggtggat tcacgagttg cggacaactc ctttgatgcc aagcgaggtg cagccggaga | 180 |
| ctggggagag cgagccaatc aggttttgaa gttcctctca gtgc | 224 |

<210> SEQ ID NO 145
<211> LENGTH: 111
<212> TYPE: DNA
<213> ORGANISM: Homo sapien

<400> SEQUENCE: 145

| agccatttac cacccatcca caaaaaaaaa aaaaaaaag aaaaatatca aggaataaaa | 60 |
| atagactttg aacaaaaagg aacatttgct ggcctgagga ggcatcaccc g | 111 |

<210> SEQ ID NO 146
<211> LENGTH: 585
<212> TYPE: DNA
<213> ORGANISM: Homo sapien

<400> SEQUENCE: 146

| tagcatgttg agcccagaca cttgtagaga gaggaggaca gttagaagaa gaagaaaagt | 60 |
| ttttaaatgc tgaaagttac tataagaaag ctttggcttt ggatgagact tttaaagatg | 120 |
| cagaggatgc tttgcagaaa cttcataaat atatgcaggt gattccttat ttcctcctag | 180 |
| aaatttagtg atatttgaaa taatgcccaa acttaatttt ctcctgagga aaactattct | 240 |
| acattactta agtaaggcat tatgaaaagt ttcttttag gtatagtttt tcctaattgg | 300 |
| gttttgacatt gcttcatagt gcctctgttt ttgtccataa tcgaaagtaa agatagctgt | 360 |
| gagaaaacta ttacctaaat ttggtatgtt gttttgagaa atgtccttat agggagctca | 420 |
| cctggtggtt tttaaattat tgttgctact ataattgagc taattataaa aacctttttg | 480 |
| agacatattt taaattgtct tttcctgtaa tactgatgat gatgttttct catgcatttt | 540 |
| cttctgaatt gggaccattg ctgctgtgtc tgggctcaca tgcta | 585 |

<210> SEQ ID NO 147
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 147

| tagcatgttg agcccagaca ctgggcagcg ggggtggcca cggcagctcc tgccgagccc | 60 |
| aagcgtgttt gtctgtgaag gaccctgacg tcacctgcca ggctagggag gggtcaatgt | 120 |
| ggagtgaatt tcaccgact ttcgcaggag tgtgcagaag ccaggtgcaa cttggtttgc | 180 |
| ttgtgttcat cacccctcaa gatatgcaca ctgctttcca aataaagcat caactgtcat | 240 |

-continued

```
ctccagatgg ggaagacttt ttctccaacc agcaggcagg tccccatcca ctcagacacc      300
agcacgtcca ccttctcggg cagcaccacg tcctccacct tctgctggta cacggtgatg      360
atgtcagcaa agccgttctg cangaccagc tgccccgtgt gctgtgccat ctcactggcc      420
tccaccgcgt acaccgctct aggccgcgca tantgtgcac agaanaaatg atgatccagt      480
cccacagccc acgtccaaga ngactttatc cgtcagggat tctttattct gcaggatgac      540
ctgtggtatt aattgttcgt gtctgggctc aacatgcta                             579
```

<210> SEQ ID NO 148
<211> LENGTH: 249
<212> TYPE: DNA
<213> ORGANISM: Homo sapien

<400> SEQUENCE: 148

```
tgacaccttg tccagcatct gcaagccagg aagagagtcc tcaccaagat ccccaccccg       60
ttggcaccag gatcttggac ttccaatctc cagaactgtg agaaataagt atttgtcgct      120
aaataaatct tgtggtttc agatatttag ctatagcaga tcaggctgac taagagaaac      180
cccataagag ttacatactc attaatctcc gtctctatcc ccaggtctca gatgctggac      240
aaggtgtca                                                             249
```

<210> SEQ ID NO 149
<211> LENGTH: 255
<212> TYPE: DNA
<213> ORGANISM: Homo sapien

<400> SEQUENCE: 149

```
tgacaccttg tccagcatct gctattttgt gacttttaa taatagccat tctgactggt       60
gtgagatggt aactcattgt gggtttggtc tgcatttctc taatgatcag tgatattaag      120 cttttttaa atatgcttgt tgaccacatg tatatcatct tttgagaagt gtctgttcat      180
atcctttgcc cacttttaa ttttttatc ttgtaaattt gtttaatttc cttacagatg      240
ctggacaagg tgtca                                                      255
```

<210> SEQ ID NO 150
<211> LENGTH: 318
<212> TYPE: DNA
<213> ORGANISM: Homo sapien

<400> SEQUENCE: 150

```
ttacgctgca acactgtgga ggccaagctg ggatcacttc ttcattctaa ctggagagga       60
gggaagttca agtccagcag agggtgggtg ggtagacagt ggcactcaga aatgtcagct      120
ggacccctgt ccccgcatag gcaggacagc aaggctgtgg ctctccaggg ccagctgaag      180
aacaggacac tgtctccgct gccacaaagc gtcagagact cccatctttg aagcacggcc      240
ttcttggtct tcctgcactt ccctgttctg ttagagacct ggttatagac aaggcttctc      300
cacagtgttg cagcgtaa                                                   318
```

<210> SEQ ID NO 151
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

```
<400> SEQUENCE: 151
tnacgcngcn acnntgtaga ganggnaagg cnttccccac attncccctt catnanagaa      60
ttattcnacc aagnntgacc natgccnttt atgacttaca tgcnnactnc ntaatctgtn     120
tcnngcctta aaagcnnntc cactacatgc ntcancactg tntgtgtnac ntcatnaact     180
gtcngnaata ggggcncata actacagaaa tgcanttcat actgcttcca ntgccatcng     240
cgtgtggcct tncctactct tcttntattc caagtagcat ctctggantg cttccccact     300
ctccacattg ttgcagcnat aat                                             323

<210> SEQ ID NO 152
<211> LENGTH: 311
<212> TYPE: DNA
<213> ORGANISM: Homo sapien

<400> SEQUENCE: 152
tcaagattcc ataggctgac cagtccaagg agagttgaaa tcatgaagga gagtctatct      60
ggagagagct gtagttttga gggttgcaaa gacttaggat ggagttggtg ggtgtggtta     120
gtctctaagg ttgattttgt tcataaattt catgccctga atgccttgct tgcctcaccc     180
tggtccaagc cttagtgaac acctaaaagt ctctgtcttc ttgctctcca aacttctcct     240
gaggatttcc tcagattgtc tacattcaga tcgaagccag ttggcaaaca agatgcagtc     300
cagagggtca g                                                          311

<210> SEQ ID NO 153
<211> LENGTH: 332
<212> TYPE: DNA
<213> ORGANISM: Homo sapien

<400> SEQUENCE: 153
caagattcca taggctgacc aggaggctat tcaagatctc tggcagttga ggaagtctct      60
ttaagaaaat agtttaaaca atttgttaaa atttttctgt cttacttcat ttctgtagca     120
gttgatatct ggctgtcctt tttataatgc agagtgggaa ctttccctac catgtttgat     180
aaatgttgtc caggctccat tgccaataat gtgttgtcca aaatgcctgt ttagttttta     240
aagacggaac tccacccttt gcttggtctt aagtatgtat ggaatgttat gataggacat     300
agtagtagcg gtggtcagcc tatggaatct tg                                   332

<210> SEQ ID NO 154
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 154
tcaagattcc ataggctgac ctggacagag atctcctggg tctggcccag gacagcaggc      60
tcaagctcag tggagaaggt ttccatgacc ctcagattcc cccaaacctt ggattgggtg     120
acattgcatc tcctcagaga gggaggagat gtangtctgg gcttccacag ggacctggta     180
ttttaggatc agggtaccgc tggcctgagg cttggatcat tcanagcctg gggtggaat      240 ggctggcagc ctgtggcccc attgaaatag gctctgggc actccctctg ttcctanttg     300
aacttgggta aggaacagga atgtggtcan cctatggaat cttga                     345
```

<210> SEQ ID NO 155
<211> LENGTH: 295
<212> TYPE: DNA
<213> ORGANISM: Homo sapien
<220> FEATURE:
<221> NAME/KEY: misc_feature
<222> LOCATION: (1)...(295)
<223> OTHER INFORMATION: n = A,T,C or G

<400> SEQUENCE: 155
gacgcttggc cacttgacac attaaacagt tttgcataat cactancatg tatttctagt    60
ttgctgtctg ctgtgatgcc ctgccctgat tctctggcgt taatgatggc aagcataatc   120
aaacgctgtt ctgttaattc caagttataa ctggcattga ttaaagcatt atctttcaca   180
actaaactgt tcttcatana acagcccata ttattatcaa attaagagac aatgtattcc   240
aatatccttt anggccaata tatttnatgt cccttaatta agagctactg tccgt         295

<210> SEQ ID NO 156
<211> LENGTH: 406
<212> TYPE: DNA
<213> ORGANISM: Homo sapien
<220> FEATURE:
<221> NAME/KEY: misc_feature
<222> LOCATION: (1)...(406)
<223> OTHER INFORMATION: n = A,T,C or G

<400> SEQUENCE: 156
gacgcttggc cacttgacac tgcagtggga aaaccagcat gagccgctgc ccccaaggaa    60
cctcgaagcc caggcagagg accagccatc ccagcctgca ggtaaagtgt gtcacctgtc   120
aggtgggctt ggggtgagtg ggtgggggaa gtgtgtgtgc aaaggggggtg tnaatgtnta  180 tgcgtgtgag catgagtgat ggctagtgtg actgcatgtc agggagtgtg aacaagcgtg   240
cggggtgtgt gtgcaagtg cgtatgcata tgagaatatg tgtctgtgga tgagtgcatt   300
tgaaagtctg tgtgtgtgcg tgtggtcatg anggtaantt antgactgcg caggatgtgt   360
gagtgtgcat ggaacactca ntgtgtgtgt caagtggccn ancgtc                  406

<210> SEQ ID NO 157
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 157
tgacgcttgg ccacttgaca cactaaaggg tgttactcat cactttcttc tctcctcggt    60
ggcatgtgag tgcatctatt cacttggcac tcatttgttt ggcagtgact gtaanccana  120
tctgatgcat acaccagctt gtaaattgaa taaatgtctc taatactatg tgctcacaat   180
anggtanggg tgaggagaag gggagaga                                      208

<210> SEQ ID NO 158
<211> LENGTH: 547
<212> TYPE: DNA
<213> ORGANISM: Homo sapien
<220> FEATURE:
<221> NAME/KEY: misc_feature
<222> LOCATION: (1)...(547)
<223> OTHER INFORMATION: n = A,T,C or G

<400> SEQUENCE: 158

```
cttcaacctc cttcaacctc cttcaacctc ctggattcaa acaatcatcc cacctcagac      60
tccttagtag ctgagactac agactcacgc cactacatct ggctaaattt ttgtagagat     120
agggtttcat catgttgccc tggctggtct caaactcctg acctcaagca atgtgcccac     180
ctcagcctcc caaagtgctg ggattacagg cataagccac catgcccagt ccatntttaa     240
tctttcctac cacattctta ccacactttc ttttatgttt agatacataa atgcttacca     300
ttatgataca attgcccaca gtattaagac agtaacatgc tgcacaggtt tgtagcctag     360
gaacagtagg caataccaca tagcttaggt gtgtggtaga ctataccatc taggtttgtg     420
taagttacac tttatgctgt ttacacaatg acaaaaccat ctaatgatgc atttctcaga     480
atgtatcctt gtcagtaagc tatgatgtac agggaacact gcccaaggac acagatattg     540
tacctgt                                                               547
```

<210> SEQ ID NO 159
<211> LENGTH: 203
<212> TYPE: DNA
<213> ORGANISM: Homo sapien

<400> SEQUENCE: 159

```
gctcctcttg ccttaccaac tcacccagta tgtcagcaat tttatcrgct ttacctacga      60
aacagcctgt atccaaacac ttaacacact cacctgaaaa gttcaggcaa caatcgcctt     120
ctcatgggtc tctctgctcc agttctgaac cttctctttt cctagaaca tgcatttarg      180
tcgatagaag ttcctctcag tgc                                             203
```

<210> SEQ ID NO 160
<211> LENGTH: 402
<212> TYPE: DNA
<213> ORGANISM: Homo sapien

<400> SEQUENCE: 160

```
tgtaagtcga gcagtgtgat gggtggaaca gggttgtaag cagtaattgc aaactgtatt      60
taaacaataa taataatatt tagcattat agagcacttt atatcttcaa agtacttgca     120
aacattayct aattaaatac cctctctgat tataatctgg atacaaatgc acttaaactc     180
aggacagggt catgagaraa gtatgcattt gaaagttggt gctagctatg ctttaaaaac     240
ctatacaatg atgggraagt tagagttcag attctgttgg actgttttg tgcatttcag      300
ttcagcctga tggcagaatt agatcatatc tgcactcgat gactytgctt gataacttat     360
cactgaaatc tgagtgttga tcatcacact gctcgactta ca                       402
```

<210> SEQ ID NO 161
<211> LENGTH: 193
<212> TYPE: DNA
<213> ORGANISM: Homo sapien

<400> SEQUENCE: 161

```
agcatgttga gcccagacac tgaccaggag aaaaaccaac caatagaaac acgcccagac      60
actgaccagg agaaaaacca accaataaaa acaggcccgg acataagaca ataataaaa     120
ttagcggaca aggacatgaa aacagctatt gtaagagcgg atatagtggt gtgtgtctgg     180
gctcaacatg cta                                                       193
```

<210> SEQ ID NO 162
<211> LENGTH: 147
<212> TYPE: DNA
<213> ORGANISM: Homo sapien

<400> SEQUENCE: 162

| | | | | | |
|---|---|---|---|---|---|
| tgttgagccc | agacactgac | caggagaaaa | accaaccaat | aaaaacaggc | ccggacataa | 60 |
| gacaaataat | aaaattagcg | acaaggaca | tgaaaacagc | tattgtaaga | gcggatatag | 120 |
| tggtgtgtgt | ctgggctcaa | catgcta | | | | 147 |

<210> SEQ ID NO 163
<211> LENGTH: 294
<212> TYPE: DNA
<213> ORGANISM: Homo sapien

<400> SEQUENCE: 163

| | | | | | |
|---|---|---|---|---|---|
| tagcatgttg | agcccagaca | caaatctttc | cttaagcaat | aaatcatttc | tgcatatgtt | 60 |
| tttaaaacca | cagctaagcc | atgattattc | aaaaggacta | ttgtattggg | tattttgatt | 120 |
| tgggttctta | tctccctcac | attatcttca | tttctatcat | tgacctctta | tcccagagac | 180 |
| tctcaaactt | ttatgttata | caaatcacat | tctgtctcaa | aaaatatctc | acccacttct | 240 |
| cttctgtttc | tgcgtgtgta | tgtgtgtgtg | tgtgtgtctg | ggctcaacat | gcta | 294 |

<210> SEQ ID NO 164
<211> LENGTH: 412
<212> TYPE: DNA
<213> ORGANISM: Homo sapien
<220> FEATURE:
<221> NAME/KEY: misc_feature
<222> LOCATION: (1)...(412)
<223> OTHER INFORMATION: n = A,T,C or G

<400> SEQUENCE: 164

| | | | | | |
|---|---|---|---|---|---|
| cgggattggc | tttgagctgc | agatgctgcc | tgtgaccgca | cccggcgtgg | aacagaaagc | 60 |
| cacctggctg | caagtgcgcc | agagccgccc | tgactacgtg | ctgctgtggg | gctggggcgt | 120 |
| gatgaactcc | accgccctga | aggaagccca | ggccaccgga | taccccgcg | acaagatgta | 180 |
| cggcgtgtgg | tgggccggtg | cggagcccga | tgtgcgtgac | gtgggcgaag | gcgccaaggg | 240 |
| ctacaacgcg | ctggctctga | acggctacgg | cacgcagtcc | aaggtgatcc | angacatcct | 300 |
| gaaacacgtg | cacgacaagg | gccagggcac | ggggcccaaa | gacgaagtgg | gctcggtgct | 360 |
| gtacacccgc | ggcgtgatca | tccagatgct | ggacaaggtg | tcaatcacta | at | 412 |

<210> SEQ ID NO 165
<211> LENGTH: 361
<212> TYPE: DNA
<213> ORGANISM: Homo sapien

<400> SEQUENCE: 165

| | | | | | |
|---|---|---|---|---|---|
| ttgacacctt | gtccagcatc | tgcatctgat | gagagcctca | gatggctacc | actaatggca | 60 |
| gaaggcaaag | gagaacaggc | attgtatggc | aagaaaggaa | gaaagagaga | ggggagaaag | 120 |
| gtgctaggtt | cttttcaaca | accagttctt | gatggaactg | agagtaagag | ctcaaggcca | 180 |
| ggtgtggtga | ctccaaccag | taatcccaac | attttaggag | gctgaggcag | gcagatgtct | 240 |
| tgaccccatg | agtttgtgac | cagcctgaac | aacatcatga | gactccatct | ctacaataat | 300 |
| tacaaaaatt | aatcaggcat | tgtggtatgc | cctgtagtcc | cagatgctgg | acaaggtgtc | 360 |
| a | | | | | | 361 |

<210> SEQ ID NO 166
<211> LENGTH: 427
<212> TYPE: DNA
<213> ORGANISM: Homo sapien

<400> SEQUENCE: 166

| twgactgact catgtccct acacccaact atcttctcca ggtggccagg catgatagaa | 60 |
|---|---|
| tctgatcctg acttagggga atattttctt tttacttccc atcttgattc cctgccggtg | 120 |
| agtttcctgg ttcagggtaa gaaaggagct caggccaaag taatgaacaa atccatcctc | 180 |
| acagacgtac agaataagag aacwtggacw tagccagcag aacmcaaktg aaamcagaac | 240 |
| mcttamctag gatracaamc mcrraratar ktgcycmcmc wtataataga aaccaaactt | 300 |
| gtatctaatt aaatatttat ccacygtcag ggcattagtg gttttgataa atacgctttg | 360 |
| gctaggattc ctgaggttag aatggaaraa caattgcamc gagggtaggg gacatgagtc | 420 |
| aktctaa | 427 |

<210> SEQ ID NO 167
<211> LENGTH: 500
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 167

| aacgtcgcat gctcccggcc gccatggccg cgggatagac tgactcatgt cccctaagat | 60 |
|---|---|
| agaggagaca cctgctaggt gtaaggagaa gatggttagg tctacggagg ctccaggtg | 120 |
| ggagtagttc cctgctaagg gagggtagac tgttcaacct gttcctgctc cggcctccac | 180 |
| tatagcagat gcgagcagga gtaggagaga gggaggtaag agtcagaagc ttatgttgtt | 240 |
| tatgcgggga aacgccrtat cggggcagc cragttatta ggggacantr tagwyartcw | 300 |
| agntagcatc caaagcgngg gagttntccc atatggttgg acctgcaggc ggccgcatta | 360 |
| gtgattagca tgtgagcccc agacacgcat agcaacaagg acctaaactc agatcctgtg | 420 |
| ctgattactt aacatgaatt attgtattta tttaacaact ttgagttatg aggcatatta | 480 |
| ttaggtccat attacctgga | 500 |

<210> SEQ ID NO 168
<211> LENGTH: 358
<212> TYPE: DNA
<213> ORGANISM: Homo sapien

<400> SEQUENCE: 168

| ttcatcgctc ggtgactcaa gcctgtaatc ccagaacttt gggaggccga ggggagcaga | 60 |
|---|---|
| tcacctgagg ttgggagttt gagaccagcc tggccaacat ggtgacaacc cgtctctgct | 120 |
| aaaaatacaa aaattagcca agcatggtgg catgcacttg taatcccagc tactcgggag | 180 |
| gctgaggcag gagaatcact tgaggccagg aggcagaggt tgcagtgagg cagaggttga | 240 |
| gatcatgcca ctgcactcca gcctgggcaa cagagtaaga ctccatctca aaaaaaaaa | 300 |
| aaaaaagaa tgatcagagc cacaaataca gaaaaccttg agtcaccgag cgatgaaa | 358 |

<210> SEQ ID NO 169
<211> LENGTH: 1265
<212> TYPE: DNA
<213> ORGANISM: Homo sapien

<400> SEQUENCE: 169

```
ttctgtccac accaatctta gagctctgaa agaatttgtc tttaaatatc tttttaatagt      60
aacatgtatt ttatggacca aattgacatt ttcgactatt ttttcccaaa aaaagtcagg     120
tgaatttcag cacactgagt tgggaatttc ttatcccaga agwcggcacg agcaatttca     180
tatttattta agattgattc catactccgt tttcaaggag aatccctgca gtctccttaa     240
aggtagaaca aatactttct atttttttttt caccattgtg ggattggact ttaagaggtg    300
actctaaaaa aacagagaac aaatatgtct cagttgtatt aagcacggac ccatattatc    360
atattcactt aaaaaaatga tttcctgtgc accttttggc aacttctctt ttcaatgtag     420
ggaaaaactt agtcaccctg aaaacccaca aaataaataa aacttgtaga tgtgggcaga    480
argtttgggg gtggacattg tatgtgttta aattaaaccc tgtatcactg agaagctgtt    540
gtatgggtca gagaaaatga atgcttagaa gctgttcaca tcttcaagag cagaagcaaa   600
ccacatgtct cagctatatt attatttatt ttttatgcat aaagtgaatc atttcttctg     660
tattaatttc caagggtttt taccctctat ttaaatgctt tgaaaaacag tgcattgaca    720
atgggttgat atttttcttt aaaagaaaaa tataattatg aaagccaaga taatctgaag    780
cctgttttat tttaaaactt tttatgttct gtggttgatg ttgtttgttt gtttgtttct    840
attttgttgg ttttttactt tgtttttttgt tttgttttgt tttggtttdg catactacat    900
gcagtttctt taaccaatgt ctgtttggct aatgtaatta agttgttaa tttatatgag     960
tgcatttcaa ctatgtcaat ggtttcttaa tatttattgt gtagaagtac tggtaatttt   1020
tttatttaca atatgtttaa agagataaca gtttgatatg ttttcatgtg tttatagcag   1080
aagttattta tttctatggc attccagcgg atattttggt gtttgcgagg catgcagtca   1140
atattttgta cagttagtgg acagtattca gcaacgcctg atagcttctt tggccttatg   1200
ttaaataaaa agacctgttt gggatgtaaa aaaaaaaaaa aaaaaaaaa aaaaaaaaa     1260
aaaaa                                                              1265
```

<210> SEQ ID NO 170
<211> LENGTH: 383
<212> TYPE: DNA
<213> ORGANISM: Homo sapien

<400> SEQUENCE: 170

```
tgtaagtcga gcagtgtgat gacgatattc ttcttattaa tgtggtaatt gaacaaatga      60
tctgtgatac tgatcctgag ctaggaggcg ctgttcagtt aatgggactt cttcgtactc    120
taattgatcc agagaacatg ctggctacaa ctaataaaac cgaaaaaagt gaatttctaa    180
attttttcta caaccattgt atgcatgttc tcacagcacc acttttgacc aatacttcag    240
aagacaaatg tgaaaggat aatatagttg gatcaaacaa aaacaacaca atttgtcccg      300
ataattatca aacagcacag ctacttgcct taattttaga gttactcaca ttttgtgtgg    360
aacatcacac tgctcgactt aca                                           383
```

<210> SEQ ID NO 171
<211> LENGTH: 383
<212> TYPE: DNA
<213> ORGANISM: Homo sapien

<400> SEQUENCE: 171

```
tgggcacctt caatatcgca agttaaaaat aatgttgagt ttattatact tttgacctgt      60
ttagctcaac agggtgaagg catgtaaaga atgtggactt ctgaggaatt ttcttttaaa    120
```

| aagaacataa tgaagtaaca ttttaattac tcaaggacta cttttggttg aagtttataa | 180 |
| tctagatacc tctactttt gttttgctg ttcgacagtt cacaaagacc ttcagcaatt | 240 |
| tacagggtaa aatcgttgaa gtagtggagg tgaaactgaa atttaaaatt attctgtaaa | 300 |
| tactataggg aaagaggctg agcttagaat cttttggttg ttcatgtgtt ctgtgctctt | 360 |
| atcatcacac tgctcgactt aca | 383 |

<210> SEQ ID NO 172
<211> LENGTH: 699
<212> TYPE: DNA
<213> ORGANISM: Homo sapien
<220> FEATURE:
<221> NAME/KEY: misc_feature
<222> LOCATION: (1)...(699)
<223> OTHER INFORMATION: n = A,T,C or G

<400> SEQUENCE: 172

| tcgggtgatg cctcctcagg cttgtcgtta gtgtacacag agctgctcat gaagcgacag | 60 |
| cggctgcccc tggcacttca gaacctcttc ctctacactt ttggtgcgct tctgaatcta | 120 |
| ggtctgcatg ctggcggcgg ctctggccca ggcctcctgg aaagtttctc aggatgggca | 180 |
| gcactcgtgg tgctgagcca ggcactaaat ggactgctca tgtctgctgt catggagcat | 240 |
| ggcagcagca tcacacgcct ctttgtggtg tcctgctcgc tggtggtcaa cgccgtgctc | 300 |
| tcagcagtcc tgctacggct gcagctcaca gccgccttct tcctggccac attgctcatt | 360 |
| ggcctggcca tgcgcctgta ctatggcagc cgctagtccc tgacaacttc caccctgatt | 420 |
| ccggaccctg tagattgggc gccaccacca gatcccctc ccaggccttc ctccctctcc | 480 |
| catcagcggc cctgtaacaa gtgccttgtg agaaaagctg gagaagtgag ggcagccagg | 540 |
| ttattctctg gaggttggtg gatgaagggg taccctagg agatgtgaag tgtgggtttg | 600 |
| gttaaggaaa tgcttaccat cccccacccc caaccaagtt nttccagact aaagaattaa | 660 |
| ggtaacatca atacctaggc ctgaggaggc atcacccga | 699 |

<210> SEQ ID NO 173
<211> LENGTH: 701
<212> TYPE: DNA
<213> ORGANISM: Homo sapien

<400> SEQUENCE: 173

| tcgggtgatg cctcctcagg ccagatcaaa cttggggttg aaaactgtgc aaagaaatca | 60 |
| atgtcggaga aagaattttg caaaagaaaa atgcctaatc agtactaatt taataggtca | 120 |
| cattagcagt ggaagaagaa atgttgatat tttatgtcag ctattttata atcaccagag | 180 |
| tgcttagctt catgtaagcc atctcgtatt cattagaaat aagaacaatt ttattcgtcg | 240 |
| gaaagaactt tcaatttat agcatcttaa ttgctcagga ttttaaattt tgataaagaa | 300 |
| agctccactt ttggcaggag tagggggcag ggagagagga ggctccatcc acaaggacag | 360 |
| agacaccagg gccagtaggg tagctggtgg ctggatcagt cacaacggac tgacttatgc | 420 |
| catgagaaga aacaacctcc aaatctcagt tgcttaatac aacacaagct catttcttgc | 480 |
| tcacgttaca tgtcctatgt agatcaacag caggtgactc agggacccag gctccatctc | 540 |
| catatgagct tccatagtca ccaggacacg ggctctgaaa gtgtcctcca tgcagggaca | 600 |
| catgcctctt cctttcattg ggcagagcaa gtcacttatg gccagaagtc acactgcagg | 660 |
| gcagtgccat cctgctgtat gcctgaggag gcatcacccg a | 701 |

<210> SEQ ID NO 174
<211> LENGTH: 700
<212> TYPE: DNA
<213> ORGANISM: Homo sapien
<220> FEATURE:
<221> NAME/KEY: misc_feature
<222> LOCATION: (1)...(700)
<223> OTHER INFORMATION: n = A,T,C or G

<400> SEQUENCE: 174

| | | |
|---|---|---|
| tcgggtgatg cctcctcang ccctaaatc agagtccagg gtcagagcca caggagacag | 60 |
| ggaaagacat agattttaac cggccccctt caggagattc tgaggctcag ttcactttgt | 120 |
| tgcagtttga acagaggcag caaggctagt ggttaggggc acggtctcta aagctgcact | 180 |
| gcctggatct gcctcccagc tctgccagga accagctgcg tggccttgag ctgctgacac | 240 |
| gcagaaagcc ccctgtggac ccagtctcct cgtctgtaag atgaggacag gactctagga | 300 |
| acccttttccc ttggttttggc ctcactttca caggctccca tcttgaactc tatctactct | 360 |
| tttcctgaaa ccttgtaaaa gaaaaaagtg ctagcctggg caacatggca aaaccctgtc | 420 |
| tctacaaaaa atacaaaaat tagttgggtg tggtggcatg tgcctgtagt cccagccact | 480 |
| tgggaggtgc tgaggtggga ggatcacttg agcccgggag gtggaggttg cagtgagcca | 540 |
| agatcatgcc actgcactcc agcctgagta atagagtaag actctgtctc aaaaacaaca | 600 |
| acaacaacag tgagtgtgcc tctgtttccg ggttggatgg ggcaccacat ttatgcatct | 660 |
| ctcagatttg gacgctgcag cctgaggagg catcacccga | 700 |

<210> SEQ ID NO 175
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 175

| | | |
|---|---|---|
| tatagggcga attgggcccg agttgcatgn tcccggccgc catggccgcg ggattcgggt | 60 |
| gatgcctcct caggcttgtc tgccacaagc tacttctctg agctcagaaa gtgcccttg | 120 |
| atgagggaaa atgtcctact gcactgcgaa tttctcagtt ccattttacc tcccagtcct | 180 |
| ccttctaaac cagttaataa attcattcca caagtattta ctgattacct gcttgtgcca | 240 |
| gggactattc tcaggctgaa gaaggtggga ggggagggcg gaacctgagg agccacctga | 300 |
| gccagcttta tatttcaacc atggctggcc catctgagag catctcccca ctctcgccaa | 360 |
| cctatcgggg catagcccag ggatgccccc aggcggccca ggttagatgc gtcccttttgg | 420 |
| cttgtcagtg atgacataca ccttagctgc ttagctggtg ctggcctgag gaggcatcac | 480 |
| ccga | 484 |

<210> SEQ ID NO 176
<211> LENGTH: 432
<212> TYPE: DNA
<213> ORGANISM: Homo sapien

<400> SEQUENCE: 176

| | | |
|---|---|---|
| tcgggtgatg cctcctcagg gctcaaggga tgagaagtga cttctttctg gagggaccgt | 60 |
| tcatgccacc caggatgaaa atggataggg acccacttgg aggacttgct gatatgtttg | 120 |
| gacaaatgcc aggtagcgga attggtactg gtccaggagt tatccaggat agattttcac | 180 |

| | |
|---|---|
| ccaccatggg acgtcatcgt tcaaatcaac tcttcaatgg ccatggggga cacatcatgc | 240 |
| ctcccacaca atcgcagttt ggagagatgg gaggcaagtt tatgaaaagc cagggctaa | 300 |
| gccagctcta ccataaccag agtcaggac tcttatccca gctgcaagga cagtcgaagg | 360 |
| atatgccacc tcggttttct aagaaaggac agcttaatgc agatgagatt agcctgagga | 420 |
| ggcatcaccc ga | 432 |

<210> SEQ ID NO 177
<211> LENGTH: 788
<212> TYPE: DNA
<213> ORGANISM: Homo sapien

<400> SEQUENCE: 177

| | |
|---|---|
| tagcatgttg agcccagaca cagtagcatt tgtgccaatt tctggttgga atggtgacaa | 60 |
| catgctggag ccaagtgcta acatgccttg gttcaaggga tggaaagtca cccgtaagga | 120 |
| tggcaatgcc agtggaacca cgctgcttga ggctctggac tgcatcctac caccaactcg | 180 |
| cccaactgac aagcccttgc gcctgcctct ccaggatgtc tacaaaattg gtggtattgg | 240 |
| tactgttcct gttggccgag tggagactgg tgttctcaaa cccggtatgg tggtcacctt | 300 |
| tgctccagtc aacgttacaa cggaagtaaa atctgtcgaa atgcaccatg aagctttgag | 360 |
| tgaagctctt cctggggaca atgtgggctt caatgtcaag aatgtgtctg tcaaggatgt | 420 |
| tcgtcgtggc aacgttgctg gtgacagcaa aaatgaccca ccaatggaag cagctggctt | 480 |
| cactgctcag gtgattatcc tgaaccatcc aggccaaata agtgccggct atgcccctgt | 540 |
| attggattgc cacacggctc acattgcatg caagtttgct gagctgaagg aaaagattga | 600 |
| tcgccgttct ggtaaaaagc tggaagatgg ccctaaattc ttgaagtctg gtgatgctgc | 660 |
| cattgttgat atggttcctg gcaagcccat gtgtgttgag agcttctcag actatccacc | 720 |
| tttgggtcgc tttgctgttc gtgatatgag acagacagtt gcggtgggtg tctgggctca | 780 |
| acatgcta | 788 |

<210> SEQ ID NO 178
<211> LENGTH: 786
<212> TYPE: DNA
<213> ORGANISM: Homo sapien

<400> SEQUENCE: 178

| | |
|---|---|
| tagcatgttg agcccagaca cctgtgtttc tgggagctct ggcagtggcg gattcatagg | 60 |
| cacttgggct gcactttgaa tgacacactt ggctttatta gattcactag ttttttaaaaa | 120 |
| attgttgttc gtttcttttc attaaaggtt taatcagaca gatcagacag cataattttg | 180 |
| tatttaatga cagaaacgtt ggtacatttc ttcatgaatg agcttgcatt ctgaagcaag | 240 |
| agcctacaaa aggcacttgt tataaatgaa agttctggct ctagaggcca gtactctgga | 300 |
| gtttcagagc agccagtgat tgttccagtc agtgatgcct agttatatag aggaggagta | 360 |
| cactgtgcac tcttctaggt gtaagggtat gcaactttgg atcttaaaat tctgtacaca | 420 |
| tacacacttt atatatatgt atgtatgtat gaaaacatga aattagtttg tcaaatatgt | 480 |
| gtgtgtttag tattttagct tagtgcaact atttccacat tatttattaa attgatctaa | 540 |
| gacactttct tgttgacacc ttgaatatta atgttcaagg gtgcaatgtg tattcctta | 600 |
| gattgttaaa gcttaattac tatgatttgt agtaaattaa cttttaaaat gtatttgagc | 660 |
| ccttctgtag tgtcgtaggg ctcttacagg gtgggaaaga ttttaatttt ccagttgcta | 720 |

```
attgaacagt atggcctcat tatatatttt gatttatagg agtttgtgtc tgggctcaac    780
atgcta                                                               786

<210> SEQ ID NO 179
<211> LENGTH: 796
<212> TYPE: DNA
<213> ORGANISM: Homo sapien

<400> SEQUENCE: 179
tagcatgttg agcccagaca ctggttacaa gaccagacct gcttcctcca tatgtaaaca     60
gcttttaaaa agccagtgaa cctttttaat actttggcaa ccttctttca caggcaaaga    120
acacccccat ccgcccctttg tttggagtgc agagtttggc tttggttctt tgccttgcct   180
ggagtatact tctaattcct gttgtcctgc acaagctgaa taccgagcta cccaccgcca    240
cccaggccag gtttccactc atttattact ttatgtttct gttccattgc tggtccacag    300
aaataagttt tcctttggag gaatgtgatt atacccctt aatttcctcc ttttgctttt     360
ttttaatatc attggtatgt gtttggccca gaggaaactg aaattcacca tcatcttgac    420
tggcaatccc attaccatgc tttttttaaa aaacgtaatt tttcttgcct tacattggca    480
gagtagccct tcctggctac tggcttaatg tagtcactca gtttctaggt ggcattaggc    540
atgagacctg aagcacagac tgtcttacca caaaaggtga caagatctca aaccttagcc    600
aaagggctat gtcaggtttc aatgctatct gcttctgttc ctgctcactg ttctggattt    660
tgtccttctt catccctagc accagaattt cccagtctcc ctccctacct tcccttgttt    720
taattctaat ctatcagcaa ataaacttt caaatgtttt aaccggtatc tccatgtgtc     780
tgggctcaac atgcta                                                    796

<210> SEQ ID NO 180
<211> LENGTH: 488
<212> TYPE: DNA
<213> ORGANISM: Homo sapien

<400> SEQUENCE: 180
ggatgtgctg caaggcgatt aagttgggta acgccagggt tttcccagtc acgacgttgt     60
aaaacgacgg ccagtgaatt gtaatacgac tcactatagg gcgaattggg cccgacgtcg    120
catgctcccg gccgccatgg ccgcgggata gcatgttgag cccagacacc tgcaggtcat    180
ttggagagat ttttcacgtt accagcttga tggtcttttt caggaggaga gacactgagc    240
actcccaagg tgaggttgaa gatttcctct agatagccgg ataagaagac taggagggat    300
gcctagaaaa tgattagcat gcaaatttct acctgccatt tcagaactgt gtgtcagccc    360
acattcagct gcttcttgtg aactgaaaag agagaggtat tgagactttt ctgatggccg    420
ctctaacatt gtaacacagt aatctgtgtg tgtgtgggtg tgtgtgtgtg tctgggctca    480
acatgcta                                                             488

<210> SEQ ID NO 181
<211> LENGTH: 317
<212> TYPE: DNA
<213> ORGANISM: Homo sapien

<400> SEQUENCE: 181
tagcatgttg agcccagaca cggcgacggt acctgatgag tgggtgatg gcacctgtga      60 aaaggaggaa cgtcatcccc catgatattg gggacccaga tgatgaacca tggctccgcg    120
tcaatgcata tttaatccat gatactgctg attggaagga cctgaacctg aagtttgtgc    180
```

| | |
|---|---|
| tgcaggttta tcgggactat tacctcacgg gtgatcaaaa cttcctgaag gacatgtggc | 240 |
| ctgtgtgtct agtaagggat gcacatgcag tggccagtgt gccagggta tggttggtgt | 300 |
| ctgggctcaa catgcta | 317 |

<210> SEQ ID NO 182
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 182

| | |
|---|---|
| tagcatgttg agcccagaca ctggctgtta gccaaatcct ctctcagctg ctccctgtgg | 60 |
| tttggtgact caggattaca gaggcatcct gtttcaggga acaaaaagat tttagctgcc | 120 |
| agcagagagc accacataca ttagaatggt aaggactgcc acctccttca agaacaggag | 180 |
| tgagggtggt ggtgaatggg aatggaagcc tgcattccct gatgcatttg tgctctctca | 240 |
| aatcctgtct tagtcttagg aaaggaagta agtttcaag gacggttccg aactgctttt | 300 |
| tgtgtctggg ctcaacatgc tatcccgcgg ccatggcggc cgggagcatg cgacgtcggg | 360 |
| cccaattcgc cctatagtga gtcgtattac aattcactgg ccgtcgtttt acaacgtcgt | 420 |
| gactgggaaa accctggcgt tacccaactt aatcgccttg cagcacatcc cccttccca | 480 |
| gctggcgtaa tancgaaaag gcccgca | 507 |

<210> SEQ ID NO 183
<211> LENGTH: 227
<212> TYPE: DNA
<213> ORGANISM: Homo sapien

<400> SEQUENCE: 183

| | |
|---|---|
| gatttacgct gcaacactgt ggaggtagcc ctggagcaag gcaggcatgg atgcttctgc | 60 |
| aatccccaaa tggagcctgg tatttcagcc aggaatctga gcagagcccc ctctaattgt | 120 |
| agcaatgata agttattctc tttgttcttc aaccttccaa tagccttgag cttccagggg | 180 |
| agtgtcgtta atcattacag cctggtctcc acagtgttgc agcgtaa | 227 |

<210> SEQ ID NO 184
<211> LENGTH: 225
<212> TYPE: DNA
<213> ORGANISM: Homo sapien

<400> SEQUENCE: 184

| | |
|---|---|
| ttacgctgca acactgtgga gcagattaac atcagacttt tctatcaaca tgactggggt | 60 |
| tactaaaaag acaacaaatc aatggcttca aaagtctaag gaataatttc gatacttcaa | 120 |
| ctttataaaa cctgacaaaa ctatcaatca agcataaaga cagatgaaga acatttccag | 180 |
| attttggcca atcagatatt ttacctccac agtgttgcag cgtaa | 225 |

<210> SEQ ID NO 185
<211> LENGTH: 597
<212> TYPE: DNA
<213> ORGANISM: Homo sapien

<400> SEQUENCE: 185

| | |
|---|---|
| ggcccgacgt cgcatgctcc cggccgccat ggccgcggga ttcgttaggg tctctatcca | 60 |
| ctgggaccca taggctagtc agagtattta gagttgagtt cctttctgct tcccagaatt | 120 |

| | |
|---|---:|
| tgaaagaaaa ggagtgaggt gatagagctg agagatcaga tttgcctctg aagcctgttc | 180 |
| aagatgtatg tgctcagacc ccaccactgg ggcctgtggg tgaggtcctg ggcatctatt | 240 |
| tgaatgaatt gctgaagggg agcactatgc caaggaaggg gaacccatcc tggcactggc | 300 |
| acagggtca ccttatccag tgctcagtgc ttctttgctg ctacctggtt ttctctcata | 360 |
| tgtgagggc aggtaagaag aagtgcccrg tgttgtgcga gttttagaac atctaccagt | 420 |
| aagtggggaa gtttcacaaa gcagcagctt tgttttgtgt attttcacct tcagttagaa | 480 |
| gaggaaggct gtgagatgaa tgttagttga gtggaaaaga cgggtaagct tagtggatag | 540 |
| agaccctaac gaatcactag tgcggccgcc ttgcaggtcg accatatggg agagctc | 597 |

<210> SEQ ID NO 186
<211> LENGTH: 597
<212> TYPE: DNA
<213> ORGANISM: Homo sapien

<400> SEQUENCE: 186

| | |
|---|---:|
| ggcccgaagt tgcatgttcc cggccgccat ggccgcggga ttcgttaggg tctctatcca | 60 |
| ctacctaaaa aatcccaaac atataactga actcctcaca cccaattgga ccaatccatc | 120 |
| accccagagg cctacagatc ctcctttgat acataagaaa atttccccaa actacctaac | 180 |
| tatatcattt tgcaagattt gttttaccaa attttgatgg cctttctgag cttgtcagtg | 240 |
| tgaaccacta ttacgaacga tcggatatta actgcccctc accgtccagg tgtagctggc | 300 |
| aacatcaagt gcagtaaata ttcattaagt tttcacctac taaggtgctt aaacacccta | 360 |
| gggtgccatg tcggtagcag atcttttgat ttgtttttat ttcccataag ggtcctgttc | 420 |
| aaggtcaatc atacatgtag tgtgagcagc tagtcactat cgcatgactt ggagggtgat | 480 |
| aatagaggcc tcctttgctg ttaaagaact cttgtcccag cctgtcaaag tggatagaga | 540 |
| ccctaacgaa tcactagtgc ggccgcctgc aggtcgacca tatgggagag ctcccaa | 597 |

<210> SEQ ID NO 187
<211> LENGTH: 324
<212> TYPE: DNA
<213> ORGANISM: Homo sapien

<400> SEQUENCE: 187

| | |
|---|---:|
| tcgttagggt ctctatccac ttgcaggtaa aatccaatcc tgtgtatatc ttatagtctt | 60 |
| ccatatgtag tggttcaaga gactgcagtt ccagaaagac tagccgagcc catccatgtc | 120 |
| ttccacttaa ccctgctttg ggttacacat cttaactttt ctgttcaagt ttctctgtgt | 180 |
| agtttatagc atgagtattg ggawaatgcc ctgaaacctg acatgagatc tgggaaacac | 240 |
| aaacttactc aataagaatt tctcccatat ttttatgatg gaaaaatttc acatgcacag | 300 |
| aggagtggat agagaccctt acga | 324 |

<210> SEQ ID NO 188
<211> LENGTH: 178
<212> TYPE: DNA
<213> ORGANISM: Homo sapien
<220> FEATURE:
<221> NAME/KEY: misc_feature
<222> LOCATION: (1)...(178)
<223> OTHER INFORMATION: n = A,T,C or G

```
<400> SEQUENCE: 188
gcgcggggat tcggggtgat acctcctcat gccaaaatac aacgtntaat ttcacaactt      60
gccttccaat ttacgcattt tcaatttgct ctccccattt gttgagtcac aacaaacacc     120
attgcccaga aacatgtatt acctaacatg cacatactct taaaactact catcccctt     178

<210> SEQ ID NO 189
<211> LENGTH: 367
<212> TYPE: DNA
<213> ORGANISM: Homo sapien

<400> SEQUENCE: 189
tgacaccttg tccagcatct gacacagtct tggctcttgg aaaatattgg ataaatgaaa      60
atgaatttct ttagcaagtg gtataagctg agaatatacg tatcacatat cctcattcta     120
agacacattc agtgtccctg aaattagaat aggacttaca ataagtgtgt tcactttctc     180
aatagctgtt attcaattga tggtaggcct taaaagtcaa agaaatgaga gggcatgtga     240
aaaaaagctc aacatcactg atcattagaa aacttccatt caaaccccca atgagatacc     300
atctcatacc agtcagaatg gctattatta aaaagtcaaa aataacaga tgctggacaa      360 ggtgtca                                                              367

<210> SEQ ID NO 190
<211> LENGTH: 369
<212> TYPE: DNA
<213> ORGANISM: Homo sapien
<220> FEATURE:
<221> NAME/KEY: misc_feature
<222> LOCATION: (1)...(369)
<223> OTHER INFORMATION: n = A,T,C or G

<400> SEQUENCE: 190
gacaccttgt ccagcatctg acaacgctaa cagcctgagg agatctttat ttatttattt      60
agtttttact ctggctaggc agatggtggc taaaacattc atttacccat ttattcattt     120
aattgttcct gcaaggccta tggatagagt attgtccagc actgctctgg aagctaggag     180
catggggatg aacaagatag gctacatcct gttcccacag aacttccact ttagtctggg     240
aaacagatga tatatacaaa tatataaatg aattcaggta gttttaagta cgaaaagaat     300
aagaaagcag agtcatgatt tanaatgctg gaaacagggg ctattgcttg agatattgaa     360
ggtgcccaa                                                            369

<210> SEQ ID NO 191
<211> LENGTH: 369
<212> TYPE: DNA
<213> ORGANISM: Homo sapien

<400> SEQUENCE: 191
tgacaccttg tccagcatct gcacagggaa agaaactat tatcagagtg aacaggcaac       60
ctacagaatg ggagaaaatt tttgcaatct atccatctga caaagggcta atatccagaa     120
tctacaaaga acttatacaa atttacaaga aacaaactaa caaacaactc ctcaaaaagt     180
gggtgaagga tgtgaacaga cacttctcaa aagaagacat ttatggggcc aacaaacata     240
tgaaaaaaag ctcatcatca ctggtcacta gataaatgca aatcaaaacc acaatgagat     300
accatctcat tccagttaga atggcaatca ttaaaaagtc aggaaacaac agatgctgga     360
caaggtgtc                                                            369
```

<210> SEQ ID NO 192
<211> LENGTH: 449
<212> TYPE: DNA
<213> ORGANISM: Homo sapien

<400> SEQUENCE: 192

| | | | | | |
|---|---|---|---|---|---|
| tgacgcttgg | ccacttgaca | cttcatcttt | gcacagaaaa | acttctttac | agatttaatt | 60 |
| caagactggt | ctagtgacag | tcctccagac | attttttcat | ttgttccata | tacgtggaat | 120 |
| tttaaaatca | tgtttcatca | gtttgaaatg | atttgggctg | ctaatcaaca | caattggatc | 180 |
| gactgttcta | ctaaacaaca | ggaaaatgtg | tatctggcag | cctgtggaga | aacactaaac | 240 |
| attgattttt | ctttgccttt | tacggacttt | gttccagcta | catgtaatac | caagttctct | 300 |
| ttaagaggag | aagatgttga | tcttcatttg | tttctaccag | actgccaccc | tagtaaatat | 360 |
| tctttattta | tgctggtaaa | aaattgccat | ccaaataaga | tgattcatga | tactggtatt | 420 |
| cctgctgagt | gtcaagtggc | caagcgtca | | | | 449 |

<210> SEQ ID NO 193
<211> LENGTH: 372
<212> TYPE: DNA
<213> ORGANISM: Homo sapien

<400> SEQUENCE: 193

| | | | | | |
|---|---|---|---|---|---|
| tgacgcttgg | ccacttgaca | ccagggatgt | akcagttgaa | tataatcctg | caattgtaca | 60 |
| tattggcaat | ttcccatcaa | acattctaga | aagagacaac | caggattgct | aggccataaa | 120 |
| agctgcaata | ataactggt | aattgcagta | atcatttcag | gccaattcaa | tccagtttgg | 180 |
| ctcagaggtg | cctttggctg | agagaagagg | tgagatataa | tgtgtttttct | tgcaacttct | 240 |
| tggaagaata | actccacaat | agtctgagga | ctagataca | acctatttgc | cattaaagca | 300 |
| ccagagtctg | ttaattccag | tactgataag | tgttggagat | tagactccag | tgtgtcaagt | 360 |
| ggccaagcgt | ca | | | | | 372 |

<210> SEQ ID NO 194
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 194

| | | | | | |
|---|---|---|---|---|---|
| tgacgcttgg | ccacttgaca | cttatgtaga | atccatcgtg | ggctgatgca | agcccttat | 60 |
| ttaggcttag | tgttgtgggc | accttcaata | tcacactaga | gacaaacgcc | acaagatctg | 120 |
| cagaaacatt | cagttctgan | cactcgaatg | gcaggataac | tttttgtgtt | gtaatccttc | 180 |
| acatatacaa | aaacaaactc | tgcantctca | cgttacaaaa | aaacgtactg | ctgtaaaata | 240 |
| ttaagaaggg | gtaaaggata | ccatctataa | caaagtaact | tacaactagt | gtcaagtggc | 300 |
| caagcgtca | | | | | | 309 |

<210> SEQ ID NO 195
<211> LENGTH: 312
<212> TYPE: DNA
<213> ORGANISM: Homo sapien
<220> FEATURE:
<221> NAME/KEY: misc_feature
<222> LOCATION: (1)...(312)
<223> OTHER INFORMATION: n = A,T,C or G

<400> SEQUENCE: 195

```
tgacgcttgg ccacttgaca cccaatctcg cacttcatcc tcccagcacc tgatgaagta      60
ggactgcaac tatccccact tcccagatga ggggaccaan gtacacatta ggacccggat     120
gggagcacag atttgtccga tcccagactc caagcactca gcgtcactcc aggacagcgg     180
ctttcagata aggtcacaaa catgaatggc tccgacaacc ggagtcagtc cgtgctgagt     240
taaggcaatg gtgacacgga tgcacgtgtn acctgtaatg gttcatcgta agtgtcaagt     300
ggccaagcgt ca                                                         312
```

<210> SEQ ID NO 196
<211> LENGTH: 288
<212> TYPE: DNA
<213> ORGANISM: Homo sapien

<400> SEQUENCE: 196

```
tgtatcgacg tagtggtctc ctcagccatg cagaactgtg actcaattaa acctctttcc      60
tttatgaatt acccaatctc gggtagtgtc tttatagtag tgtgagaatg gactaataca     120
agtacatttt acttagtaat aataataaac aaatatatta catttttgtg tatttactac     180
accatatttt ttattgttat tgtagtgtac accttctact tattaaaaga aataggcccg     240
aggcgggcag atcacgaggt caggagatgg agaccactac gtcgatac                 288
```

<210> SEQ ID NO 197
<211> LENGTH: 289
<212> TYPE: DNA
<213> ORGANISM: Homo sapien

<400> SEQUENCE: 197

```
ttgggcacct tcaatatcat gacaggtgat gtgataacca agaaggctac taagtgatta      60
atgggtgggt aatgtataca gagtaggtac actggacaga ggggtaattc atagccaagg     120
caggagaagc agaatggcaa acatttcat cacactactc aggatagcat gcagtttaaa     180
acctataagt agtttatttt tggaattttc cacttaatat tttcagactg caggtaacta     240
aactgtggaa cacaagaaca tagataaggg gagaccacta cgtcgatac                289
```

<210> SEQ ID NO 198
<211> LENGTH: 288
<212> TYPE: DNA
<213> ORGANISM: Homo sapien

<400> SEQUENCE: 198

```
gtatcgacgt agtggtctcc caagcagtgg gaagaaaacg tgaaccaatt aaaatgtatc      60 agataccccca agaaaggcg cttgagtaaa gattccaagt gggtcacaat ctcagatctt     120
aaaattcagg ctgtcaaaga gatttgctat gaggttgctc tcaatgactt caggcacagt     180
cggcaggaga ttgaagccct ggccattgtc aagatgaagg agctttgtgc catgtatggc     240
aagaaagacc ccaatgagcg ggactcctgg agaccactac gtcgatac                 288
```

<210> SEQ ID NO 199
<211> LENGTH: 1027
<212> TYPE: DNA
<213> ORGANISM: Homo sapien
<220> FEATURE:
<221> NAME/KEY: misc_feature
<222> LOCATION: (1)...(1027)
<223> OTHER INFORMATION: n = A,T,C or G

<400> SEQUENCE: 199

```
gcttttggg aaaaacncaa ntgggggaaa ggggggnttnn tngcaagggg ataaaggggg      60
aancccaggg tttccccatt cagggaggtg taaaaagncg gccaggggat tgtaanagga     120
ttcaataata gggggaatgg gcccngaagt tgcaaggttc cngcccgcca tgnccgcggg     180
atttagtgac attacgacgs tggtaataaa gtgggsccaa waaatatttg tgatgtgatt     240
tttsgaccag tgaacccatt gwacaggacc tcatttccty tgagatgrta gccataatca     300
gataaaagrt tagaagtytt tctgcacgtt aacagcatca ttaaatggag tggcatcacc     360
aatttcaccc tttgttagcc gataccttcc ccttgaaggc attcaattaa gtgaccaatc     420
gtcatacgag aggggatggc atggggattg atgatgatat cagggggtgat accttcacag    480
gtgaaaggca tatcctcttg tctatactga ataccacaag taccctttg accatgtcga      540
ctagcaaatt tgtctccaat ctgtgtwatc cctaacagag cgtacccta tttacaaaa      600
tttatatcct tcctgattga gagttaccat aacctgatca caatgcccg tctcgctwgt     660
tctgagaaaa gtgctacagt ctctcttggt atagcgtcta ttggtgctct ccaattcatc    720
ttcattttc aggcaaggtg aactgttttg cctataataa cmtcatctcc tgatacmcga    780
aacccckgga rctatcaaac catcatcatc cagcgttckt watgtymcta aatccctatt    840
gcggccgcct gcaggtcaac atatngggaaa acccccccacc ccttnggagc ntaccttgaa   900
ttttccatat gtcccntaaa ttanctngnc ttanccctggc cntaacctnt tccggtttaa   960
attgtttccg ccccnttcc ccnccttnna accggaaacc ttaatttna accngggggtt  1020
cctatcc                                                            1027
```

<210> SEQ ID NO 200
<211> LENGTH: 207
<212> TYPE: DNA
<213> ORGANISM: Homo sapien

<400> SEQUENCE: 200

```
agtgacatta cgacgctggc catcttgaat cctagggcat gaagttgccc caaagttcag      60
cacttggtta agcctgatcc ctctggttta tcacaaagaa taggatggga taaagaaagt    120
ggacacttaa ataagctata aattatatgg tccttgtcta gcaggagaca actgcacagg    180
tatactacca gcgtcgtaat gtcacta                                        207
```

<210> SEQ ID NO 201
<211> LENGTH: 209
<212> TYPE: DNA
<213> ORGANISM: Homo sapien

<400> SEQUENCE: 201

```
tgggcacctt caatatctat taaaagcaca aatactgaag aacacaccaa gactatcaat      60
gaggttacat ctggagtcct cgatatatca ggaaaaaatg aagtgaacat tcacagagtt    120
ttacttcttt gggaactcaa atgctagaaa agaaaagggt gccctctttc tctggcttcc    180
tggtcctatc cagcgtcgta atgtcacta                                      209
```

<210> SEQ ID NO 202
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 202

```
ntacgctgca acactgtgga gccactggtt tttattcccg gcaggttatc cagcaaacag    60
tcactgaaca caccgaagac cgtggtatgg taaccgttca cagtaatcgt tccagtcgtc   120
tgcgggaccc cgacgagcgt cactgggtac agaccagatt cagccggaag agaaagcgcc   180
gcagggagag actcgaactc cactccgctg gtgagcagcc ccatgttttc aactcgaagt   240
tcaaacggca ttgggttata taccatcagc tgaacttcac acacatctcc ttgaacccac   300
tggaaatcta ttttcttgtt ccgctcttct ccacagtgtt gcagcgtaa               349
```

<210> SEQ ID NO 203
<211> LENGTH: 241
<212> TYPE: DNA
<213> ORGANISM: Homo sapien

<400> SEQUENCE: 203

```
tgctcctctt gccttaccaa cccaaagccc actgtgaaat atgaagtgaa tgacaaaatt    60
cagttttcaa cgcaatatag tatagtttat ctgattcttt tgatctccag gacactttaa   120
acaactgcta ccaccaccac caacctaggg atttaggatt ctccacagac cagaaattat   180
ttctcctttg agtttcaggc tcctctggga ctcctgttca tcaatgggtg gtaaatggct   240
a                                                                    241
```

<210> SEQ ID NO 204
<211> LENGTH: 248
<212> TYPE: DNA
<213> ORGANISM: Homo sapien

<400> SEQUENCE: 204

```
tagccattta ccacccatct gcaaaccswg acmwwcargr cywgwackya ggcgatttga    60
agtactggta atgctctgat catgttagtt acataagtgt ggtcagttta caaaaattca   120
cagaactaaa tactcaatgc tatgtgttca tgtctgtgtt tatgtgtgtg taatgtttca   180
attaagtttt tttaaaaaaa agagatgatt tccaaataag aaagccgtgt tggtaaggca   240
agaggagc                                                             248
```

<210> SEQ ID NO 205
<211> LENGTH: 505
<212> TYPE: DNA
<213> ORGANISM: Homo sapien
<220> FEATURE:
<221> NAME/KEY: misc_feature
<222> LOCATION: (1)...(505)
<223> OTHER INFORMATION: n = A,T,C or G

<400> SEQUENCE: 205

```
tacgctgcaa cactgtggag ccattcatac aggtccctaa ttaaggaaca agtgattatg    60
ctacctttgc acgttaggg taccgcggcc gttaaacatg tgtcactggg caggcggtgc   120
ctctaatact ggtgatgcta gaggtgatgt ttttggtaaa caggcggggt aagatttgcc   180
gagttccttt tacttttttt aacctttcct tatgagcatg cctgtgttgg gttgacagtg   240
ggggtaataa tgacttgttg gttgattgta gatattgggc tgttaattgt cagttcagtg   300
ttttaatctg acgcaggctt atgcggagga gaatgttttc atgttactta tactaacatt   360
agttcttcta tagggtgata gattggtcca attgggtgtg aggagttcag ttatatgttt   420
gggatttttt aggtagtggg tgttganctt gaacgctttc ttaattggtg gctgcttta   480
rgcctactat gggtggtaaa tggct                                          505
```

```
<210> SEQ ID NO 206
<211> LENGTH: 179
<212> TYPE: DNA
<213> ORGANISM: Homo sapien

<400> SEQUENCE: 206
tagactgact catgtcccct accaaagccc atgtaaggag ctgagttctt aaagactgaa      60
gacagactat tctctggaga aaataaaat ggaaattgta cttttaaaaaa aaaaaaaatc     120 ggccgggcat ggtagcacac acctgtaatc ccagctacta ggggacatga gtcagtcta     179

<210> SEQ ID NO 207
<211> LENGTH: 176
<212> TYPE: DNA
<213> ORGANISM: Homo sapien

<400> SEQUENCE: 207
agactgactc atgtccccta ccccaccttc tgctgtgctg ccgtgttcct aacaggtcac      60
agactggtac tggtcagtgg cctggggggtt ggggacctct attatatggg atacaaattt   120
aggagttgga attgacacga tttagtgact gatgggatat gggtggtaaa tggcta        176

<210> SEQ ID NO 208
<211> LENGTH: 196
<212> TYPE: DNA
<213> ORGANISM: Homo sapien

<400> SEQUENCE: 208
agactgactc atgtccccta tttaacaggg tctctagtgc tgtgaaaaaa aaaaatgctg      60
aacattgcat ataacttata ttgtaagaaa tactgtacaa tgactttatt gcatctgggt    120
agctgtaagg catgaaggat gccaagaagt ttaaggaata tgggtggtaa atggctaggg    180
gacatgagtc agtcta                                                     196

<210> SEQ ID NO 209
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 209
gacgcttggc cacttgacac cttttatttt ttaaggattc ttaagtcatt tangtnactt      60 tgtaagttttt tcctgtgccc ccataagaat gatagcttta aaaattatgc tggggtagca    120
aagaagatac ttctagcttt agaatgtgta ggtatagcca ggattcttgt gaggaggggt    180
gatttagagc aaatttctta ttctccttgc ctcatctgta acatggggat aataatagaa    240
ctggcttgac aaggttggaa ttagtattac atggtaaata catgtaaaat gtttagaatg    300
gtgccaagta tctaggaagt acttgggcat gggtggtaaa tggct                    345

<210> SEQ ID NO 210
<211> LENGTH: 178
<212> TYPE: DNA
<213> ORGANISM: Homo sapien
```

<400> SEQUENCE: 210

| | | | |
|---|---|---|---|
| gacgcttggc cacttgacac tagagtaggg tttggccaac ttttctata aaggaccaga | 60 | | |
| gagtaaatat ttcaggcttt gtgggttgtg cagtctctct tgcaactact cagctctgcc | 120 | | |
| attgtagcat agaaatcagc catagacagg acagaaatga atgggtggta aatggcta | 178 | | |

<210> SEQ ID NO 211
<211> LENGTH: 454
<212> TYPE: DNA
<213> ORGANISM: Homo sapien

<400> SEQUENCE: 211

| | |
|---|---|
| tgggcacctt caatatctat ccagcgcatc taaattcgct tttttcttga ttaaaattt | 60 |
| caccacttgc tgttttgct catgtatacc aagtagcagt ggtgtgaggc catgcttgtt | 120 |
| ttttgattcg atatcagcac cgtataagag cagtgctttg ccattaatt tatcttcatt | 180 |
| gtagacagca tagtgtagag tggtatctcc atactcatct ggaatatttg gatcagtgcc | 240 |
| atgttccagc aacattaacg cacattcatc ttcctggcat tgtacggcct ttgtcagagc | 300 |
| tgtcctcttt ttgttgtcaa ggacattaag ttgacatcgt ctgtccagca cgagttttac | 360 |
| tacttctgaa ttcccattgg cagaggccag atgtagagca gtcctctttt gcttgtccct | 420 |
| cttgttcaca tcagtgtccc tgagcataac ggaa | 454 |

<210> SEQ ID NO 212
<211> LENGTH: 337
<212> TYPE: DNA
<213> ORGANISM: Homo sapien

<400> SEQUENCE: 212

| | |
|---|---|
| tccgttatgc cacccagaaa acctactgga gttacttatt aacatcaagg ctggaaccta | 60 |
| tttgcctcag tcctatctga ttcatgagca catggttatt actgatcgca ttgaaaacat | 120 |
| tgatcacctg ggtttctta tttatcgact gtgtcatgac aaggaaactt acaaactgca | 180 |
| acgcagagaa actattaaag gtattcagaa acgtgaagcc agcaattgtt tcgcaattcg | 240 |
| gcattttgaa aacaaatttg ccgtggaaac tttaatttgt tcttgaacag tcaagaaaaa | 300 |
| cattattgag gaaaattaat atcacagcat aacggaa | 337 |

<210> SEQ ID NO 213
<211> LENGTH: 715
<212> TYPE: DNA
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 213

| | |
|---|---|
| tcgggtgatg cctcctcagg catcttccat ccatctcttc aagattagct gtcccaaatg | 60 |
| ttttccttc tcttctttac tgataaattt ggactccttc ttgacactga tgacagcttt | 120 |
| agtatccttc ttgtcacctt gcagacttta aacataaaaa tactcattgg ttttaaaagg | 180 |
| aaaaagtat acattagcac tattaagctt ggccttgaaa catttctat cttttattaa | 240 |
| atgtcggtta gctgaacaga attcatttta caatgcagag tgagaaaaga agggagctat | 300 |
| atgcatttga gaatgcaagc attgtcaaat aaacatttta aatgctttct taaagtgagc | 360 |
| acatacagaa atacattaag atattagaaa gtgttttgc ttgtgtacta ctaattaggg | 420 |
| aagcaccttg tatagttcct cttctaaaat tgaagtagat tttaaaaacc catgtaattt | 480 |

```
aattgagctc tcagttcaga ttttaggaga attttaacag ggatttggtt ttgtctaaat      540
tttgtcaatt tntttagtta atctgtataa ttttataaat gtcaaactgt atttagtccg      600
ttttcatgct gctatgaaag aaatacccan gacagggtta tttataaang gaaagangtt      660
aatttgactc ccagttcaca ggcctgagga ngnatcnccc gaaatcctta ttgcg          715
```

<210> SEQ ID NO 214
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 214

```
ggtaangngc atacntcggt gctccggccg ccggagtcgg gggattcggg tgatgcctcc       60
tcaggcccac ttgggcctgc ttttcccaaa tggcagctcc tctggacatg ccattccttc      120
tcccacctgc ctgattcttc atatgttggg tgtccctgtt tttctggtgc tatttcctga      180
ctgctgttca gctgccactg tcctgcaaag cctgcctttt taaatgcctc accattcctt      240
catttgtttc ttaaatatgg gaagtgaaag tgccacctga ggccgggcac agtggctcac      300
gcctgtaatc ccagcacttt gggagcctga ggaggcatca cccga                     345
```

<210> SEQ ID NO 215
<211> LENGTH: 429
<212> TYPE: DNA
<213> ORGANISM: Homo sapien

<400> SEQUENCE: 215

```
ggtgatgcct cctcaggcga agctcaggga ggacagaaac ctcccgtgga gcagaagggc       60
aaaagctcgc ttgatcttga ttttcagtac gaatacagac cgtgaaagcg gggcctcacg      120
atccttctga ccttttgggt tttaagcagg aggtgtcaga aaagttacca cagggataac      180
tggcttgtgg cggccaagcg ttcatagcga cgtcgctttt tgatccttcg atgtcggctc      240
ttcctatcat tgtgaagcag aattcaccaa gcgttggatt gttcacccac taatagggaa      300
cgtgagctgg gtttagaccg tcgtgagaca ggttagtttt accctactga tgatgtgtkg      360
ttgccatggt aatcctgctc agtacgagag gaaccgcagg ttcasacatt tggtgtatgt      420
gcttgcctt                                                             429
```

<210> SEQ ID NO 216
<211> LENGTH: 593
<212> TYPE: DNA
<213> ORGANISM: Homo sapien
<220> FEATURE:
<221> NAME/KEY: misc_feature
<222> LOCATION: (1)...(593)
<223> OTHER INFORMATION: n = A,T,C or G

<400> SEQUENCE: 216

```
tgacacctat gtccngcatc tgttcacagt ttccacaaat agccagcctt tggccacctc       60
tctgtcctga ggtatacaag tatatcagga ggtgtatacc ttctcttctc ttccccacca      120
aagagaacat gcaggctctg gaagctgtct taggagcctt tgggctcaga atttcagagt      180
cttgggtacc ttggatgtgg tctggaagga gaaacattgg ctctggataa ggagtacagc      240
cggaggaggg tcacagagcc ctcagctcaa gcccctgtgc cttagtctaa aagcagcttt      300
ggatgaggaa gcaggttaag taacatacgt aagcgtacac aggtagaaag tgctgggagt      360
```

| cagaattgca cagtgtgtag gagtagtacc tcaatcaatg agggcaaatc aactgaaaga | 420 |
| agaagaccna ttaatgaatt gcttangggg aaggatcaag gctatcatgg agatctttct | 480 |
| aggaagatta ttgtttanaa ttatgaaagg antagggcag ggacagggcc agaagtanaa | 540 |
| ganaacattg cctatanccc ttgtcttgca cccagatgct ggacaaggtg tca | 593 |

<210> SEQ ID NO 217
<211> LENGTH: 335
<212> TYPE: DNA
<213> ORGANISM: Homo sapien

<400> SEQUENCE: 217

| tgacaccttg tccagcatct gacgtgaaga tgagcagctc agaggaggtg tcctggattt | 60 |
| cctggttctg tgggctccgt ggcaatgaat tcttctgtga agtggatgaa gactacatcc | 120 |
| aggacaaatt taatcttact ggactcaatg agcaggtccc tcactatcga caagctctag | 180 |
| acatgatctt ggacctggag cctgatgaag aactggaaga caaccccaac cagagtgacc | 240 |
| tgattgagca ggcagccgag atgctttatg gattgatcca cgcccgctac atccttacca | 300 |
| accgtggcat cgcccagatg ctggacaagg tgtca | 335 |

<210> SEQ ID NO 218
<211> LENGTH: 248
<212> TYPE: DNA
<213> ORGANISM: Homo sapien

<400> SEQUENCE: 218

| tacgtactgg tcttgaaggt cttaggtaga gaaaaaatgt gaatatttaa tcaaagacta | 60 |
| tgtatgaaat gggactgtaa gtacagaggg aagggtggcc cttatcgcca gaagttggta | 120 |
| gatgcgtccc cgtcatgaaa tgttgtgtca ctgccccgaca tttgccgaat tactgaaatt | 180 |
| ccgtagaatt agtgcaaatt ctaacgttgt tcatctaaga ttatggttcc atgtttctag | 240 |
| tactttta | 248 |

<210> SEQ ID NO 219
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 219

| tgacgcttgg ccacttgaca caagtagggg ataaggacaa agacccatna ggtggcctgt | 60 |
| cagccttttg ttactgttgc ttccctgtca ccacggcccc ctctgtaggg gtgtgctgtg | 120 |
| ctctgtggac attggtgcat tttcacacat accattctct ttctgcttca cagcagtcct | 180 |
| gaggcgggag cacacaggac taccttgtca gatgangata atgatgtctg ccaactcac | 240 |
| cccccaacct tctcactagt tatangaaga gccangccta naaccttcta tcctgncccc | 300 |
| ttgccctatg acctcatccc tgttccatgc cctattctga tttctggtga actttggagc | 360 |
| agcctggttt ntcctcctca ctccagcctc tctccatacc atggtangg ggtgctgttc | 420 |
| cacncaaang gtcaggtgtg tctggggaat cctnanancct gccnggagtt tccnangcat | 480 |
| tcttaaaaac cttcttgcct aatcanatng tgtccagtgg ccaaccntcn | 530 |

<210> SEQ ID NO 220
<211> LENGTH: 531
<212> TYPE: DNA
<213> ORGANISM: Homo sapien

<400> SEQUENCE: 220

| | | | | | | |
|---|---|---|---|---|---|---|
| tgacgcttgg | ccacttgaca | ctaaatagca | tcttctaaag | gcctgattca | gagttgtgga | 60 |
| aaattctccc | agtgtcaggg | attgtcagga | acagggctgc | tcctgtgctc | actttacctg | 120 |
| ctgtgtttct | gctggaaaag | gagggaagag | gaatggctga | ttttttaccta | atgtctccca | 180 |
| gtttttcata | ttcttcttgg | atcctcttct | ctgacaactg | ttccctttg | gtcttcttct | 240 |
| tcttgctcag | agagcaggtc | tctttaaaac | tgagaaggga | gaatgagcaa | atgattaaag | 300 |
| aaaacacact | tctgaggccc | agagatcaaa | tattaggtaa | atactaaacc | gcttgcctgc | 360 |
| tgtggtcact | tttctcctct | ttcacatgct | ctatccctct | atccccacc | tattcatatg | 420 |
| gcttttatct | gccaagttat | ccggcctctc | atcaaccttc | tccctagcc | tactggggga | 480 |
| tatccatctg | ggtctgtctc | tggtgtattg | gtgtcaagtg | gccaagcgtc | a | 531 |

<210> SEQ ID NO 221
<211> LENGTH: 530
<212> TYPE: DNA
<213> ORGANISM: Homo sapien

<400> SEQUENCE: 221

| | | | | | | |
|---|---|---|---|---|---|---|
| attgacgctt | ggccacttga | cacccgcctg | cctgcaatac | tggggcaagg | gccttcactg | 60 |
| cttcctgcc | accagctgcc | actgcacaca | gagatcagaa | atgctaccaa | ccaagactgt | 120 |
| tggtcctcag | cctctctgag | gagaaagagc | agaagcctgg | aagtcagaag | agaagctaga | 180 |
| tcggctacgg | ccttggcagc | cagcttcccc | acctgtggca | ataaagtcgt | gcatggctta | 240 |
| acaatggggg | cacctcctga | gaaacacatt | gttaggcaat | tcggcgtgtg | ttcatcagag | 300 |
| catatttaca | caaacctcga | tagtgcagcc | tactatccac | tattgctcct | acgctgcaaa | 360 |
| cctgaacagc | atgggactgt | actgaatact | ggaagcagct | ggtgatggta | cttatttgtg | 420 |
| tatctaaaca | cagagaaggt | acagtaagaa | tatggtatca | taaacttaca | gggaccgcca | 480 |
| tcctatatgc | agtctgttgt | gaccaaaatg | tgtcaagtgg | ccaagcgtca | | 530 |

<210> SEQ ID NO 222
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 222

| | | | | | | |
|---|---|---|---|---|---|---|
| tgtatcgacg | tagtggtctc | cgggctacta | ggccgttgtg | tgctggtagt | acctggttca | 60 |
| ctgaaaggcg | catctccctc | cccgcgtcgc | cctgaagcag | ggggaggact | tcgcccagcc | 120 |
| aaggcagttg | tatgagttttt | agctgcggca | cttcgagacc | tctgagccca | cctccttcag | 180 |
| gagccttccc | cgattaagga | agccagggta | aggattcctt | cctcccccag | acaccacgaa | 240 |
| caaaccacca | ccccccctat | tctggcagcc | catatacatc | agaacgaaac | aaaaataaca | 300 |
| aataaacnaa | aaccaaaaaa | aaaagagaag | gggaaatgta | tatgtctgtc | catcctgttg | 360 |
| ctttagcctg | tcagctccta | nagggcaggg | accgtgtctt | ccgaatggtc | tgtgcagcgc | 420 |
| cgactgcggg | aagtatcgga | ggaggaagca | gagtcagcag | aagttgaacg | gtgggcccgg | 480 |

-continued

| | |
|---|---|
| cggctcttgg gggctggtgt tgtacttcga gaccgctttc gcttttttgtc ttagatttac | 540 |
| gtttgctctt tggagtggga naccactacn tcnataca | 578 |

<210> SEQ ID NO 223
<211> LENGTH: 578
<212> TYPE: DNA
<213> ORGANISM: Homo sapien

<400> SEQUENCE: 223

| | |
|---|---|
| tgtatcgacg tagtggtctc ctcttgcaaa ggactggctg gtgaatggtt tccctgaatt | 60 |
| atggacttac cctaaacata tcttatcatc attaccagtt gcaaaatatt agaatgtgtt | 120 |
| gtcactgttt catttgattc ctagaaggtt agtcttagat atgttacttt aacctgtatg | 180 |
| ctgtagtgct ttgaatgcat ttttttgtttg catttttgtt tgcccaacct gtcaattata | 240 |
| gctgcttagg tctggactgt cctggataaa gctgttaaaa tattccaccag tccagccatc | 300 |
| ttacaagcta attaagtcaa ctaaatgctt ccttgttttg ccagacttgt tatgtcaatc | 360 |
| ctcaatttct gggttcattt tgggtgccct aaatcttagg gtgtgacttt cttagcatcc | 420 |
| tgtaacatcc attcccaagc aagcacaact tcacataata ctttccagaa gttcattgct | 480 |
| gaagcctttc cttcacccag cggagcaact tgattttcta caacttccct catcagagcc | 540 |
| acaagagtat gggatatgga gaccactacg tcgataca | 578 |

<210> SEQ ID NO 224
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 224

| | |
|---|---|
| tgtatcgacg tantggtctc ccaaggtgct gggattgcag gcatgagcca ccactcccag | 60 |
| gtggatcttt ttcttatac ttacttcatt aggtttctgt tattcaagaa gtgtagtggt | 120 |
| aaaagtcttt tcaatctaca tggttaaata atgatagcct gggaaataaa tagaaatttt | 180 |
| ttcttcatc tttaggttga ataaagaaac agaaaaaata gaacatactg aaaataatct | 240 |
| aagttccaac catagaagaa ctgcagaaga aatgaagaaa gtgatgatga tttagatttt | 300 |
| gatattgatt tagaagacac aggaggagac cactacgtcg ataca | 345 |

<210> SEQ ID NO 225
<211> LENGTH: 347
<212> TYPE: DNA
<213> ORGANISM: Homo sapien

<400> SEQUENCE: 225

| | |
|---|---|
| tgtatcgacg tagtggtctc caaactgagg tatgtgtgcc actagcacac aaagccttcc | 60 |
| aacagggacg caggcacagg cagtttaaag ggaatctgtt tctaaattaa tttccacctt | 120 |
| ctctaagtat tctttcctaa aactgatcaa ggtgtgaagc ctgtgctctt tcccaactcc | 180 |
| cctttgacaa cagccttcaa ctaacacaag aaaaggcatg tctgacactc ttcctgagtc | 240 |
| tgactctgat acgttgttct gatgtctaaa gagctccaga acaccaaagg gacaattcag | 300 |
| aatgctggtg tataacagac tccaatggag accactacgt cgataca | 347 |

```
<210> SEQ ID NO 226
<211> LENGTH: 281
<212> TYPE: DNA
<213> ORGANISM: Homo sapien
<220> FEATURE:
<221> NAME/KEY: misc_feature
<222> LOCATION: (1)...(281)
<223> OTHER INFORMATION: n = A,T,C or G

<400> SEQUENCE: 226 aggngngga ntgtatcgac gtagtggtct cccaacagtc tgtcattcag tctgcaggtg      60
tcagtgtttt ggacaatgag gcaccattgt cacttattga ctcctcagct ctaaatgctg   120
aaattaaatc ttgtcatgac aagtctggaa ttcctgatga ggttttacaa agtattttgg   180
atcaatactc caacaaatca gaaagccaga aagaggatcc tttcaatatt gcagaaccac   240
gagtggattt acacacctca ggagaccact acgtcgatac a                        281

<210> SEQ ID NO 227
<211> LENGTH: 3646
<212> TYPE: DNA
<213> ORGANISM: Homo sapien

<400> SEQUENCE: 227
gggaaacact tcctcccagc cttgtaaggg ttggagccct ctccagtata tgctgcagaa      60
tttttctctc ggtttctcag aggattatgg agtccgcctt aaaaaaggca agctctggac   120
actctgcaaa gtagaatggc caaagttttgg agttgagtgg cccccttgaag ggtcactgaa   180 cctcacaatt gttcaagctg tgtggcgggt tgttactgaa actcccggcc tccctgatca   240
gtttccctac attgatcaat ggctgagttt ggtcaggagc accccttccg tggctccact   300
catgcaccat tcataatttt acctccaagg tcctcctgag ccagaccgtg ttttcgcctc   360
gaccctcagc cggttcggct cgccctgtac tgcctctctc tgaagaagag gagagtctcc   420
ctcacccagt cccaccgcct taaaaccagc ctactccctt agggtcatcc catgtctcct   480
cggctatgtc ccctgtaggc tcatcaccca ttgcctcttg gttgcaaccg tggtgggagg   540
aagtagcccc tctactacca ctgagagagg cacaagtccc tctgggtgat gagtgctcca   600 ccccccttcct ggtttatgtc ccttctttct acttctgact tgtataattg gaaaacccat   660
aatcctccct tctctgaaaa gccccaggct ttgacctcac tgatggagtc tgtactctgg   720
acacattggc ccacctggga tgactgtcaa cagctccttt tgacccttt cacctctgaa   780 gagagggaaa gtatccaaag agaggccaaa aagtacaacc tcacatcaac caataggccg   840
gaggaggaag ctagaggaat agtgattaga gacccaattg ggacctaatt gggacccaaa   900
tttctcaagt ggagggagaa cttttgacga tttccaccgg tatctcctcg tgggtattca   960
gggagctgct cagaaaccta taaacttgtc taaggcgact gaagtcgtcc aggggcatga  1020
tgagtcacca ggagtgtttt tagagcacct ccaggaggct tatcagattt acacccctt   1080 tgacctggca gccccgaaa atagccatgc tcttaatttg gcatttgtgg ctcaggcagc   1140
cccagatagt aaaaggaaac tccaaaaact agagggattt tgctggaatg aataccagtc   1200
agcttttaga gatagcctaa aaggttttgg acagtcaaga ggttgaaaaa caaaacaag   1260 cagctcaggc agctgaaaaa agccactgat aaagcatcct ggagtatcag agtttactgt   1320
tagatcagcc tcatttgact tcccctccca catggtgttt aaatccagct acactacttc   1380
ctgactcaaa ctccactatt cctgttcatg actgtcagga actgttggaa actactgaaa   1440
ctggccgacc tgatcttcaa aatgtgcccc taggaaaggt ggatgccacc atgttcacag   1500
```

-continued

```
acagtagcag cttcctcgag aagggactac gaaaggccgg tgcagctgtt accatggaga      1560
cagatgtgtt gtgggctcag gctttaccag caaacacctc agcacaaaag gctgaattga      1620
tcgccctcac tcaggctctc cgatggggta aggatattaa cgttaacact gacagcaggt      1680
acgcctttgc tactgtgcat gtacgtggag ccatctacca ggagcgtggg ctactcacct      1740
cagcaggtgg ctgtaatcca ctgtaaagga catcaaaagg aaaacacggc tgttgcccgt      1800
ggtaaccaga aagctgattc agcagctcaa gatgcagtgt gactttcagt cacgcctcta      1860
aacttgctgc ccacagtctc ctttccacag ccagatctgc ctgacaatcc cgcatactca      1920
acagaagaag aaaactggcc tcagaactca gagccaataa aaatcaggaa ggttggtgga      1980
ttcttcctga ctctagaatc ttcatacccc gaactcttgg gaaaacttta atcagtcacc      2040
tacagtctac cacccattta ggaggagcaa agctacctca gctcctccgg agccgtttta      2100
agatccccca tcttcaaagc ctaacagatc aagcagctct ccggtgcaca acctgcgccc      2160
aggtaaatgc caaaaaaggt cctaaaccca gcccaggcca ccgtctccaa gaaaactcac      2220
caggagaaaa gtgggaaatt gactttacag aagtaaaacc acccgggct gggtacaaat       2280
accttctagt actggtagac accttctctg gatgactga agcatttgct accaaaaacg       2340
aaactgtcaa tatggtagtt aagttttac tcaatgaaat catccctcga catgggctgc       2400
ctgtttgcca tagggtctga taatggaccg gccttcgcct tgtctatagt ttagtcagtc       2460
agtaaggcgt taaacattca atggaagctc cattgtgcct atcgacccca gagctctggg       2520
caagtagaac gcatgaactg caccctaaaa aacactctta caaattaat cttagaaacc        2580
ggtgtaaatt gtgtaagtct ccttcctta gccctactta gagtaaggtg cacccttac        2640
tgggctgggt tcttaccttt tgaaatcatg tatgggaggg tgctgcctat cttgcctaag     2700
ctaagagatg cccaattggc aaaatatca caaactaatt tattacagta cctacagtct      2760
ccccaacagg tacaagatat catcctgcca cttgttcgag gaacccatcc caatccaatt     2820
cctgaacaga cagggccctg ccattcattc ccgccaggtg acctgttgtt tgttaaaaag     2880
ttccagagag aaggactccc tcctgcttgg aagagacctc acaccgtcat cacgatgcca     2940
acggctctga agtggatgg cattcctgcg tggattcatc actcccgcat caaaaaggcc     3000
aacagagccc aactagaaac atgggtcccc agggctgggt caggcccctt aaaactgcac    3060
ctaagttggg tgaagccatt agattaattc tttttcttaa ttttgtaaaa caatgcatag    3120
cttctgtcaa acttatgtat cttaagactc aatataaccc ccttgttata actgaggaat    3180
caatgatttg attcccccaa aaacacaagt ggggaatgta gtgtccaacc tggttttac     3240
taaccctgtt tttagactct cccttcctt taatcactca gcttgtttcc acctgaattg      3300
actctccctt agctaagagc gccagatgga ctccatcttg gtctttcac tggcagccgc      3360
ttcctcaagg acttaacttg tgcaagctga ctcccagcac atccaagaat gcaattaact      3420
gataagatac tgtggcaagc tatatccgca gttcccagga attcgtccaa ttgatcacag      3480
ccccctctacc cttcagcaac caccaccctg atcagtcagc agccatcagc accgaggcaa     3540
ggccctccac cagcaaaaag attctgactc actgaagact tggatgatca ttagtatttt     3600
tagcagtaaa gttttttttt cttttctttt ccttttttct cgtgcc                      3646
```

<210> SEQ ID NO 228
<211> LENGTH: 419
<212> TYPE: DNA
<213> ORGANISM: Homo sapien

```
<220> FEATURE:
<221> NAME/KEY: misc_feature
<222> LOCATION: (1)...(419)
<223> OTHER INFORMATION: n = A,T,C or G

<400> SEQUENCE: 228
taagagggta caagatctaa gcacagccgt caatgcagaa cacagaacgt agcctggtaa      60
gtgtgttaag agtgggaatt tttggagtac agagtaaggc acctaaccct agctggggtt    120
tggtgacggt cccagatggc ttacagaaga agtgtcctg  agatgagttt ttaagaatga    180
ataaggatag acacaagtga ggactgactt ggcagtggtg aatggtgggt ggcaaaaaac    240
ttcgcatgta tggaaactgc acgtacagga atgaagaatg agactgtgtg gtgtttaatg    300
agctgcaaat actaatttta tcctgaaagt tttgaagagt taactaaaaa gtattttta    360 gtaaggaaat aaccctacat ttcagggtta ttgtttgttt anatattgaa ggtgcccaa     419

<210> SEQ ID NO 229
<211> LENGTH: 148
<212> TYPE: DNA
<213> ORGANISM: Homo sapien

<400> SEQUENCE: 229
aagagggtac ctgtatgtag ccatggtggc aatgagagac tgattactac ctgctggaga     60
ttgtttaagt gagttaatat attaaggata aagggagcca ggttttttga ctgttggaga   120
aggaaattac agatattgaa ggtcccaa                                       148

<210> SEQ ID NO 230
<211> LENGTH: 257
<212> TYPE: DNA
<213> ORGANISM: Homo sapien

<400> SEQUENCE: 230
taagagggta cmaaaaaaaa aaaatagaac gaatgagtaa gacctactat ttgatagtac     60
aacagggtga ctatagtcaa tgataactta attatacatt taacatagag tgtaattgga   120
ttgtttgtaa ctcgaaggat aaatgcttga gaggatggat accccattct ccatgatgta   180
cttatttcac attacatgcc tgtatcaaag catctcatat accctataaa tatgtacacc   240
tactatgtac cctctta                                                   257

<210> SEQ ID NO 231
<211> LENGTH: 260
<212> TYPE: DNA
<213> ORGANISM: Homo sapien

<400> SEQUENCE: 231
taagagggta cgggtatttg ctgatgggat ttttttttct ttcttttct  ttggaaaaca     60 aaatgaaagc cagaacaaaa ttattgaaca aaagacaggg actaaatctg gagaaatgaa   120
gtcccctcac ctgactgcca tttcattcta tctgaccttc cagtctaggt taggagaata   180
gggggtggag gggattaatc tgatacaggt atatttaaag caactctgca tgtgtgccag   240
aagtccatgg taccctctta                                               260

<210> SEQ ID NO 232
<211> LENGTH: 596
<212> TYPE: DNA
<213> ORGANISM: Homo sapien
```

```
<220> FEATURE:
<221> NAME/KEY: misc_feature
<222> LOCATION: (1)...(596)
<223> OTHER INFORMATION: n = A,T,C or G

<400> SEQUENCE: 232
tgctcctctt gccttaccaa ccacaaatta gaaccataat gagatgtcac ctcatacctg      60
gtgggattaa cattatttaa aaaatcagaa gtattgacaa ggatgtgaag aaattagaac    120
atctgtgcac tgttggtggg aatgtaaaaa aggtgtggcc actatgggta acagcatgaa    180
ggttcctcaa aaaaaatttt ttttaatcta ctctatgatc gatcttgagg ttgtttatgc    240
aaaagaactg aaatcaggat tttgaggaaa tattcacatt cccacatcca tttctgcttt    300
attcataata ctcaagagat ggaaacaacc taaatgtcca tcccgggatg aatggataaa    360
cacagtgtgg tatatgcata caatggaata ttatttagtc tttaaaaaga aaaattctat    420
catatactac aacttanatn aaccttgagg acacaatgct nagtgaaata agccacggaa    480
ggacgaatac tgcattattc ccttatatga agtatctaaa gtggtcaaac tcttanagca    540
naaagtaaaa atgggtggtt gccanacagt tggttaggcn agaaganaan cctant        596

<210> SEQ ID NO 233
<211> LENGTH: 96
<212> TYPE: DNA
<213> ORGANISM: Homo sapien

<400> SEQUENCE: 233
tcttctgaag acctttcgcg actcttaagc tcgtggttgg taaggcaaga ggagcgttgg     60
taaggcaaga ggagcgttgg taaggcaaga ggagca                               96

<210> SEQ ID NO 234
<211> LENGTH: 313
<212> TYPE: DNA
<213> ORGANISM: Homo sapien

<400> SEQUENCE: 234
tgtaagtcga gcagtgtgat gataaaactt gaatggatca atagttgctt cttatggatg     60
agcaaagaaa gtagtttctt gtgatggaat ctgctcctgg caaaaatgct gtgaacgttg    120
ttgaaaagac aacaaagagt ttagagtagt acataaattt agaatagtac ataaacttag    180
aatagtacat aaacttagta cataaataat gcacgaagca ggggcagggc ttgagagaat    240
tgacttcaat ttggaaagag tatctactgt aggttagatg ctctcaaaca gcatcacact    300
gctcgactta caa                                                       313

<210> SEQ ID NO 235
<211> LENGTH: 550
<212> TYPE: DNA
<213> ORGANISM: Homo sapien

<400> SEQUENCE: 235
aacgaggaca gatccttaaa aagaatgttg agtgaaaaaa gtagaaaata agataatctc     60
caaagtccag tagcattatt taaacatttt taaaaaatac actgataaaa attttgtaca    120
tttcccaaaa atacatatgg aagcacagca gcatgaatgc ctatgggrtt gaggataggg    180
gttgggagta gggatgggga taaggggga aaataaaacc agagaggagt cttacacatt    240
tcatgaacca aggagtataa ttatttcaac tatttgtacc wgaagtccag aaagagtgga    300
ggcagaaggg ggagaagagg gcgaagaaac gttttgggga gaggggtccc asaagagaga    360
```

```
ttttcgcgat gtggcgctac atacgttttt ccaggatgcc ttaagctctg caccctattt      420
ttctcatcac taatattaga ttaaaccctt tgaagacagc gtctgtggtt tctctacttc      480
agctttccct ccgtgtcttg cacacagtag ctgttttaca agggttgaac tgactgaagt      540
gagattattc                                                            550
```

<210> SEQ ID NO 236
<211> LENGTH: 325
<212> TYPE: DNA
<213> ORGANISM: Homo sapien

<400> SEQUENCE: 236

```
tagactgact catgtcccct accagagtag ctagaattaa tagcacaagc ctctacaccc       60
aggaactcac tattgaatac ataaatggaa tttattcagc cttaaaaagt ttggaaggaa      120
attctgacat atgctaaaac atggatgaac cttgaagact ttatgataag taaaagaagc      180
cagtcataaa aggaaaaata ttgcatgatt ccacttatat gaggtaccta gagtagtcaa      240
tttcatagaa acacaaaata gaatggtgtt tgccagggct tttgaggaaa agggaatgac      300
aagttagggg acatgagtca gtcta                                           325
```

<210> SEQ ID NO 237
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 237

```
tagactgact catgtcccct atctactcaa catttccact tgaagtctga taggcatctc       60 agcttatct tgtcccaaag caaactcttt atttcttttc atcctagtct ttatttcttg      120
tgctgtctta cccatctcaa aagagtgcca aaatccacca agttgctgaa acagaaatct      180
aagaaatatc cttgattctt cttttttccca tctacttcac ttctaattca ttagtaaata      240
atctgtttca gaaaaccaaa caccctcatgt tctcactcat aaggggagt tgaacaatga      300 gaacacacag acacagggag gggaacatca cacaccacgg cccgtcaggg agtangggac      360
atgagtcagt cta                                                        373
```

<210> SEQ ID NO 238
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 238

```
tagactgact catgtcccct ataatgctcc caggcatcag aaagcatctc aaactggagc       60
tgacaccatg gcagaggttt caggtaagtc acaaaagggg tcctaaagaa tttgccctca      120
atatcagagt gattagaaga agtggacaga gctacccaag ttaaacatat gcgagataaa      180
aaaaatatgg cacttgtgaa cacacactac aggaggaaaa taaggaacat aatagcatat      240
tgtgctatta tgatgatgaa gaacctctct anaagaaaac ataaccaaag aaacaaagaa      300
aattcctgcn aatgttttaat gctatagaag aaattaacaa aaacatatat tcaatgaatt      360
cagaaaagtt agcaggtcan aagaaaacaa atcaaagacc agaataatcc cattttagat      420
```

```
tgtcgagtaa actanaacag aaagaatacc actggaaatt gaattcctac gtangggaca      480
tgantcantc ta                                                         492

<210> SEQ ID NO 239
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 239
tggaaagtat taatgatgg gcaacttgct gtttacttcc tacatatccc atcatcttct       60 gtatttttt aaataacttt tttttggatt tttaaagtaa ccttattctg agaggtaaca      120
tggattacat acttctaagc cattaggaga ctctatgtta aaccaaaagg aaatgttact     180
agatcttcat ttgatcaata ggatgtgata atcatcatct ttctgctcta atggaaaagt    240
actanaaaca tggaaccata atcttagatg aacaacgtta gaatttgcac taattctacg    300
gaatttcagt aattcggcaa atgtcgggca gtgacacaac atttcatgac ggggacgcat    360
ctaccaactt ctggcgataa gggccaccct tccctctgta cttacagtcc catttcatac    420
acagtctttg attaaatatt cacattttt ctctacctaa agaccttcaa gaccagtacg     480
ta                                                                   482

<210> SEQ ID NO 240
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 240
tgtatcgacg tagtggtctc cccatgtgat agtctgaaat atagcctcat gggatgagag      60
gctgtgcccc agcccgacac ccgtaaaggg tctgtgctga ggtggattag taaaagagga    120
aagccttgca gttgagatag aggaagggca ctgtctcctg cctgcccctg ggaactgaat    180
gtctcggtat aaaacccgat tgtacatttg ttcaattctg agataggaga aaaaccaccc    240
tatggcggga ggcgagacat gttggcagca atgctgcctt gttatgcttt actccacaga    300
tgtttgggcg gagggaaaca taaatctggc ctacgtcac atccaggcat agtacctccc     360
tttgaactta attatgacac agattccttt gctcacatgt ttttttgctg accttctcct    420
tattatcacc ctgctctcct accgcattcc ttgtgctgag ataatgaaaa taatatcaat    480
aaaaacttga nggaactcgg agaccactac gtcgataca                            519

<210> SEQ ID NO 241
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 241
tgtatcgacg tagtggtctc cactcccgcc ttgacggggc tgctatctgc cttccaggcc      60
actgtcacgg ctcccgggta gaagtcactt atgagacaca ccagtgtggc cttgttggct    120
```

```
tgaagctcct cagaggaggg tgggaacaga gtgaccgagg gggcagcctt gggctgacct        180
aggacggtca gcttggtccc tccgccaaac acgagagtgc tgctgcttgt atatgagctg        240
cagtaataat cagcctcgtc ctcagcctgg agcccagaga tggtcaggga ggccgtgttg        300
ccanacttgg agccagagaa gcgattagaa acccctgagg gccgattacc gacctcataa        360
atcatgaatt tggggctttt gcctgggtgc tgttggtacc angagacatt attataacca        420
ccaacgtcac tgctggttcc antgcaggga aaatggttga tcnaactgtc caagaaaacc        480
actacgtcca taccaatcca ctaattgccn gccgcctgca ggttcaacca tattggggaa        540
naactccccn ccgccgtttg ggattgncat naacctttga aatttttttcc tattanttgt        600 cccctaaaa taaaccnttg ggcnttaatc cattgggtcc atancttntt tncccggttt         660
ttaaaanttg tttatcccgc cncccnattt cccccccaac tttccaaaac ccgaaaaccnt       720 tnaaatttnt tnaaacccctg gggggttccc nnaattnnan ttnaanctnc c                771

<210> SEQ ID NO 242
<211> LENGTH: 167
<212> TYPE: DNA
<213> ORGANISM: Homo sapien

<400> SEQUENCE: 242
tgggcacctt caatatcggg ctcatcgata acatcacgct gctgatgctg ctgttgctgg         60
tcctctctag gaacctctgg attttcaaat tctttgagga attcatccaa attatctgcc        120
tctcctcctt tcctcctttt tctaaggtct tctggtacaa gcggtca                     167

<210> SEQ ID NO 243
<211> LENGTH: 338
<212> TYPE: DNA
<213> ORGANISM: Homo sapien

<400> SEQUENCE: 243
ttgggcacct tcaatatcta ctgatctaaa tagtgtggtt tgaggcctct tgttcctggc         60
taaaaatcct tggcaagagt caatctccac tttacaatag aggtaaaaat cttacaatgg       120
atattcttga caaagctagc atagagacag caatttttaca caaggtatttt ttcacctgtt     180 taataacagt ggttttccta cacccatagg gtgccaccaa gggaggagtg cacagttgca       240
gaaacaaatt aagatactga agacaacact acttaccatt tcccgtatag ctaaccacca      300
gttcaactgt acatgtatgt tcttatgggc aatcaaga                               338

<210> SEQ ID NO 244
<211> LENGTH: 346
<212> TYPE: DNA
<213> ORGANISM: Homo sapien

<400> SEQUENCE: 244
tttttggctc ccatacagca cactctcatg ggaaatgtct gttctaaggt caacccataa        60
tgcaaaaatc atcaatatac ttgaagatcc ccgtgtaagg tacaatgtat ttaatattat      120
cactgataca attgatccaa taccagttttt agtctggcat tgaatcaaat cactgttttt    180
gttgtataaa aagagaaata tttagcttat atttaagtac catattgtaa gaaaaagat       240 gcttatcttt acatgctaaa atcatgatct gtacattggt gcagtgaata ttactgtaaa      300
agggaagaag gaatgaagac gagctaagga tattgaaggt gcccaa                     346
```

```
<210> SEQ ID NO 245
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 245
accaatccca cacggatact gagggacaag tatatcatcc catttcatcc ctacagcagc      60
aacttcatga ggcaggagtt attagtccca ttttacagaa gaggaaactg agacttaggg     120
agatcaagta atttgcccag gtcgcacaat tagtgataga gccagggctt gaagcgacgt     180
ctgtcttaag ccaatgaccc ctgcagatta ttagagcaac tgttctccac aacagtgtaa     240
gcctcttgct anaagctcag gtccacaagg gcagagattt ttgtctgttt tgctcattgc     300
tccttcccca ttgcttagag cagggtctgc cacgaancag gttctcaatg catagttatt     360
aaatgtatat aagagcaaac atatgttaca gagaactttc tgtatgcttg tcacttacat     420
gaatcacctg tganatgggt atgcttgttc cccantgttg cagatnaaga tattgaangt     480
gcccaaatca ctanttgcgg gcgcctgcan gtccancata t                          521

<210> SEQ ID NO 246
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 246
tggaaccaat ccaaataccc atcaatgata gactggataa agaaaatttg gcacatgttc      60
accatgaaat actatgcagc cataaaaaag gatgagttca tcctttgc agggacatgg      120 atgaagctgg agaccatcat tctcagcaaa ctaacaaggg aacagaaaac caaacactgc     180
atgttctcac tcttaagtgg gagctgaaca atgagaacac atggacacag ggaggggaac     240
atcacacagt ggggcctgct ggtgggtagg ggtctagggg agggatagca ttaggagaaa     300
tacctaatgt agatgacggg ttgatgggtg cagcaaacca ccatgacacg tgtataccta     360
tgtaacaaac ctgcatgttc tgcacatgta ccccagaact taaagtgtta ataaaaaaat     420
taagaaaaaa gttaagtatg tcatagatac ataaaatatt gtanatattg aaggtgccca     480
aa                                                                     482

<210> SEQ ID NO 247
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 247
ttcgatacag gcacagagta agcagaaaaa tggctgtggt ttaaccaagt gagtacagtt      60
aagtgagaga ggggcagaga agacaagggc atatgcaggg ggtgattata acaggtggtt     120
gtgctgggaa gtgagggtac tcgggatga ggaacagtga aaaagtggca aaagtggta     180 agatcagtga attgtacttc tccagaattt gatttctggn ggagtcaaat aactatccag     240
```

```
tttggggtat catanggcaa cagttgaggt ataggaggta gaagtcncag tgggataatt    300
gaggttatga anggtttggt actgactggt actgacaang tctgggttat gaccatggga    360
atgaatgact gtanaagcgt anaggatgaa actattccac ganaaagggg tccnaaaact    420
aaaaannnaa gnnnnnggggg aatattattt atgtggatat tgaangtgcc caaa         474

<210> SEQ ID NO 248
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 248
ttcgatacag gcaaacatga actgcaggag ggtggtgacg atcatgatgt tgccgatggt     60
ccggatggnc acgaagacgc actggancac gtgcttacgt ccttttgctc tgttgatggc    120
cctgagggga cgcaggaccc ttatgaccct cagaatcttc acaacgggag atggcactgg    180
attgantccc antgacacca gagacacccc aaccaccagn atatcantat attgatgtag    240
ttcctgtaga nggcccccctt gtggaggaaa gctccatnag ttggtcatct tcaacaggat    300
ctcaacagtt tccgatggct gtgatgggca tagtcatant taaccntgtn tcgaa         355

<210> SEQ ID NO 249
<211> LENGTH: 434
<212> TYPE: DNA
<213> ORGANISM: Homo sapien

<400> SEQUENCE: 249
ttggattggt cctccaggag aacaagggga aaaaggtgac cgagggctcc ctggaactca     60
aggatctcca ggagcaaaag gggatggggg aattcctggt cctgctggtc ccttaggtcc    120
acctggtcct ccaggcttac caggtcctca aggcccaaag ggtaacaaag gctctactgg    180
acccgctggc cagaaaggtg acagtggtct tccagggcct cctgggcctc caggtccacc    240
tggtgaagtc attcagcctt taccaatctt gtcctccaaa aaaacgagaa gacatactga    300
aggcatgcaa gcagatgcag atgataatat tcttgattac tcggatggaa tggaagaaat    360
atttggttcc ctcaattccc tgaaacaaga catcgagcat atgaaatttc caatgggtac    420
tcagaccaat ccaa                                                      434

<210> SEQ ID NO 250
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 250
tggattggtc acatggcaga gacaggattc caaggcagtg agaggaggat acaatgcttc     60
tcactagtta ttattattta ttttatttt gagatgaagt ctcgctttgt ctcccaggct    120
ggagagcggt ggtgcgatct tggctctctg caaccccgc ctcaagcaat tctcctgtct    180
tagcctcgcg ggtagatgga attacaggcg cccaccgcca tgcccaacta atttttttgt    240
gtcttcagta gagacaggggt ttcgccatgt tgggcaggct ggtcttgaac tcctgacctc    300
nagtgatctg ccctcctcgg cctcacaaag tgctggaatt acaggcatgg gctgctgcac    360
```

```
ccagtcaact tctcactagt tatggcctta tcattttcac cacattctat tggcccaaaa    420 aaaaaaaaan                                                          430
```

<210> SEQ ID NO 251
<211> LENGTH: 329
<212> TYPE: DNA
<213> ORGANISM: Homo sapien

<400> SEQUENCE: 251

```
tggtactcca ccatyatggg gtcaaccgcc atcctcgccc tcctcctggc tgttctccaa     60
ggagtctgtg ccgaggtgca gctgrtgcag tctggagcag aggtgaaaaa gtccggggag   120
tctctgaaga tctcctgtaa gggttctgga tacaccttta agatctactg gatcgcctgg   180
gtgcgccagt tgcccgggaa aggcctggag tggatggggc tcatctttcc tgatgactct   240
gataccagat acagcccgtc cttccaaggc caggtcacca tctcagtcga taagtccatc   300
agcaccgcct atctgcagtg gagtaccaa                                      329
```

<210> SEQ ID NO 252
<211> LENGTH: 536
<212> TYPE: DNA
<213> ORGANISM: Homo sapien

<400> SEQUENCE: 252

```
tggtactcca ctcagcccaa ccttaattaa gaattaagag ggaacctatt actattctcc     60
caggctcctc tgctctaacc aggcttctgg gacagtatta gaaaggatg tctcaacaag    120 tatgtagatc ctgtactggc ctaagaagtt aaactgagaa tagcataaat cagaccaaac    180
ttaatggtcg ttgagacttg tgtcctggag cagctgggat aggaaaactt ttgggcagca    240
agaggaagaa ctgcctggaa gggggcatca tgttaaaaat tacaagggga acccacacca    300 ggccccttc ccagctctca gcctagagta ttagcatttc tcagctagag actcacaact    360
tccttgctta gaatgtgcca ccggggggag tccctgtggg tgatgaggct ctcaagagtg    420
agagtggcat cctatcttct gtgtgcccac aggagcctgg cccgagactt agcaggtgaa    480
gtttctggtc caggcttttgc ccttgactca ctatgtgacc tctggtggag taccaa       536
```

<210> SEQ ID NO 253
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 253

```
ntgttgcgat cccagtaact cgggaagctg aggcgggagg atcacctgag ctcaggaggt     60
tgaggccgca gtgagccggg accacgccac tacactccag cctggggcat agagtgagac    120
cctccaagac agaaaagaaa agaaaggaag ggaaagggaa agggaaaagg aaaaggaaaa    180
ggaaaaggaa aaggaaaaga caagacaaaa caagacttga atttggatct cctgacttca    240
attttatgtt ctttctacac cacaattcct ctgcttacta agatgataat ttagaaaccc    300
ctcgttccat tcttttacagc aagctggaag tttggtcaag taattacaat aatagtaaca    360
aatttgaata ttatatgcca ggtgtttttc attcctgctc tcacttaatt ctcaccactc    420
tgatataaat acaattgctg ccgggtgtgg tggctcatgc ctgtaatccc ggcactttgg    480
gagaccgagg tgggcggats gcaacaa                                        507
```

<210> SEQ ID NO 254
<211> LENGTH: 222
<212> TYPE: DNA
<213> ORGANISM: Homo sapien
<220> FEATURE:
<221> NAME/KEY: misc_feature
<222> LOCATION: (1)...(222)
<223> OTHER INFORMATION: n = A,T,C or G

<400> SEQUENCE: 254

| | | | | | |
|---|---|---|---|---|---|
| ttggattggt | cactgtgagg | aagccaaatc | ggatccgaga | gtcttttct | 60 aaaggccagt |
| actggccaca | ctttctcctg | ccgccttcct | caaagctgaa | gacacacaga | 120 gcaaggcgct |
| tctgttttac | tccccaatgg | taactccaaa | ccatagatgg | ttagctnccc | 180 tgctcatctt |
| tccacatccc | tgctattcag | tatagtccgt | ggaccaatcc | aa | 222 |

<210> SEQ ID NO 255
<211> LENGTH: 463
<212> TYPE: DNA
<213> ORGANISM: Homo sapien

<400> SEQUENCE: 255

| | | | | | |
|---|---|---|---|---|---|
| tgttgcgatc | cataaatgct | gaaatggaaa | taaacaacat | gatgagggag | 60 gattaagttg |
| gggagggagc | acattaaggt | ggccatgaag | tttgttggaa | gaagtgactt | 120 ttgaacaagg |
| ccttggtgtt | aagagctgat | gagagtgtcc | cagacagagg | ggccactggt | 180 acaatagacg |
| agatgggaga | gggcttggaa | ggtgtgcgaa | ataggaagga | gtttgttctg | 240 gtatgagtct |
| agtgaacaca | gaggcgagag | gccctggtgg | gtgcagctgg | agagttatgc | 300 agaataacat |
| taggccctgt | gggggactgt | agactgtcag | caataatcca | cagtttggat | 360 tttattctaa |
| gagtgatggg | aagccgtgga | aaggggggtta | agcaaggagt | gaaattatca | 420 gatttacagt |
| gataaaaata | aattggtctg | gctactgggg | aaaaaaaaa | aaa | 463 |

<210> SEQ ID NO 256
<211> LENGTH: 262
<212> TYPE: DNA
<213> ORGANISM: Homo sapien

<400> SEQUENCE: 256

| | | | | | |
|---|---|---|---|---|---|
| ttggattggt | caacctgctc | aactctacyt | ttcctccttc | ttcctaaaaa | 60 attaatgaat |
| ccaatacatt | aatgccaaaa | cccttgggtt | ttatcaatat | ttctgttaaa | 120 aagtattatc |
| cagaactgga | cataatacta | cataataata | cataacaacc | ccttcatctg | 180 gatgcaaaca |
| tctattaata | tagcttaaga | tcactttcac | tttacagaag | caacatcctg | 240 ttgatgttat |
| tttgatgttt | ggaccaatcc | aa | | | 262 |

<210> SEQ ID NO 257
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 257

| | | | | | |
|---|---|---|---|---|---|
| gnggnnnnnn | nnncaattcg | actcngttcc | cntggtancc | ggtcgacatg | 60 gccgcgggat |
| taccgcttgt | nnctgggggt | gtatggggga | ctatgaccgc | ttgtagctgg | 120 ggtgtatgg |
| gggactatga | ccgcttgtag | mtggkggtgt | atggggggact | atgaccgctt | 180 gtcgggtggt |

```
cggataaacc gacgcaaggg acgtgatcga agctgcgttc ccgctctttc gcatcggtag     240
ggatcatgga cagcaatatc cgcattcgyc tgaaggcgtt cgaccatcgc gtgctcgatc     300
aggcgaccgg cgacatcgcc gacaccgcac gccgtaccgg cgcgctcatc cgcggtccga     360
tcccgcttcc cacgcgcatc gagaagttca cggtcaaccg tggcccgcac gtcgacaaga     420
agtcgcgcga gcagttcgag gtgcgtacct acaagcggtc a                         461
```

<210> SEQ ID NO 258
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 258

```
tgaccgcttg tagctggggg tgtatggggg actacgaccg cttgtagctg ggggtgtatg      60
ggggactatg accgcttgta gctgggggtg tatgggggac tatgaccgct tgtagctggg     120
ggtgtatggg ggactaggac cgcttgtagc tgggggtgta tggggactat gaccgcttg     180 tagctggggg tgtatggggg actacgaccg cttgtagctg ggggtgtatg ggggactatg     240
accgcttgta nctgggggtg tatgggggac tatgaccgct tgtgctgcct ggggatggg     300 aggagagttg tggttgggga aaaaaaaaaa aa                                   332
```

<210> SEQ ID NO 259
<211> LENGTH: 291
<212> TYPE: DNA
<213> ORGANISM: Homo sapien
<220> FEATURE:
<221> NAME/KEY: misc_feature
<222> LOCATION: (1)...(291)
<223> OTHER INFORMATION: n = A,T,C or G

<400> SEQUENCE: 259

```
taccgcttgt gaccgcttgt gaccgcttgt gaccgcttgt gaccgcttgt gaccgcttgt      60
gaccgcttgt gaccgcttgt gaccgcttgt gaccgcttgt gaccgcttgt gaccgcttgt     120
gaccgcttgt gaccgcttgt nacnggggt gtctggggga ctatgannga ntgtnactgg      180
gggtgtctgg gggnctatga nngantgtna cnggggggtgt ctgggggact atganngact     240 gtcnncctg ggggatcnga ggagantngn ggntagngat ggttngggan a               291
```

<210> SEQ ID NO 260
<211> LENGTH: 238
<212> TYPE: DNA
<213> ORGANISM: Homo sapien

<400> SEQUENCE: 260

```
taagagggta ctggttaaaa tacaggaaat ctggggtaat gaggcagaga accaggatac      60
tttgaggtca gggatgaaaa ctagaatttt tttctttttt tttgcctgag aaacttgctg     120
ctctgaagag gcccatgtat taattgcttt gatcttcctt ttcttacagc cctttcaagg     180
gcagagccct ccttatcctg aaggaatctt atccttagct atagtatgta ccctctta       238
```

<210> SEQ ID NO 261
<211> LENGTH: 746
<212> TYPE: DNA
<213> ORGANISM: Homo sapien
<220> FEATURE:
<221> NAME/KEY: misc_feature
<222> LOCATION: (1)...(746)
<223> OTHER INFORMATION: n = A,T,C or G

<400> SEQUENCE: 261

| | | | | | |
|---|---|---|---|---|---|
| ttgggcacct | tcaatatcaa | tagctaacat | ttattgagtg | tttatcgtat | cataaaacac | 60 |
| tgttctaagc | ctttaaacgt | actaattcat | ttaatgctca | taatcacttt | agaaggtggg | 120 |
| tactagtatt | agtctcattt | acagatgcaa | catgcaggca | cagagaggtt | aattaacttg | 180 |
| cccaaggtaa | cacagctaag | aaatagaaaa | aatattgaat | ctggaaagtt | gggcttctgg | 240 |
| gtaacccaca | gagtcttcaa | tgagcctggg | gcctcactca | gtttgctttt | acaaagcgaa | 300 |
| tgagtaacat | cacttaattc | agtgagtagg | ccaaatggag | gtcagctacg | agtttctgct | 360 |
| gttcttgcag | tggactgaca | gatgtttaca | acgtctggcc | atcagtwaat | ggactgatta | 420 |
| tcattgggaw | gtgggtgggc | tgaatgttgg | ccagtgaagt | ttattcawgc | catattttta | 480 |
| tgtttaggat | gacttttggc | tggtcctagg | gcaagctctg | tctgscacgg | aacacagaat | 540 |
| wacacaggga | cccctcaat | ttctggtgtg | gctagaacca | tgaaccactg | gttgggggaa | 600 |
| caagcggtca | aaacctaagt | gcggccggct | ggcagggtcc | acccatatgg | ggaaaactcc | 660 |
| cnacgcgttt | ggaatgcctn | agctngaatt | attctaanag | ttgtccncnt | aaaattagcc | 720 |
| tgggcgttaa | tcangggtcn | naagcc | | | | 746 |

<210> SEQ ID NO 262
<211> LENGTH: 588
<212> TYPE: DNA
<213> ORGANISM: Homo sapien
<220> FEATURE:
<221> NAME/KEY: misc_feature
<222> LOCATION: (1)...(588)
<223> OTHER INFORMATION: n = A,T,C or G

<400> SEQUENCE: 262

| | | | | | |
|---|---|---|---|---|---|
| tgaccgcttg | tcatctcaca | tggggtcctg | cacgcttttg | cctttgtagg | aaacctgaca | 60 |
| tttgtctgtt | tcttctttct | cttttccttc | ccatatcctc | ctaatttacg | tttgacttgt | 120 |
| ttgctgagga | ggcaggagct | agagactgct | gtgagctcat | aggggtggga | agtttatcct | 180 |
| tcaagtcccg | cccactcatc | actgcttctc | accttcccct | gaccaggctt | acaagtgggt | 240 |
| tcttgcctgc | tttcccttg | gacccaacaa | gccctgtaa | tgagtgtgca | tgactctgac | 300 |
| agctgtggac | tcagggtcct | tggctacagc | tgccatgtaa | aatatctcat | ccagttctcg | 360 |
| caaattgtta | aaataaccac | atttcttaga | ttccagtacc | caaatcatgt | ctttacgaac | 420 |
| tgctcctcac | acccagaagt | ggcacaataa | ttcttgggga | attattactt | ttttttttct | 480 |
| ctctnttnnc | gnnngnnnng | gnnngnccag | gaattaccac | nttggaagac | ctggccngaa | 540 |
| tttattatan | agggagccg | attnttttc | ctaacacaaa | gcgggtca | | 588 |

<210> SEQ ID NO 263
<211> LENGTH: 730
<212> TYPE: DNA
<213> ORGANISM: Homo sapien
<220> FEATURE:
<221> NAME/KEY: misc_feature
<222> LOCATION: (1)...(730)
<223> OTHER INFORMATION: n = A,T,C or G

<400> SEQUENCE: 263

```
ttttttttttt tttggcctga gcaactgaaa ttatgaaatt tccatatact caaagagta      60
agactgcaaa aagattaaat gtaaaagttg tcttgtatac agtaatgttt aagatacct    120
ttanatttat aaatggaaaa ttagggcatt tggatataca agttgaaaat tcaggagtga    180
ggttgggctg gctgggtata tactgaaaac tgtcagtaca cagatgacat ctaaaaccac    240
aaatctggtt ttattttagc agtgatatgt gtcactccca caaaagcctt cccaattggc    300
ctcagcatac acaacaagtc acctccccac agccctctac acataaacaa attccttagt    360
ttagttcagg aggaaatgcg cccttttcct tccgctctag gtgaccgcaa ggcccagttc    420
tcgtcaccaa gatgttaagg gaagtctgcc aaagaggcat ctgaaggaa ataaggggaa     480
tgggagtgac cacaaaggaa agccaaggan aaactttgga gaccgtttct aganccctgg    540
catttcacaa caaaactcng gaacaaacct tgtctcatca atcatttaag cccttcgttt    600
ggannagact ttctgaactg ggcgctgaac ataanccctca ttgaatgtct tcacagtctc   660
ccagctgaag gcacaccttg ggccagaagg ggaatcttcc aggtcctcaa nacagggctc    720
gcccttgnc                                                            730
```

<210> SEQ ID NO 264
<211> LENGTH: 715
<212> TYPE: DNA
<213> ORGANISM: Homo sapien
<220> FEATURE:
<221> NAME/KEY: misc_feature
<222> LOCATION: (1)...(715)
<223> OTHER INFORMATION: n = A,T,C or G

<400> SEQUENCE: 264

```
ttttttttttt tttggccagt atgatagtct ctaccactat attgaagctc ttaggtcatt    60
tacacttaat gtggttatag atgctgttga gcttacttct accaccttgc tatttctccc    120
gtctctttt tgttcctttt ctcttctttt cctcccttat tttataattg aatttttag    180
gattctattt tatatagatt tatcagctat aacactttgt attcttttgt tttgtggttc    240
ttctgtcatt tcaatgtgca tcttaaactc atcacaatct attttcaaat aatatcatat    300
aaccttacat ataatgtaag aatctaccac catatatttc catttctccc ttccatccta    360
tgtntgtcat attttttcct ttatatatgt tttaaagaca taatagtata tgggaggttt    420
ttgcttaaaa tgtgatcaat attccttcaa ngaaacgtaa aaattcaaaa taaatntctg    480
tttattctca aatnnaccta atatttccta ccatntctna tacntttcaa gaatctgaag    540
gcattggttt tttccggctt aagaacctcc tctaaagcac tctaagcaga attaagtctt    600
ctgggagagg aattctccca agcttgggcc ttnanntgta ctccntnang gttaaantttt   660
ggccgggaaa tagaaattcc aagttaacag gntantttt nttttntnn tcncc           715
```

<210> SEQ ID NO 265
<211> LENGTH: 152
<212> TYPE: DNA
<213> ORGANISM: Homo sapien

<400> SEQUENCE: 265

```
ttttttttttt tttcccaaca caaagcacca ttatctttcc tcacaatttt caacatagtt     60
tgattcccat gaagaggtta tgatttctaa agaaaacatg gctactatac tatcaatcag    120
ggttaaatct ttttttttg agacggagtt ta                                    152
```

```
<210> SEQ ID NO 266
<211> LENGTH: 193
<212> TYPE: DNA
<213> ORGANISM: Homo sapien
<220> FEATURE:
<221> NAME/KEY: misc_feature
<222> LOCATION: (1)...(193)
<223> OTHER INFORMATION: n = A,T,C or G

<400> SEQUENCE: 266
taaactccgt cccttctta atcaatatgg aggctaccca ctccacatta ccttcttttc      60
aagggactgt ttccgtaact gttgtgggta ttcacgacca ggcttctaaa cctcttaaaa    120
ctccccaatt ctggtgccaa cttggacaac atgctttttt tttttttttt ttttttttn    180 gagacggagt tta                                                        193

<210> SEQ ID NO 267
<211> LENGTH: 460
<212> TYPE: DNA
<213> ORGANISM: Homo sapien

<400> SEQUENCE: 267
tgttgcgatc ccttaagcat gggtgctatt aaaaaaatgg tggagaagaa aatacctgga     60
atttacgtct tatctttaga gattgggaag accctgatgg aggacgtgga gaacagcttc   120
ttcttgaatg tcaattccca agtaacaaca gtgtgtcagg cacttgctaa ggatcctaaa   180
ttgcagcaag gctacaatgc tatgggattc tcccagggag gccaatttct gagggcagtg   240
gctcagagat gcccttcacc tcccatgatc aatctgatct cggttggggg acaacatcaa   300
ggtgtttttg gactccctcg atgcccagga gagagctctc acatctgtga cttcatccga   360
aaaacactga atgctggggc gtactccaaa gttgttcagg aacgcctcgt gcaagccgaa   420
tactggcatg acccataaaa ggaggatgtg gatcgcaaca                          460

<210> SEQ ID NO 268
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 268
tgttgcgatc cgttgataga atagcgacgt ggtaatgagt gcatggcacg cctccgactt     60
accttcgccc gtggggaccc cgagtacgtc tacggcgtcg tcacttagag taccctctgg   120
acgcccgggc gcgttcgatt taccggaagc gcgagctgca gtgggcttgc gccccggcc    180 aaattctttg gggggtttaa ggccgcgggg aatttgaggt atctctatca gtatgtagcc   240
aagttggaac agtcgccatt cccgaaatcg ctttctttga atccgcaccg cctccagcat   300
tgcctcattc atcaacctga aggcacgcat aagtgacggt tgtgtcttca gcagctccac   360
tccataacta gcgcgctcga cctcgtcttc gtacgcgcca ggtccgtgcg tgcgaattcc   420
caactccgtt gagttgcgca tttcaagttn cgaaactgtt cgcctccacn atttggcatg   480
ttcacgcatg acacggaata aactcgtcca gtaccgggaa tgggatcgca aca          533

<210> SEQ ID NO 269
<211> LENGTH: 50
<212> TYPE: DNA
<213> ORGANISM: Homo sapien
```

<400> SEQUENCE: 269

| | | |
|---|---|---|
| tttttttttt ttcgcctgaa ttagctacag atcctcctca caagcggtca | 50 | |

<210> SEQ ID NO 270
<211> LENGTH: 519
<212> TYPE: DNA
<213> ORGANISM: Homo sapien

<400> SEQUENCE: 270

| | |
|---|---|
| tgttgcgatc caaataaccc accagcttct tgcacacttc gcagaagcca ccgtcctttg | 60 |
| gctgagtcac gtgaacggtc agtgcaagca gccgcgtgcc agagcagagg tgcagcatgc | 120 |
| tgcacaccag ctcagggctg acctcctcca gcaggatgga caggatggag ctgccgtacg | 180 |
| tgtccaccac ctcctggcac tcttccgaca gggacttcgg cagcttcgag cacattttgt | 240 |
| caaaagcgtc gagtatttct ttctcagtct tgttgttgtc aatcagcttg gtcacctcct | 300 |
| tcaccaggaa ttcacacacc tcacagtaaa catcagactt tgctgggacc tcgtgcttct | 360 |
| taatgggctc caccagttcc agggcaggga tgacattctt ggaggccact ttggcgggga | 420 |
| ccagagtctg catgggcatc tctttcacct catcacagaa cccaaccagc gcacagatct | 480 |
| ccttgggttg catgtgcatc atcatctggg atcgcaaca | 519 |

<210> SEQ ID NO 271
<211> LENGTH: 457
<212> TYPE: DNA
<213> ORGANISM: Homo sapien

<400> SEQUENCE: 271

| | |
|---|---|
| tttttttttt tcgggcggc gaccggacgt gcactcctcc agtagcggct gcacgtcgtg | 60 |
| ccaatggccc gctatgagga ggtgagcgtg tccggcttcg aggagttcca ccgggccgtg | 120 |
| gaacagcaca atggcaagac cattttcgcc tactttacgg gttctaagga cgccgggggg | 180 |
| aaaagctggt gccccgactg cgtgcaggct gaaccagtcg tacgagaggg gctgaagcac | 240 |
| attagtgaag gatgtgtgtt catctactgc caagtaggag aagagcctta ttggaaagat | 300 |
| ccaaataatg acttcagaaa aaacttgaaa gtaacagcag tgcctacact acttaagtat | 360 |
| ggaacacctc aaaaactggt agaatctgag tgtcttcagg ccaacctggt ggaaatgttg | 420 |
| ttctctgaag attaagattt taggatggca atcaaga | 457 |

<210> SEQ ID NO 272
<211> LENGTH: 102
<212> TYPE: DNA
<213> ORGANISM: Homo sapien

<400> SEQUENCE: 272

| | |
|---|---|
| tttttttttt ttgggcaaca acctgaatac cttttcaagg ctctggcttg ggctcaagcc | 60 |
| cgcagggaa atgcaactgg ccaggtcaca gggcaatcaa ga | 102 |

<210> SEQ ID NO 273
<211> LENGTH: 455
<212> TYPE: DNA
<213> ORGANISM: Homo sapien
<220> FEATURE:
<221> NAME/KEY: misc_feature
<222> LOCATION: (1)...(455)
<223> OTHER INFORMATION: n = A,T,C or G

<400> SEQUENCE: 273

```
tttttttttt ttggcaatca acaggtttaa gtcttcggcc gaagttaatc tcgtgttttt      60
ggcaatcaac aggtttaagt cttcggccga agttaatctc gtgttttTGG caatcaacag     120
gtttaagtct tcggccgaag ttaatctcgt gttttTGGca atcaacaggt ttaagtcttc     180
ggccgaagtt aatctcgtgt tttTGGcaat caacaggttt aagtcttcgg ccgaagttaa     240
tctcgtgttt tTGGcaatca acaggtttaa gtcttcggcc gaagttaatc tcgtgttttt     300
ggcaatcaag aggtttaagt cttcggccga agttaatctc gtgttttTGG caatcaacag     360
gtttaagtct tcggccgaan ttaatctcgt gttttTGGca atcaacaggt ttaantcttc     420
ggccgaagtt aatctcgtgt tttTGGcaat caana                                455
```

<210> SEQ ID NO 274
<211> LENGTH: 461
<212> TYPE: DNA
<213> ORGANISM: Homo sapien

<400> SEQUENCE: 274

```
tttttttttt ttggccaata cccttgatga acatcaatgt gaaaatcctc ggtaaaatac      60
tggcaaacca atccagcag cacatcaaaa agcttatcca ccatgatcaa gtgggcttca     120
tccctgggat gcaaggctgg ttcaacataa gaaaatcaat aaatgtaatc catcacataa     180
acagaaccaa agacaaaaac cacatgatta tctcaataga tgcagaaaag gccttggaca     240
aattcaacag cccttcatgc taaacactct taataaaacta gatattgatg gaatgtatct     300
caaaataata agagctattt atgacaaacc cacagccaat atcatactga atgggcaaag     360
actggaagca ttccctttga aaactggcac aagacaagga tgccctctct caccgctcct     420
attcaacata gtattggaag ttctggccag ggcaatcaag a                        461
```

<210> SEQ ID NO 275
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 275

```
tttttttttt ttggccaaca ccaagtcttc cacgtgggag gttttattat gttttacaac      60
catgaaaaca taggaaggtg gctgttacag caaacatttc agatagacga atcggccaag     120
ctccccaaac cccaccttca cagcctcttc cacacgtctc ccanagattg ttgtccttca     180
cttgcaaatt canggatgtt ggaagtngac atttnnagtn gcnggaaccc catcagtgaa     240
ncantaagca gaantacgat gactttgana nacanctgat gaagaacacn ctacnganaa     300
ccctttctnt cgtgttanga tctcnngtcc ntcactaatg cggcccctg cnggtccacc     360
atttgggaga actccccccn cgttggatcc ccccttgagt ntcccattct ngtccccan     420
accngncttg ngngncantn cnncctcnca ccntgtttcc ctgnngtnaa aatnngtttt     480
nccgccnccc naattccac ccnaatcaca gcgaanccng aaggccttcn naagtgttta     540
angcccngng gtttcctcnt ntanttgcag cctaccctcc cncttnnnnt tncgngttgg     600
tcgcgccctg gncncgcctn gttcctcttt nnggnnacaa cctngntcnn nggcncntcn     660
nnnctnttcc tnnnactagc tngcctntcc ncnccgnggn ncanngcaca ttncncnnac     720
tntgtnncc                                                              729
```

<210> SEQ ID NO 276
<211> LENGTH: 339
<212> TYPE: DNA
<213> ORGANISM: Homo sapien

<400> SEQUENCE: 276

```
tgacctgaca tgtagtagat acttaataaa tatttgtgga atgaatggat gaagtggagt      60
tacagagaaa aatagaaaag tacaaattgt tgtcagtgtt ttgaaggaaa attatgatct     120
ttcccaaagt tctgacttca ttctaagaca gggttagtat ctccatacat aattttactt     180
gcttttgaaa atcaaatgag ataatctatt tagattgata atttatttag actggctata     240
aactattaag tgctagcaaa tatacatttt aatctcattt tccacctctt gtgatatagc     300
tatgtaggtg ttgactttaa tggatgtcag gtcaatccc                            339
```

<210> SEQ ID NO 277
<211> LENGTH: 664
<212> TYPE: DNA
<213> ORGANISM: Homo sapien
<220> FEATURE:
<221> NAME/KEY: misc_feature
<222> LOCATION: (1)...(664)
<223> OTHER INFORMATION: n = A,T,C or G

<400> SEQUENCE: 277

```
tgacctgaca tccataacaa aatctttctc cattatattc ttctagggga atttcttgaa      60
aagcatccaa aggaaacaaa tgatggtaag accgtgccaa gtggggagca gacaccaaag     120
taagaccaca gattttacat tcaacaggta gctcacagta cttcgcccga cactgtgggc     180
agaaatagcc tcctaatgta agccctggct cagtattgcc atccaaatgc gccatgctga     240
aagagggttt tgcatcctgg tcagatnaag aagcaatggt gtgctgagga atcccatac     300 gaataagtga gcattcagaa cttgagctag caggaggagg actaagatga tgtgtgagca     360
actctttgta atggctttca tctaaaataa catggtacgt gccaccagtt tcacgagcaa     420
gtacagtgca aacgcgaact tctgcagaca atccaataac agatactcta attttagctg     480
cctttagggt cttgattaaa tcataaatat tagatggatc gcaagttgta aggntgctaa     540
aagatgatta gtacttctcg acttgtatgt ccaggcatgt tgttttaaan tctgccttag     600
nccctgctta ggggaatttt taaagaagat ggctctccat gttcanggtc aatcacnaat     660
tgcc                                                                  664
```

<210> SEQ ID NO 278
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 278

```
tgacctgaca ttgaggaaga gcacacacct ctgaaattcc ttaggttcag aagggcattt      60
gacacagagt gggcctctga taattcatga aatgcattct gaagtcatcc agaatggagg     120
ctgcaatctg ctgtgctttg ggggttgcct cactgtgctc ctggatatca cacaaaagct     180
gcaatccttc ttcttcaact aacatttgc agtatttgct gggattttta ctgcagacat      240
gatacatagc ccatagtgcc cagagctgaa cctctggttg agagaagttg ccaaggagcg     300
ggaaaaatgt cttgaaagat ctataggtca ccaatgctgt catcttacaa cttgaacttg     360
```

```
gccaattctg tatggttgca tgcagatctt ggagaagagt acgcctctgg aagtcacggg        420
atatccaaan ctgtctgtca gatgtcaggt ca                                      452

<210> SEQ ID NO 279
<211> LENGTH: 274
<212> TYPE: DNA
<213> ORGANISM: Homo sapien

<400> SEQUENCE: 279
tttttttttt ttcggcaagg caaatttact tctgcaaaag ggtgctgctt gcacttttgg         60
ccactgcgag agcacaccaa acaaagtagg gaagggg ttt ttatccctaa cgcggttatt       120
ccctggttct gtgtcgtgtc cccattggct ggagtcagac tgcacaatct acactgaccc       180
aactggctac tgtttaaaat tgaatatgaa taattaggta ggaaggggga ggctgtttgt       240
tacggtacaa gacgtgtttg ggcatgtcag gtca                                    274

<210> SEQ ID NO 280
<211> LENGTH: 272
<212> TYPE: DNA
<213> ORGANISM: Homo sapien

<400> SEQUENCE: 280
tacctgacat ggagaaataa cttgtagtat tttgcgtgca atggaatact atatgagggt         60
gaaaatgaat gaactagcaa tgcgtgtatc aacatgaata aatccccaaa acataataat       120
gttgaatgga aaaggtgagt ttcagaagga tatatatgcc ctctaaatcc atttatgtaa       180
acctttaaaa aactacatta tttatggtca taagtccatc cagaaaatat ttaaaaacct       240
acatgggatt gataactact gatgtcaggt ca                                      272

<210> SEQ ID NO 281
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 281
tttttttttt ttggccaata gcatgattta aacattggaa aaagtcaaat gagcaatgcg         60
aatttttatg ttctcttgaa taatcaaaag agtaggcaac attggttcct cattcttgaa       120
tagcattaat cagaaaatat tgcatagcct ctagcctcct tagagtaggt gtgctctctc       180
aaatatatca tagtcccaca gtttatttca tgtatatttt ctgcctgaat cacatagaca       240
tttgaatttg caacgcctga tgtaaatata taaattctta ccaatcagaa acatagcaag       300
aaattcaggg acttggtcat yatcagggta tgacagcana tccctgtara aacactgata       360
cacactcaca cacgtatgca acgtggagat gtcgcyttww kkktwywcwm rmrycrwcgn       420
aatcacttan n                                                             431

<210> SEQ ID NO 282
<211> LENGTH: 98
<212> TYPE: DNA
<213> ORGANISM: Homo sapien

<400> SEQUENCE: 282
attcgattcg atgcttgagc ccaggagttc aagactgcag tgagccactg cacttcaggc         60
tggacaacag agcgagtccc tgtgccaaaa aaaaaaaa                                 98
```

<210> SEQ ID NO 283
<211> LENGTH: 764
<212> TYPE: DNA
<213> ORGANISM: Homo sapien
<220> FEATURE:
<221> NAME/KEY: misc_feature
<222> LOCATION: (1)...(764)
<223> OTHER INFORMATION: n = A,T,C or G

<400> SEQUENCE: 283

| | | | | | |
|---|---|---|---|---|---|
| tttttttttt | ttcgcaagca | cgtgcacttt | attgaatgac | actgtagaca | ggtgtgtggg | 60 |
| tataaactgc | tgtatctagg | ggcaggacca | aggggggcagg | ggcaacagcc | ccagcgtgca | 120 |
| gggccascat | tgcacagtgg | astgcaaagg | ttgcaggcta | tgggcggcta | ctavtaaccc | 180 |
| cgtttttcct | gtattatctg | taacataata | tggtagactg | tcacagagcc | gaatwccart | 240 |
| hacasgatga | atccaawggt | caygaggatg | cccasaatca | gggcccasat | sttcaggcac | 300 |
| ttggcggtgg | gggcatasgc | ctgkgcccg | gtcacgtcsc | caaccwtcty | cctgtcccta | 360 |
| cmcttgawtc | cncnccttnn | nntnccntna | tntgcccgcc | cncctcctng | ngtcaaccng | 420 |
| natctgcact | anctccctcn | cccttntgg | antctcntcc | ttcaantaan | nttatccttn | 480 |
| acncccccct | cnccttcc | ctnccnccn | tnatcccngn | nccntatca | ntcntnccct | 540 |
| cnctntnctn | cnnatcgttc | cncctnntaa | ctacncttn | nacnanncct | cactnatncc | 600 |
| ngnnanttct | ttccttccct | cccnacgcnn | tgcgtgcgcc | cgtctngcct | nnnctncgna | 660 |
| cccnnacttt | atttaccttt | ncaccctagc | nctctactn | acccanccnc | tcctacctcc | 720 |
| nggnccaccc | nncccnatc | nctnnctctn | tcnnctcntt | cccc | | 764 |

<210> SEQ ID NO 284
<211> LENGTH: 157
<212> TYPE: DNA
<213> ORGANISM: Homo sapien

<400> SEQUENCE: 284

| | | | | | |
|---|---|---|---|---|---|
| caagtgtagg | cacagtgatg | aaagcctgga | gcaaacacaa | tctgtgggta | attaacgttt | 60 |
| atttctcccc | ttccaggaac | gtcttgcatg | gatgatcaaa | gatcagctcc | tggtcaacat | 120 |
| aaataagcta | gtttaagata | cgttcccta | cacttga | | | 157 |

<210> SEQ ID NO 285
<211> LENGTH: 150
<212> TYPE: DNA
<213> ORGANISM: Homo sapien

<400> SEQUENCE: 285

| | | | | | |
|---|---|---|---|---|---|
| attcgattgt | actcagacaa | caatatgcta | agtggaagaa | gtcagtcaca | aaagaccaca | 60 |
| tactgtatga | cttcatttac | attaagtgtc | cagaataggc | aaatccgtag | agacagaaag | 120 |
| tagatgagca | gctgcctagg | tctgagtaca | | | | 150 |

<210> SEQ ID NO 286
<211> LENGTH: 219
<212> TYPE: DNA
<213> ORGANISM: Homo sapien

<400> SEQUENCE: 286

| | | | | | |
|---|---|---|---|---|---|
| attcgatttt | ttttttttg | gccatgatga | aattcttact | ccctcagatt | ttttgtctgg | 60 |
| ataaatgcaa | gtctcaccac | cagatgtgaa | attacagtaa | actttgaagg | aatctcctga | 120 |

```
gcaaccttgg ttaggatcaa tccaatattc accatctggg aagtcaggat ggctgagttg    180
caggtcttta caagttcggg ctggattggt ctgagtaca                            219

<210> SEQ ID NO 287
<211> LENGTH: 196
<212> TYPE: DNA
<213> ORGANISM: Homo sapien

<400> SEQUENCE: 287
attcgattct tgaggctacc aggagctagg agaagaggca tggaacaaat tttccctcat    60
atccatactc agaaggaacc aaccctgctg acaccttaat ttcagcttct ggcctctaga    120
actgtgagag agtacatttc tcttggttta agccaagaga atctgtcttt tggtacttta    180
tatcatagcc tcaaga                                                    196

<210> SEQ ID NO 288
<211> LENGTH: 199
<212> TYPE: DNA
<213> ORGANISM: Homo sapien

<400> SEQUENCE: 288
attcgatttc agtccagtcc cagaacccac attgtcaatt actactctgt araagattca    60
tttgttgaaa ttcattgagt aaaacattta tgatccctta atatatgcca attaccatgc    120
taggtactga agattcaagt gaccgagatg ctagcccttg ggttcaagtg atccctctcc    180
cagagtgcac tggactgaa                                                 199

<210> SEQ ID NO 289
<211> LENGTH: 182
<212> TYPE: DNA
<213> ORGANISM: Homo sapien

<400> SEQUENCE: 289
attcgattct tgaggctaca aacctgtaca gtatgttact ctactgaata ctgtaggcaa    60
tagtaataca gaagcaagta tctgtatatg taaacattaa aaaggtacag tgaaacttca    120
gtattataat cttagggacc accattatat atgtggtcca tcattggcca aaaaaaaaaa    180
aa                                                                   182

<210> SEQ ID NO 290
<211> LENGTH: 1646
<212> TYPE: DNA
<213> ORGANISM: Homo sapien

<400> SEQUENCE: 290
ggcacgagga gaaatgtaat tccatatttt atttgaaact tattccatat tttaattgga    60
tattgagtga ttgggttatc aaacacccac aaactttaat tttgttaaat ttatatggct    120
ttgaaataga agtataagtt gctaccatttt tttgataaca ttgaaagata gtattttacc    180
atctttaatc atcttggaaa atacaagtcc tgtgaacaac cactctttca cctagcagca    240
tgaggccaaa agtaaaggct ttaaattata acatatggga ttcttagtag tatgtttttt    300
tcttgaaact cagtggctct atctaacctt actatctcct cactctttct ctaagactaa    360
actctaggct cttaaaaatc tgcccacacc aatcttagaa gctctgaaaa gaatttgtct    420
ttaaatatct tttaatagta acatgtattt tatggaccaa attgacattt tcgactattt    480
tttccaaaaa agtcaggtga atttcagcac actgagttgg gaatttctta tcccagaaga    540
ccaaccaatt tcatatttat ttaagattga ttccatactc cgttttcaag gagaatccct    600
```

-continued

```
gcagtctcct taaaggtaga acaaatactt tctatttttt tttcaccatt gtgggattgg      660
actttaagag gtgactctaa aaaaacagag aacaaatatg tctcagttgt attaagcacg      720
gacccatatt atcatattca cttaaaaaaa tgatttcctg tgcaccttt ggcaacttct       780 cttttcaatg tagggaaaaa cttagtcacc ctgaaaaccc acaaaataaa taaaacttgt     840
agatgtgggc agaaggtttg ggggtggaca ttgtatgtgt ttaaattaaa ccctgtatca      900
ctgagaagct gttgtatggg tcagagaaaa tgaatgctta gaagctgttc acatcttcaa     960
gagcagaagc aaaccacatg tctcagctat attattattt atttttatg cataaagtga      1020 atcatttctt ctgtattaat ttccaaaggg ttttaccctc tatttaaatg ctttgaaaaa     1080
cagtgcattg acaatgggtt gatatttttc tttaaaagaa aaatataatt atgaaagcca     1140
agataatctg aagcctgttt tattttaaaa cttttttatgt tctgtggttg atgttgtttg     1200
tttgtttgtt tctatttgt tggttttta ctttgttttt tgttttgttt tgttttgttt        1260
kgcatactac atgcagttct ttaaccaatg tctgtttggc taatgtaatt aaagttgtta     1320
atttatatga gtgcatttca actatgtcaa tggtttctta atatttattg tgtagaagta     1380
ctggtaattt ttttatttac aatatgttta aagagataac agtttgatat gttttcatgt     1440
gtttatagca gaagttattt atttctatgg cattccagcg gatattttgg tgtttgcgag     1500
gcatgcagtc aatattttgt acagttagtg gacagtattc agcaacgcct gatagcttct     1560
ttggccttat gttaaataaa aagacctgtt tgggatgtat ttttttatttt taaaaaaaaa     1620 aaaaaaaaaa aaaaaaaaaa aaaaa                                            1646
```

<210> SEQ ID NO 291
<211> LENGTH: 1851
<212> TYPE: DNA
<213> ORGANISM: Homo sapien

<400> SEQUENCE: 291

```
tcatcaccat tgccagcagc ggcaccgtta gtcaggtttt ctgggaatcc cacatgagta       60
cttccgtgtt cttcattctt cttcaatagc cataaatctt ctagctctgg ctggctgttt     120
tcacttcctt taagcctttg tgactcttcc tctgatgtca gctttaagtc ttgttctgga     180
ttgctgtttt cagaagagat ttttaacatc tgttttctt tgtagtcaga aagtaactgg      240
caaattacat gatgatgact agaaacagca tactctctgg ccgtctttcc agatcttgag     300
aagatacatc aacattttgc tcaagtagag ggctgactat acttgctgat ccacaacata     360
cagcaagtat gagagcagtt cttccatatc tatccagcgc atttaaattc gcttttttct     420
tgattaaaaa tttcaccact tgctgttttt gctcatgtat accaagtagc agtggtgtga     480
ggccatgctt gttttttgat tcgatatcag caccgtataa gagcagtgct ttggccatta     540
atttatcttc attgtagaca gcatagtgta gagtggtatt tccatactca tctggaatat     600
ttggatcagt gccatgttcc agcaacatta acgcacatta atcttcctgg cattgtacgg      660 ccttttgtcag agctgtcctc ttttgttgt caaggacatt aagttgacat cgtctgtcca     720
gcacgagttt tactacttct gaattcccat ggcagaggc cagatgtaga gcagtcctct    780
tttgcttgtc cctcttgttc acatccgtgt ccctgagcat gacgatgaga tcctttctgg    840
ggactttacc ccaccaggca gctctgtgga gcttgtccag atcttctcca tggacgtggt    900
acctgggatc catgaaggcg ctgtcatcgt agtctcccca agcgaccacg ttgctcttgc     960
cgctcccctg cagcagggga agcagtggca gcaccacttg cacctcttgc tcccaagcgt    1020
cttcacagag gagtcgttgt ggtctccaga agtgcccacg ttgctcttgc cgctccccct    1080
```

```
gtccatccag ggaggaagaa atgcaggaaa tgaaagatgc atgcacgatg gtatactcct      1140
cagccatcaa acttctggac agcaggtcac ttccagcaag gtggagaaag ctgtccaccc      1200
acagaggatg agatccagaa accacaatat ccattcacaa acaaacactt ttcagccaga      1260
cacaggtact gaaatcatgt catctgcggc aacatggtgg aacctaccca atcacacatc      1320
aagagatgaa gacactgcag tatatctgca caacgtaata ctcttcatcc ataacaaaat      1380
aatataattt tcctctggag ccatatggat gaactatgaa ggaagaactc cccgaagaag      1440
ccagtcgcag agaagccaca ctgaagctct gtcctcagcc atcagcgcca cggacaggar      1500
tgtgtttctt ccccagtgat gcagcctcaa gttatcccga agctgccgca gcacacggtg      1560
gctcctgaga aacaccccag ctcttccggt ctaacacagg caagtcaata aatgtgataa      1620
tcacataaac agaattaaaa gcaaagtcac ataagcatct caacagacac agaaaaggca      1680
tttgacaaaa tccagcatcc ttgtatttat tgttgcagtt ctcagaggaa atgcttctaa      1740
cttttcccca tttagtatta tgttggctgt gggcttgtca taggtggttt ttattacttt      1800
aaggtatgtc ccttctatgc ctgttttgct gagggtttta attctcgtgc c              1851

<210> SEQ ID NO 292
<211> LENGTH: 1851
<212> TYPE: DNA
<213> ORGANISM: Homo sapien

<400> SEQUENCE: 292
tcatcaccat tgccagcagc ggcaccgtta gtcaggtttt ctgggaatcc cacatgagta       60
cttccgtgtt cttcattctt cttcaatagc cataaatctt ctagctctgg ctggctgttt      120
tcacttcctt taagcctttg tgactcttcc tctgatgtca gctttaagtc ttgttctgga      180
ttgctgtttt cagaagagat ttttaacatc tgttttctt tgtagtcaga aagtaactgg      240
caaattacat gatgatgact agaaacagca tactctctgg ccgtctttcc agatcttgag      300
aagatacatc aacattttgc tcaagtagag ggctgactat acttgctgat ccacaacata      360
cagcaagtat gagagcagtt cttccatatc tatccagcgc atttaaattc gcttttttct      420
tgattaaaaa tttcaccact tgctgttttt gctcatgtat accaagtagc agtggtgtga      480
ggccatgctt gttttttgat tcgatatcag caccgtataa gagcagtgct ttggccatta      540
atttatcttc attgtagaca gcatagtgta gagtggtatt tccatactca tctggaatat      600
ttggatcagt gccatgttcc agcaacatta acgcacattc atcttcctgg cattgtacgg      660
cctttgtcag agctgtcctc tttttgttgt caaggacatt aagttgacat cgtctgtcca      720
gcacgagttt tactacttct gaattcccat tggcagaggc cagatgtaga gcagtcctct      780
tttgcttgtc cctcttgttc acatccgtgt ccctgagcat gacgatgaga tccttctctgg      840 ggactttacc ccaccaggca gctctgtgga gcttgtccag atcttctcca tggacgtggt      900
acctgggatc catgaaggcg ctgtcatcgt agtctcccca agcgaccacg ttgctcttgc      960
cgctcccctg cagcagggga agcagtggca gcaccacttg cacctcttgc tcccaagcgt     1020
cttcacagag gagtcgttgt ggtctccaga agtgcccacg ttgctcttgc cgctcccct      1080 gtccatccag ggaggaagaa atgcaggaaa tgaaagatgc atgcacgatg gtatactcct     1140
cagccatcaa acttctggac agcaggtcac ttccagcaag gtggagaaag ctgtccaccc     1200
acagaggatg agatccagaa accacaatat ccattcacaa acaaacactt ttcagccaga     1260
cacaggtact gaaatcatgt catctgcggc aacatggtgg aacctaccca atcacacatc     1320
aagagatgaa gacactgcag tatatctgca caacgtaata ctcttcatcc ataacaaaat     1380
```

-continued

| | |
|---|---|
| aatataattt tcctctggag ccatatggat gaactatgaa ggaagaactc cccgaagaag | 1440 |
| ccagtcgcag agaagccaca ctgaagctct gtcctcagca atcagcgcca cggacaggar | 1500 |
| tgtgtttctt ccccagtgat gcagcctcaa gttatcccga agctgccgca gcacacggtg | 1560 |
| gctcctgaga aacaccccag ctcttccggt ctaacacagg caagtcaata aatgtgataa | 1620 |
| tcacataaac agaattaaaa gcaaagtcac ataagcatct caacagacac agaaaaggca | 1680 |
| tttgacaaaa tccagcatcc ttgtatttat tgttgcagtt ctcagaggaa atgcttctaa | 1740 |
| cttttcccca tttagtatta tgttggctgt gggcttgtca taggtggttt ttattacttt | 1800 |
| aaggtatgtc ccttctatgc ctgttttgct gagggtttta attctcgtgc c | 1851 |

<210> SEQ ID NO 293
<211> LENGTH: 668
<212> TYPE: DNA
<213> ORGANISM: Homo sapien

<400> SEQUENCE: 293

| | |
|---|---|
| cttgagcttc caaataygga agactggccc ttacacasgt caatgttaaa atgaatgcat | 60 |
| ttcagtattt tgaagataaa attrgtagat ctataccttg ttttttgatt cgatatcagc | 120 |
| accrtataag agcagtgctt tggccattaa tttatctttc attrtagaca gcrtagtgya | 180 |
| gagtggtatt tccatactca tctggaatat ttggatcagt gccatgttcc agcaacatta | 240 |
| acgcacattc atcttcctgg cattgtacgg cctgtcagta ttagacccaa aaacaaatta | 300 |
| catatcttag gaattcaaaa taacattcca cagcttttcac caactagtta tatttaaagg | 360 |
| agaaaactca tttttatgcc atgtattgaa atcaaaccca cctcatgctg atatagttgg | 420 |
| ctactgcata cctttatcag agctgtcctc ttttttgttgt caaggacatt aagttgacat | 480 |
| cgtctgtcca gcaggagttt tactacttct gaattcccat tggcagaggc cagatgtaga | 540 |
| gcagtcctat gagagtgaga agacttttta ggaaaattgta gtgcactagc tacagccata | 600 |
| gcaatgattc atgtaactgc aaaacactgaa tagcctgcta ttactctgcc ttcaaaaaaa | 660 |
| aaaaaaaa | 668 |

<210> SEQ ID NO 294
<211> LENGTH: 1512
<212> TYPE: DNA
<213> ORGANISM: Homo sapien

<400> SEQUENCE: 294

| | |
|---|---|
| gggtcgccca gggggsgcgt gggctttcct cgggtgggtg tgggttttcc ctgggtgggg | 60 |
| tgggctgggc trgaatcccc tgctggggtt ggcaggtttt ggctgggatt gactttttytc | 120 |
| ttcaaacaga ttggaaaccc ggagttacct gctagttggt gaaactggtt ggtagacgcg | 180 |
| atctgttggc tactactggc ttctcctggc tgttaaaagc agatggtggt tgaggttgat | 240 |
| tccatgccgg ctgcttcttc tgtgaagaag ccatttggtc tcaggagcaa gatgggcaag | 300 |
| tggtgctgcc gttgcttccc ctgctgcagg gagagcggca agagcaacgt gggcacttct | 360 |
| ggagaccacg acgactctgc tatgaagaca ctcaggagca agatgggcaa gtggtgccgc | 420 |
| cactgcttcc cctgctgcag ggggagtggc aagagcaacg tgggcgcttc tggagaccac | 480 |
| gacgaytctg ctatgaagac actcaggaac aagatggcaa gtggtgctg ccactgcttc | 540 |
| ccctgctgca gggggagcrg caagagcaag gtgggcgctt ggggagacta cgatgacagt | 600 |
| gccttcatgg agcccaggta ccacgtccgt ggagaagatc tggacaagct ccacagagct | 660 |
| gcctggtggg gtaaagtccc cagaaaggat ctcatcgtca tgctcaggga cactgacgtg | 720 |

```
aacaagaagg acaagcaaaa gaggactgct ctacatctgg cctctgccaa tgggaattca    780
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tatayggtgc tgatatcgaa   1020
tcaaaaaaca aggtatagat ctactaattt tatcttcaaa atactgaaat gcattcattt   1080
taacattgac gtgtgtaagg gccagtcttc cgtatttgga agctcaagca taacttgaat   1140
gaaaatattt tgaaatgacc taattatctm agactttatt ttaaatattg ttattttcaa   1200
agaagcatta gagggtacag ttttttttt ttaaatgcac ttctggtaaa tacttttgtt   1260
gaaaacactg aatttgtaaa aggtaatact tactatttt caattttcc ctcctaggat    1320 ttttttcccc taatgaatgt aagatggcaa aatttgccct gaaataggtt ttacatgaaa   1380
actccaagaa aagttaaaca tgtttcagtg aatagagatc ctgctccttt ggcaagttcc   1440
taaaaaacag taatagatac gaggtgatgc gcctgtcagt ggcaaggttt aagatatttc   1500
tgatctcgtg cc                                                      1512

<210> SEQ ID NO 295
<211> LENGTH: 1853
<212> TYPE: DNA
<213> ORGANISM: Homo sapien

<400> SEQUENCE: 295
gggtcgccca gggggsgcgt gggctttcct cgggtgggtg tgggttttcc ctgggtgggg     60
tgggctgggc trgaatcccc tgctggggtt ggcaggtttt ggctgggatt gacttttytc    120
ttcaaacaga ttggaaaccc ggagttacct gctagttggt gaaactggtt ggtagacgcg    180
atctgttggc tactactggc ttctcctggc tgttaaaagc agatggtggt tgaggttgat    240
tccatgccgg ctgcttcttc tgtgaagaag ccatttggtc tcaggagcaa gatgggcaag    300
tggtgctgcc gttgcttccc ctgctgcagg gagagcggca agagcaacgt gggcacttct    360
ggagaccacg acgactctgc tatgaagaca ctcaggagca agatgggcaa gtggtgccgc    420
cactgcttcc cctgctgcag ggggagtggc aagagcaacg tgggcgcttc tggagaccac    480
gacgaytctg ctatgaagac actcaggaac aagatgggca agtggtgctg ccactgcttc    540
ccctgctgca gggggagcrg caagagcaag gtgggcgctt gggagactac gatgacagy    600 gccttcatgg akcccaggta ccacgtccrt ggagaagatc tggacaagct ccacagagct    660
gcctggtggg gtaaagtccc cagaaaggat ctcatcgtca tgctcaggga cackgaygtg    720
aacaagargg acaagcaaaa gaggactgct ctacatctgg cctctgccaa tgggaattca    780
gaagtagtaa aactcstgct ggacagacga tgtcaactta atgtccttga caacaaaaag    840
aggacagctc tgayaaaggc cgtacaatgc caggaagatg aatgtgcgtt aatgttgctg    900
gaacatggca ctgatccaaa tattccagat gagtatggaa ataccactct rcactaygct    960
rtctayaatg aagataaatt aatggccaaa gcactgctct tatayggtgc tgatatcgaa   1020
tcaaaaaaca agcatggcct cacaccactg ytacttggtr tacatgagca aaaacagcaa   1080
gtsgtgaaat ttttaatyaa gaaaaagcg aatttaaaat gcrctggata gatatggaag   1140
ractgctctc atacttgctg tatgttgtgg atcagcaagt atagtcagcc ytctacttga   1200
gcaaaatrtt gatgtatctt ctcaagatct ggaaagacgg ccagagagta tgctgtttct   1260
agtcatcatc atgtaatttg ccagttactt tctgactaca aagaaaaaca gatgttaaaa   1320
```

-continued

```
atctcttctg aaaacagcaa tccagaacaa gacttaaagc tgacatcaga ggaagagtca    1380
caaaggctta aaggaagtga aaacagccag ccagaggcat ggaaactttt aaatttaaac    1440
ttttggttta atgtttttttt ttttgcctt aataatatta gatagtccca aatgaaatwa    1500
cctatgagac taggctttga gaatcaatag attcttttt taagaatctt ttggctagga     1560
gcggtgtctc acgcctgtaa ttccagcacc ttgagaggct gaggtgggca gatcacgaga    1620
tcaggagatc gagaccatcc tggctaacac ggtgaaaccc catctctact aaaaatacaa    1680
aaacttagct gggtgtggtg gcgggtgcct gtagtcccag ctactcagga rgctgaggca    1740
ggagaatggc atgaacccgg gaggtggagg ttgcagtgag ccgagatccg ccactacact    1800
ccagcctggg tgacagagca agactctgtc tcaaaaaaaa aaaaaaaaa aaa            1853
```

<210> SEQ ID NO 296
<211> LENGTH: 2184
<212> TYPE: DNA
<213> ORGANISM: Homo sapien

<400> SEQUENCE: 296

```
ggcacgagaa ttaaaaccct cagcaaaaca ggcatagaag ggacatacct taaagtaata     60 aaaccacct atgacaagcc cacagccaac ataatactaa atggggaaaa gttagaagca     120
tttcctctga gaactgcaac aataaataca aggatgctga attttgtcaa atgccttttc    180
tgtgtctgtt gagatgctta tgtgactttg cttttaattc tgtttatgtg attatcacat    240
ttattgactt gcctgtgtta gaccggaaga gctggggtgt ttctcaggag ccaccgtgtg    300
ctgcggcagc ttcgggataa cttgaggctg catcactggg gaagaaacac aytcctgtcc    360
gtggcgctga tggctgagga cagagcttca gtgtggcttc tctgcgactg gcttcttcgg    420
ggagttcttc cttcatagtt catccatatg gctccagagg aaaattatat tattttgtta    480
tggatgaaga gtattacgtt gtgcagatat actgcagtgt cttcatctct tgatgtgtga    540
ttgggtaggt tccaccatgt tgccgcagat gacatgattt cagtacctgt gtctggctga    600
aaagtgtttg tttgtgaatg gatattgtgg tttctggatc tcatcctctg tgggtggaca    660
gctttctcca ccttgctgga agtgacctgc tgtccagaag tttgatggct gaggagtata    720
ccatcgtgca tgcatctttc atttcctgca tttcttcctc cctggatgga caggggagc     780 ggcaagagca acgtgggcac ttctggagac cacaacgact cctctgtgaa gacgcttggg    840
agcaagaggt gcaagtggtg ctgccactgc ttcccctgct gcaggggagc ggcaagagca    900
acgtggtcgc ttggggagac tacgatgaca gcgccttcat ggatcccagg taccacgtcc    960
atggagaaga tctggacaag ctccacagag ctgcctggtg gggtaaagtc cccagaaagg    1020
atctcatcgt catgctcagg gacacggatg tgaacaagag ggacaagcaa aagaggactg    1080
ctctacatct ggcctctgcc aatgggaatt cagaagtagt aaaactcgtg ctggacagac    1140
gatgtcaact taatgtcctt gacaacaaaa agaggacagc tctgacaaag gccgtacaat    1200
gccaggaaga tgaatgtgcg ttaatgttgc tggaacatgg cactgatcca atattccag     1260 atgagtatgg aaataccact ctacactatg ctgtctacaa tgaagataaa ttaatggcca    1320
aagcactgct cttatacggt gctgatatcg aatcaaaaaa caagcatggc ctcacaccac    1380
tgctacttgg tatacatgag caaaacagc aagtggtgaa attttaatc aagaaaaaag      1440 cgaatttaaa tgcgctggat agatatggaa gaactgctct catacttgct gtatgttgtg    1500
gatcagcaag tatagtcagc cctctacttg agcaaaatgt tgatgtatct tctcaagatc    1560
tggaaagacg gccagagagt atgctgtttc tagtcatcat catgtaattt gccagttact    1620
```

| | |
|---|---:|
| ttctgactac aaagaaaaac agatgttaaa aatctcttct gaaaacagca atccagaaca | 1680 |
| agacttaaag ctgacatcag aggaagagtc acaaaggctt aaaggaagtg aaaacagcca | 1740 |
| gccagaggca tggaaacttt taaatttaaa cttttggttt aatgttttt tttttttgcct | 1800 |
| taataatatt agatagtccc aaatgaaatw acctatgaga ctaggctttg agaatcaata | 1860 |
| gattcttttt ttaagaatct tttggctagg agcggtgtct cacgcctgta attccagcac | 1920 |
| cttgagaggc tgaggtgggc agatcacgag atcaggagat cgagaccatc ctggctaaca | 1980 |
| cggtgaaacc ccatctctac taaaaataca aaaacttagc tgggtgtggt ggcgggtgcc | 2040 |
| tgtagtccca gctactcagg argctgaggc aggagaatgc catgaacccg ggaggtggag | 2100 |
| gttgcagtga gccgagatcc gccactacac tccagcctgg gtgacagagc aagactctgt | 2160 |
| ctcaaaaaaa aaaaaaaaa aaaa | 2184 |

<210> SEQ ID NO 297
<211> LENGTH: 1855
<212> TYPE: DNA
<213> ORGANISM: Homo sapien
<220> FEATURE:
<221> NAME/KEY: misc_feature
<222> LOCATION: (1)...(1855)
<223> OTHER INFORMATION: n = A,T,C or G

<400> SEQUENCE: 297

| | |
|---|---:|
| tgcacgcatc ggccagtgtc tgtgccacgt acactgacgc cccctgagat gtgcacgccg | 60 |
| cacgcgcacg ttgcacgcgc ggcagcggct tggctggctt gtaacggctt gcacgcgcac | 120 |
| gccgcccccg cataaccgtc agactggcct gtaacggctt gcaggcgcac gccgcacgcg | 180 |
| cgtaacggct tggctgccct gtaacggctt gcacgtgcat gctgcacgcg cgttaacggc | 240 |
| ttggctggca tgtagccgct tggcttggct ttgcattytt tgctkggctk ggcgttgkty | 300 |
| tcttggattg acgcttcctc cttggatkga cgtttcctcc ttggatkgac gtttccytyty | 360 |
| tcgcgttcct ttgctggact tgacctttty tctgctgggt ttggcattcc tttggggtgg | 420 |
| gctgggtgtt ttctccgggg gggktkgccc ttcctggggt gggcgtgggk cgcccccagg | 480 |
| gggcgtgggc tttccccggg tgggtgtggg ttttcctggg gtgggggtggg ctgtgctggg | 540 |
| atcccccctgc tggggttggc agggattgac ttttttcttc aaacagattg gaaacccgga | 600 |
| gtaacntgct agttggtgaa actggttggt agacgcgatc tgctggtact actgttttctc | 660 |
| ctggctgtta aaagcagatg gtggctgagg ttgattcaat gccggctgct tcttctgtga | 720 |
| agaagccatt tggtctcagg agcaagatgg gcaagtggtg cgccactgct tcccctgctg | 780 |
| caggggggagc ggcaagagca acgtgggcac ttctggagac cacaacgact cctctgtgaa | 840 |
| gacgcttggg agcaagaggt gcaagtggtg ctgcccactg cttcccctgc tgcaggggag | 900 |
| cggcaagagc aacgtggkcg cttggggaga ctacgatgac agcgccttca tggakcccag | 960 |
| gtaccacgtc crtggagaag atctggacaa gctccacaga gctgcctggt ggggtaaagt | 1020 |
| ccccagaaag gatctcatcg tcatgctcag ggacactgay gtgaacaaga rggacaagca | 1080 |
| aaagaggact gctctacatc tggcctctgc caatgggaat tcagaagtag taaaactcgt | 1140 |
| gctggacaga cgatgtcaac ttaatgtcct tgacaacaaa aagaggacag ctctgacaaa | 1200 |
| ggccgtacaa tgccaggaag atgaatgtgc gttaatgttg ctgaacatg gcactgatcc | 1260 |
| aaatattcca gatgagtatg gaaataccac tctacactat gctgtctaca atgaagataa | 1320 |
| attaatggcc aaagcactgc tcttatacgg tgctgatatg gaatcaaaaa acaaggtata | 1380 |
| gatctactaa ttttatcttc aaaatactga aatgcattca ttttaacatt gacgtgtgta | 1440 |

-continued

```
agggccagtc ttccgtattt ggaagctcaa gcataacttg aatgaaaata ttttgaaatg    1500
acctaattat ctaagacttt attttaaata ttgttatttt caaagaagca ttagagggta    1560 cagtttttt ttttaaatg cacttctggt aaatactttt gttgaaaaca ctgaatttgt      1620
aaaaggtaat acttactatt tttcaatttt tccctcctag gatttttttc ccctaatgaa    1680
tgtaagatgg caaatttgc cctgaaatag gttttacatg aaaactccaa gaaaagttaa     1740
acatgtttca gtgaatagag atcctgctcc tttggcaagt tcctaaaaaa cagtaataga    1800
tacgaggtga tgcgcctgtc agtggcaagg tttaagatat ttctgatctc gtgcc         1855
```

<210> SEQ ID NO 298
<211> LENGTH: 1059
<212> TYPE: DNA
<213> ORGANISM: Homo sapien

<400> SEQUENCE: 298

```
gcaacgtggg cacttctgga gaccacaacg actcctctgt gaagacgctt gggagcaaga      60
ggtgcaagtg gtgctgccca ctgcttcccc tgctgcaggg gagcggcaag agcaacgtgg     120
gcgcttgrgg agactmcgat gacagygcct tcatggagcc caggtaccac gtccgtggag     180
aagatctgga caagctccac agagctgccc tggtgggta aagtccccag aaaggatctc      240
atcgtcatgc tcagggacac tgaygtgaac aagargacc agcaaaagag gactgctcta     300
catctggcct ctgccaatgg gaattcagaa gtagtaaaac tcstgctgga cagacgatgt    360
caacttaatg tccttgacaa caaaaagagg acagctctga yaaaggccgt acaatgccag    420
gaagatgaat gtgcgttaat gttgctggaa catggcactg atccaaatat tccagatgag   480
tatggaaata ccactctrca ctaygctrtc tayaatgaag ataaattaat ggccaaagca    540
ctgctcttat ayggtgctga tatcgaatca aaaaacaagg tatagatcta ctaattttat   600
cttcaaaata ctgaaatgca ttcattttaa cattgacgtg tgtaagggcc agtcttccgt    660
atttggaagc tcaagcataa cttgaatgaa atatttga aatgacctaa ttatctaaga     720
ctttatttta aatattgtta ttttcaaaga agcattagag ggtacagttt tttttttta    780 aatgcacttc tggtaaatac ttttgttgaa aacactgaat ttgtaaaagg taatacttac    840 tattttcaa ttttccctc ctaggatttt tttccctaa tgaatgtaag atggcaaaat     900
ttgccctgaa ataggtttta catgaaaact ccaagaaaag ttaaacatgt ttcagtgaat    960
agagatcctg ctcctttggc aagttcctaa aaaacagtaa tagatacgag gtgatgcgcc   1020
tgtcagtggc aaggtttaag atatttctga tctcgtgcc                          1059
```

<210> SEQ ID NO 299
<211> LENGTH: 329
<212> TYPE: PRT
<213> ORGANISM: Homo sapien

<400> SEQUENCE: 299

```
Met Asp Ile Val Val Ser Gly Ser His Pro Leu Trp Val Asp Ser Phe
  1               5                  10                  15

Leu His Leu Ala Gly Ser Asp Leu Leu Ser Arg Ser Leu Met Ala Glu
                 20                  25                  30

Glu Tyr Thr Ile Val His Ala Ser Phe Ile Ser Cys Ile Ser Ser Ser
             35                  40                  45

Leu Asp Gly Gln Gly Glu Arg Gln Glu Gln Arg Gly His Phe Trp Arg
         50                  55                  60
```

```
Pro Gln Arg Leu Leu Cys Glu Asp Ala Trp Glu Gln Val Gln Val
 65                  70                  75                  80

Val Leu Pro Leu Leu Pro Leu Leu Gln Gly Ser Gly Lys Ser Asn Val
                 85                  90                  95

Val Ala Trp Gly Asp Tyr Asp Ser Ala Phe Met Asp Pro Arg Tyr
            100                 105                 110

His Val His Gly Glu Asp Leu Asp Lys Leu His Arg Ala Ala Trp Trp
            115                 120                 125

Gly Lys Val Pro Arg Lys Asp Leu Ile Val Met Leu Arg Asp Thr Asp
            130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
                165                 170                 175

Gln Leu Asn Val Leu Asp Asn Lys Lys Arg Thr Ala Leu Thr Lys Ala
                180                 185                 190

Val Gln Cys Gln Glu Asp Glu Cys Ala Leu Met Leu Leu Glu His Gly
            195                 200                 205

Thr Asp Pro Asn Ile Pro Asp Glu Tyr Gly Asn Thr Thr Leu His Tyr
            210                 215                 220

Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
                245                 250                 255

Leu Gly Ile His Glu Gln Lys Gln Gln Val Val Lys Phe Leu Ile Lys
                260                 265                 270

Lys Lys Ala Asn Leu Asn Ala Leu Asp Arg Tyr Gly Arg Thr Ala Leu
                275                 280                 285

Ile Leu Ala Val Cys Cys Gly Ser Ala Ser Ile Val Ser Pro Leu Leu
            290                 295                 300

Glu Gln Asn Val Asp Val Ser Ser Gln Asp Leu Glu Arg Arg Pro Glu
305                 310                 315                 320

Ser Met Leu Phe Leu Val Ile Ile Met
                325

<210> SEQ ID NO 300
<211> LENGTH: 148
<212> TYPE: PRT
<213> ORGANISM: Homo sapien
<220> FEATURE:
<221> NAME/KEY: VARIANT
<222> LOCATION: (1)...(148)
<223> OTHER INFORMATION: Xaa = Any Amino Acid

<400> SEQUENCE: 300

Met Thr Xaa Pro Ser Trp Ser Pro Gly Thr Thr Ser Val Glu Lys Ile
 1               5                  10                  15

Trp Thr Ser Ser Thr Glu Leu Pro Trp Trp Gly Lys Val Pro Arg Lys
                20                  25                  30

Asp Leu Ile Val Met Leu Arg Asp Thr Asp Val Asn Lys Xaa Asp Lys
            35                  40                  45

Gln Lys Arg Thr Ala Leu His Leu Ala Ser Ala Asn Gly Asn Ser Glu
        50                  55                  60

Val Val Lys Leu Xaa Leu Asp Arg Arg Cys Gln Leu Asn Val Leu Asp
65                  70                  75                  80
```

-continued

```
Asn Lys Lys Arg Thr Ala Leu Xaa Lys Ala Val Gln Cys Gln Glu Asp
                85                  90                  95

Glu Cys Ala Leu Met Leu Leu Glu His Gly Thr Asp Pro Asn Ile Pro
            100                 105                 110

Asp Glu Tyr Gly Asn Thr Thr Leu His Tyr Ala Xaa Tyr Asn Glu Asp
        115                 120                 125

Lys Leu Met Ala Lys Ala Leu Leu Tyr Gly Ala Asp Ile Glu Ser
    130                 135                 140

Lys Asn Lys Val
145
```

<210> SEQ ID NO 301
<211> LENGTH: 1155
<212> TYPE: DNA
<213> ORGANISM: Homo sapien

<400> SEQUENCE: 301

| | | |
|---|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |
| ggcgcttctg gagaccacga cgactctgct atgaagacac tcaggaacaa gatgggcaag | 300 |
| tggtgctgcc actgcttccc ctgctgcagg gggagcggca agagcaaggt gggcgcttgg | 360 |
| ggagactacg atgacagtgc cttcatggag cccaggtacc acgtccgtgg agaagatctg | 420 |
| gacaagctcc acagagctgc ctggtggggt aaagtcccca gaaaggatct catcgtcatg | 480 |
| ctcagggaca ctgacgtgaa caagaaggac aagcaaaaga ggactgctct acatctggcc | 540 |
| tctgccaatg ggaattcaga agtagtaaaa ctcctgctgg acagacgatg tcaacttaat | 600 |
| gtccttgaca acaaaaagag gacagctctg ataaaggccg tacaatgcca ggaagatgaa | 660 |
| tgtgcgttaa tgttgctgga acatggcact gatccaaata ttccagatga gtatggaaat | 720 |
| accactctgc actacgctat ctataatgaa gataaattaa tggccaaagc actgctctta | 780 |
| tatggtgctg atatcgaatc aaaaaacaag catggcctca caccactgtt acttggtgta | 840 |
| catgagcaaa acagcaagt cgtgaaattt ttaatcaaga aaaagcgaa tttaaatgca | 900 |
| ctggatagat atggaaggac tgctctcata cttgctgtat gttgtggatc agcaagtata | 960 |
| gtcagccttc tacttgagca aaatattgat gtatcttctc aagatctatc tggacagacg | 1020 |
| gccagagagt atgctgtttc tagtcatcat catgtaattt gccagttact ttctgactac | 1080 |
| aaagaaaaac agatgctaaa aatctcttct gaaaacagca atccagaaaa tgtctcaaga | 1140 |
| accagaaata aataa | 1155 |

<210> SEQ ID NO 302
<211> LENGTH: 2000
<212> TYPE: DNA
<213> ORGANISM: Homo sapien

<400> SEQUENCE: 302

| | | |
|---|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |

-continued

| | |
|---|---|
| ggcgcttctg gagaccacga cgactctgct atgaagacac tcaggaacaa gatgggcaag | 300 |
| tggtgctgcc actgcttccc ctgctgcagg gggagcggca agagcaaggt gggcgcttgg | 360 |
| ggagactacg atgacagtgc cttcatggag cccaggtacc acgtccgtgg agaagatctg | 420 |
| gacaagctcc acagagctgc ctggtggggt aaagtcccca gaaaggatct catcgtcatg | 480 |
| ctcagggaca ctgacgtgaa caagaaggac aagcaaaaga ggactgctct acatctggcc | 540 |
| tctgccaatg ggaattcaga agtagtaaaa ctcctgctgg acagacgatg tcaacttaat | 600 |
| gtccttgaca caaaaagag gacagctctg ataaaggccg tacaatgcca ggaagatgaa | 660 |
| tgtgcgttaa tgttgctgga acatggcact gatccaaata ttccagatga gtatggaaat | 720 |
| accactctgc actacgctat ctataatgaa gataaattaa tggccaaagc actgctctta | 780 |
| tatggtgctg atatcgaatc aaaaaacaag catggcctca caccactgtt acttggtgta | 840 |
| catgagcaaa acagcaagt cgtgaaattt ttaatcaaga aaaagcgaa tttaaatgca | 900 |
| ctggatagat atgaaggac tgctctcata cttgctgtat gttgtggatc agcaagtata | 960 |
| gtcagccttc tacttgagca aaatattgat gtatcttctc aagatctatc tggacagacg | 1020 |
| gccagagagt atgctgtttc tagtcatcat catgtaattt gccagttact ttctgactac | 1080 |
| aaagaaaaac agatgctaaa aatctcttct gaaaacagca atccagaaca agacttaaag | 1140 |
| ctgacatcag aggaagagtc acaaggttc aaagcagta aaatagcca gccagagaaa | 1200 |
| atgtctcaag aaccagaaat aaataaggat ggtgatagag aggttgaaga agaaatgaag | 1260 |
| aagcatgaaa gtaataatgt gggattacta gaaaaccctga ctaatggtgt cactgctggc | 1320 |
| aatggtgata atggattaat tcctcaaagg aagagcagaa cacctgaaaa tcagcaattt | 1380 |
| cctgacaacg aaagtgaaga gtatcacaga atttgcgaat tagtttctga ctacaaagaa | 1440 |
| aaacagatgc caaaatactc ttctgaaaac agcaacccag aacaagactt aaagctgaca | 1500 |
| tcagaggaag agtcacaaag gcttgagggc agtgaaaatg ccagccaga gctagaaaat | 1560 |
| tttatggcta tcgaagaaat gaagaagcac ggaagtactc atgtcggatt cccagaaaac | 1620 |
| ctgactaatg gtgccactgc tggcaatggt gatgatggat taattcctcc aaggaagagc | 1680 |
| agaacacctg aaagccagca atttcctgac actgagaatg aagagtatca cagtgacgaa | 1740 |
| caaaatgata ctcagaagca attttgtgaa gaacagaaca ctggaatatt acacgatgag | 1800 |
| attctgattc atgaagaaa gcagatagaa gtggttgaaa aaatgaattc tgagctttct | 1860 |
| cttagttgta agaaagaaaa agacatcttg catgaaaata gtacgttgcg ggaagaaatt | 1920 |
| gccatgctaa gactggagct agacacaatg aaacatcaga gccagctaaa aaaaaaaaaa | 1980 |
| aaaaaaaaaa aaaaaaaaa | 2000 |

```
<210> SEQ ID NO 303
<211> LENGTH: 2040
<212> TYPE: DNA
<213> ORGANISM: Homo sapien

<400> SEQUENCE: 303
```

| | |
|---|---|
| atggtggttg aggttgattc catgccggct gcctcttctg tgaagaagcc atttggtctc | 60 |
| aggagcaaga tgggcaagtg gtgctgccgt tgcttcccct gctgcaggga gagcggcaag | 120 |
| agcaacgtgg gcacttctgg agaccacgac gactctgcta tgaagacact caggagcaag | 180 |
| atgggcaagt ggtgccgcca ctgcttcccc tgctgcaggg ggagtggcaa gagcaacgtg | 240 |
| ggcgcttctg gagaccacga cgactctgct atgaagacac tcaggaacaa gatgggcaag | 300 |
| tggtgctgcc actgcttccc ctgctgcagg gggagcggca agagcaaggt gggcgcttgg | 360 |

```
ggagactacg atgacagtgc cttcatggag cccaggtacc acgtccgtgg agaagatctg    420
gacaagctcc acagagctgc ctggtggggt aaagtcccca gaaaggatct catcgtcatg    480
ctcagggaca ctgacgtgaa caagaaggac aagcaaaaga ggactgctct acatctggcc    540
tctgccaatg ggaattcaga agtagtaaaa ctcctgctgg acagacgatg tcaacttaat    600
gtccttgaca caaaaagag gacagctctg ataaaggccg tacaatgcca ggaagatgaa     660
tgtgcgttaa tgttgctgga acatggcact gatccaaata ttccagatga gtatggaaat    720
accactctgc actacgctat ctataatgaa gataaattaa tggccaaagc actgctctta    780
tatggtgctg atatcgaatc aaaaaacaag catggcctca caccactgtt acttggtgta    840
catgagcaaa acagcaagt cgtgaaattt ttaatcaaga aaaagcgaa tttaaatgca      900
ctggatagat atgaaggac tgctctcata cttgctgtat gttgtggatc agcaagtata    960
gtcagccttc tacttgagca aaatattgat gtatcttctc aagatctatc tggacagacg   1020
gccagagagt atgctgtttc tagtcatcat catgtaattt gccagttact ttctgactac   1080
aaagaaaaac agatgctaaa aatctcttct gaaaacagca atccagaaca agacttaaag   1140
ctgacatcag aggaagagtc acaaaggttc aaaggcagtg aaaatagcca gccagagaaa   1200
atgtctcaag aaccagaaat aaataaggat ggtgatagag aggttgaaga gaaatgaag    1260
aagcatgaaa gtaataatgt gggattacta gaaaacctga ctaatggtgt cactgctggc   1320
aatggtgata atggattaat tcctcaaagg aagagcagaa cacctgaaaa tcagcaattt   1380
cctgacaacg aaagtgaaga gtatcacaga atttgcgaat tagtttctga ctacaaagaa   1440
aaacagatgc caaatactc ttctgaaaac agcaacccag aacaagactt aaagctgaca   1500
tcagaggaag agtcacaaag gcttgagggc agtgaaaatg ccagccaga gaaagatct    1560
caagaaccag aaataaataa ggatggtgat agagagctag aaaattttat ggctatcgaa   1620
gaaatgaaga agcacggaag tactcatgtc ggattcccga aaaacctgac taatggtgcc   1680
actgctggca atggtgatga tggattaatt cctccaagga gagcagaac acctgaaagc    1740
cagcaatttc ctgacactga aatgaagag tatcacagtg acgaacaaaa tgatactcag    1800
aagcaatttt gtgaagaaca gaacactgga atattacacg atgagattct gattcatgaa   1860
gaaaagcaga tagaagtggt tgaaaaaatg aattctgagc tttctcttag ttgtaagaaa   1920
gaaaaagaca tcttgcatga aaatagtacg ttgcgggaag aaattgccat gctaagactg   1980
gagctagaca caatgaaaca tcagagccag ctaaaaaaaa aaaaaaaaaa aaaaaaaaa    2040
```

<210> SEQ ID NO 304
<211> LENGTH: 384
<212> TYPE: PRT
<213> ORGANISM: Homo sapien

<400> SEQUENCE: 304

```
Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80
```

```
Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
        115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

<210> SEQ ID NO 305
<211> LENGTH: 656
<212> TYPE: PRT
<213> ORGANISM: Homo sapien

<400> SEQUENCE: 305

Met Val Val Glu Val Asp Ser Met Pro Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80
```

-continued

```
Gly Ala Ser Gly Asp His Asp Asp Ser Ala Met Lys Thr Leu Arg Asn
                 85                  90                  95
Lys Met Gly Lys Trp Cys Cys His Cys Phe Pro Cys Cys Arg Gly Ser
            100                 105                 110
Gly Lys Ser Lys Val Gly Ala Trp Gly Asp Tyr Asp Asp Ser Ala Phe
            115                 120                 125
Met Glu Pro Arg Tyr His Val Arg Gly Glu Asp Leu Asp Lys Leu His
    130                 135                 140
Arg Ala Ala Trp Trp Gly Lys Val Pro Arg Lys Asp Leu Ile Val Met
145                 150                 155                 160
Leu Arg Asp Thr Asp Val Asn Lys Lys Asp Gln Lys Arg Thr Ala
                165                 170                 175
Leu His Leu Ala Ser Ala Asn Gly Asn Ser Glu Val Val Lys Leu Leu
                180                 185                 190
Leu Asp Arg Arg Cys Gln Leu Asn Val Leu Asp Asn Lys Lys Arg Thr
                195                 200                 205
Ala Leu Ile Lys Ala Val Gln Cys Gln Glu Asp Glu Cys Ala Leu Met
    210                 215                 220
Leu Leu Glu His Gly Thr Asp Pro Asn Ile Pro Asp Glu Tyr Gly Asn
225                 230                 235                 240
Thr Thr Leu His Tyr Ala Ile Tyr Asn Glu Asp Lys Leu Met Ala Lys
                245                 250                 255
Ala Leu Leu Leu Tyr Gly Ala Asp Ile Glu Ser Lys Asn Lys His Gly
                260                 265                 270
Leu Thr Pro Leu Leu Leu Gly Val His Glu Gln Lys Gln Gln Val Val
    275                 280                 285
Lys Phe Leu Ile Lys Lys Ala Asn Leu Asn Ala Leu Asp Arg Tyr
290                 295                 300
Gly Arg Thr Ala Leu Ile Leu Ala Val Cys Cys Gly Ser Ala Ser Ile
305                 310                 315                 320
Val Ser Leu Leu Leu Glu Gln Asn Ile Asp Val Ser Ser Gln Asp Leu
                325                 330                 335
Ser Gly Gln Thr Ala Arg Glu Tyr Ala Val Ser Ser His His Val
                340                 345                 350
Ile Cys Gln Leu Leu Ser Asp Tyr Lys Glu Lys Gln Met Leu Lys Ile
    355                 360                 365
Ser Ser Glu Asn Ser Asn Pro Glu Gln Asp Leu Lys Leu Thr Ser Glu
    370                 375                 380
Glu Glu Ser Gln Arg Phe Lys Gly Ser Glu Asn Ser Gln Pro Glu Lys
385                 390                 395                 400
Met Ser Gln Glu Pro Glu Ile Asn Lys Asp Gly Asp Arg Glu Val Glu
                405                 410                 415
Glu Glu Met Lys Lys His Glu Ser Asn Asn Val Gly Leu Leu Glu Asn
                420                 425                 430
Leu Thr Asn Gly Val Thr Ala Gly Asn Gly Asp Asn Gly Leu Ile Pro
                435                 440                 445
Gln Arg Lys Ser Arg Thr Pro Glu Asn Gln Gln Phe Pro Asp Asn Glu
    450                 455                 460
Ser Glu Glu Tyr His Arg Ile Cys Glu Leu Val Ser Asp Tyr Lys Glu
465                 470                 475                 480
Lys Gln Met Pro Lys Tyr Ser Ser Glu Asn Ser Asn Pro Glu Gln Asp
                485                 490                 495
```

```
Leu Lys Leu Thr Ser Glu Glu Ser Gln Arg Leu Glu Gly Ser Glu
            500                 505                 510

Asn Gly Gln Pro Glu Leu Glu Asn Phe Met Ala Ile Glu Glu Met Lys
            515                 520                 525

Lys His Gly Ser Thr His Val Gly Phe Pro Glu Asn Leu Thr Asn Gly
            530                 535                 540

Ala Thr Ala Gly Asn Gly Asp Asp Gly Leu Ile Pro Pro Arg Lys Ser
545                 550                 555                 560

Arg Thr Pro Glu Ser Gln Gln Phe Pro Asp Thr Glu Asn Glu Glu Tyr
            565                 570                 575

His Ser Asp Glu Gln Asn Asp Thr Gln Lys Gln Phe Cys Glu Glu Gln
            580                 585                 590

Asn Thr Gly Ile Leu His Asp Glu Ile Leu Ile His Glu Glu Lys Gln
            595                 600                 605

Ile Glu Val Val Glu Lys Met Asn Ser Glu Leu Ser Leu Ser Cys Lys
            610                 615                 620

Lys Glu Lys Asp Ile Leu His Glu Asn Ser Thr Leu Arg Glu Glu Ile
625                 630                 635                 640

Ala Met Leu Arg Leu Glu Leu Asp Thr Met Lys His Gln Ser Gln Leu
            645                 650                 655

<210> SEQ ID NO 306
<211> LENGTH: 671
<212> TYPE: PRT
<213> ORGANISM: Homo sapien

<400> SEQUENCE: 306

Met Val Val Glu Val Asp Ser Met Pro Ala Ala Ser Ser Val Lys Lys
1               5                   10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
            35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Ser Ala Met Lys Thr Leu Arg Asn
            85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
            115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
            165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
            195                 200                 205

Ala Leu Ile Lys Ala Val Gln Cys Gln Glu Asp Glu Cys Ala Leu Met
    210                 215                 220
```

```
Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
    370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
        435                 440                 445

Gln Arg Lys Ser Arg Thr Pro Glu Asn Gln Gln Phe Pro Asp Asn Glu
    450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
                485                 490                 495

Leu Lys Leu Thr Ser Glu Glu Ser Gln Arg Leu Glu Gly Ser Glu
            500                 505                 510

Asn Gly Gln Pro Glu Lys Arg Ser Gln Glu Pro Glu Ile Asn Lys Asp
        515                 520                 525

Gly Asp Arg Glu Leu Glu Asn Phe Met Ala Ile Glu Glu Met Lys Lys
    530                 535                 540

His Gly Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
                565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Glu Lys Gln Ile
    610                 615                 620

Glu Val Val Glu Lys Met Asn Ser Glu Leu Ser Leu Ser Cys Lys Lys
625                 630                 635                 640
```

-continued

Glu Lys Asp Ile Leu His Glu Asn Ser Thr Leu Arg Glu Glu Ile Ala
            645                 650                 655

Met Leu Arg Leu Glu Leu Asp Thr Met Lys His Gln Ser Gln Leu
            660                 665                 670

<210> SEQ ID NO 307
<211> LENGTH: 800
<212> TYPE: DNA
<213> ORGANISM: Homo sapien

<400> SEQUENCE: 307

| | | |
|---|---|---|
| atkagcttcc gcttctgaca acactagaga tccctcccct ccctcagggt atggccctcc | 60 |
| acttcatttt tggtacataa catctttata ggacaggggt aaaatcccaa tactaacagg | 120 |
| agaatgctta ggactctaac aggttttga gaatgtgttg gtaagggcca ctcaatccaa | 180 |
| tttttcttgg tcctccttgt ggtctaggag gacaggcaag ggtgcagatt tcaagaatg | 240 |
| catcagtaag ggccactaaa tccgaccttc ctcgttcctc cttgtggtct gggaggaaaa | 300 |
| ctagtgtttc tgttgctgtg tcagtgagca caactattcc gatcagcagg gtccagggac | 360 |
| cactgcaggt tcttgggcag ggggagaaac aaaacaaacc aaaaccatgg gcrgttttgt | 420 |
| ctttcagatg ggaaacactc aggcatcaac aggctcacct ttgaaatgca tcctaagcca | 480 |
| atgggacaaa tttgacccac aaaccctgga aaagaggtg gctcattttt tttgcactat | 540 |
| ggcttggccc caacattctc tctctgatgg ggaaaaatgg ccacctgagg gaagtacaga | 600 |
| ttacaatact atcctgcagc ttgaccttt ctgtaagagg gaaggcaaat ggagtgaaat | 660 |
| accttatgtc caagctttct tttcattgaa ggagaataca ctatgcaaag cttgaaattt | 720 |
| acatcccaca ggaggacctc tcagcttacc cccatatcct agcctcccta tagctcccct | 780 |
| tcctattagt gataagcctc | 800 |

<210> SEQ ID NO 308
<211> LENGTH: 102
<212> TYPE: PRT
<213> ORGANISM: Homo sapien
<220> FEATURE:
<221> NAME/KEY: VARIANT
<222> LOCATION: (1)...(102)
<223> OTHER INFORMATION: Xaa = Any Amino Acid

<400> SEQUENCE: 308

Met Gly Xaa Phe Val Phe Gln Met Gly Asn Thr Gln Ala Ser Thr Gly
 1               5                  10                  15

Ser Pro Leu Lys Cys Ile Leu Ser Gln Trp Asp Lys Phe Asp Pro Gln
            20                  25                  30

Thr Leu Glu Lys Glu Val Ala His Phe Phe Cys Thr Met Ala Trp Pro
        35                  40                  45

Gln His Ser Leu Ser Asp Gly Glu Lys Trp Pro Pro Glu Gly Ser Thr
    50                  55                  60

Asp Tyr Asn Thr Ile Leu Gln Leu Asp Leu Phe Cys Lys Arg Glu Gly
65                  70                  75                  80

Lys Trp Ser Glu Ile Pro Tyr Val Gln Ala Phe Phe Ser Leu Lys Glu
                85                  90                  95

Asn Thr Leu Cys Lys Ala
            100

<210> SEQ ID NO 309
<211> LENGTH: 9
<212> TYPE: PRT
<213> ORGANISM: Artificial Sequence
<220> FEATURE:
<223> OTHER INFORMATION: Made in the lab

<400> SEQUENCE: 309

Leu Met Ala Glu Glu Tyr Thr Ile Val
 1               5

<210> SEQ ID NO 310
<211> LENGTH: 9
<212> TYPE: PRT
<213> ORGANISM: Artificial Sequence
<220> FEATURE:
<223> OTHER INFORMATION: Made in the lab

<400> SEQUENCE: 310

Lys Leu Met Ala Lys Ala Leu Leu Leu
 1               5

<210> SEQ ID NO 311
<211> LENGTH: 9
<212> TYPE: PRT
<213> ORGANISM: Artificial Sequence
<220> FEATURE:
<223> OTHER INFORMATION: Made in the lab

<400> SEQUENCE: 311

Gly Leu Thr Pro Leu Leu Leu Gly Ile
 1               5

<210> SEQ ID NO 312
<211> LENGTH: 10
<212> TYPE: PRT
<213> ORGANISM: Artificial Sequence
<220> FEATURE:
<223> OTHER INFORMATION: Made in the lab

<400> SEQUENCE: 312

Lys Leu Val Leu Asp Arg Arg Cys Gln Leu
 1               5                  10

<210> SEQ ID NO 313
<211> LENGTH: 1852
<212> TYPE: DNA
<213> ORGANISM: Homo sapiens

<400> SEQUENCE: 313
ggcacgagaa ttaaaaccct cagcaaaaca ggcatagaag ggacatacct taaagtaata      60 aaaccacct atgacaagcc cacagccaac ataatactaa atggggaaaa gttagaagca     120
tttcctctga gaactgcaac aataaataca aggatgctgg attttgtcaa atgccttttc    180
tgtgtctgtt gagatgctta tgtgactttg cttttaattc tgtttatgtg attatcacat    240
ttattgactt gcctgtgtta gaccggaaga gctggggtgt ttctcaggag ccaccgtgtg    300
ctgcggcagc ttcgggataa cttgaggctg catcactggg gaagaaacac aytcctgtcc    360
gtggcgctga tggctgagga cagagcttca gtgtggcttc tctgcgactg gcttcttcgg    420
ggagttcttc cttcatagtt catccatatg gctccagagg aaaattatat tatttttgtta   480 tggatgaaga gtattacgtt gtgcagatat actgcagtgt cttcatctct tgatgtgtga    540
ttgggtaggt tccaccatgt tgccgcagat gacatgattt cagtacctgt gtctggctga    600

-continued

| | | | |
|---|---|---|---|
| aaagtgtttg | tttgtgaatg | gatattgtgg | tttctggatc tcatcctctg tgggtggaca | 660 |
| gctttctcca | ccttgctgga | agtgacctgc | tgtccagaag tttgatggct gaggagtata | 720 |
| ccatcgtgca | tgcatctttc | atttcctgca | tttcttcctc cctggatgga caggggagc | 780 |
| ggcaagagca | acgtgggcac | ttctggagac | cacaacgact cctctgtgaa gacgcttggg | 840 |
| agcaagaggt | gcaagtggtg | ctgccactgc | ttcccctgct gcaggggag cggcaagagc | 900 |
| aacgtggtcg | cttggggaga | ctacgatgac | agcgccttca tggatcccag gtaccacgtc | 960 |
| catggagaag | atctggacaa | gctccacaga | gctgcctggt ggggtaaagt ccccagaaag | 1020 |
| gatctcatcg | tcatgctcag | ggacacggat | gtgaacaaga gggacaagca aaagaggact | 1080 |
| gctctacatc | tggcctctgc | caatgggaat | tcagaagtag taaaactcgt gctggacaga | 1140 |
| cgatgtcaac | ttaatgtcct | tgacaacaaa | aagaggacac tctgacaaa ggccgtacaa | 1200 |
| tgccaggaag | atgaatgtgc | gttaatgttg | ctggaacatg gcactgatcc aaatattcca | 1260 |
| gatgagtatg | gaaataccac | tctacactat | gctgtctaca atgaagataa attaatggcc | 1320 |
| aaagcactgc | tcttatacgg | tgctgatatc | gaatcaaaaa acaagcatgg cctcacacca | 1380 |
| ctgctacttg | gtatacatga | gcaaaaacag | caagtggtga aattttttaat caagaaaaaa | 1440 |
| gcgaatttaa | atgcgctgga | tagatatgga | agaactgctc tcatacttgc tgtatgttgt | 1500 |
| ggatcagcaa | gtatagtcag | ccctctactt | gagcaaaatg ttgatgtatc ttctcaagat | 1560 |
| ctggaaagac | ggccagagag | tatgctgttt | ctagtcatca tcatgtaatt tgccagttac | 1620 |
| tttctgacta | caaagaaaaa | cagatgttaa | aaatctcttc tgaaaacagc aatccagaac | 1680 |
| aagacttaaa | gctgacatca | gaggaagagt | cacaaaggct taaggaagt gaaaacagcc | 1740 |
| agccagagct | agaagattta | tggctattga | agaagatga agaacacgga agtactcatg | 1800 |
| tgggattccc | agaaaacctg | actaacggtg | ccgctgctgg caatggtgat ga | 1852 |

<210> SEQ ID NO 314
<211> LENGTH: 879
<212> TYPE: DNA
<213> ORGANISM: Homo sapiens

<400> SEQUENCE: 314

| | | | |
|---|---|---|---|
| atgcatcttt | catttcctgc | atttcttcct | ccctggatgg acaggggag cggcaagagc | 60 |
| aacgtgggca | cttctggaga | ccacaacgac | tcctctgtga agacgcttgg gagcaagagg | 120 |
| tgcaagtggt | gctgccactg | cttcccctgc | tgcaggggga gcggcaagag caacgtggtc | 180 |
| gcttggggag | actacgatga | cagcgccttc | atggatccca ggtaccacgt ccatggagaa | 240 |
| gatctggaca | agctccacag | agctgcctgg | tggggtaaag tccccagaaa ggatctcatc | 300 |
| gtcatgctca | gggacacgga | tgtgaacaag | agggacaagc aaaagaggac tgctctacat | 360 |
| ctggcctctg | ccaatgggaa | ttcagaagta | gtaaaactcg tgctggacag acgatgtcaa | 420 |
| cttaatgtcc | ttgacaacaa | aaagaggaca | ctctgacaa aggccgtaca atgccaggaa | 480 |
| gatgaatgtg | cgttaatgtt | gctggaacat | ggcactgatc caaatattcc agatgagtat | 540 |
| ggaaatacca | ctctacacta | tgctgtctac | aatgaagata aattaatggc caaagcactg | 600 |
| ctcttatacg | gtgctgatat | cgaatcaaaa | acaagcatg gcctcacacc actgctactt | 660 |
| ggtatacatg | agcaaaaaca | gcaagtggtg | aattttttaa tcaagaaaaa agcgaatta | 720 |
| aatgcgctgg | atagatatgg | aagaactgct | ctcatacttg ctgtatgttg tggatcagca | 780 |
| agtatagtca | gccctctact | tgagcaaaat | gttgatgtat cttctcaaga tctggaaaga | 840 |
| cggccagaga | gtatgctgtt | tctagtcatc | atcatgtaa | 879 |

<210> SEQ ID NO 315
<211> LENGTH: 292
<212> TYPE: PRT
<213> ORGANISM: Homo sapiens

<400> SEQUENCE: 315

Met His Leu Ser Phe Pro Ala Phe Leu Pro Pro Trp Met Asp Arg Gly
1               5                   10                  15
Ser Gly Lys Ser Asn Val Gly Thr Ser Gly Asp His Asn Asp Ser Ser
            20                  25                  30
Val Lys Thr Leu Gly Ser Lys Arg Cys Lys Trp Cys Cys His Cys Phe
        35                  40                  45
Pro Cys Cys Arg Gly Ser Gly Lys Ser Asn Val Val Ala Trp Gly Asp
    50                  55                  60
Tyr Asp Asp Ser Ala Phe Met Asp Pro Arg Tyr His Val His Gly Glu
65                  70                  75                  80
Asp Leu Asp Lys Leu His Arg Ala Ala Trp Trp Gly Lys Val Pro Arg
                85                  90                  95
Lys Asp Leu Ile Val Met Leu Arg Asp Thr Asp Val Asn Lys Arg Asp
            100                 105                 110
Lys Gln Lys Arg Thr Ala Leu His Leu Ala Ser Ala Asn Gly Asn Ser
        115                 120                 125
Glu Val Val Lys Leu Val Leu Asp Arg Arg Cys Gln Leu Asn Val Leu
    130                 135                 140
Asp Asn Lys Lys Arg Thr Ala Leu Thr Lys Ala Val Gln Cys Gln Glu
145                 150                 155                 160
Asp Glu Cys Ala Leu Met Leu Leu Glu His Gly Thr Asp Pro Asn Ile
                165                 170                 175
Pro Asp Glu Tyr Gly Asn Thr Thr Leu His Tyr Ala Val Tyr Asn Glu
            180                 185                 190
Asp Lys Leu Met Ala Lys Ala Leu Leu Tyr Gly Ala Asp Ile Glu
        195                 200                 205
Ser Lys Asn Lys His Gly Leu Thr Pro Leu Leu Leu Gly Ile His Glu
    210                 215                 220
Gln Lys Gln Gln Val Val Lys Phe Leu Ile Lys Lys Ala Asn Leu
225                 230                 235                 240
Asn Ala Leu Asp Arg Tyr Gly Arg Thr Ala Leu Ile Leu Ala Val Cys
                245                 250                 255
Cys Gly Ser Ala Ser Ile Val Ser Pro Leu Leu Glu Gln Asn Val Asp
            260                 265                 270
Val Ser Ser Gln Asp Leu Glu Arg Arg Pro Glu Ser Met Leu Phe Leu
        275                 280                 285
Val Ile Ile Met
    290

<210> SEQ ID NO 316
<211> LENGTH: 584
<212> TYPE: DNA
<213> ORGANISM: Homo sapiens

<400> SEQUENCE: 316
agttgggcca aattcccctc ccctacagc ttgaagggga cataaccaat agcctgggt        60 ttttttgtgg tccttggag atttctttgc ttattttctt ctgggtgggg gtgattagag      120
gaggcttatc actaatagga aggggagcta taggaggct aggatatggg ggtaagctga     180
gaggtcctcc tgtgggatgt aaatttcaag ctttgcatag tgtattctcc ttcaatgaaa    240

-continued

```
agaaagcttg gacataaggt atttcactcc atttgccttc cctcttacag aaaaggtcaa    300
gctgcaggat agtattgtaa tctgtacttc cctcaggtgg ccattttcc ccatcagaga     360
gagaatgttg gggccaagcc atagtgcaga aaaaaaaatg agccacctct ttttccaggg    420
tttgtgggtc aaatttgtcc cattggctta ggatgcattt caaaggtgag cctgttgatg    480
cctgagtgtt tcccatctga aagacaaaac tgcccatggt tttggtttgt tttgtttctc    540
cccctgccca agaactatca aactcctgag ccaacaacta aaaa                    584

<210> SEQ ID NO 317
<211> LENGTH: 829
<212> TYPE: DNA
<213> ORGANISM: Homo sapiens

<400> SEQUENCE: 317
attagcttcc gcttctgaca acactagaga tccctcccct ccctcagggt atggccctcc     60
acttcatttt tggtacataa catctttata ggacaggggt aaaatcccaa tactaacagg    120
agaatgctta ggactctaac aggtttttga gaatgtgttg gtaagggcca ctcaatccaa    180
tttttcttgg tcctccttgt ggtctaggag gacaggcaag ggtgcagatt ttcaagaatg    240
catcagtaag ggccactaaa tccgaccttc ctcgttcctc cttgtggtct gggaggaaaa    300
ctagtgtttc tgttgctgtg tcagtgagca caactattcc gatcagcagg gtccagggac    360
cactgcaggt tcttgggcag ggggagaaac aaaacaaacc aaaaccatgg gcagttttgt    420
ctttcagatg ggaaacactc aggcatcaac aggctcacct ttgaaatgca tcctaagcca    480
atgggacaaa tttgacccac aaaccctgga aaaagaggtg gctcattttt tttgcactat    540
ggcttggccc caacattctc tctctgatgg ggaaaaatgg ccacctgagg gaagtacaga    600
ttacaatact atcctgcagc ttgaccttt ctgtaagagg gaaggcaaat ggagtgaaat     660
accttatgtc caagctttct tttcattgaa ggagaataca ctatgcaaag cttgaaattt    720
acatcccaca ggaggacctc tcagcttacc cccatatcct agcctcccta tagctcccct    780
tcctattagt gataagcctc ctctaatcac ccccacccag aagaaaata                829
```

COMPOSITIONS AND METHODS FOR THE TREATMENT AND DIAGNOSIS OF BREAST CANCER

CROSS REFERENCE TO RELATED APPLICATIONS

This application is a continuation-in-part of U.S. patent application Ser. No. 09/429,755, filed Oct. 28, 1999, which is a continuation-in-part of U.S. patent application Ser. No. 09/289,198, filed Apr. 9, 1999, which is a continuation-in-part of U.S. patent application Ser. No. 09/062,451, filed Apr. 17, 1998, which is a continuation in part of U.S. patent application Ser. No. 08/991,789, filed Dec. 11, 1997, which is a continuation-in-part of U.S. patent application Ser. No. 08/838,762, filed Apr. 9, 1997 Now Abandoned, which claims priority from International Patent Application No. PCT/US97/00485, filed Jan. 10, 1997, and is a continuation-in-part of U.S. patent application Ser. No. 08/700,014, filed Aug. 20, 1996, which is a continuation-in-part of U.S. patent application Ser. No. 08/585,392, filed Jan. 1, 1996.

TECHNICAL FIELD

The present invention relates generally to the detection and therapy of breast cancer. The invention is more specifically related to nucleotide sequences that are preferentially expressed in breast tumor tissue and to polypeptides encoded by such nucleotide sequences. The nucleotide sequences and polypeptides may be used in vaccines and pharmaceutical compositions for the prevention and treatment of breast cancer. The polypeptides may also be used for the production of compounds, such as antibodies, useful for diagnosing and monitoring the progression of breast cancer in a patient.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific-tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

Briefly stated, the subject invention provides compositions and methods for the diagnosis and therapy of breast cancer. In one aspect, isolated polynucleotides are provided, comprising (a) a nucleotide sequence preferentially expressed in breast cancer tissue, relative to normal tissue; (b) a variant of such a sequence, as defined below; or (c) a nucleotide sequence encoding an epitope of a polypeptide encoded by at least one of the above sequences. In one embodiment, the isolated polynucleotide comprises a human endogenous retroviral sequence recited in SEQ ID NO: 1. In other embodiments, the isolated polynucleotide comprises a sequence recited in any one of SEQ ID NO: 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317.

In related embodiments, the isolated polynucleotide encodes an epitope of polypeptide, wherein the polypeptide is encoded by a nucleotide sequence that: (a) hybridizes to a sequence recited in any one of SEQ ID NO: 1, 3–26, 28–77, 142, 143, 46–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317 under stringent conditions; and (b) is at least 80% identical to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317.

In another embodiment, the present invention provides an isolated polynucleotide encoding an epitope of a polypeptide, the polypeptide being encoded by: (a) a nucleotide sequence transcribed from the sequence of SEQ ID NO: 141; or (b) a variant of said nucleotide sequence that contains one or more nucleotide substitutions, deletions, insertions and/or modifications at no more than 20% of the nucleotide positions, such that the antigenic and/or immunogenic properties of the polypeptide encoded by the nucleotide sequence are retained. Isolated DNA and RNA molecules comprising a nucleotide sequence complementary to a polynucleotide as described above are also provided.

In related aspects, the present invention provides recombinant expression vectors comprising a polynucleotide as described above and host cells transformed or transfected with such expression vectors.

In further aspects, polypeptides comprising an amino acid sequence encoded by a polynucleotide as described above, and monoclonal antibodies that bind to such polypeptides are provided. In certain embodiments, the inventive polypeptides comprise an amino acid sequence selected from the group consisting of SEQ ID NO: 299, 300, 304–306, 308 and 315, and variants thereof as defined below.

In yet another aspect, methods are provided for determining the presence of breast cancer in a patient. In one embodiment, the method comprises detecting, within a biological sample, a polypeptide as described above. In another embodiment, the method comprises detecting, within a biological sample, an RNA molecule encoding a polypeptide as described above. In yet another embodiment, the method comprises (a) intradermally injecting a patient with a polypeptide as described above; and (b) detecting an immune response on the patient's skin and therefrom detecting the presence of breast cancer in the patient. In further embodiments, the present invention provides methods for determining the presence of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In a related aspect, diagnostic kits useful in the determination of breast cancer are provided. The diagnostic kits generally comprise either one or more monoclonal antibodies as described above, or one or more monoclonal antibodies that bind to a polypeptide encoded by a nucleotide sequence selected from the group consisting of sequences provided in SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and a detection reagent.

Diagnostic kits are also provided that comprise a first polymerase chain reaction primer and a second polymerase chain reaction primer, at least one of the primers being specific for a polynucleotide described herein. In one embodiment, at least one of the primers comprises at least about 10 contiguous nucleotides of a polynucleotide as described above, or a polynucleotide encoding a polypeptide encoded by a sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289 and 290.

Within another related aspect, the diagnostic kit comprises at least one oligonucleotide probe, the probe being specific for a polynucleotide described herein. In one embodiment, the probe comprises at least about 15 contiguous nucleotides of a polynucleotide as described above, or a polynucleotide selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289 and 290.

In another related aspect, the present invention provides methods for monitoring the progression of breast cancer in a patient. In one embodiment, the method comprises: (a) detecting an amount, in a biological sample, of a polypeptide as described above at a first point in time; (b) repeating step (a) at a subsequent point in time; and (c) comparing the amounts of polypeptide detected in steps (a) and (b), and therefrom monitoring the progression of breast cancer in the patient. In another embodiment, the method comprises (a) detecting an amount, within a biological sample, of an RNA molecule encoding a polypeptide as described above at a first point in time; (b) repeating step (a) at a subsequent point in time; and (c) comparing the amounts of RNA molecules detected in steps (a) and (b), and therefrom monitoring the progression of breast cancer in the patient. In yet other embodiments, the present invention provides methods for monitoring the progression of breast cancer in a patient as described above wherein the polypeptide is encoded by a nucleotide sequence selected from the group consisting of SEQ ID NO: 78–86, 144, 145, 153, 167, 177, 193, 199, 205, 208, 215, 217, 220, 241, 242, 246, 248, 249, 252, 256, 267, 270, 274, 277, 279, 282, 283, 285–287, 289, 290 and sequences that hybridize thereto under stringent conditions.

In still other aspects, pharmaceutical compositions, which comprise a polypeptide as described above in combination with a physiologically acceptable carrier, and vaccines, which comprise a polypeptide as described above in combination with an immunostimulant or adjuvant, are provided. In yet other aspects, the present invention provides pharmaceutical compositions and vaccines comprising a polypeptide encoded by a nucleotide sequence selected from the group consisting of SEQ ID NO: 78–86, 144, 145, 153, 167, 177, 193, 199, 205, 208, 215, 217, 220, 241, 242 and 246, 248, 249, 252, 256, 267, 270, 274, 277, 279, 282, 283, 285–287, 289, 290 and sequences that hybridize thereto under stringent conditions.

In related aspects, the present invention provides methods for inhibiting the development of breast cancer in a patient, comprising administering to a patient a pharmaceutical composition or vaccine as described above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 5A and 5B show the sequencing strategy, genomic organization and predicted open reading frame for the retroviral element containing B18Ag1.

FIG. 6 shows the nucleotide sequence of the representative breast tumor-specific cDNA B18Ag1.

FIG. 7 shows the nucleotide sequence of the representative breast tumor-specific cDNA B17Ag1.

FIG. 8 shows the nucleotide sequence of the representative breast tumor-specific cDNA B17Ag2.

FIG. 9 shows the nucleotide sequence of the representative breast tumor-specific cDNA B13Ag2a.

FIG. 10 shows the nucleotide sequence of the representative breast tumor-specific cDNA B13Ag1b.

FIG. 11 shows the nucleotide sequence of the representative breast tumor-specific cDNA B13Ag1a.

FIG. 12 shows the nucleotide sequence of the representative breast tumor-specific cDNA B11Ag1.

FIG. 13 shows the nucleotide sequence of the representative breast tumor-specific cDNA B3CA3c.

FIG. 14 shows the nucleotide sequence of the representative breast tumor-specific cDNA B9CG1.

FIG. 15 shows the nucleotide sequence of the representative breast tumor-specific cDNA B9CG3.

FIG. 16 shows the nucleotide sequence of the representative breast tumor-specific cDNA B2CA2.

FIG. 17 shows the nucleotide sequence of the representative breast tumor-specific cDNA B3CA1.

FIG. 18 shows the nucleotide sequence of the representative breast tumor-specific cDNA B3CA2.

FIG. 19 shows the nucleotide sequence of the representative breast tumor-specific cDNA B3CA3.

FIG. 20 shows the nucleotide sequence of the representative breast tumor-specific cDNA B4CA1.

DETAILED DESCRIPTION OF THE INVENTION

Figure 1:
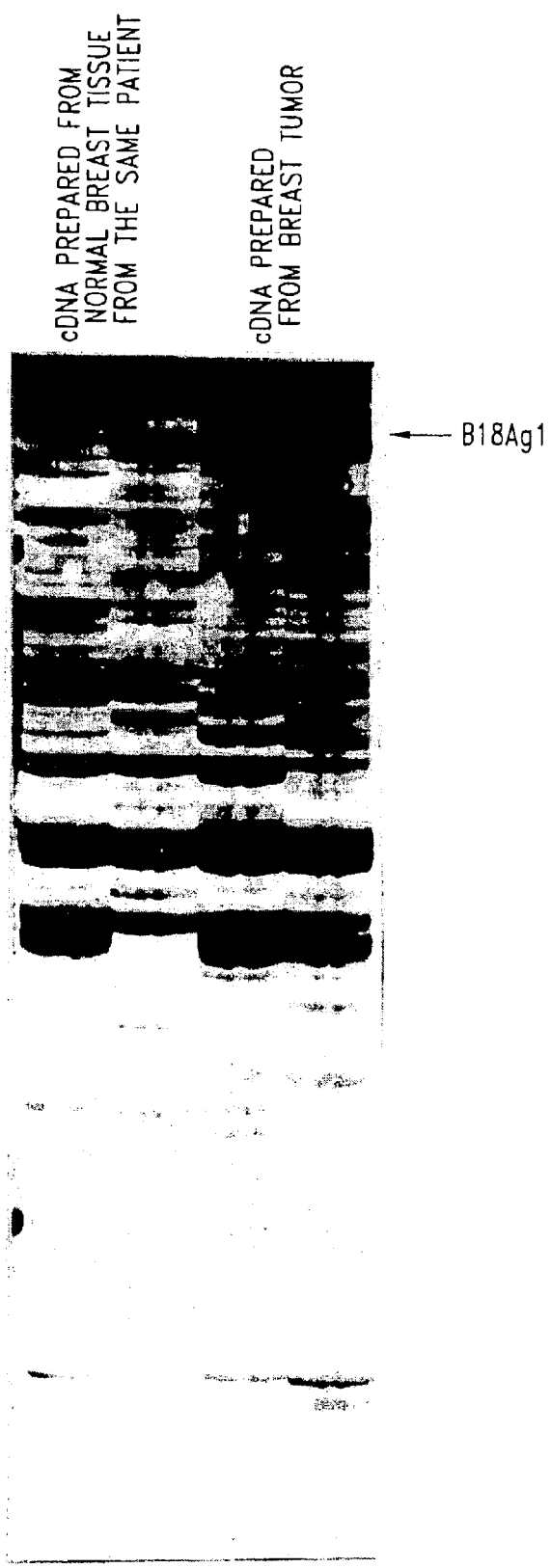
FIG. 1 shows the differential display PCR products, separated by gel electrophoresis, obtained from cDNA prepared from normal breast tissue (lanes 1 and 2) and from cDNA prepared from breast tumor tissue from the same patient (lanes 3 and 4). The arrow indicates the band corresponding to B18Ag1.

As noted above, the present invention is generally directed to compositions and methods for the diagnosis, monitoring and therapy of breast cancer. The compositions described herein include polypeptides, polynucleotides and antibodies. Polypeptides of the present invention generally comprise at least a portion of a protein that is expressed at a greater level in human breast tumor tissue than in normal breast tissue (i.e., the level of RNA encoding the polypeptide is at least 2-fold higher in tumor tissue). Such polypeptides are referred to herein as breast tumor-specific polypeptides, and cDNA molecules encoding such polypeptides are referred to as breast tumor-specific cDNAs. Polynucleotides of the subject invention generally comprise a DNA or RNA sequence that encodes all or a portion of a polypeptide as described above, or that is complementary to such a sequence. Antibodies are generally immune system proteins, or fragments thereof, that are capable of binding to a portion of a polypeptide as described above. Antibodies can be produced by cell culture techniques, including the generation of monoclonal antibodies as described herein, or via transfection of antibody genes into suitable bacterial or mammalian cell hosts, in order to allow for the production of recombinant antibodies.

Polypeptides within the scope of this invention include, but are not limited to, polypeptides (and epitopes thereof) encoded by a human endogenous retroviral sequence, such as the sequence designated B18Ag1 (FIG. 5 and SEQ ID NO: 1). Also within the scope of the present invention are polypeptides encoded by other sequences within the retroviral genome containing B18Ag1 (SEQ ID NO: 141). Such sequences include, but are not limited to, the sequences recited in SEQ ID NO:3–SEQ ID NO:10. B18Ag1 has homology to the gag p30 gene of the endogenous human retroviral element S71, as described in Werner et al., *Virology* 174:225–238 (1990) and also shows homology to about thirty other retroviral gag genes. As discussed in more detail below, the present invention also includes a number of additional breast tumor-specific polypeptides, such as those encoded by the nucleotide sequences recited in SEQ ID NO: 11–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317.

As used herein, the term "polypeptide" encompasses amino acid chains of any length, including full length proteins containing the sequences recited herein. A polypeptide comprising an epitope of a protein containing a sequence as described herein may consist entirely of the epitope, or may contain additional sequences. The additional sequences may be derived from the native protein or may be heterologous, and such sequences may (but need not) possess immunogenic or antigenic properties.

An "epitope," as used herein is a portion of a polypeptide that is recognized (i.e., specifically bound) by a B-cell and/or T-cell surface antigen receptor. Epitopes may generally be identified using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones. An epitope of a polypeptide is a portion that reacts with such antisera and/or T-cells at a level that is similar to the reactivity of the full length polypeptide (e.g., in an ELISA and/or T-cell reactivity assay). Such screens may generally be performed using methods well known to those of ordinary skill in the art, such as those described in Harlow and Lane, *Antibodies: A Laboratory Manual*, Cold Spring Harbor Laboratory, 1988. B-cell and T-cell epitopes may also be predicted via computer analysis. Polypeptides comprising an epitope of a polypeptide that is preferentially expressed in a tumor tissue (with or without additional amino acid sequence) are within the scope of the present invention.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (I) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer CABIOS 5:151–153; Myers, E. W. and Muller W. (1988) Optimal alignments in linear space CABIOS 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity. In general, polynucleotides encoding all or a portion of the polypeptides described herein may be prepared using any of several techniques. For example, cDNA molecules encoding such polypeptides may be cloned on the basis of the breast tumor-specific expression of the corresponding mRNAs, using differential display PCR. This technique compares the amplified products from RNA template prepared from normal and breast tumor tissue. cDNA may be prepared by reverse transcription of RNA using a $(dT)_{12}AG$ primer. Following amplification of the cDNA using a random primer, a band corresponding to an amplified product specific to the tumor RNA may be cut out from a silver stained gel and subcloned into a suitable vector (e.g., the T-vector, Novagen, Madison, Wis.). Polynucleotides encoding all or a portion of the breast tumor-specific polypeptides disclosed herein may be amplified from cDNA prepared as described above using the random primers shown in SEQ ID NO.:87–125.

Alternatively, a polynucleotide encoding a polypeptide as described herein (or a portion thereof) may be amplified from human genomic DNA, or from breast tumor cDNA, via polymerase chain reaction. For this approach, B18Ag1 sequence-specific primers may be designed based on the sequence provided in SEQ ID NO:1, and may be purchased or synthesized. One suitable primer pair for amplification from breast tumor cDNA is (5' ATG GCT ATT TTC GGG GGC TGA CA) (SEQ ID NO: 126) and (5' CCG GTA TCT CCT CGT GGG TAT T) (SEQ ID NO:127). An amplified portion of B18Ag1 may then be used to isolate the full length gene from a human genomic DNA library or from a breast tumor cDNA library, using well known techniques, such as those described in Sambrook et al., *Molecular Cloning. A Laboratory Manual*, Cold Spring Harbor Laboratories, Cold Spring Harbor, N.Y. (1989). Other sequences within the retroviral genome of which B18Ag1 is a part may be similarly prepared by screening human genomic libraries using B18Ag1-specific sequences as probes. Nucleotides translated into protein from the retroviral genome shown in SEQ ID NO: 141 may then be determined by cloning the corresponding cDNAs, predicting the open reading frames and cloning the appropriate cDNAs into a vector containing a viral promoter, such as T7. The resulting constructs can be employed in a translation reaction, using techniques known to those of skill in the art, to identify nucleotide sequences which result in expressed protein. Similarly, primers specific for the remaining breast tumor-specific polypeptides described herein may be designed based on the nucleotide sequences provided in SEQ ID NO:11–86, 142–298, 301–303, 307, 313, 314, 316 and 317.

Recombinant polypeptides encoded by the DNA sequences described above may be readily prepared from the DNA sequences. For example, supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

In general, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line such as COS or CHO.

Such techniques may also be used to prepare polypeptides comprising epitopes or variants of the native polypeptides. For example, variants of a native polypeptide may generally be prepared using standard mutagenesis techniques, such as oligonucleotide-directed site-specific mutagenesis, and sections of the DNA sequence may be removed to permit preparation of truncated polypeptides. Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. *Am. Chem. Soc.* 85:2149–2146 (1963). Equipment for automated synthesis of polypeptides is commercially available from suppliers such as Perkin Elmer/Applied BioSystems Division, Foster City, Calif., and may be operated according to the manufacturer's instructions.

In specific embodiments, polypeptides of the present invention encompass amino acid sequences encoded by a polynucleotide having a sequence recited in any one of SEQ ID NO:1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317, and variants of such polypeptides. Polypeptides within the scope of the present invention also include polypeptides (and epitopes thereof) encoded by DNA sequences that hybridize to a sequence recited in any one of SEQ ID NO: 1, 3–26, 28–77, 142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288, 291–298, 301–303, 307, 313, 314, 316 and 317 under stringent conditions, wherein the DNA sequences are at least 80% identical in overall sequence to a recited sequence and wherein RNA corresponding to the nucleotide sequence is expressed at a greater level in human breast tumor tissue than in normal breast tissue. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. Polynucleotides according to the present invention include molecules that encode any of the above polypeptides.

In another aspect of the present invention, antibodies are provided. Such antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used, for example, in methods for detecting breast cancer in a patient. Such methods involve using an antibody to detect the presence or absence of a breast tumor-specific polypeptide as described herein in a suitable biological sample. As used herein, suitable biological samples include tumor or normal tissue biopsy, mastectomy, blood, lymph node, serum or urine samples, or other tissue, homogenate, or extract thereof obtained from a patient.

There are a variety of assay formats known to those of ordinary skill in the art for using an antibody to detect polypeptide markers in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody, immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of antibody ranging from about 10 ng to about 1 $\mu$g, and preferably about 100–200 ng, is sufficient to immobilize an adequate amount of polypeptide.

Covalent attachment of antibody to a solid support may also generally be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value established from non-tumor tissue. In one preferred embodiment, the cut-off value is the average mean signal obtained when the immobilized antibody is incubated with samples from patients without breast cancer. In general, a sample generating a signal that is three standard deviations above the predetermined cut-off value may be considered positive for breast cancer. In an alternate preferred embodiment, the cut-off value is determined using a Receiver Operator Curve, according to the method of Sackett et al., *Clinical Epidemiology: A Basic Sciencefor Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 1 µg. Such tests can typically be performed with a very small amount of biological sample.

The presence or absence of breast cancer in a patient may also be determined by evaluating the level of mRNA encoding a breast tumor-specific polypeptide as described herein within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction.

For example, polymerase chain reaction may be used to amplify sequences from cDNA prepared from RNA that is isolated from one of the above biological samples. Sequence-specific primers for use in such amplification may be designed based on the sequences provided in any one of SEQ ID NO: 1, 11–86, 142–298. 301–303, 307, 313, 314, 316 and 317, and may be purchased or synthesized. In the case of B18Ag1, as noted herein, one suitable primer pair is B18Ag1-2 (5' ATG GCT ATT TTC GGG GGC TGA CA) (SEQ ID NO:126) and B18Ag1-3 (5' CCG GTA TCT CCT CGT GGG TAT T) (SEQ ID NO:127). The PCR reaction products may then be separated by gel electrophoresis and visualized according to methods well known to those of ordinary skill in the art. Amplification is typically performed on samples obtained from matched pairs of tissue (tumor and non-tumor tissue from the same individual) or from unmatched pairs of tissue (tumor and non-tumor tissue from different individuals). The amplification reaction is preferably performed on several dilutions of cDNA spanning two orders of magnitude. A two-fold or greater increase in expression in several dilutions of the tumor sample as compared to the same dilution of the non-tumor sample is considered positive.

As used herein, the term "primer/probe specific for a polynucleotide" means an oligonucleotide sequence that has at least about 80% identity, preferably at least about 90% and more preferably at least about 95%, identity to the polynucleotide in question, or an oligonucleotide sequence that is anti-sense to a sequence that has at least about 80% identity, preferably at least about 90% and more preferably at least about 95%, identity to the polynucleotide in question. Primers and/or probes which may be usefully employed in the inventive diagnostic methods preferably have at least about 10–40 nucleotides. In a preferred embodiment, the polymerase chain reaction primers comprise at least about 10 contiguous nucleotides of a polynucleotide that encodes one of the polypeptides disclosed herein or that is anti-sense to a sequence that encodes one of the polypeptides disclosed herein. Preferably, oligonucleotide probes for use in the inventive diagnostic methods comprise at least about 15 contiguous oligonucleotides of a polynucleotide that encodes one of the polypeptides disclosed herein or that is anti-sense to a sequence that encodes one of the polypeptides disclosed herein. Techniques for both PCR based assays and in situ hybridization assays are well known in the art.

Conventional RT-PCR protocols using agarose and ethidium bromide staining, while important in defining gene specificity, do not lend themselves to diagnostic kit development because of the time and effort required in making them quantitative (i.e., construction of saturation and/or titration curves), and their sample throughput. This problem is overcome by the development of procedures such as real time RT-PCR which allows for assays to be performed in single tubes, and in turn can be modified for use in 96 well plate formats. Instrumentation to perform such methodologies are available from Perkin Elmer/Applied Biosystems Division. Alternatively, other high throughput assays using labeled probes (e.g., digoxygenin) in combination with labeled (e.g., enzyme fluorescent, radioactive) antibodies to such probes can also be used in the development of 96 well plate assays.

In yet another method for determining the presence or absence of breast cancer in a patient, one or more of the breast tumor-specific polypeptides described may be used in a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to a test antigen (i.e., an immunogenic portion of a polypeptide employed, or a variant thereof). The response may measured visually, using a ruler. In general, a response that is greater than about 0.5 cm in diameter, preferably greater than about 5.0 cm in diameter, is a positive response, indicative of breast cancer.

The breast tumor-specific polypeptides described herein are preferably formulated, for use in a skin test, as pharmaceutical compositions containing at least one polypeptide and a physiologically acceptable carrier, such as water, saline, alcohol, or a buffer. Such compositions typically contain one or more of the above polypeptides in an amount ranging from about 1 $\mu$g to 100 $\mu$g, preferably from about 10 $\mu$g to 50 $\mu$g in a volume of 0.1 mL. Preferably, the carrier employed in such pharmaceutical compositions is a saline solution with appropriate preservatives, such as phenol and/or Tween 80™.

In other aspects of the present invention, the progression and/or response to treatment of a breast cancer may be monitored by performing any of the above assays over a period of time, and evaluating the change in the level of the response (i.e., the amount of polypeptide or mRNA detected or, in the case of a skin test, the extent of the immune response detected). For example, the assays may be performed every month to every other month for a period of 1 to 2 years. In general, breast cancer is progressing in those patients in whom the level of the response increases over time. In contrast, breast cancer is not progressing when the signal detected either remains constant or decreases with time.

In further aspects of the present invention, the compounds described herein may be used for the immunotherapy of breast cancer. In these aspects, the compounds (which may be polypeptides, antibodies or polynucleotides) are preferably incorporated into pharmaceutical compositions or vaccines. Pharmaceutical compositions comprise one or more such compounds and a physiologically acceptable carrier. Vaccines may comprise one or more such compounds in combination with an immunostimulant, such as an adjuvant or a liposome (into which the compound is incorporated). An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Alternatively, a vaccine may contain DNA encoding one or more of the polypeptides as described above, such that the polypeptide is generated in situ. In such vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749 (1993), and reviewed by Cohen, *Science* 259:1691–1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th 1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Ribi ImmunoChem Research Inc., Hamilton, Mont.), RC-529 (Ribi ImmunoChem Research Inc., Hamilton, Mont.) and Aminoalkyl glucosaminide 4-phosphates (AGPs).

Any vaccine provided herein may be prepared using well known methods that result in a combination of antigen, immunostimulant and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macropliages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class 1 and class 11 MHC, adhesion molecules (e.g., CD54 and CD11) and costimulatory molecules (e.g., CD40, CD80, CD86 and 4-I BB).

APCs may generally be transfected with a polynucleotide encoding a polypeptide of the present invention (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

The above pharmaceutical compositions and vaccines may be used, for example, for the therapy of breast cancer in a patient. As used herein, a "patient" refers to any warm-blooded animal, preferably a human. A patient may or may not be afflicted with breast cancer. Accordingly, the above pharmaceutical compositions and vaccines may be used to prevent the development of breast cancer or to treat a patient afflicted with breast cancer. In a preferred embodiment, the compounds are administered either prior to or following surgical removal of primary tumors and/or treatment by administration of radiotherapy and conventional chemotherapeutic drugs. To prevent or slow the development of breast cancer, a pharmaceutical composition or vaccine comprising one or more polypeptides as described herein may be administered to a patient. Alternatively, naked DNA or plasmid or viral vector encoding the polypeptide may be administered. For treating a patient with breast cancer, the pharmaceutical composition or vaccine may comprise one or more polypeptides, antibodies or polynucleotides complementary to DNA encoding a polypeptide as described herein (e.g., antisense RNA or antisense deoxyribonucleotide oligonucleotides).

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered for a 52-week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg. Suitable dose sizes will vary with the size of the patient, but will typically range from about 0.1 mL to about 5 mL.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. *Ibid*).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.*, 22(3), 213, 1996).

In another embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," Immunological Reviews, 157:177, 1997).

Additionally vectors expressing the disclosed polynucleotides may be introduced into stem cells taken from the patient and clonally propagated in vitro for autologous transplant back into the same patient. In one embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

The following Examples are offered by way of illustration and not by way of limitation.

EXAMPLES

Example 1

Preparation of Breast Tumor-Specific cDNAs Using Differential Display RT-PCR

This Example illustrates the preparation of cDNA molecules encoding breast tumor-specific polypeptides using a differential display screen.

A. Preparation of B18Ag1 cDNA and Characterization of mRNA Expression

Tissue samples were prepared from breast tumor and normal tissue of a patient with breast cancer that was confirmed by pathology after removal from the patient. Normal RNA and tumor RNA was extracted from the samples and mRNA was isolated and converted into cDNA using a $(dT)_{12}AG$ (SEQ ID NO:130) anchored 3' primer. Differential display PCR was then executed using a randomly chosen primer (CTTCAACCTC) (SEQ ID NO:103). Amplification conditions were standard buffer containing 1.5 mM $MgCl_2$, 20 pmol of primer, 500 pmol dNTP, and 1 unit of Taq DNA polymerase (Perkin-Elmer, Branchburg, N.J.). Forty cycles of amplification were performed using 94° C. denaturation for 30 seconds, 42° C. annealing for 1 minute, and 72° C extension for 30 seconds. An RNA fingerprint containing 76 amplified products was obtained. Although the RNA fingerprint of breast tumor tissue was over 98% identical to that of the normal breast tissue, a band was repeatedly observed to be specific to the RNA fingerprint pattern of the tumor. This band was cut out of a silver stained gel, subcloned into the T-vector (Novagen, Madison, Wis.) and sequenced.

The sequence of the cDNA, referred to as B18Ag1, is provided in SEQ ID NO:1. A database search of GENBANK and EMBL revealed that the B 18Ag1 fragment initially cloned is 77% identical to the endogenous human retroviral Element S71, which is a truncated retroviral element homologous to the Simian Sarcoma Virus (SSV). S71 contains an incomplete gag gene, a portion of the pol gene and an LTR-like structure at the 3' terminus (see Werner et al., *Virology* 174:225–238 (1990)). B18Ag1 is also 64% identical to SSV in the region corresponding to the P30 (gag) locus. B18Ag1 contains three separate and incomplete reading frames covering a region which shares considerable homology to a wide variety of gag proteins of retroviruses which infect mammals. In addition, the homology to S71 is not just within the gag gene, but spans several kb of sequence including an LTR.

Figure 2:
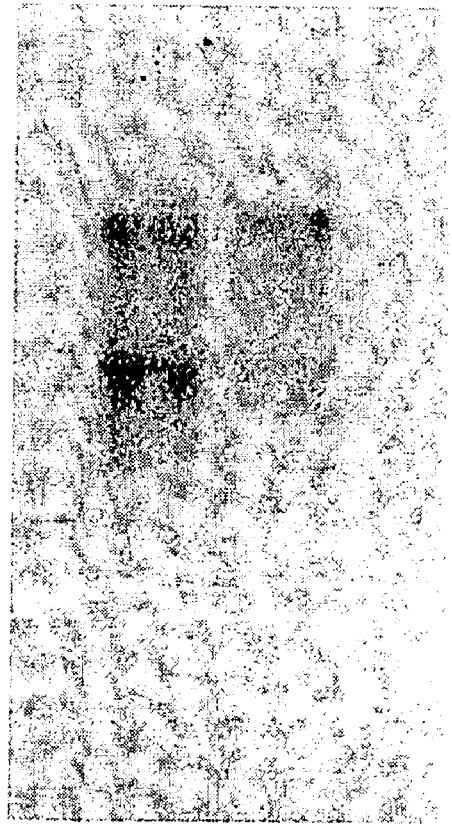
FIG. 2 is a northern blot comparing the level of B18Ag1 mRNA in breast tumor tissue (lane 1) with the level in normal breast tissue.

B18Ag1-specific PCR primers were synthesized using computer analysis guidelines. RT-PCR amplification (94° C., 30 seconds; 60° C.→42° C., 30 seconds; 72° C., 30 seconds for 40 cycles) confirmed that B18Ag1 represents an actual mRNA sequence present at relatively high levels in the patient's breast tumor tissue. The primers used in amplification were B18Ag1-1 (CTG CCT GAG CCA CAA ATG) (SEQ ID NO:128) and B18Ag1-4 (CCG GAG GAG GAA GCT AGA GGA ATA) (SEQ ID NO:129) at a 3.5 mM magnesium concentration and a pH of 8.5, and B18Ag1-2 (ATG GCT ATT TTC GGG GCC TGA CA) (SEQ ID NO:126) and B18Ag1-3 (CCG GTA TCT CCT CGT GGG TAT T) (SEQ ID NO:127) at 2 mM magnesium at pH 9.5. The same experiments showed exceedingly low to nonexistent levels of expression in this patient's normal breast tissue (see FIG. 1). RT-PCR experiments were then used to show that B 18Ag1 mRNA is present in nine other breast tumor samples (from Brazilian and American patients) but absent in, or at exceedingly low levels in, the normal breast tissue corresponding to each cancer patient. RT-PCR analysis has also shown that the B18Ag1 transcript is not present in various normal tissues (including lymph node, myocardium and liver) and present at relatively low levels in PBMC and lung tissue. The presence of B18Ag1 mRNA in breast tumor samples, and its absence from normal breast tissue, has been confirmed by Northern blot analysis, as shown in FIG. 2.

Figure 3:
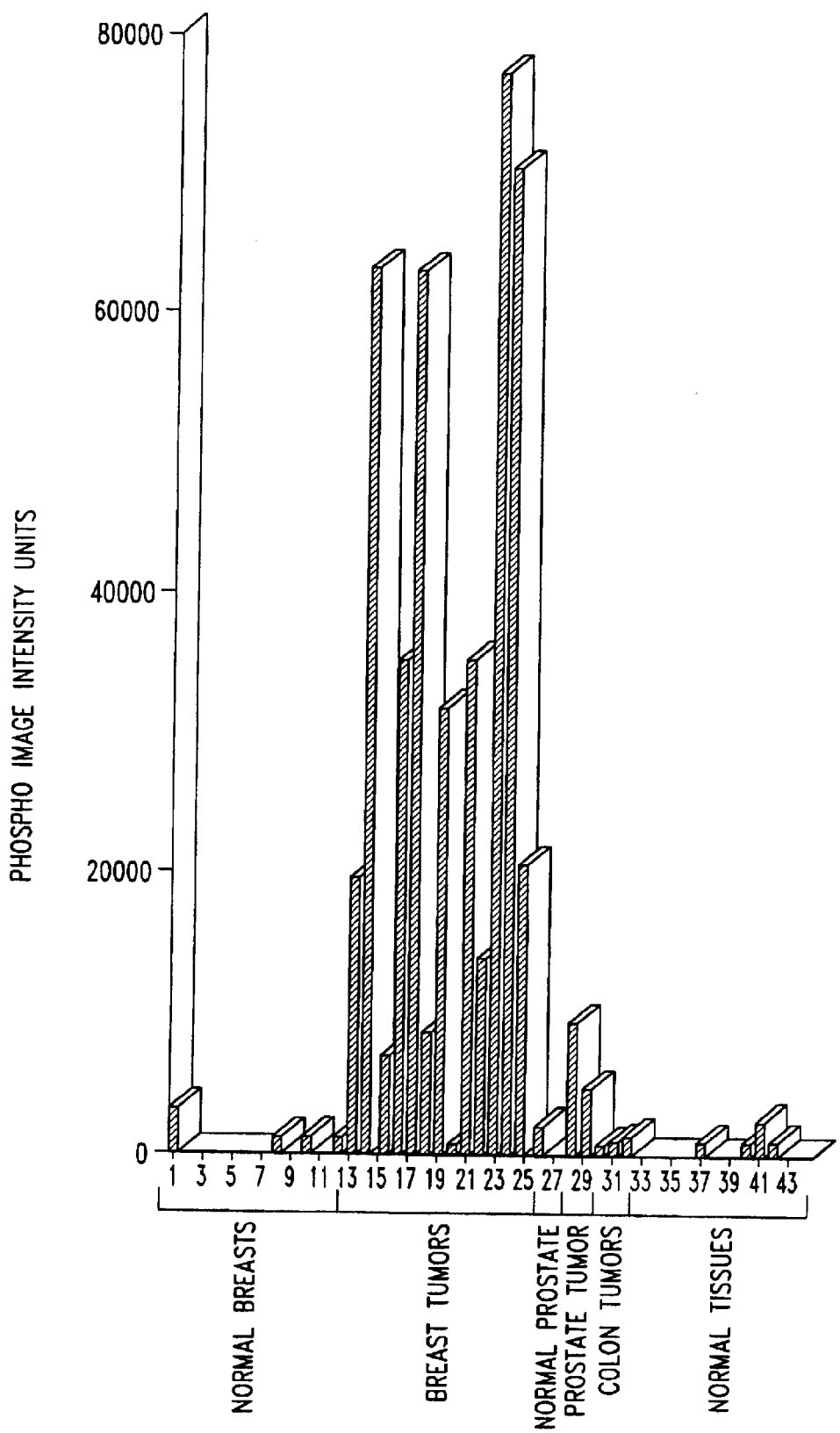
FIG. 3 shows the level of B18Ag1 mRNA in breast tumor tissue compared to that in various normal and non-breast tumor tissues as determined by RNase protection assays.

The differential expression of B18Ag1 in breast tumor tissue was also confirmed by RNase protection assays. FIG. 3 shows the level of B18Ag1 mRNA in various tissue types as determined in four different RNase protection assays. Lanes 1–12 represent various normal breast tissue samples, lanes 13–25 represent various breast tumor samples; lanes 26–27 represent normal prostate samples; lanes 28–29 represent prostate tumor samples; lanes 30–32 represent colon tumor samples; lane 33 represents normal aorta; lane 34 represents normal small intestine; lane 35 represents normal skin, lane 36 represents normal lymph node; lane 37 represents normal ovary; lane 38 represents normal liver; lane 39 represents normal skeletal muscle; lane 40 represents a first normal stomach sample, lane 41 represents a second normal stomach sample; lane 42 represents a normal lung; lane 43 represents normal kidney; and lane 44 represents normal pancreas. Interexperimental comparison was facilitated by including a positive control RNA of known ε-actin message abundance in each assay and normalizing the results of the different assays with respect to this positive control.

Figure 4:
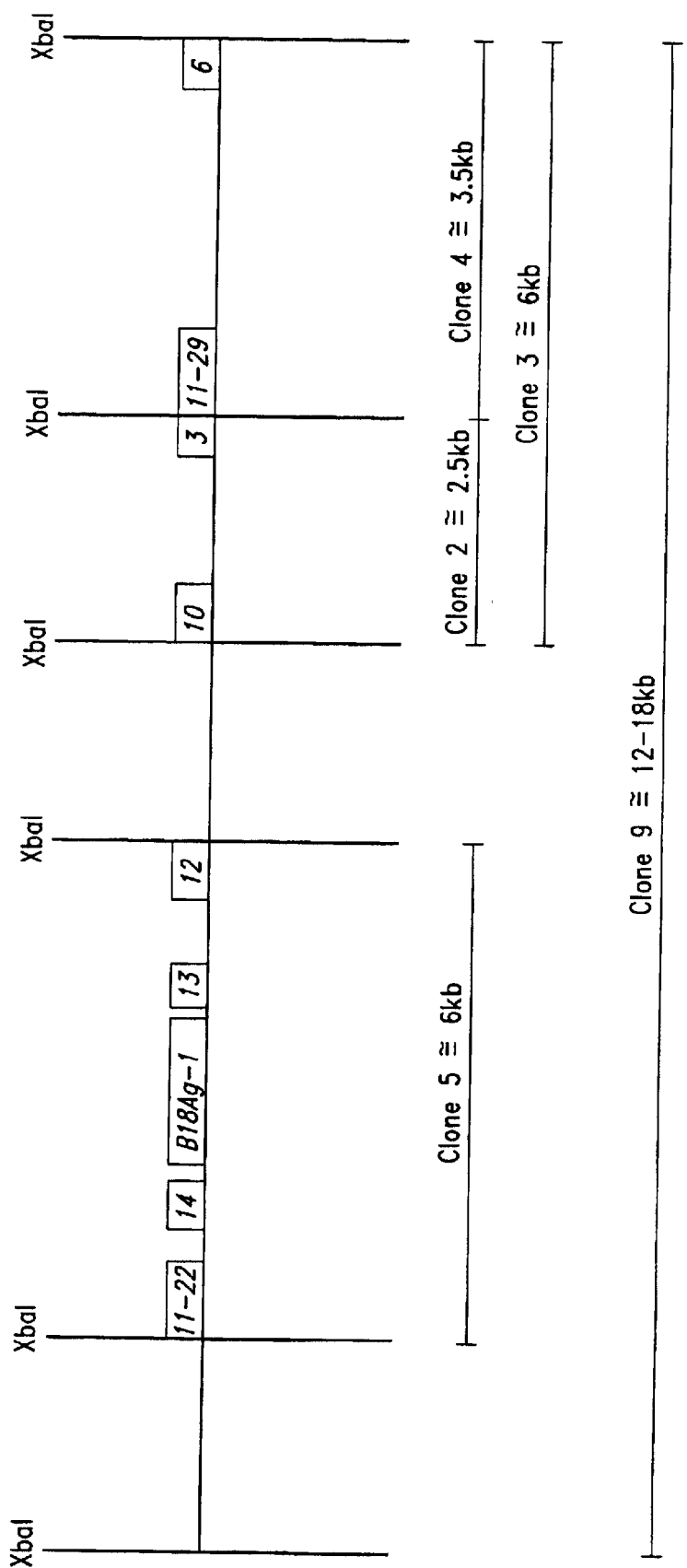
FIG. 4 is a genomic clone map showing the location of additional retroviral sequences obtained from ends of XbaI restriction digests (provided in SEQ ID NO:3–SEQ ID NO:10) relative to B18 Ag1.

RT-PCR and Southern Blot analysis has shown the B18Ag1 locus to be present in human genomic DNA as a single copy endogenous retroviral element. A genomic clone of approximately 12–18 kb was isolated using the initial B18Ag1 sequence as a probe. Four additional subclones were also isolated by XbaI digestion. Additional retroviral sequences obtained from the ends of the XbaI digests of these clones (located as shown in FIG. 4) are shown as SEQ ID NO:3–SEQ ID NO:10, where SEQ ID NO:3 shows the location of the sequence labeled 10 in FIG. 4, SEQ ID NO:4 shows the location of the sequence labeled 11–29, SEQ ID NO:5 shows the location of the sequence labeled 3, SEQ ID NO:6 shows the location of the sequence labeled 6, SEQ ID NO:7 shows the location of the sequence labeled 12, SEQ ID NO:8 shows the location of the sequence labeled 13, SEQ ID NO:9 shows the location of the sequence labeled 14 and SEQ ID NO: 0 shows the location of the sequence labeled 11–22.

Subsequent studies demonstrated that the 12–18 kb genomic clone contains a retroviral element of about 7.75 kb, as shown in FIGS. 5A and 5B. The sequence of this retroviral element is shown in SEQ ID NO: 141. The numbered line at the top of FIG. 5A represents the sense strand sequence of the retroviral genomic clone. The box below this line shows the position of selected restriction sites. The arrows depict the different overlapping clones used to sequence the retroviral element. The direction of the arrow shows whether the single-pass subclone sequence corresponded to the sense or anti-sense strand. FIG. 5B is a schematic diagram of the retroviral element containing B18Ag1 depicting the organization of viral genes within the element. The open boxes correspond to predicted reading frames, starting with a methionine, found throughout the element. Each of the six likely reading frames is shown, as indicated to the left of the boxes, with frames 1–3 corresponding to those found on the sense strand.

Using the cDNA of SEQ ID NO:1 as a probe, a longer cDNA was obtained (SEQ ID NO:227) which contains minor nucleotide differences (less than 1%) compared to the genomic sequence shown in SEQ ID NO:141.

B. Preparation of cDNA Molecules Encoding Other Breast Tumor-Specific Polypeptides Normal RNA and tumor RNA was prepared and mRNA was isolated and converted into cDNA using a $(dT)_{12}AG$ anchored 3' primer, as described above. Differential display PCR was then executed using the randomly chosen primers of SEQ ID NO: 87–125. Amplification conditions were as noted above, and bands observed to be specific to the RNA fingerprint pattern of the tumor were cut out of a silver stained gel, subcloned into either the T-vector (Novagen, Madison, Wis.) or the pCRII vector (Invitrogen, San Diego, Calif.) and sequenced. The sequences are provided in SEQ ID NO:11–SEQ ID NO:86. Of the 79 sequences isolated, 67 were found to be novel (SEQ ID NO:11–26 and 28–77) (see also FIGS. 6–20).

An extended DNA sequence (SEQ ID NO: 290) for the antigen B15Ag1 (originally identified partial sequence provided in SEQ ID NO: 27) was obtained in further studies. Comparison of the sequence of SEQ ID NO: 290 with those in the gene bank as described above, revealed homology to the known human β-A activin gene. Further studies led to the isolation of the full-length cDNA sequence for the antigen B21GT2 (also referred to as B311D; originally identified partial cDNA sequence provided in SEQ ID NO: 56). The full-length sequence is provided in SEQ ID NO: 307, with the corresponding amino acid sequence being provided in SEQ ID NO: 308. Further studies led to the isolation of a splice variant of B311D. The B311D clone of SEQ ID NO: 316 was sequenced and a XhoI/NotI fragment from this clone was gel purified and 32P-cDTP labeled by random priming for use as a probe for further screening to obtain additional B311D gene sequence. Two fractions of a human breast tumor cDNA bacterial library were screened using standard techniques. One of the clones isolated in this manner yielded additional sequence which includes a poly A+ tail. The determined cDNA sequence of this clone (referred to as B311D_BT1_1A) is provided in SEQ ID NO: 317. The sequences of SEQ ID NO: 316 and 317 were found to share identity over a 464 bp region, with the sequences diverging near the poly A+ sequence of SEQ ID NO: 317.

Subsequent studies identified an additional 146 sequences (SEQ ID NOS:142–289), of which 115 appeared to be novel (SEQ ID NOS:142, 143, 146–152, 154–166, 168–176, 178–192, 194–198, 200–204, 206, 207, 209–214, 216, 218, 219, 221–240, 243–245, 247, 250, 251, 253, 255, 257–266, 268, 269, 271–273, 275, 276, 278, 280, 281, 284, 288 and 291). To the best of the inventors' knowledge none of the previously identified sequences have heretofore been shown to be expressed at a greater level in human breast tumor tissue than in normal breast tissue.

In further studies, several different splice forms of the antigen B11Ag1 (also referred to as B305D) were isolated, with each of the various splice forms containing slightly different versions of the B11Ag1 coding frame. Splice junction sequences define individual exons which, in various patterns and arrangements, make up the various splice forms. Primers were designed to examine the expression pattern of each of the exons using RT-PCR as described below. Each exon was found to show the same expression pattern as the original B11Ag1 clone, with expression being breast tumor-, normal prostate- and normal testis-specific. The determined cDNA sequences for the isolated protein coding exons are provided in SEQ ID NO: 292–298, respectively. The predicted amino acid sequences corresponding to the sequences of SEQ ID NO: 292 and 298 are provided in SEQ ID NO: 299 and 300. Additional studies using rapid amplification of cDNA ends (RACE), a 5' specific primer to one of the splice forms of B11Ag1 provided above and a breast adenocarcinoma, led to the isolation of three additional, related, splice forms referred to as isoforms B11C-15, B11C-8 and B11C-9,16. The determined cDNA sequences for these isoforms are provided in SEQ ID NO: 301–303, with the corresponding predicted amino acid sequences being provided in SEQ ID NO: 304–306.

In subsequent studies on B305D isoform A (cDNA sequence provided in SEQ ID NO: 292), the cDNA sequence (provided in SEQ ID NO: 313) was foul contain an additional guanine residue at position 884, leading to a frameshift in the open reading frame. The determined DNA sequence of this ORF is provided in SEQ ID NO: 314. This frameshift generates a protein sequence (provided in SEQ ID NO: 315) of 293 amino acids that contains the C-terminal domain common to the other isoforms of B305D but that differs in the N-terminal region.

Example 2

Preparation of B18AG1 DNA from Human Genomic DNA

This Example illustrates the preparation of B18Ag1 DNA by amplification from human genomic DNA.

B18Ag1 DNA may be prepared from 250 ng human genomic DNA using 20 pmol of B18Ag1 specific primers, 500 pmol dNTPS and 1 unit of Taq DNA polymerase (Perkin Elmer, Branchburg, N.J.) using the following amplification parameters: 94° C. for 30 seconds denaturing, 30 seconds 60° C. to 42° C. touchdown annealing in 2° C. increments every two cycles and 72° C. extension for 30 seconds. The last increment (a 42° C. annealing temperature) should cycle 25 times. Primers were selected using computer analysis. Primers synthesized were B18Ag1-1, B18Ag1-2, B11Ag1-3, and B18Ag1-4. Primer pairs that may be used are 1+3, 1+4, 2+3, and 2+4.

Following gel electrophoresis, the band corresponding to B18Ag1 DNA may be excised and cloned into a suitable vector.

Example 3

Preparation of B 18AG1 DNA from Breast Tumor cDNA

This Example illustrates the preparation of B18Ag1 DNA by amplification from human breast tumor cDNA.

First strand cDNA is synthesized from RNA prepared from human breast tumor tissue in a reaction mixture containing 500 ng poly A+ RNA, 200 pmol of the primer $(T)_{12}AG$(i.e., TTT TTT TTT TTT AG) (SEQ ID NO: 130), IX first strand reverse transcriptase buffer, 6.7 mM DTT, 500 mmol dNTPs, and 1 unit AMV or MMLV reverse transcriptase (from any supplier, such as Gibco-BRL (Grand Island, N.Y.)) in a final volume of 30 µl. After first strand synthesis, the cDNA is diluted approximately 25 fold and 1 µl is used for amplification as described in Example 2. While some primer pairs can result in a heterogeneous population of transcripts, the primers B18Ag1-2 (5'ATG GCT ATT TTC GGG GGC TGA CA) (SEQ ID NO: 126) and B18Ag1-3 (5'CCG GTA TCT CCT CGT GGG TAT T) (SEQ ID NO: 127) yield a single 151 bp amplification product.

Example 4

Identification of B-Cell and T-Cell Epitopes or B 18AG1

This Example illustrates the identification of B18Ag1 epitopes.

The B18 µl sequence can be screened using a variety of computer algorithms. To determine B-cell epitopes, the sequence can be screened for hydrophobicity and hydrophilicity values using the method of Hopp, *Prog. Clin. Biol. Res.* 172B:367–77 (1985) or, alternatively, Cease et al., *J. Exp. Med.* 164:1779–84 (1986) or Spouge et al., *J. Immunol.* 138:204–12 (1987). Additional Class II MHC (antibody or B-cell) epitopes can be predicted using programs such as AMPHI (e.g., Margalit et al., *J. Immunol.* 138:2213 (1987)) or the methods of Rothbard and Taylor (e.g., *EMBO J.* 7:93 (1988)).

Once peptides (15–20 amino acids long) are identified using these techniques, individual peptides can be synthesized using automated peptide synthesis equipment (available from manufacturers such as Perkin Elmer/ Applied Biosystems Division, Foster City, Calif.) and techniques such as Merrifield synthesis. Following synthesis, the peptides can used to screen sera harvested from either normal or breast cancer patients to determine whether patients with breast cancer possess antibodies reactive with the peptides. Presence of such antibodies in breast cancer patient would confirm the immunogenicity of the specific B-cell epitope in question. The peptides can also be tested for their ability to generate a serologic or humoral immune in animals (mice, rats, rabbits, chimps etc.) following immunization in vivo. Generation of a peptide-specific antiserum following such immunization further confirms the immunogenicity of the specific B-cell epitope in question.

To identify T-cell epitopes, the B18Ag1 sequence can be screened using different computer algorithms which are useful in identifying 8-10 amino acid motifs within the B18Ag1 sequence which are capable of binding to HLA Class 1 MHC molecules. (see, e.g., Rammensee et al., *Immunogenetics* 41:178–228 (1995)). Following synthesis such peptides can be tested for their ability to bind to class 1 MHC using standard binding assays (e.g., Sette et al., *J. Immunol.* 153:5586–92 (1994)) and more importantly can be tested for their ability to generate antigen reactive cytotoxic T-cells following in vitro stimulation of patient or normal peripheral mononuclear cells using, for example, the methods of Bakker et al., *Cancer Res.* 55:5330–34 (1995), Visseren et al., *J. Immunol.* 154:3991–98 (1995); Kawakami et al., *J. Immunol.* 154:3961–68 (1995); and Kast et al., *J. Immunol.* 152:3904–12 (1994). Successful in vitro generation of T-cells capable of killing autologous (bearing the same Class I MHC molecules) tumor cells following in vitro peptide stimulation further confirms the immunogenicity of the B18Ag1 antigen. Furthermore, such peptides may be used to generate murine peptide and B18Ag1 reactive cytotoxic T-cells following in vivo immunization in mice rendered transgenic for expression of a particular human MHC Class I haplotype (Vitiello et al., *J. Exp. Med.* 173:1007–15 (1991). A representative list of predicted B18Ag1 B-cell and T-cell epitopes, broken down according to predicted HLA Class I MHC binding antigen, is shown below:

Predicted Th Motifs (B-cell epitopes) (SEQ ID NOS.: 131–133)

SSGGRTFDDFHRYLLVGI
QGAAQKPINLSKXIEVVQGHDF
SPGVFLEHLQEAYRIYTPFDLSA

Predicted HLA A2.1 Motifs (T-cell epitopes) (SEQ ID NOS.: 134–140)

YLLVGIQGA
GAAQKPINL
NLSKXIEVV
EVVQGHDES
HLQEAYRIY
NLAFVAQAA
FVAQAAPDS

Example 5

Identification of T-Cell Epitopes of B11 AG1

This Example illustrates the identification of B11Ag1 (also referred to as B305D) epitopes. Four peptides, referred to as B 11-8, B11-1, B11-5 and B 11-12 (SEQ ID NO: 309–312, respectfully) were derived from the B1Ag1 gene.

Figure 22:
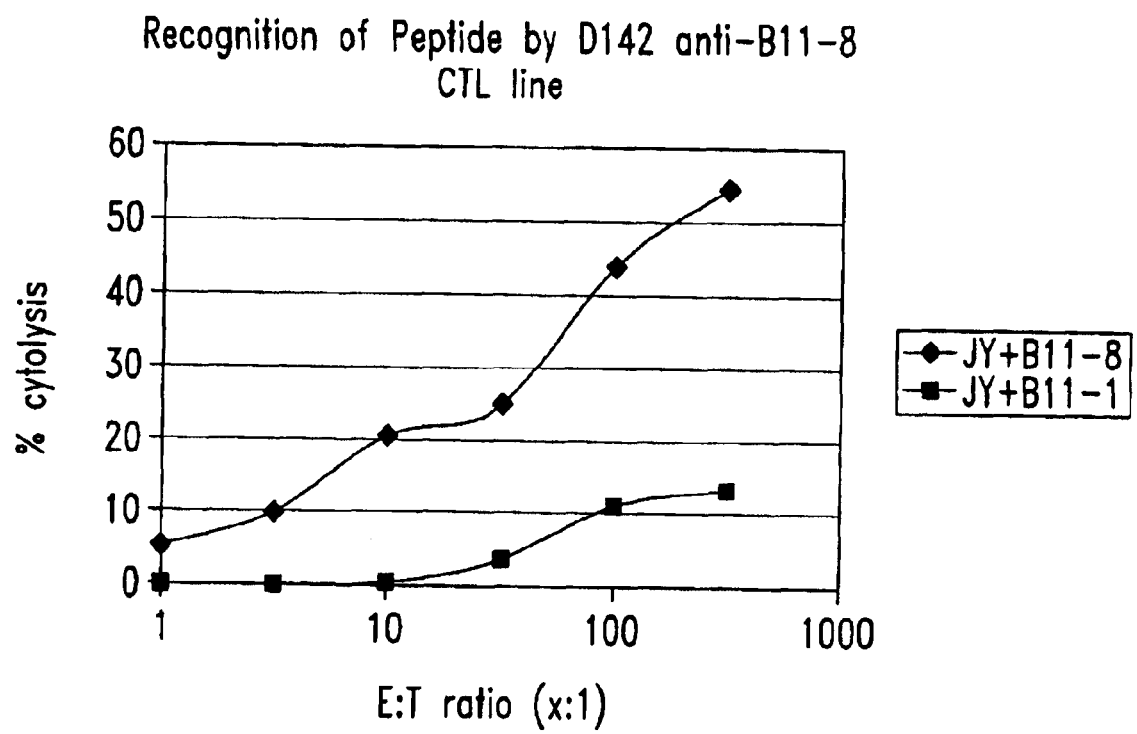
FIG. 22 shows the recognition of a B11Ag1 peptide (referred to as B11-8) by an anti-B11-8 CTL line.

Human CD8 T cells were primed in vitro to the peptide B13-8 using dendritic cells according to the protocol of Van Tsai et al. (*Critical Reviews in Immunology* 18:65–75, 1998). The resulting CD8 T cell cultures were tested for their ability to recognize the B 11-8 peptide or a negative control peptide, presented by the B-LCL line, JY. Briefly, T cells were incubated with autologous monocytes in the presence of 10 ug/ml peptide, 10 ng/ml IL-7 and 10 ug/ml IL-2, and assayed for their ability to specifically lyse target cells in a standard 51-Cr release assay. As shown in FIG. 22, the bulk culture line demonstrated strong recognition of the B11-8 peptide with weaker recognition of the peptide B 11-1.

Figure 23:
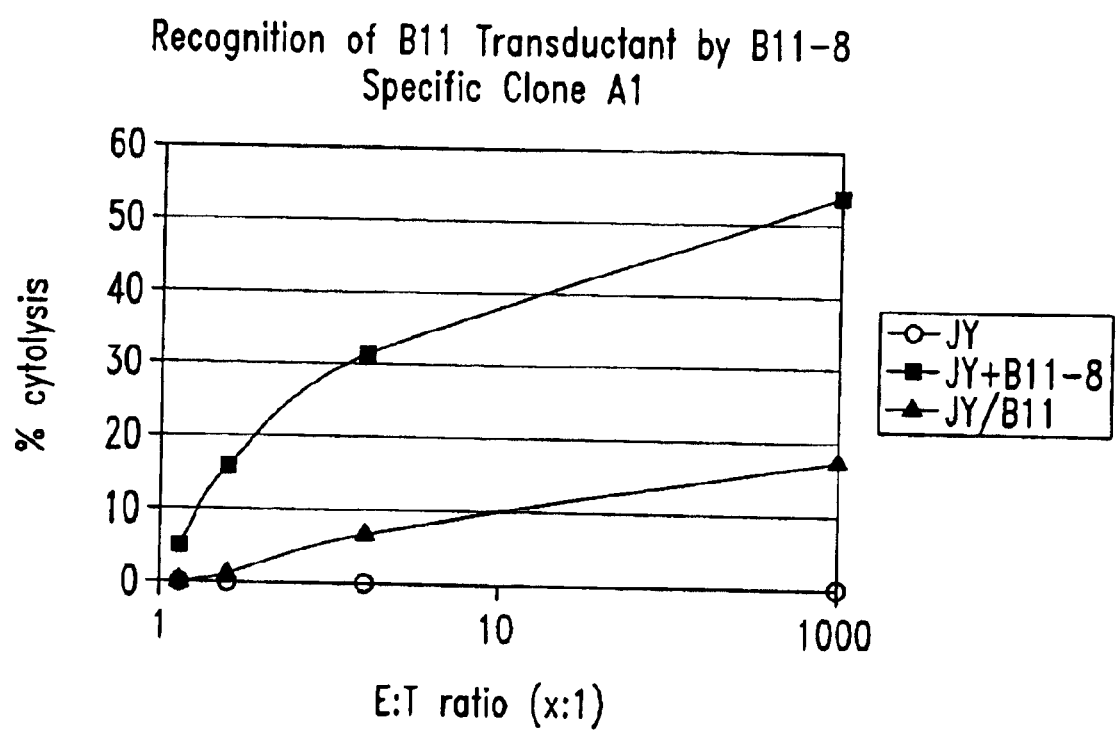
FIG. 23 shows the recognition of a cell line transduced with the antigen B11Ag1 by the B11-8 specific clone A1.
Figure 24:
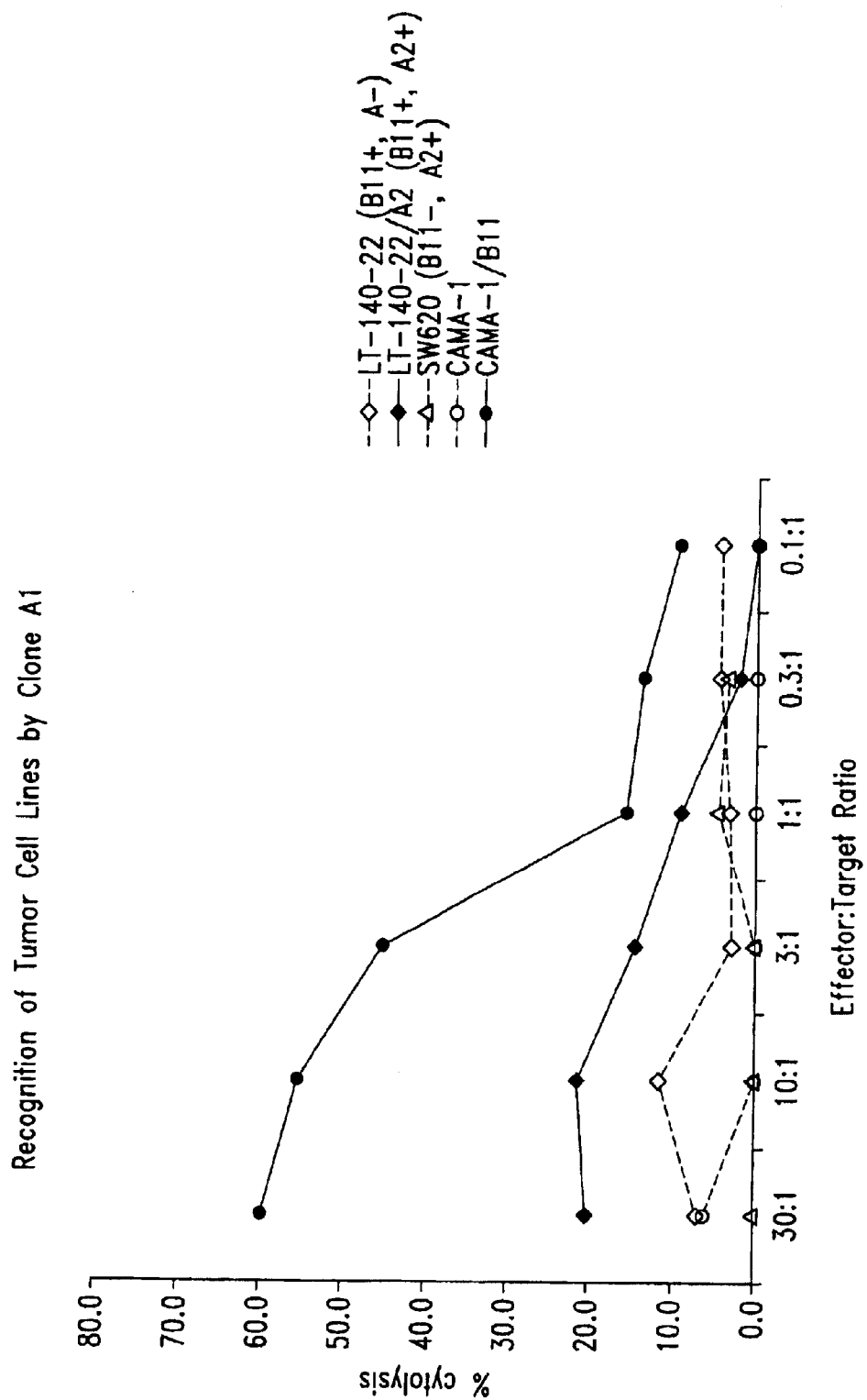
FIG. 24 shows recognition of a lung adenocarcinoma line (LT-140-22) and a breast adenocarcinoma line (CAMA-1) by the B11-8 specific clone A1.

A clone from this CTL line was isolated following rapid expansion using the monoclonal antibody OKT3 and human IL-2. As shown in FIG. 23, this clone (referred to as A1), in addition to being able to recognize specific peptide, recognized JY LCL transduced with the B11Ag1 gene. This data demonstrates that B11-8 is a naturally processed epitope of the B11Ag1 gene. In addition these T cells were further found to recognize and lyse, in an HLA-A2 restricted manner, an established tumor cell line naturally expressing B11Ag1 (FIG. 24). The T cells strongly recognize a lung adenocarcinoma (LT-140-22) naturally expressing B11Ag1 transduced with HLA-A2, as well as an A2+ breast carcinoma (CAMA-1) transduced with B11Ag1, but not untransduced lines or another negative tumor line (SW620). These data clearly demonstrate that these human T cells recognize not only B11-specific peptides but also transduced cells, as well as naturally expressing tumor lines.

CTL lines raised against the antigens B11-5 and B11-12, using the procedures described above, were found to recognize corresponding peptide-coated targets.

Example 6

Characterization of Breast Tumor Genes Discovered by Differential Display PCR

The specificity and sensitivity of the breast tumor genes discovered by differential display PCR were determined using RT-PCR. This procedure enabled the rapid evaluation of breast tumor gene mRNA expression semiquantitatively without using large amounts of RNA. Using gene specific primers, mRNA expression levels in a variety of tissues were examined, including 8 breast tumors, 5 normal breasts, 2 prostate tumors, 2 colon tumors, 1 lung tumor, and 14 other normal adult human tissues, including normal prostate, colon, kidney, liver, lung, ovary, pancreas, skeletal muscle, skin, stomach and testes.

To ensure the semiquantitative nature of the RT-PCR, β-actin was used as internal control for each of the tissues examined. Serial dilutions of the first strand cDNAs were prepared and RT-PCR assays performed using β-actin specific primers. A dilution was then selected that enabled the linear range amplification of β-actin template, and which was sensitive enough to reflect the difference in the initial copy number. Using this condition, the β-actin levels were determined for each reverse transcription reaction from each tissue. DNA contamination was minimized by DNase treatment and by assuring a negative result when using first strand cDNA that was prepared without adding reverse transcriptase.

Figure 21A:
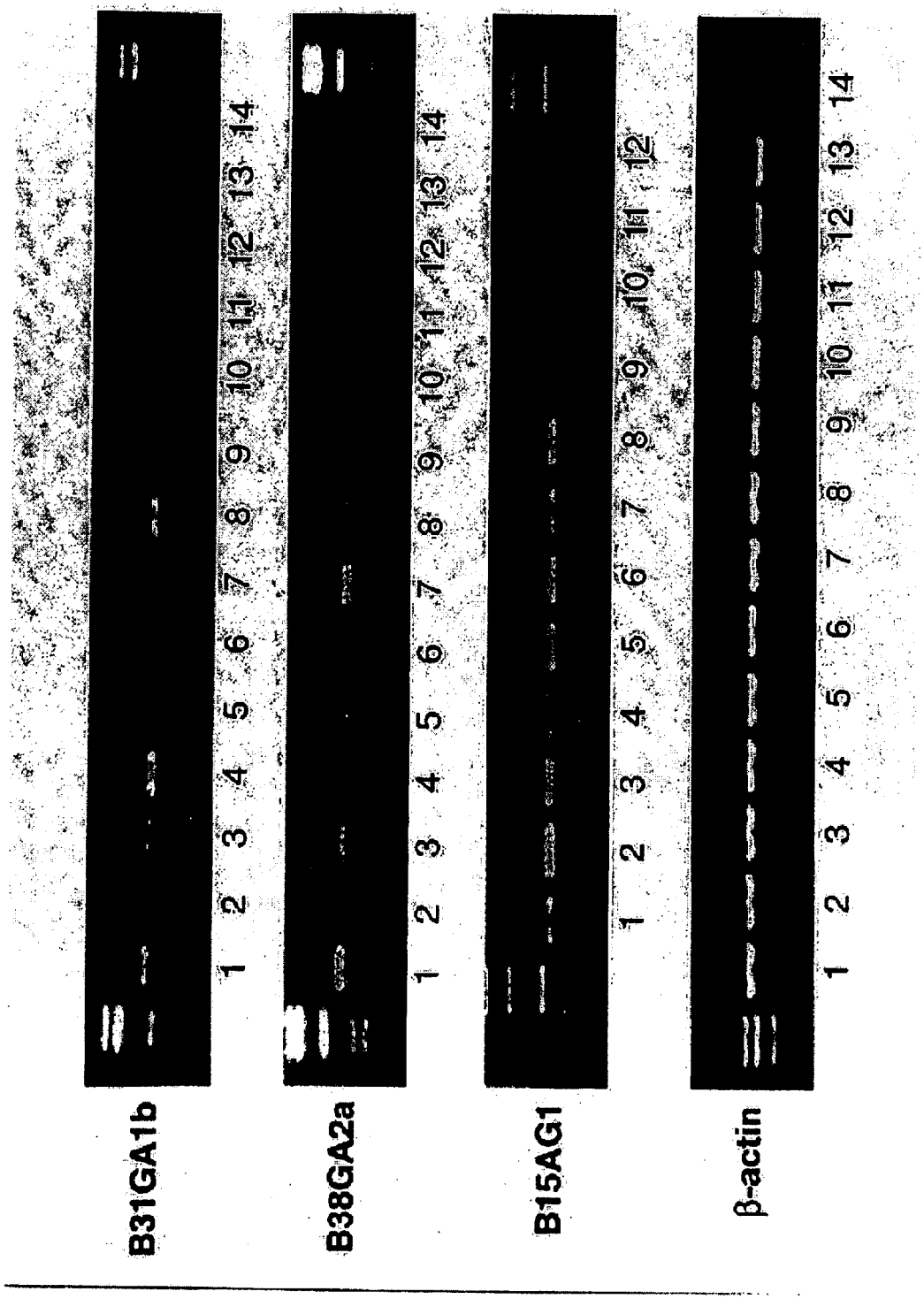
FIG. 21A depicts RT-PCR analysis of breast tumor genes in breast tumor tissues (lanes 1–8) and normal breast tissues (lanes 9–13) and H$_2$O (lane 14).
Figure 21B:
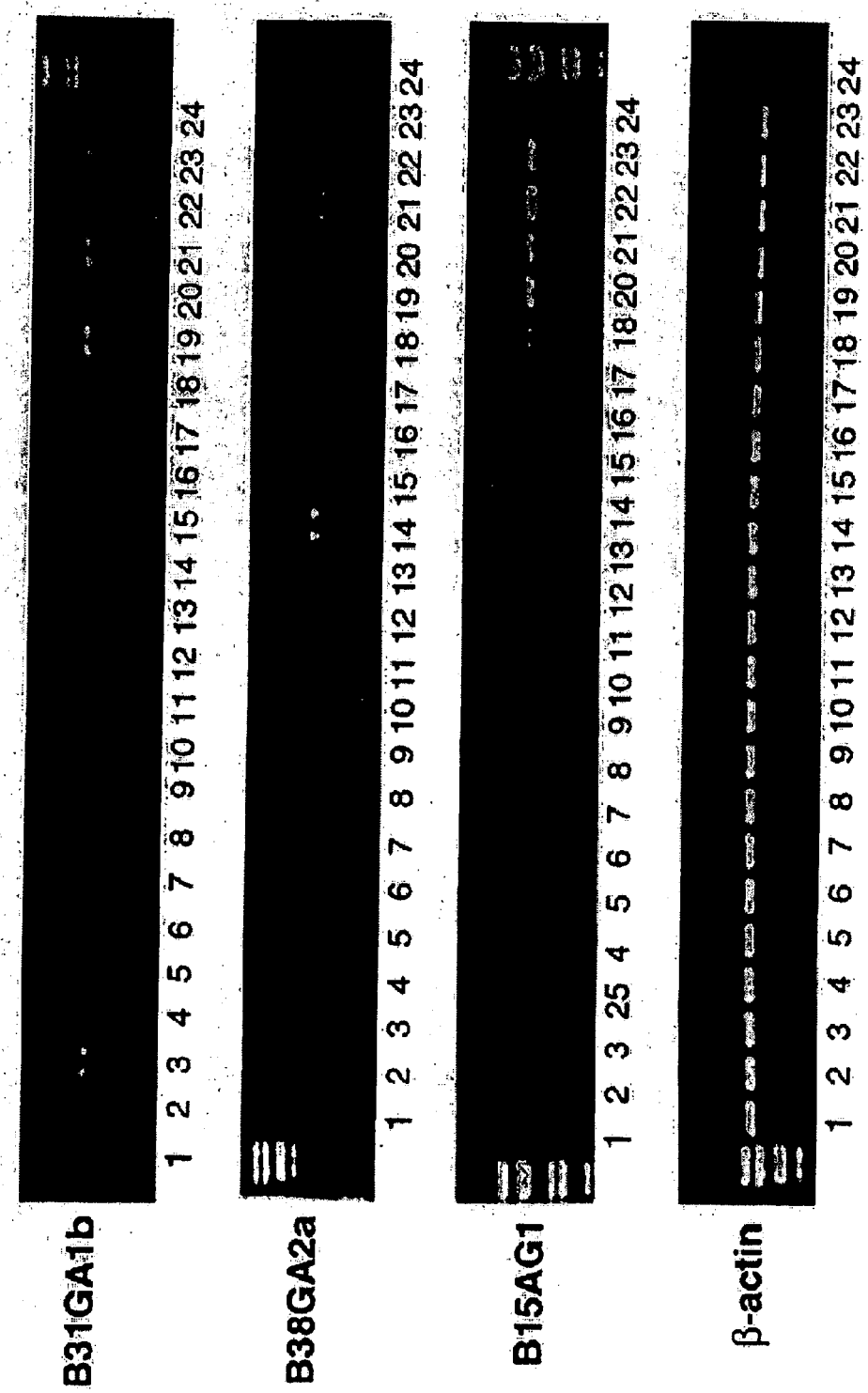
FIG. 21B depicts RT-PCR analysis of breast tumor genes in prostate tumors (lane 1, 2), colon tumors (lane 3), lung tumor (lane 4), normal prostate (lane 5), normal colon (lane 6), normal kidney (lane 7), normal liver (lane 8), normal lung (lane 9), normal ovary (lanes 10, 18), normal pancreases (lanes 11, 12), normal skeletal muscle (lane 13), normal skin (lane 14), normal stomach (lane 15), normal testes (lane 16), normal small intestine (lane 17), HBL-100 (lane 19), MCF-12A (lane 20), breast tumors (lanes 21–23), H$_2$O (lane 24), and colon tumor (lane 25).

Using gene specific primers, the mRNA expression levels were determined in a variety of tissues. To date, 38 genes have been successfully examined by RT-PCR, five of which exhibit good specificity and sensitivity for breast tumors (B15AG-1, B31GA1b, B38GA2a, B11A1a and B18AG1a). FIGS. 21A and 21B depict the results for three of these genes: B15AG-1 (SEQ ID NO:27), B31GA1b (SEQ ID NO:148) and B38GA2a (SEQ ID NO: 157). Table I summarizes the expression level of all the genes tested in normal breast tissue and breast tumors, and also in other tissues.

TABLE I

| | Percentage of Breast Cancer Antigens that are Expressed in Various Tissues | |
|---|---|---|
| Breast Tissues | Over-expressed in Breast Tumors | 84% |
| | Equally Expressed in Normals and Tumor | 16% |
| Other Tissues | Over-expressed in Breast Tumors but not in any Normal Tissues | 9% |
| | Over-expressed in Breast Tumors but Expressed in Some Normal Tissues | 30% |
| | Over-expressed in Breast Tumors but Equally Expressed in All Other Tissues | 61% |

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising the amino acid sequence of SEQ ID NO:299, wherein said polypeptide is expressed in breast tumor tissue.

2. An isolated polypeptide that is at least 90% identical to the amino acid sequence of SEQ ID NO:299, wherein said polypeptide is expressed in breast tumor tissue.

3. An isolated polypeptide according to claim 2, wherein said polypeptide is at least 95% identical to the amino acid sequence of SEQ ID NO:299.

4. An isolated polypeptide comprising the amino acid sequence encoded by the polynucleotide sequence of SEQ ID NO:292.

5. An isolated polypeptide comprising the amino acid sequence of SEQ ID NO:299.

6. An isolated polypeptide according to any one of claims 1–5, in combination with a physiologically acceptable carrier.

7. An isolated polypeptide according to any one of claims 1–5, in combination with an immunostimulant.

8. An isolated polypeptide according to claim 7, wherein said immunostimulant is an adjuvant.

9. An isolated polypeptide according to claim 7, wherein said immunostimulant induces a predominantly Type I response.

* * * * *

UNITED STATES PATENT AND TRADEMARK OFFICE
CERTIFICATE OF CORRECTION

PATENT NO.    : 6,861,506 B1
DATED         : March 1, 2005
INVENTOR(S)   : Tony N. Frudakis et al.

It is certified that error appears in the above-identified patent and that said Letters Patent is hereby corrected as shown below:

Title page,
Item [56] References Cited, U.S. PATENT DOCUMENTS, insert the following:
-- 5,912,143    06/15/99    Bandman et al
   6,225,054    05/01/01    Frudakis et al.
   6,344,550    02/05/02    Frudakis et al. --.

FOREIGN PATENT DOCUMENTS
  "WO   98/11514     5/1994" should read as
-- WO   94/11514     05/26/94 --.
Insert the following:
-- EP   1033401 A2   09/06/00
   WO   99/06550     02/11/99
   WO   99/31236     06/24/99
   WO   01/51628     07/19/01 --.

OTHER PUBLICIATONS, insert the following:
-- Ahn and Kunkel, "The structural and functional diversity of dystrophin," *Nature Genetics* 3:283-291, April 1993

Attwood, T.K., "The Babel of Bioinformatices," *Science 290*: 471-473, October 20, 2000

Boon, T., "Toward a Genetic Analysis of Tumor Rejection Antigens," *Adv. Cancer Res.* 58:177-210

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology 111*: 2129-2138, November 1990

Cawthon et al., "cDNA Sequence and Genomic Structure of *EVI2B*, a Gene Lying with an Intron of the Neurofibromatosis Type 1 gene," *Genomics 9*: 446-460, 1991

Curti, B.D., "Physical barriers to drug delivery in tumors," *Critical Reviews in Oncology/Hematology 14*:29-39, 1993

Dermer, G.B., "Another Anniversary for the War on Cancer," *Bio/Technology 12*: 320, March 1994

UNITED STATES PATENT AND TRADEMARK OFFICE
CERTIFICATE OF CORRECTION

PATENT NO. : 6,861,506 B1
DATED : March 1, 2005
INVENTOR(S) : Tony N. Frudakis et al.

It is certified that error appears in the above-identified patent and that said Letters Patent is hereby corrected as shown below:

Title page (cont'd),
Drexler, H. "Recent Results on the Biology of Hodgkin and Reed-Sternberg cells. II. Continuous Cell Lines," *Leukemia and Lymphoma 9*: 1-25, 1993

Embleton, M.J., "Monoclonal Antibodies to Osteogenic Sarcoma Antigens," in Monoclonal Antibodies and Cancer, *Immunology Series 23*, Wright, Jr. G.L. (ed.), Marcel Dekker, New York, NY, 1984, pp. 181-207

Freshney, R.I., *Culture of Animal Cells: A Manual of Basic Technique*, Alan R. Liss, Inc., New York, 1983, pp.3-4

GenBank Accession No. AA533501, August 1, 1997

GenBank Accession No. AC018804, February 11, 2003

GenBank Accession No. A1804733, July 6, 1999

GenBank Accession No. AQ063365, July 30, 1998

GenBank Accession No. AQ124119, August 31, 1998

Geneseq (Derwent) Accession No. AAV68996, January 22, 1999

Genseq (Derwent) Accession No. AAL10921, December 7, 2001

Genseq (Derwent) Accession No. AAL11383, December 7, 2001

Genseq (Derwent) Accession No. AAL11455, December 7, 2001

Genseq (Derwent) Accession No. AAL13620, December 7, 2001

Genseq (Derwent) Accession No. AAL18685, December 7, 2001

Genseq (Derwent) Accession No. AAL20282, December 7, 2001

Genseq (Derwent) Accession No. AAL20354, December 7, 2001

Genseq (Derwent) Accession No. AAL22489, December 7, 2001

UNITED STATES PATENT AND TRADEMARK OFFICE
CERTIFICATE OF CORRECTION

PATENT NO. : 6,861,506 B1
DATED : March 1, 2005
INVENTOR(S) : Tony N. Frudakis et al.

It is certified that error appears in the above-identified patent and that said Letters Patent is hereby corrected as shown below:

Title page (cont'd),
Gerhold and Caskey, "It's the genes! EST access to human genome content," *BioEssays* *18*(12): 973-981, 1996

Geysen et al., "Gognitive Features of Continuous Antigenic Determinants," *Journal of Molecular Recognition* *1*(1): 32-41, 1988

Gillies and Wesolowski et al., "Antigen binding and biological activities of engineered mutant chimeric antibodies with human tumor specificities," *Hum. Antibod. Hybridomas* *1*(1): 47-54, 1990

Harris et al., "Polycystic Kidney Disease 1: Identification and Analysis of the Primary Defect," *Journal of the American Society of Nephrology* *6*(4): 1125-1133, October 1995

Hartwell et al., "Integrating Genetic Approaches into the Discovery of Anticancer Drugs," *Science* *278*: 1064-1068, November 7, 1997

Hsu, T.C., "Karyology of Cells in Culture," in Tissue Culture: Methods and Applications, Kurse, Jr et al. (eds.), Academic Press, New York, 1973, pp . 764-767

Jain, R. K., "Barriers to Drug Delivery in Solid Tumors," *Scientific American* *271*(1): 58-65, July 1994

Johnstone and Thorpe (eds.), *Immunochemistry in Practice*, Second Edition, Blackwell Scientific Publications, Oxford England, 1987, pp 49-50

Lazar et al., "Transforming Growth Factor α: Mutation of Aspartic Acid 47 and Leucine 48 Results in Different Biological Activities," *Molecular and Cellular Biology* *8*: 1247-1252, March 1988

Russell and Barton , "Structural Features can be Unconserved in Proteins with Similar Folds. An Analysis of Side-chain to Side-chain Contacts Secondary Structure and Accessibility," *J. Mol. Biol.* *244*: 332-350, 1994

Tao and Morrison, "Studies of Aglycosylated Chimeric Mouse-Human IgG. Role of Carbohydrate in the Structure and Effector Functions Mediated by the Human IgG Constant Region," *Journal of Immunity* *143*(8): 2595-2601, October 15, 1989

UNITED STATES PATENT AND TRADEMARK OFFICE
CERTIFICATE OF CORRECTION

PATENT NO. : 6,861,506 B1
DATED : March 1, 2005
INVENTOR(S) : Tony N. Frudakis et al.

It is certified that error appears in the above-identified patent and that said Letters Patent is hereby corrected as shown below:

Title page (cont'd),
Venter et al., "Geneme sequence analysis: scientific objectives and practical strategies," *Trends in Biotechnology 10*: 8-11, Jan/Feb 1992

Walter, G., "Production of use of antibodies against synthetic peptides," *Journal of Immunological Methods 88*: 149-161, 1986

Wei et al., "Protection against mammary tumor growth by vaccination with full-length, modified human *ErbB-2* DNA," *Int. J. Cancer 81*: 748-754, 1999

Wells and Peitsch, "The chemokine information source: identification and characterization of novel chemokines using the WorldWideWeb and Expressed Sequence Tag Databases," *Journal of Leukocyte Biology 61*: 545-550, May 1997 --.

Signed and Sealed this

Eighth Day of November, 2005

JON W. DUDAS
*Director of the United States Patent and Trademark Office*